(12) United States Patent
Vazquez et al.

(10) Patent No.: US 10,966,980 B2
(45) Date of Patent: *Apr. 6, 2021

(54) PYRROLO[2,3-D]PYRIMIDINE DERIVATIVES

(71) Applicant: Pfizer Inc., New York, NY (US)

(72) Inventors: Michael L. Vazquez, Billerica, MA (US); Neelu Kaila, Lexington, MA (US); Jamison B. Tuttle, Marblehead, MA (US); Patrick Robert Verhoest, Newton, MA (US); Matthew R. Reese, Mystic, CT (US); Karen J. Coffman, Pawcatuck, CT (US); Tarek Samad, Chestnut Hill, MA (US); James M. Duerr, Quincy, MA (US); Simone Sciabola, Cambridge, MA (US); Mihir D. Parikh, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/822,265

(22) Filed: Aug. 10, 2015

(65) Prior Publication Data

US 2016/0045508 A1 Feb. 18, 2016

Related U.S. Application Data

(60) Provisional application No. 62/189,347, filed on Jul. 7, 2015, provisional application No. 62/036,276, filed on Aug. 12, 2014.

(51) Int. Cl.
| | |
|---|---|
| *C07D 487/04* | (2006.01) |
| *C07D 519/00* | (2006.01) |
| *C07D 491/052* | (2006.01) |
| *C07D 498/08* | (2006.01) |
| *C07D 491/044* | (2006.01) |
| *A61K 45/06* | (2006.01) |
| *A61K 31/519* | (2006.01) |
| *A61K 31/5377* | (2006.01) |
| *A61K 31/5386* | (2006.01) |

(52) U.S. Cl.
CPC ........ *A61K 31/519* (2013.01); *A61K 31/5377* (2013.01); *A61K 31/5386* (2013.01); *A61K 45/06* (2013.01); *C07D 487/04* (2013.01); *C07D 491/044* (2013.01); *C07D 491/052* (2013.01); *C07D 498/08* (2013.01); *C07D 519/00* (2013.01)

(58) Field of Classification Search
CPC ............................ C07D 487/04; A61K 31/519
USPC ....................................... 544/280; 514/265.1
See application file for complete search history.

(56) References Cited

U.S. PATENT DOCUMENTS

| | | | |
|---|---|---|---|
| 3,037,980 A | 6/1962 | Hitchings et al. | |
| 6,051,578 A | 4/2000 | Chen | |
| 6,232,320 B1 | 5/2001 | Stewart et al. | |
| 6,284,766 B1 | 9/2001 | Horvath | |
| 6,384,039 B1 | 5/2002 | Fossa | |
| 6,552,192 B1 | 4/2003 | Hanuš et al. | |
| 6,610,847 B2 | 8/2003 | Blumenkopf et al. | |
| 6,664,252 B2 | 12/2003 | Castelhano et al. | |
| 6,673,802 B2 | 1/2004 | Castelhano et al. | |
| 6,680,324 B2 | 1/2004 | Castelhano et al. | |
| 6,686,366 B1 | 2/2004 | Castelhano et al. | |
| 6,696,567 B2 | 2/2004 | Blumenkopf et al. | |
| 6,765,008 B1 | 7/2004 | Chen | |
| 7,335,667 B2 | 2/2008 | Rodgers et al. | |
| 7,504,407 B2 | 3/2009 | Castelhano et al. | |
| 8,133,899 B2 | 3/2012 | Mitton-Fry et al. | |
| 8,372,854 B2 | 2/2013 | Xie et al. | |
| 8,426,411 B2 | 4/2013 | Wishart et al. | |
| 8,633,206 B2 | 1/2014 | Promo et al. | |
| 8,946,239 B2 | 2/2015 | Gangjee et al. | |
| 9,035,074 B2 | 5/2015 | Brown et al. | |
| 9,050,334 B2 | 6/2015 | Gaweco et al. | |
| 2003/0139427 A1 | 7/2003 | Castelhano et al. | |
| 2003/0187261 A1 | 10/2003 | Havlicek et al. | |
| 2008/0051404 A1 | 2/2008 | Claiborne et al. | |
| 2008/0194557 A1 | 8/2008 | Barbosa et al. | |
| 2008/0200458 A1 | 8/2008 | Barbosa et al. | |
| 2010/0273776 A1 | 10/2010 | Lindquist et al. | |
| 2010/0331297 A1 | 12/2010 | Bulawa et al. | |
| 2012/0322782 A1 | 12/2012 | Narishetty et al. | |
| 2014/0018361 A1 | 1/2014 | Harriman et al. | |
| 2014/0057895 A1 | 2/2014 | Mizuno et al. | |
| 2014/0243312 A1 | 8/2014 | Brown et al. | |

(Continued)

FOREIGN PATENT DOCUMENTS

| | | | |
|---|---|---|---|
| JP | 6-329674 A | 11/1994 | |
| JP | 6-329675 A | 11/1994 | |

(Continued)

OTHER PUBLICATIONS

Flanagan et al, "Discovery of CP-690,550: A Potent and Selective Janus Kinase (JAK) Inhibitor for the Treatment of Autoimmune Diseases and Organ Transplant Rejection", Journal of Medicinal Chemistry 53(24):8468-8484 (2010).

PCT International Search Report and Written Opinion for PCT/IB2015/055823 dated Oct. 30, 2015.

Kisseleva et al, "Signaling through the JAK/STAT pathway, recent advances and future challenges", Gene 285:1-24 (2002).

Murray, "The JAK-STAT Signaling Pathway: Input and Output Integration", The Journal of Immunology 178:2623-2629 (2007).

Neubauer et al, "Jak2 Deficiency Defines an Essential Developmental Checkpoint in Definitive Hematopoiesis", Cell 93:397-409 (1998).

O'Shea et al, "Cytokine Signaling in 2002: New Surprises in the Jak/Stat Pathway", Cell 109:S121-S131 (2002).

(Continued)

*Primary Examiner* — Susanna Moore

(74) *Attorney, Agent, or Firm* — A. David Joran

(57) ABSTRACT

Described herein are pyrrolo{2,3-d}pyrimidine derivatives, their use as Janus Kinase (JAK) inhibitors, pharmaceutical compositions containing them, and therapeutic uses thereof.

2 Claims, No Drawings

(56) References Cited

U.S. PATENT DOCUMENTS

| | | | | |
|---|---|---|---|---|
| 2015/0225408 A1* | 8/2015 | Brown | ................ | C07D 519/00 514/210.21 |
| 2015/0246048 A1* | 9/2015 | Brown | ................ | C07D 519/00 514/210.21 |
| 2016/0045508 A1 | 2/2016 | Vazquez et al. | | |

FOREIGN PATENT DOCUMENTS

| | | |
|---|---|---|
| JP | 8-134068 A | 5/1996 |
| JP | 2007-91649 A | 4/2007 |
| JP | 2013-10719 A | 1/2013 |
| JP | 2014-133739 A | 7/2014 |
| WO | 99/65908 A1 | 12/1999 |
| WO | 99/65909 A1 | 12/1999 |
| WO | 01/42246 A2 | 6/2001 |
| WO | 02/00661 A1 | 1/2002 |
| WO | 02/096909 A1 | 12/2002 |
| WO | 2004/032834 A2 | 4/2004 |
| WO | 2004/046112 A2 | 6/2004 |
| WO | 2007/012953 A2 | 2/2007 |
| WO | 2009/060278 A1 | 5/2009 |
| WO | 2010/020905 A1 | 2/2010 |
| WO | 2010/032200 A1 | 3/2010 |
| WO | 2011/045702 A1 | 4/2011 |
| WO | 2011/06881 A1 | 6/2011 |
| WO | 2011/075334 A1 | 6/2011 |
| WO | 2011/086053 A1 | 7/2011 |
| WO | 2012/009678 A1 | 1/2012 |
| WO | 2012/075381 A1 | 6/2012 |
| WO | 2012/117000 A1 | 9/2012 |
| WO | 2014/015107 A1 | 1/2014 |
| WO | 2014/128591 A1 | 8/2014 |

OTHER PUBLICATIONS

Parganas et al, "Jak2 Is Essential for Signaling through a Variety of Cytokine Receptors", Cell 93:385-395 (1998).

Winkler et al, "Nitrilases Catalyze Key Step to Conformationally Constrained GABA Analogous g-Amino Acids in High Optical Purity", J. Org. Chem. 72:7423-7426 (2007).

Yamaoka et al, "The Janus kinases (Jaks)", Genome Biology 5:253 (2004).

Aberg et al, "Characterization and Validation of a Canine Pruritic Model", Drug Development Research 76:246-250 (2015).

Chiba et al, "Stat3 inhibition in neural lineage cells", Hormone Molecular Biology and Clinical Investigation 10 (2):255-263 (2012).

Collard et al, "The pharmacokinetics of oclacitinib maleate, a Janus kinase inhibitor, in the dog", Journal of Veterinary Pharmacology and Therapeutics 37:279-285 (2013).

Fernandes et al, "Lymphotoxin-β receptor in microenvironmental cells promotes the development of T-cell acute lymphoblastic leukaemia with cortical/mature immunophenotype", British Journal of Haematology 171:736-751 (2015).

Fukunishi et al, "Prediction of Synthetic Accessibility Based on Commercially Available Compound Databases", Journal of Chemical Information and Modeling 54:3259-3267 (2014).

Fukuyama et al, "Aggression behaviour induced by oral administration of the Janus-kinase inhibitor tofacitinib, but not oclacitinib, under stressful conditions", European Journal of Pharmacology 764:278-282 (2015).

Fukuyama et al, Topically Administered Janus-Kinase Inhibitors Tofacitinib and Oclacitinib Display Impressive Antipruritic and Anti-Inflammatory Responses in a Model of Allergic Dermatitis, The Journal of Pharmacology and Experimental Therapeutics 354:394-405 (2015).

Gehringer et al, "Novel Hinge-Binding Motifs for Janus Kinase 3 Inhbitors: A Comprehensive Structure-Activity Relationship Study on Tofacitinib Bioisosteres", ChemMedChem 9:2516-2527 (2014).

Gonzales et al, "Oclacitinib (APOQUEL®) is a novel Janus kinase inhibitor with activity against cytokines involved in allergy", Journal of Veterinary Pharmacology and Therapeutics 37:317-324 (2014).

Hau et al, "Antimycotics suppress the Malassezia extract-induced production of CXC chemokine ligand 10 in human keratinocytes", The Journal of Dermatology 41:124-134 (2014).

Keohane et al, "JAK inhibition induces silencing of T Helper cytokine secretion and a profound reduction in T regulatory cells", British Journal of Haematology 171:60-73 (2015).

Olivry et al, "Treatment of canine atopic dermatitis: 2015 updated guidelines from the International Committee on Allergic Diseases of Animals (ICADA)", BMC Veterinary Research 11:210 (2015) 15 pages.

Saridomichelakis et al, "An update on the treatment of canine atopic dermatitis", The Veterinary Journal 207:29-37 (2016).

* cited by examiner

PYRROLO[2,3-D]PYRIMIDINE DERIVATIVES

RELATED APPLICATIONS

This application claims the benefit of U.S. Provisional Application No. 62/036,276, filed Aug. 12, 2014, and U.S. Provisional Application No. 62/189,347, filed Jul. 7, 2015, which are hereby incorporated by referenced in their entireties.

FIELD OF THE INVENTION

The present invention provides pharmaceutically active pyrrolo[2,3-d]pyrimidine compounds and analogues. Such compounds are useful for inhibiting Janus Kinase (JAK). This invention also is directed to compositions comprising methods for making such compounds, and methods for treating and preventing conditions mediated by JAK.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or deregulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases.

Thus, protein kinases have emerged as an important class of enzymes as targets for therapeutic intervention. In particular, the JAK family of cellular protein tyrosine kinases (JAK1, JAK2, JAK3, and Tyk2) play a central role in cytokine signaling (Kisseleva et al., Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the IFN family (IFN-alpha, IFN-beta, IFN-omega, Limitin, IFN-gamma, IL-10, IL-19, IL-20, IL-22), the gp130 family (IL-6, IL-11, OSM, LIF, CNTF, NNT-1/BSF-3, G-CSF, CT-1, Leptin, IL-12, IL-23), gamma C family (IL-2, IL-7, TSLP, IL-9, IL-15, IL-21, IL-4, IL-13), IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

There remains a need for new compounds that effectively and selectively inhibit specific JAK enzymes, and JAK1 in particular, vs. JAK2. JAK1 is a member of the Janus family of protein kinases composed of JAK1, JAK2, JAK3 and TYK2. JAK1 is expressed to various levels in all tissues. Many cytokine receptors signal through pairs of JAK kinases in the following combinations: JAK1/JAK2, JAK1/JAK3, JAK1/TYK2, JAK2/TYK2 or JAK2/JAK2. JAK1 is the most broadly paired JAK kinase in this context and is required for signaling by γ-common (IL-2Rγ) cytokine receptors, IL-6 receptor family, Type I, II and III receptor families and IL-10 receptor family. Animal studies have shown that JAK1 is required for the development, function and homeostasis of the immune system. Modulation of immune activity through inhibition of JAK1 kinase activity can prove useful in the treatment of various immune disorders (Murray, P. J.

J. Immunol., 178, 2623-2629 (2007); Kisseleva, T., et al., Gene, 285, 1-24 (2002); O'Shea, J. J., et al., Cell, 109, (suppl.) S121-S131 (2002)) while avoiding JAK2 dependent erythropoietin (EPO) and thrombopoietin (TPO) signaling (Neubauer H., et al., Cell, 93(3), 397-409 (1998); Parganas E., et al., Cell, 93(3), 385-95 (1998)).

SUMMARY OF THE INVENTION

The present invention provides a compound of formula I having the structure:

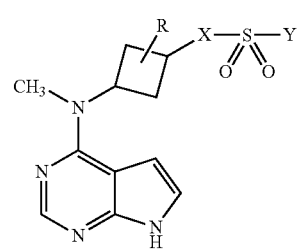

or a pharmaceutically acceptable salt thereof, wherein

R is selected from hydrogen, deuterium, $C_1$-$C_6$ linear or branched alkyl, $C_1$-$C_6$ linear or branched perfluoroalkyl, aryl, and alkylaryl;

X is selected from —NH— and —$CR_aR_b$—, where (a) $R_a$ and $R_b$ are independently hydrogen, deuterium, $C_1$-$C_6$ linear or branched alkyl, $C_3$-$C_6$ cycloalkyl, aryl, (aryl)$C_1$-$C_6$ linear or branched alkyl, heteroaryl, ($C_1$-$C_6$ linear or branched alkyl)heteroaryl, (heteroaryl)$C_1$-$C_6$ linear or branched alkyl, (heterocyclic)$C_1$-$C_6$ linear or branched alkyl, where said alkyl, aryl, heteroaryl and cycloalkyl may be optionally substituted with one or more $R_c$, or (b) $R_a$ and $R_b$ together form a chain comprising —$(CR_cR_d)_j$—, where $R_c$ and $R_d$ are independently hydrogen, deuterium, $C_1$-$C_6$ linear or branched alkyl, aryl, ($C_1$-$C_6$ linear or branched alkyl)aryl, heteroaryl, ($C_1$-$C_6$ linear or branched alkyl)heteroaryl, halo, CN, $CF_3$, hydroxyl, alkoxy, —$CONH_2$, —$NHCO(C_1$-$C_6$ alkyl), —$CONH(C_1$-$C_6$ alkyl), $C_1$-$C_6$ alkoxycarbonyl, or $SO_2CH_3$;

Y is A-$R_1$, where A is a bond, —NH—, —$(CH_2)_k$— or —$(CD_2)_k$- and $R_1$ is $C_1$-$C_6$ linear or branched alkyl, $C_3$-$C_6$ cycloalkyl, aryl, or —$NR_aR_b$, or is an unsaturated, saturated or partially saturated monocyclic or bicyclic ring structure containing a total of four to eleven atoms having one to four heteroatoms independently selected from the group consisting of oxygen, nitrogen, and sulfur, wherein said alkyl, cycloalkyl, aryl, or monocyclic or bicyclic ring structure is further optionally substituted with one or more substituents independently selected from the group consisting of deuterium, halo, $C_1$-$C_6$ linear or branched alkyl, —$C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, CN, hydroxyl, $CF_3$, —$OR_e$, —$CO(C_1$-$C_6$ linear or branched alkyl), —$CO(C_3$-$C_6$ cycloalkyl), —$NR_eR_f$, an unsaturated, saturated or partially saturated monocyclic or bicyclic ring structure containing a total of four to eleven atoms as defined above, and —S(O)$_2$R$_e$ and where said alkyl, alkoxy, and cycloalkyl may be optionally substituted with one or more substituents independently selected from the group consisting of C$_1$-C$_6$ linear or branched alkyl, C$_3$-C$_6$ cycloalkyl, halo, CN, hydroxyl, —OR$_e$, CONH$_2$, and SO$_2$CH$_3$, where (a) R$_a$ and R$_b$ are independently hydrogen, deuterium, C$_1$-C$_6$ linear or branched alkyl, C$_3$-C$_6$ cycloalkyl, C$_1$-C$_6$ linear or branched alkoxy-(C$_3$-C$_6$ cycloalkyl), C$_1$-C$_6$ linear or branched alkoxy-(C$_1$-C$_6$ linear or branched alkyl)-, aryl, (aryl)C$_1$-C$_6$ linear or branched alkyl, heteroaryl, heterocyclic, (C$_1$-C$_6$ linear or branched alkyl)heteroaryl, (heteroaryl)C$_1$-C$_6$ linear or branched alkyl, (heterocyclic)C$_1$-C$_6$ linear or branched alkyl where said alkyl, aryl, heteroaryl and cycloalkyl may be optionally substituted with one or more R$_c$;

(b) R$_a$ and R$_b$ together form a chain comprising —(CR$_c$R$_d$)$_j$—, where R$_c$ and R$_d$ are independently hydrogen, deuterium, C$_1$-C$_6$ linear or branched alkyl, C$_3$-C$_6$ cycloalkyl, C$_1$-C$_6$ linear or branched alkoxy-(C$_3$-C$_6$ cycloalkyl), C$_1$-C$_6$ linear or branched alkoxy-(C$_1$-C$_6$ linear or branched alkyl)-, aryl, (C$_1$-C$_6$ linear or branched alkyl)aryl, heteroaryl, (C$_1$-C$_6$ linear or branched alkyl)heteroaryl, halo, CN, hydroxyl, CF$_3$, —NHCO(alkyl), —CONH(alkyl), alkoxycarbonyl, CONH$_2$, —OR$_e$, —NR$_e$R$_f$, or —S(O)$_2$R$_e$ in which any alkyl, cycloalkyl or alkoxy moiety may be optionally substituted with one or more halogen atoms;

(c) R$_a$ and R$_b$ together form a chain comprising four to six atoms having one or two heteroatoms independently selected from nitrogen, oxygen and sulfur in which any carbon atom may optionally be substituted with a substituent selected from the group consisting of C$_1$-C$_6$ linear or branched alkyl, C$_3$-C$_6$ cycloalkyl, C$_1$-C$_6$ linear or branched alkoxy-(C$_3$-C$_6$ cycloalkyl), C$_1$-C$_6$ linear or branched alkoxy-(C$_1$-C$_6$ linear or branched alkyl)-, aryl, (C$_1$-C$_6$ linear or branched alkyl)aryl, heteroaryl, (C$_1$-C$_6$ linear or branched alkyl)heteroaryl, heterocyclic, halo, CN, hydroxyl, CF$_3$, —NHCO(C$_1$-C$_6$ linear or branched alkyl), —CONH(C$_1$-C$_6$ linear or branched alkyl), C$_1$-C$_6$ linear or branched alkoxycarbonyl, CONH$_2$, —OR$_e$, —NR$_e$R$_f$, or —S(O)$_2$R$_e$, in which any of said alkyl, alkoxy, or cycloalkyl moieties may be optionally substituted with one or more halogen atoms and any nitrogen atom, if chemically permissible, may be optionally substituted with C$_1$-C$_6$ linear or branched alkyl, C$_3$-C$_6$ cycloalkyl, C$_1$-C$_6$ linear or branched alkoxy-(C$_3$-C$_6$ cycloalkyl), C$_1$-C$_6$ linear or branched alkoxy-(C$_1$-C$_6$ linear or branched alkyl)-, aryl, (C$_1$-C$_6$ linear or branched alkyl)aryl, —C(O)C$_1$-C$_6$ linear or branched alkyl, —CONH(C$_1$-C$_6$ linear or branched alkyl), C$_1$-C$_6$ alkoxycarbonyl, CONH$_2$, or —S(O)$_2$R$_e$ in which any of said alkyl or cycloalkyl moieties may be optionally substituted with one or more halogen atoms; or, (d) R$_a$ and R$_b$ together form a 5 to 10 membered bicycloalkyl ring in which any atom of said ring may be optionally substituted with a substituent selected from the group consisting of C$_1$-C$_6$ linear or branched alkyl, C$_3$-C$_6$ cycloalkyl, C$_1$-C$_6$ linear or branched alkoxy-(C$_3$-C$_6$ cycloalkyl), C$_1$-C$_6$ linear or branched alkoxy-(C$_1$-C$_6$ linear or branched alkyl)-, aryl, (C$_1$-C$_6$ linear or branched alkyl)aryl, heteroaryl, (C$_1$-C$_6$ linear or branched alkyl)heteroaryl, heterocyclic, halo, CN, hydroxyl, CF$_3$, —NHCO(C$_1$-C$_6$ linear or branched alkyl), —CONH(C$_1$-C$_6$ linear or branched alkyl), C$_1$-C$_6$ linear or branched alkoxycarbonyl, CONH$_2$, —OR$_e$, —NR$_e$R$_f$, or —S(O)$_2$R$_e$, in which any of said alkyl, alkoxy or cycloalkyl moieties may be optionally substituted with one or more halogen atoms;

where R$_e$ and R$_f$ are independently hydrogen, deuterium, C$_1$-C$_6$ linear or branched alkyl, C$_1$-C$_6$ alkoxy, or C$_3$-C$_6$ cycloalkyl, where said alkyl and cycloalkyl may be optionally substituted with one or more substituents independently selected from the group consisting of halo, CN, hydroxyl, C$_1$-C$_6$ linear or branched haloalkyl, and CONH$_2$; and, j is 2, 3, 4 or 5; and, k is 0, 1, 2; 3, or 4.

In other aspects, the present invention also provides:

pharmaceutical compositions which comprise a pharmaceutically acceptable carrier and a compound of formula I;

methods for treating conditions or disorders including myositis, vasculitis, pemphigus, Crohn's disease, lupus, nephritis, psoriasis, multiple sclerosis, major depression disorder, allergy, asthma, Sjogren's disease, dry eye syndrome, transplant rejection, cancer, inflammatory bowel disease, septic shock, cardiopulmonary dysfunction, acute respiratory disease, or cachexia by administering to a subject in need a therapeutically effective amount of a compound of formula I or a pharmaceutically acceptable salt thereof;

methods for treating conditions or disorders including atopic dermatitis, eczema, psoriasis, scleroderma, lupus, pruritus, other pruritic conditions, allergic reactions including allergic dermatitis in mammal, horse allergic diseases including bite hypersensitivity, summer eczema, sweet itch in horses, heaves, inflammatory airway disease, recurrent airway obstruction, airway hyper-responsiveness, and chronic obstruction pulmonary disease by administering to a mammal in need a therapeutically effective amount of a compound of formula I, or a pharmaceutically acceptable salt thereof; and, methods for the preparation of compounds of the present invention.

A review of the chemical and medical literature uncovers numerous JAK inhibitors. While these compounds have shown activity in numerous inflammatory conditions, the literature does not show the same activity in diseases of the central nervous system. This lack of activity is directly related to the difficulty of getting JAK inhibitors across the blood-brain barrier. Selected compounds of formula I cross the blood brain barrier and therefore can be used in the treatment of a number neurological disease and conditions such as epilepsy, dementia, etc.

The present invention will be further understood from the following description given by way of example only. The present invention is directed to a class of pyrrolo[2,3-d]pyrimidine derivatives. In particular, the present invention is directed to pyrrolo[2,3-d]pyrimidine compounds useful as inhibitors of JAK, and particularly JAK1. While the present invention is not so limited, an appreciation of various aspects of the invention will be gained through the following discussion and the examples.

The term "alkyl", alone or in combination, means an acyclic, saturated hydrocarbon group of the formula C$_n$H$_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms. The carbon atom content of alkyl and various other hydrocarbon-containing moieties is indicated by a prefix designating a lower and upper number of carbon atoms in the moiety, that is, the prefix C$_i$-C$_j$ indicates a moiety of the integer "i" to the integer "j" carbon atoms, inclusive. Thus, for example, C$_1$-C$_6$ alkyl refers to alkyl of one to six carbon atoms, inclusive. The term"haloalkyl" refers to an alkyl moiety as described above in which one or more hydrogen atoms is replaced by a halogen atom (as defined below).

The term "($C_1$-$C_6$)alkoxy" as used herein, means a ($C_1$-$C_6$)alkyl group, as defined above, attached to the parent molecular moiety through an oxygen atom. Examples include, but are not limited to, methoxy, ethoxy, propoxy, 2-propoxy, butoxy, tert-butoxy, pentyloxy, and hexyloxy. The term "haloalkoxy" refers to an alkoxy moiety as immediately described above in which one or more hydrogen atoms is replaced by a halogen atom.

The term "hydroxy," as used herein, means an OH radical. The term "heterocyclic" refers to a saturated or partially saturated (i.e., nonaromatic) heterocycle which contains five to ten ring atoms where one or more, preferably, one, two or three ring atoms, are heteroatom(s) selected from N, O and S, the remaining being carbon, and which may be attached via a ring nitrogen atom or a ring carbon atom. Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

The term "aryl" refers to an aromatic monocyclic or bicyclic hydrocarbon containing six to ten ring carbon atoms which may be attached via one of the ring carbon atoms. Equally, when substituted, the substituent may be located on a ring carbon atom. Equally, when substituted, the substituent may be located on a ring carbon atom. Specific examples include phenyl, toluyl, xylyl, trimethylphenyl, and naphthyl. Examples of aryl substituents include alkyl, hydroxyl, halo, nitrile, alkoxy, trifluoromethyl, carboxamido, $SO_2Me$, benzyl, and substituted benzyl.

The term "heteroaryl" refers to a monovalent aromatic monocyclic or bicyclic heterocycle of five to ten ring atoms where one or more, preferably, one, two or three ring atoms, are heteroatom(s) selected from N, O and S, the remaining being carbon, and which may be attached via a ring carbon atom or a ring nitrogen atom with an appropriate valency. Equally, when substituted, the substituent may be located on a ring carbon atom (in all cases) or a ring nitrogen atom with an appropriate valency (if the substituent is joined through a carbon atom). Specific examples include thienyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl. The term "cycloalkyl" means a monocyclic, saturated hydrocarbon group of the formula $C_nH_{2n-1}$. Examples include cyclopropyl, cyclobutyl, cyclopentyl, cyclohexyl, and cycloheptyl. Unless otherwise specified, a cycloalkyl group comprises from 3 to 8 carbon atoms.

The terms "halo" and "halogen" refer to fluoride (F), chloride (Cl), bromide (Br) or iodide (I).

The term "mammal" refers to human, livestock or companion animals.

The term "companion animal" or "companion animals" refers to animals kept as pets or household animal. Examples of companion animals include dogs, cats, and rodents including hamsters, guinea pigs, gerbils and the like, rabbits, ferrets and birds.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits, as well as birds, such as chickens, ducks and turkeys.

The term "treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation of the present invention in combination with other therapies.

The term "therapeutically-effective" indicates the capability of an agent to prevent, or improve the severity of, the disorder, while avoiding adverse side effects typically associated with alternative therapies. The phrase "therapeutically-effective" is to be understood to be equivalent to the phrase "effective for the treatment, prevention, or amelioration", and both are intended to qualify the amount of each agent for use in the combination therapy which will achieve the goal of improvement in the severity of cancer, cardiovascular disease, or pain and inflammation and the frequency of incidence over treatment of each agent by itself, while avoiding adverse side effects typically associated with alternative therapies.

"Pharmaceutically acceptable" means suitable for use in mammals, companion animals or livestock animals.

The term "neurological" refers to the central nervous system. The treatment of neurological conditions refers to the treatment of a condition, disease, ailment, etc. impacting the central nervous system ("CNS"). Such diseases can impact tissues in the periphery as well as the central nervous system.

If substituents are described as being "independently selected" from a group, each substituent is selected independent of the other. Each substituent therefore may be identical to or different from the other substituent(s).

DETAILED DESCRIPTION OF THE INVENTION

The present invention is related to novel compounds which are selective JAK1 modulators useful for the treatment of diseases and conditions associated with dysregulation of the JAK1. The present invention further provides pharmaceutical compositions comprising such JAK1 modulators as well as methods of treating and/or preventing such diseases and conditions. Accordingly, the present invention provides a compound of formula I having the structure:

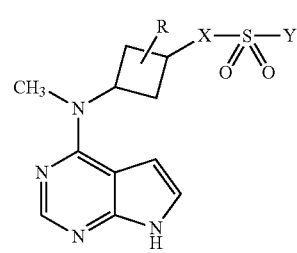

I or a pharmaceutically acceptable salt thereof, wherein

R is selected from hydrogen, deuterium, $C_1$-$C_6$ linear or branched alkyl, $C_1$-$C_6$ linear or branched perfluoroalkyl, aryl, and alkylaryl;

X is selected from —NH— and —$CR_aR_b$—, where (a) $R_a$ and $R_b$ are independently hydrogen, deuterium, $C_1$-$C_6$ linear or branched alkyl, $C_3$-$C_6$ cycloalkyl, aryl, (aryl)$C_1$-$C_6$ linear or branched alkyl, heteroaryl, ($C_1$-$C_6$ linear or branched alkyl)heteroaryl, (heteroaryl)$C_1$-$C_6$ linear or branched alkyl, (heterocyclic)$C_1$-$C_6$ linear or branched alkyl, where said alkyl, aryl, heteroaryl and cycloalkyl may be optionally substituted with one or more $R_c$, or (b) $R_a$ and $R_b$ together form a chain comprising —$(CR_cR_d)_j$—, where $R_c$ and $R_d$ are independently hydrogen, deuterium, $C_1$-$C_6$ linear or branched alkyl, aryl, ($C_1$-$C_6$ linear or branched alkyl)aryl, heteroaryl, ($C_1$-$C_6$ linear or branched alkyl)heteroaryl, halo, CN, $CF_3$, hydroxyl, alkoxy, —$CONH_2$, —$NHCO(C_1$-$C_6$ alkyl), —$CONH(C_1$-$C_6$ alkyl), $C_1$-$C_6$ alkoxycarbonyl, or $SO_2CH_3$;

Y is A-$R_1$, where A is a bond, —NH—, —$(CH_2)_k$— or —$(CD_2)_k$- and $R_1$ is $C_1$-$C_6$ linear or branched alkyl, $C_3$-$C_6$ cycloalkyl, aryl, or —$NR_aR_b$, or is an unsaturated, saturated or partially saturated monocyclic or bicyclic ring structure containing a total of four to eleven atoms having one to four heteroatoms independently selected from the group consisting of oxygen, nitrogen, and sulfur, wherein said alkyl, cycloalkyl, aryl, or monocyclic or bicyclic ring structure is further optionally substituted with one or more substituents independently selected from the group consisting of deuterium, halo, $C_1$-$C_6$ linear or branched alkyl, —$C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, CN, hydroxyl, $CF_3$, —$OR_e$, —$CO(C_1$-$C_6$ linear or branched alkyl), —$CO(C_3$-$C_6$ cycloalkyl), —$NR_eR_f$, an unsaturated, saturated or partially saturated monocyclic or bicyclic ring structure containing a total of four to eleven atoms as defined above, and —$S(O)_2R_e$ and where said alkyl, alkoxy, and cycloalkyl may be optionally substituted with one or more substituents independently selected from the group consisting of $C_1$-$C_6$ linear or branched alkyl, $C_3$-$C_6$ cycloalkyl, halo, CN, hydroxyl, —$OR_e$, $CONH_2$, and $SO_2CH_3$, where (a) $R_a$ and $R_b$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, (aryl)$C_1$-$C_6$ linear or branched alkyl, heteroaryl, heterocyclic, ($C_1$-$C_6$ linear or branched alkyl)heteroaryl, (heteroaryl)$C_1$-$C_6$ linear or branched alkyl, (heterocyclic)$C_1$-$C_6$ linear or branched alkyl where said alkyl, aryl, heteroaryl and cycloalkyl may be optionally substituted with one or more $R_c$;

(b) $R_a$ and $R_b$ together form a chain comprising —$(CR_cR_d)_j$—, where $R_c$ and $R_d$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, halo, CN, hydroxyl, $CF_3$, —NHCO(alkyl), —CONH(alkyl), alkoxycarbonyl, $CONH_2$, —$OR_e$, —$NR_eR_f$, or —$S(O)_2R_e$ in which any alkyl, cycloalkyl or alkoxy moiety may be optionally substituted with one or more halogen atoms;

(c) $R_a$ and $R_b$ together form a chain comprising four to six atoms having one or two heteroatoms independently selected from nitrogen, oxygen and sulfur in which any carbon atom may optionally be substituted with a substituent selected from the group consisting of $C_1$-$C_6$ linear or branched alkyl, —$C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —$NHCO(C_1$-$C_6$ linear or branched alkyl), —$CONH(C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy, or cycloalkyl moities may be optionally substituted with one or more halogen atoms and any nitrogen atom, if chemically permissible, may be optionally substituted with $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, —$C(O)C_1$-$C_6$ linear or branched alkyl, —$CONH(C_1$-$C_6$ linear or branched alkyl), $C_1$-$C_6$ alkoxycarbonyl, $CONH_2$, or —$S(O)_2R_e$ in which any of said alkyl or cycloalkyl moities may be optionally substituted with one or more halogen atoms; or, (d) $R_a$ and $R_b$ together form a 5 to 10 membered bicycloalkyl ring in which any atom of said ring may be optionally substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —$NHCO(C_1$-$C_6$ linear or branched alkyl), —$CONH(C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy or cycloalkyl moieties may be optionally substituted with one or more halogen atoms;

where $R_e$ and $R_f$ are independently hydrogen, deuterium, $C_1$-$C_6$ linear or branched alkyl, $C_1$-$C_6$ alkoxy, or $C_3$-$C_6$ cycloalkyl, where said alkyl and cycloalkyl may be optionally substituted with one or more substituents independently selected from the group consisting of halo, CN, hydroxyl, $C_1$-$C_6$ linear or branched haloalkyl, and $CONH_2$; and, j is 2, 3, 4 or 5; and, k is 0, 1, 2; 3, or 4.

In one embodiment, the invention provides a compound of having the structure:

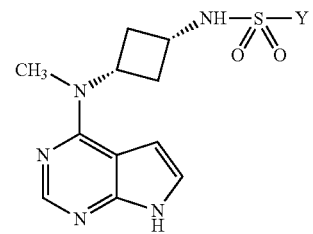

or a pharmaceutically acceptable salt thereof, wherein

Y is A-$R_1$, where A is a bond, —NH—, —$(CH_2)_k$— or —$(CD_2)_k$- and $R_1$ is $C_1$-$C_6$ linear or branched alkyl, $C_3$-$C_6$ cycloalkyl, aryl, or —$NR_aR_b$, or is an unsaturated, saturated or partially saturated monocyclic or bicyclic ring structure containing a total of four to eleven atoms having one to four heteroatoms independently selected from the group consisting of oxygen, nitrogen, and sulfur, wherein said alkyl, cycloalkyl, aryl, or monocyclic or bicyclic ring structure is further optionally substituted with one or more substituents independently selected from the group consisting of deuterium, halo, $C_1$-$C_6$ linear or branched alkyl, —$C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, CN, hydroxyl, $CF_3$, —$OR_e$, —$CO(C_1$-$C_6$ linear or branched alkyl), —$CO(C_3$-$C_6$ cycloalkyl), —$NR_eR_f$, an unsaturated, saturated or partially saturated monocyclic or bicyclic ring structure containing a total of four to eleven atoms as defined above, and —$S(O)_2R_e$ and where said alkyl, alkoxy, and cycloalkyl may be optionally substituted with one or more substituents independently selected from the group consisting of $C_1$-$C_6$ linear or branched alkyl, $C_3$-$C_6$ cycloalkyl, halo, CN, hydroxyl, —$OR_e$, $CONH_2$, and $SO_2CH_3$, where (a) $R_a$ and $R_b$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, (aryl)$C_1$-$C_6$ linear or branched alkyl, heteroaryl, heterocyclic, ($C_1$-$C_6$ linear or branched alkyl)heteroaryl, (heteroaryl)$C_1$-$C_6$ linear or branched alkyl, (heterocyclic)$C_1$-$C_6$ linear or branched alkyl where said alkyl, aryl, heteroaryl and cycloalkyl may be optionally substituted with one or more $R_c$;

(b) $R_a$ and $R_b$ together form a chain comprising —$(CR_cR_d)_j$—, where $R_c$ and $R_d$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, halo, CN, hydroxyl, $CF_3$, —NHCO(alkyl), —CONH(alkyl), alkoxycarbonyl, $CONH_2$, —$OR_e$, —$NR_eR_f$, or —$S(O)_2R_e$ in which any alkyl, cycloalkyl or alkoxy moiety may be optionally substituted with one or more halogen atoms;

(c) $R_a$ and $R_b$ together form a chain comprising four to six atoms having one or two heteroatoms independently selected from nitrogen, oxygen and sulfur in which any carbon atom may optionally be substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —NHCO($C_1$-$C_6$ linear or branched alkyl), —CONH($C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy, or cycloalkyl moieties may be optionally substituted with one or more halogen atoms and any nitrogen atom, if chemically permissible, may be optionally substituted with $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, —$C(O)C_1$-$C_6$ linear or branched alkyl, —CONH($C_1$-$C_6$ linear or branched alkyl), $C_1$-$C_6$ alkoxycarbonyl, $CONH_2$, or —$S(O)_2R_e$ in which any of said alkyl or cycloalkyl moieties may be optionally substituted with one or more halogen atoms; or, (d) $R_a$ and $R_b$ together form a 5 to 10 membered bicycloalkyl ring in which any atom of said ring may be optionally substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —NHCO($C_1$-$C_6$ linear or branched alkyl), —CONH($C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy or cycloalkyl moieties may be optionally substituted with one or more halogen atoms; where $R_e$ and $R_f$ are independently hydrogen, deuterium, $C_1$-$C_6$ linear or branched alkyl, $C_1$-$C_6$ alkoxy, or $C_3$-$C_6$ cycloalkyl, where said alkyl and cycloalkyl may be optionally substituted with one or more substituents independently selected from the group consisting of halo, CN, hydroxyl, $C_1$-$C_6$ linear or branched haloalkyl, and $CONH_2$; and, j is 2, 3, 4 or 5; and, k is 1, 2; 3, or 4.

In another embodiment, the invention provides the compound of formula I wherein A is a bond and $R_1$ is $C_1$-$C_6$ linear or branched alkyl, $C_3$-$C_6$ cycloalkyl, aryl, or —$NR_aR_b$, or is an unsaturated, saturated or partially saturated monocyclic or bicyclic ring structure containing a total of four to eleven atoms having one to four heteroatoms independently selected from the group consisting of oxygen, nitrogen, and sulfur, wherein said alkyl, cycloalkyl, aryl, or monocyclic or bicyclic ring structure is further optionally substituted with one or more substituents independently selected from the group consisting of deuterium, halo, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, CN, hydroxyl, $CF_3$, —$OR_e$, —$CO(C_1$-$C_6$ linear or branched alkyl), —$CO(C_3$-$C_6$ cycloalkyl), —$NR_eR_f$, an unsaturated, saturated or partially saturated monocyclic or bicyclic ring structure containing a total of four to eleven atoms as defined above, and —$S(O)_2R_e$ and where said alkyl, alkoxy, and cycloalkyl may be optionally substituted with one or more substituents independently selected from the group consisting of $C_1$-$C_6$ linear or branched alkyl, $C_3$-$C_6$ cycloalkyl, halo, CN, hydroxyl, —$OR_e$, $CONH_2$, and $SO_2CH_3$, where (a) $R_a$ and $R_b$ are independently hydrogen, deuterium, $C_1$-$C_6$ linear or branched alkyl, —($C_1$-$C_6$ linear or branched alkyl)-O—($C_1$-$C_6$ linear or branched alkyl)-, $C_3$-$C_6$ cycloalkyl, aryl, (aryl)$C_1$-$C_6$ linear or branched alkyl, heteroaryl, heterocyclic, ($C_1$-$C_6$ linear or branched alkyl)heteroaryl, (heteroaryl)$C_1$-$C_6$ linear or branched alkyl, (heterocyclic)$C_1$-$C_6$ linear or branched alkyl where said alkyl, aryl, heteroaryl and cycloalkyl may be optionally substituted with one or more $R_c$; or, (b) $R_a$ and $R_b$ together form a chain comprising —$(CR_cR_d)_j$—, where $R_c$ and $R_d$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, halo, CN, hydroxyl, $CF_3$, —NHCO(alkyl), —CONH(alkyl), alkoxycarbonyl, $CONH_2$, —$OR_e$, —$NR_eR_f$, or —$S(O)_2R_e$ in which any alkyl, cycloalkyl or alkoxy moiety may be optionally substituted with one or more halogen atoms; or, (c) $R_a$ and $R_b$ together form a chain comprising four to six atoms having one or two heteroatoms independently selected from nitrogen, oxygen and sulfur in which any carbon atom may optionally be substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —NHCO($C_1$-$C_6$ linear or branched alkyl), —CONH($C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy, or cycloalkyl moieties may be optionally substituted with one or more halogen atoms and any nitrogen atom, if chemically permissible, may be optionally substituted with $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, —$C(O)C_1$-$C_6$ linear or branched alkyl, —CONH($C_1$-$C_6$ linear or branched alkyl), $C_1$-$C_6$ alkoxycarbonyl, CONH₂, or —S(O)₂Rₑ in which any of said alkyl or cycloalkyl moieties may be optionally substituted with one or more halogen atoms; or, (d) Rₐ and R_b together form a 5 to 10 membered bicycloalkyl ring in which any atom of said ring may be optionally substituted with a substituent selected from the group consisting of C₁-C₆ linear or branched alkyl, C₃-C₆ cycloalkyl, C₁-C₆ linear or branched alkoxy-(C₃-C₆ cycloalkyl), C₁-C₆ linear or branched alkoxy-(C₁-C₆ linear or branched alkyl)-, aryl, (C₁-C₆ linear or branched alkyl)aryl, heteroaryl, (C₁-C₆ linear or branched alkyl)heteroaryl, heterocyclic, halo, CN, hydroxyl, CF₃, —NHCO(C₁-C₆ linear or branched alkyl), —CONH(C₁-C₆ linear or branched alkyl), C₁-C₆ linear or branched alkoxycarbonyl, CONH₂, —ORₑ, —NRₑR_f, or —S(O)₂Rₑ, in which any of said alkyl, alkoxy or cycloalkyl moieties may be optionally substituted with one or more halogen atoms;

where Rₑ and R_f are independently hydrogen, deuterium, C₁-C₆ linear or branched alkyl, C₁-C₆ alkoxy, or C₃-C₆ cycloalkyl, where said alkyl and cycloalkyl may be optionally substituted with one or more substituents independently selected from the group consisting of halo, CN, hydroxyl, C₁-C₆ linear or branched haloalkyl, and CONH₂; and, j is 2, 3, 4 or 5, or a pharmaceutically acceptable salt thereof.

In another embodiment, the invention provides the compound of formula I having the structure:

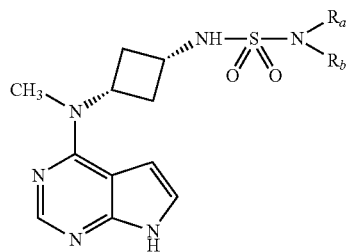

or a pharmaceutically acceptable salt thereof, wherein (a) Rₐ and R_b are independently hydrogen, deuterium, C₁-C₆ linear or branched alkyl, C₃-C₆ cycloalkyl, C₁-C₆ linear or branched alkoxy-(C₃-C₆ cycloalkyl), C₁-C₆ linear or branched alkoxy-(C₁-C₆ linear or branched alkyl)-, aryl, (aryl)C₁-C₆ linear or branched alkyl, heteroaryl, heterocyclic, (C₁-C₆ linear or branched alkyl)heteroaryl, (heteroaryl) C₁-C₆ linear or branched alkyl, (heterocyclic)C₁-C₆ linear or branched alkyl where said alkyl, aryl, heteroaryl and cycloalkyl may be optionally substituted with one or more R_c;

(b) Rₐ and R_b together form a chain comprising —(CR_cR_d)_j—, where R_c and R_d are independently hydrogen, deuterium, C₁-C₆ linear or branched alkyl, —(C₁-C₆ linear or branched alkyl)-O—(C₁-C₆ linear or branched alkyl)-, C₃-C₆ cycloalkyl, C₁-C₆ linear or branched alkoxy-(C₃-C₆ cycloalkyl), C₁-C₆ linear or branched alkoxy-(C₁-C₆ linear or branched alkyl)-, aryl, (C₁-C₆ linear or branched alkyl)aryl, heteroaryl, (C₁-C₆ linear or branched alkyl)heteroaryl, halo, CN, hydroxyl, CF₃, —NHCO(alkyl), —CONH(alkyl), alkoxycarbonyl, CONH₂, —ORₑ, —NRₑR_f, or —S(O)₂Rₑ in which any alkyl, cycloalkyl or alkoxy moiety may be optionally substituted with one or more halogen atoms;

(c) Rₐ and R_b together form a chain comprising four to six atoms having one or two heteroatoms independently selected from nitrogen, oxygen and sulfur in which any carbon atom may optionally be substituted with a substituent selected from the group consisting of C₁-C₆ linear or branched alkyl, C₃-C₆ cycloalkyl, C₁-C₆ linear or branched alkoxy-(C₃-C₆ cycloalkyl), C₁-C₆ linear or branched alkoxy-(C₁-C₆ linear or branched alkyl)-, aryl, (C₁-C₆ linear or branched alkyl)aryl, heteroaryl, (C₁-C₆ linear or branched alkyl)heteroaryl, heterocyclic, halo, CN, hydroxyl, CF₃, —NHCO(C₁-C₆ linear or branched alkyl), —CONH(C₁-C₆ linear or branched alkyl), C₁-C₆ linear or branched alkoxycarbonyl, CONH₂, —ORₑ, —NRₑR_f, or —S(O)₂Rₑ, in which any of said alkyl, alkoxy, or cycloalkyl moieties may be optionally substituted with one or more halogen atoms and any nitrogen atom, if chemically permissible, may be optionally substituted with C₁-C₆ linear or branched alkyl, C₃-C₆ cycloalkyl, C₁-C₆ linear or branched alkoxy-(C₃-C₆ cycloalkyl), C₁-C₆ linear or branched alkoxy-(C₁-C₆ linear or branched alkyl)-, aryl, (C₁-C₆ linear or branched alkyl) aryl, —C(O)C₁-C₆ linear or branched alkyl, —CONH(C₁-C₆ linear or branched alkyl), C₁-C₆ alkoxycarbonyl, CONH₂, or —S(O)₂Rₑ in which any of said alkyl or cycloalkyl moieties may be optionally substituted with one or more halogen atoms; or, (d) Rₐ and R_b together form a 5 to 10 membered bicycloalkyl ring in which any atom of said ring may be optionally substituted with a substituent selected from the group consisting of C₁-C₆ linear or branched alkyl, C₃-C₆ cycloalkyl, C₁-C₆ linear or branched alkoxy-(C₃-C₆ cycloalkyl), C₁-C₆ linear or branched alkoxy-(C₁-C₆ linear or branched alkyl)-, aryl, (C₁-C₆ linear or branched alkyl)aryl, heteroaryl, (C₁-C₆ linear or branched alkyl)heteroaryl, heterocyclic, halo, CN, hydroxyl, CF₃, —NHCO(C₁-C₆ linear or branched alkyl), —CONH(C₁-C₆ linear or branched alkyl), C₁-C₆ linear or branched alkoxycarbonyl, CONH₂, —ORₑ, —NRₑR_f, or —S(O)₂Rₑ, in which any of said alkyl, alkoxy or cycloalkyl moieties may be optionally substituted with one or more halogen atoms;

where Rₑ and R_f are independently hydrogen, deuterium, C₁-C₆ linear or branched alkyl, C₁-C₆ alkoxy, or C₃-C₆ cycloalkyl, where said alkyl and cycloalkyl may be optionally substituted with one or more substituents independently selected from the group consisting of halo, CN, hydroxyl, C₁-C₆ linear or branched haloalkyl, and CON H₂; and, j is 2, 3, 4 or 5.

In another embodiment, the invention provides the compound having the structure:

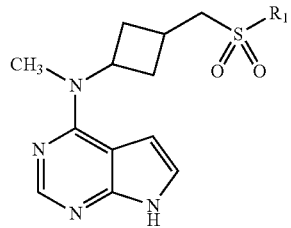

or a pharmaceutically acceptable salt thereof, wherein

R₁ is C₁-C₆ linear or branched alkyl, C₃-C₆ cycloalkyl, aryl, or —NRₐR_b, or is an unsaturated, saturated or partially saturated monocyclic or bicyclic ring structure containing a total of four to eleven atoms having one to four heteroatoms independently selected from the group consisting of oxygen, nitrogen, and sulfur, wherein said alkyl, cycloalkyl, aryl, or monocyclic or bicyclic ring structure is further optionally substituted with one or more substituents independently selected from the group consisting of deuterium, halo, C₁-C₆ linear or branched alkyl, C₃-C₆ cycloalkyl, C₁-C₆ linear or branched alkoxy-(C₃-C₆ cycloalkyl), C₁-C₆ linear or branched alkoxy-($C_1$-$C_6$ linear or branched alkyl)-, CN, hydroxyl, $CF_3$, —$OR_e$, —$CO(C_1$-$C_6$ linear or branched alkyl), —$CO(C_3$-$C_6$ cycloalkyl), —$NR_eR_f$, an unsaturated, saturated or partially saturated monocyclic or bicyclic ring structure containing a total of four to eleven atoms as defined above, and —$S(O)_2R_e$ and where said alkyl, alkoxy, and cycloalkyl may be optionally substituted with one or more substituents independently selected from the group consisting of $C_1$-$C_6$ linear or branched alkyl, $C_3$-$C_6$ cycloalkyl, halo, CN, hydroxyl, —$OR_e$, CON $H_2$, and $SO_2CH_3$, where (a) $R_a$ and $R_b$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, (aryl)$C_1$-$C_6$ linear or branched alkyl, heteroaryl, heterocyclic, ($C_1$-$C_6$ linear or branched alkyl)heteroaryl, (heteroaryl)$C_1$-$C_6$ linear or branched alkyl, (heterocyclic)$C_1$-$C_6$ linear or branched alkyl where said alkyl, aryl, heteroaryl and cycloalkyl may be optionally substituted with one or more $R_c$;

(b) $R_a$ and $R_b$ together form a chain comprising —$(CR_cR_d)_j$—, where $R_c$ and $R_d$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, halo, CN, hydroxyl, $CF_3$, —NHCO(alkyl), —CONH(alkyl), alkoxycarbonyl, $CONH_2$, —$OR_e$, —$NR_eR_f$, or —$S(O)_2R_e$ in which any alkyl, cycloalkyl or alkoxy moiety may be optionally substituted with one or more halogen atoms;

(c) $R_a$ and $R_b$ together form a chain comprising four to six atoms having one or two heteroatoms independently selected from nitrogen, oxygen and sulfur in which any carbon atom may optionally be substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —NHCO($C_1$-$C_6$ linear or branched alkyl), —CONH($C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy, or cycloalkyl moieties may be optionally substituted with one or more halogen atoms and any nitrogen atom, if chemically permissible, may be optionally substituted with $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl) aryl, —$C(O)C_1$-$C_6$ linear or branched alkyl, —CONH($C_1$-$C_6$ linear or branched alkyl), $C_1$-$C_6$ alkoxycarbonyl, $CONH_2$, or —$S(O)_2R_e$ in which any of said alkyl or cycloalkyl moieties may be optionally substituted with one or more halogen atoms; or, (d) $R_a$ and $R_b$ together form a 5 to 10 membered bicycloalkyl ring in which any atom of said ring may be optionally substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —NHCO($C_1$-$C_6$ linear or branched alkyl), —CONH($C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy or cycloalkyl moities may be optionally substituted with one or more halogen atoms;

where $R_e$ and $R_f$ are independently hydrogen, deuterium, $C_1$-$C_6$ linear or branched alkyl, $C_1$-$C_6$ alkoxy, or $C_3$-$C_6$ cycloalkyl, where said alkyl and cycloalkyl may be optionally substituted with one or more substituents independently selected from the group consisting of halo, CN, hydroxyl, $C_1$-$C_6$ linear or branched haloalkyl, and $CONH_2$; and, j is 2, 3, 4 or 5.

In one embodiment, the invention provides the compound of formula I having the structure:

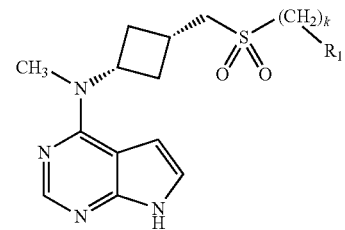

or a pharmaceutically acceptable salt thereof, wherein $R_1$ is $C_1$-$C_6$ linear or branched alkyl, $C_3$-$C_6$ cycloalkyl, aryl, or —$NR_aR_b$, or is an unsaturated, saturated or partially saturated monocyclic or bicyclic ring structure containing a total of four to eleven atoms having one to four heteroatoms independently selected from the group consisting of oxygen, nitrogen, and sulfur, wherein said alkyl, cycloalkyl, aryl, or monocyclic or bicyclic ring structure is further optionally substituted with one or more substituents independently selected from the group consisting of deuterium, halo, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, CN, hydroxyl, $CF_3$, —$OR_e$, —$CO(C_1$-$C_6$ linear or branched alkyl), —$CO(C_3$-$C_6$ cycloalkyl), —$NR_eR_f$, an unsaturated, saturated or partially saturated monocyclic or bicyclic ring structure containing a total of four to eleven atoms as defined above, and —$S(O)_2R_e$ and where said alkyl, alkoxy, and cycloalkyl may be optionally substituted with one or more substituents independently selected from the group consisting of $C_1$-$C_6$ linear or branched alkyl, $C_3$-$C_6$ cycloalkyl, halo, CN, hydroxyl, —$OR_e$, $CONH_2$, and $SO_2CH_3$, where (a) $R_a$ and $R_b$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, (aryl)$C_1$-$C_6$ linear or branched alkyl, heteroaryl, heterocyclic, ($C_1$-$C_6$ linear or branched alkyl)heteroaryl, (heteroaryl) $C_1$-$C_6$ linear or branched alkyl, (heterocyclic)$C_1$-$C_6$ linear or branched alkyl where said alkyl, aryl, heteroaryl and cycloalkyl may be optionally substituted with one or more $R_c$;

(b) $R_a$ and $R_b$ together form a chain comprising —$(CR_cR_d)_j$—, where $R_c$ and $R_d$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, halo, CN, hydroxyl, $CF_3$, —NHCO(alkyl), —CONH(alkyl), alkoxycarbonyl, $CONH_2$, —$OR_e$, —$NR_eR_f$, or —$S(O)_2R_e$ in which any alkyl, cycloalkyl or alkoxy moiety may be optionally substituted with one or more halogen atoms;

(c) $R_a$ and $R_b$ together form a chain comprising four to six atoms having one or two heteroatoms independently selected from nitrogen, oxygen and sulfur in which any carbon atom may optionally be substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —NHCO($C_1$-$C_6$ linear or branched alkyl), —CONH($C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy, or cycloalkyl moities may be optionally substituted with one or more halogen atoms and any nitrogen atom, if chemically permissible, may be optionally substituted with $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl) aryl, —C(O)$C_1$-$C_6$ linear or branched alkyl, —CONH($C_1$-$C_6$ linear or branched alkyl), $C_1$-$C_6$ alkoxycarbonyl, $CONH_2$, or —$S(O)_2R_e$ in which any of said alkyl or cycloalkyl moieties may be optionally substituted with one or more halogen atoms; or, (d) $R_a$ and $R_b$ together form a 5 to 10 membered bicycloalkyl ring in which any atom of said ring may be optionally substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —NHCO($C_1$-$C_6$ linear or branched alkyl), —CONH($C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy or cycloalkyl moities may be optionally substituted with one or more halogen atoms;

where $R_e$ and $R_f$ are independently hydrogen, deuterium, $C_1$-$C_6$ linear or branched alkyl, $C_1$-$C_6$ alkoxy, or $C_3$-$C_6$ cycloalkyl, where said alkyl and cycloalkyl may be optionally substituted with one or more substituents independently selected from the group consisting of halo, CN, hydroxyl, $C_1$-$C_6$ linear or branched haloalkyl, and $CONH_2$; and, j is 2, 3, 4 or 5; and, k is 0 or 1.

In another embodiment, the invention provides the compound of formula I having the structure:

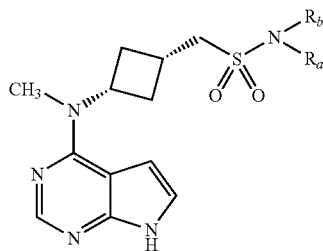

or a pharmaceutically acceptable salt thereof, wherein (a) $R_a$ and $R_b$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, (aryl)$C_1$-$C_6$ linear or branched alkyl, heteroaryl, heterocyclic, ($C_1$-$C_6$ linear or branched alkyl)heteroaryl, (heteroaryl) $C_1$-$C_6$ linear or branched alkyl, (heterocyclic)$C_1$-$C_6$ linear or branched alkyl where said alkyl, aryl, heteroaryl and cycloalkyl may be optionally substituted with one or more $R_c$;

(b) $R_a$ and $R_b$ together form a chain comprising —($CR_cR_d)_j$—, where $R_c$ and $R_d$ are independently hydrogen, deuterium, $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, halo, CN, hydroxyl, $CF_3$, —NHCO(alkyl), —CONH(alkyl), alkoxycarbonyl, $CONH_2$, —$OR_e$, —$NR_eR_f$, or —$S(O)_2R_e$ in which any alkyl, cycloalkyl or alkoxy moiety may be optionally substituted with one or more halogen atoms;

(c) $R_a$ and $R_b$ together form a chain comprising four to six atoms having one or two heteroatoms independently selected from nitrogen, oxygen and sulfur in which any carbon atom may optionally be substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —NHCO($C_1$-$C_6$ linear or branched alkyl), —CONH($C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy, or cycloalkyl moities may be optionally substituted with one or more halogen atoms and any nitrogen atom, if chemically permissible, may be optionally substituted with $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl) aryl, —C(O)$C_1$-$C_6$ linear or branched alkyl, —CONH($C_1$-$C_6$ linear or branched alkyl), $C_1$-$C_6$ alkoxycarbonyl, $CONH_2$, or —$S(O)_2R_e$ in which any of said alkyl or cycloalkyl moieties may be optionally substituted with one or more halogen atoms; or, (d) $R_a$ and $R_b$ together form a 5 to 10 membered bicycloalkyl ring in which any atom of said ring may be optionally substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —NHCO($C_1$-$C_6$ linear or branched alkyl), —CONH($C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy or cycloalkyl moities may be optionally substituted with one or more halogen atoms; where $R_e$ and $R_f$ are independently hydrogen, deuterium, $C_1$-$C_6$ linear or branched alkyl, $C_1$-$C_6$ alkoxy, or $C_3$-$C_6$ cycloalkyl, where said alkyl and cycloalkyl may be optionally substituted with one or more substituents independently selected from the group consisting of halo, CN, hydroxyl, $C_1$-$C_6$ linear or branched haloalkyl, and $CONH_2$; and, j is 2, 3, 4 or 5.

In certain other embodiments, the invention provides a compound as above wherein $R_a$ and $R_b$ together form a chain comprising four to six atoms having one or two heteroatoms independently selected from nitrogen, oxygen and sulfur in which any carbon atom may optionally be substituted with a substituent selected from the group consisting of $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl)aryl, heteroaryl, ($C_1$-$C_6$ linear or branched alkyl)heteroaryl, heterocyclic, halo, CN, hydroxyl, $CF_3$, —NHCO($C_1$-$C_6$ linear or branched alkyl), —CONH($C_1$-$C_6$ linear or branched alkyl), $C_1$-$C_6$ linear or branched alkoxycarbonyl, $CONH_2$, —$OR_e$, —$NR_eR_f$, or —$S(O)_2R_e$, in which any of said alkyl, alkoxy, or cycloalkyl moieties may be optionally substituted with one or more halogen atoms and any nitrogen atom, if chemically permissible, may be optionally substituted with $C_1$-$C_6$ linear or branched alkyl, $C_3$-$C_6$ cycloalkyl, $C_1$-$C_6$ linear or branched alkoxy-($C_3$-$C_6$ cycloalkyl), $C_1$-$C_6$ linear or branched alkoxy-($C_1$-$C_6$ linear or branched alkyl)-, aryl, ($C_1$-$C_6$ linear or branched alkyl) aryl, —C(O)$C_1$-$C_6$ linear or branched alkyl, —CONH($C_1$-$C_6$ linear or branched alkyl), $C_1$-$C_6$ alkoxycarbonyl, $CONH_2$, or —$S(O)_2R_e$ in which any of said alkyl or cycloalkyl moieties may be optionally substituted with one or more halogen atoms; where $R_e$ and $R_f$ are independently hydrogen, deuterium, $C_1$-$C_6$ linear or branched alkyl, $C_1$-$C_6$ alkoxy, or $C_3$-$C_6$ cycloalkyl, where said alkyl and cycloalkyl may be optionally substituted with one or more substituents independently selected from the group consisting of halo, CN, hydroxyl, $CF_3$, and $CONH_2$; and, j is 2, 3, 4 or 5.

In another embodiment, the invention provides a compound selected from the group consisting of:
4-cyano-N-{cis-3-[methyl(7H-pyrrolo[2,3-d]pyrimidin-4-yl)amino]cyclobutyl}pyridine-2-sulfonamide;
2,2,2-Trifluoro-N-{cis-3-[methyl(7H-pyrrolo[2,3-d]pyrimidin-4-yl)amino]cyclo-butyl}ethanesulfonamide;
N-{cis-3-[Methyl(7H-pyrrolo[2,3-d]pyrimidin-4-yl)amino]cyclobutyl}-propane-1-sulfonamide;
2-Methyl-N-{cis-3-[methyl(7H-pyrrolo[2,3-d]pyrimidin-4-yl)amino]-cyclobutyl}propane-1-sulfonamide;
cis-3-(Cyanomethyl)-N-{cis-3-[methyl(7H-pyrrolo[2,3-d]pyrimidin-4-yl)amino]cyclobutyl}cyclo-butanesulfonamide;
trans-3-(Cyanomethyl)-N-{cis-3-[methyl(7H-pyrrolo[2,3-d]pyrimidin-4-yl)amino]cyclobutyl}cyclo-butanesulfonamide;
1-[3-(Cyanomethyl)oxetan-3-yl]-N-{cis-3-[methyl(7H-pyrrolo[2,3-d]pyrimidin-4-yl)amino]cyclo-butyl}methanesulfonamide;
N-{cis-3-[methyl(7H-pyrrolo[2,3-d]pyrimidin-4-yl)amino]cyclobutyl}-1-oxetan-3-ylmethanesulfonamide;
cis-3-(Cyanomethyl)-3-methyl-N-{cis-3-[methyl(7H-pyrrolo[2,3-d]pyrimidin-4-yl)amino]cyclo-butyl}cyclobutanesulfonamide;
trans-3-(Cyanomethyl)-3-methyl-N-{cis-3-[methyl(7H-pyrrolo[2,3-d]pyrimidin-4-yl)amino]cyclo-butyl}cyclobutanesulfonamide;
4-Cyano-N-{cis-3-[methyl(7H-pyrrolo[2,3-d]pyrimidin-4-yl)amino]cyclobutyl}pyridine-2-sulfonamide;
3-(1-Hydroxy-1-methylethyl)-N-{cis-3-[methyl(7H-pyrrolo[2,3-d]pyrimidin-4-yl)amino]cyclo-butyl}benzenesulfonamide;
1-Cyclopropyl-N-{trans-3-[methyl(7H-pyrrolo[2,3-d]pyrimidin-4-yl)amino]cyclo-butyl}methanesulfonamide;
N-{(1S,3R)-3-[Methyl(7H-pyrrolo[2,3-d]pyrimidin-4-yl)amino]cyclopentyl}propane-1-sulfonamide;
1-(3,3-Difluorocyclobutyl)-N-{cis-3-[methyl(7H-pyrrolo[2,3-d]pyrimidin-4-yl)amino]cyclobutyl}methanesulfonamide;
3,3-Difluoro-N-{cis-3-[methyl(7H-pyrrolo[2,3-d]pyrimidin-4-yl)amino]cyclobutyl}cyclobutane-sulfonamide;
1-Cyclopropyl-N-{cis-3-[methyl(7H-pyrrolo[2,3-d]pyrimidin-4-yl)amino]cyclobutyl}methane-sulfonamide;
1-Cyclopropyl-N-{cis-3-[methyl(7H-pyrrolo[2,3-d]pyrimidin-4-yl)amino]cyclobutyl}azetidine-3-sulfonamide;
N-(Cyclopropylmethyl)-N'-{cis-3-[methyl(7H-pyrrolo[2,3-d]pyrimidin-4-yl)amino]cyclo-butyl}sulfamide;
(R)-3-Cyano-N-{cis-3-[methyl(7H-pyrrolo[2,3-d]pyrimidin-4-yl)amino]cyclobutyl}pyrrolidine-1-sulfonamide;
(S)-3-Cyano-N-{cis-3-[methyl(7H-pyrrolo[2,3-d]pyrimidin-4-yl)amino]cyclobutyl}pyrrolidine-1-sulfonamide;
2-Methyl-N-{cis-3-[methyl(7H-pyrrolo[2,3-d]pyrimidin-4-yl)amino]cyclobutyl}2,6-dihydropyrrolo[3,4-c]pyrazole-5(4H)-sulfonamide;
N-{cis-3-[Methyl(7H-pyrrolo[2,3-d]pyrimidin-4-yl)amino]cyclobutyl}-6-oxa-3-azabicyclo[3.1.1]hept-ane-3-sulfonamide;
3-Cyano-N-{cis-3-[methyl(7H-pyrrolo[2,3-d]pyrimidin-4-yl)amino]-cyclobutyl}azetidine-1-sulfonamide;
N-{cis-3-[Methyl(7H-pyrrolo[2,3-d]pyrimidin-4-yl)amino]cyclobutyl}-4-(1H-pyrazol-3-yl)piperidine-1-sulfonamide;
N-(2-Cyanoethyl)-N-methyl-N'-{cis-3-[methyl(7H-pyrrolo[2,3-d]pyrimidin-4-yl)amino]cyclo-butyl}sulfamide;
(1S,5S)-1-Cyano-N-{cis-3-[methyl(7H-pyrrolo[2,3-d]pyrimidin-4-yl)amino]cyclobutyl}-3-azabicyclo-[3.1.0]hexane-3-sulfonamide;
(1R,5R)-1-Cyano-N-{cis-3-[methyl(7H-pyrrolo[2,3-d]pyrimidin-4-yl)amino]cyclobutyl}-3-azabicyclo-[3.1.0]hexane-3-sulfonamide;
3-cyano-N-{trans-3-[methyl(7H-pyrrolo[2,3-d]pyrimidin-4-yl)amino]cyclobutyl}pyrrolidine-1-sulfonamide;
N-(cis-3-{[(4,4-Difluoropiperidin-1-yl)sulfonyl]methyl}cyclobutyl)-N-methyl-7H-pyrrolo[2,3-d]pyrimidin-4-amine;
1-[({cis-3-[Methyl(7H-pyrrolo[2,3-d]pyrimidin-4-yl)amino]cyclobutyl}-methyl)sulfonyl]-4-(trifluoromethyl)piperidin-4-ol;
(3R)-1-[({cis-3-[Methyl(7H-pyrrolo[2,3-d]pyrimidin-4-yl)amino]cyclobutyl}methyl)sulfon-yl]pyrrolidine-3-carbonitrile;
(3S)-1-[({cis-3-[Methyl(7H-pyrrolo[2,3-d]pyrimidin-4-yl)amino]cyclobutyl}methyl)sulfon-yl]pyrrolidine-3-carbonitrile;
N-{cis-3-[(Butylsulfonyl)methyl]cyclobutyl}-N-methyl-7H-pyrrolo[2,3-d]pyrimidin-4-amine;
N-Methyl-N-(trans-3-((propylsulfonyl)methyl)cyclobutyl)-7H-pyrrolo[2,3-d]pyrimidin-4-amine;
N-(cis-3-{[(2-Cyclopropylethyl)sulfonyl]methyl}cyclobutyl)-N-methyl-7H-pyrrolo[2,3-d]pyrimidin-4-amine;
N-[cis-3-({[(3,3-Difluorocyclobutyl)methyl]sulfonyl}-methyl)cyclobutyl]-N-methyl-7H-pyrrolo[2,3-d]pyrimidin-4-amine;
(1R,3R)-[({cis-3-[methyl(7H-pyrrolo[2,3-d]pyrimidin-4-yl)amino]cyclobutyl}methyl)sulfon-yl]cyclopentane-carbonitrile;
(1s,3S)-[({cis-3-[methyl(7H-pyrrolo[2,3-d]pyrimidin-4-yl)amino]cyclobutyl}methyl)sulfon-yl]cyclopentane-carbonitrile;
N-methyl-N-[cis-3-({[1-(propan-2-yl)pyrrolidin-3-yl]sulfonyl}methyl)cyclobutyl]-7H-pyrrolo[2,3-d]pyrimidin-4-amine;
N-(cis-3-{[(3-Chloro-4-fluorophenyl)sulfonyl]methyl}cyclobutyl)-N-methyl-7H-pyrrolo[2,3-d]pyrimidin-4-amine;

2-[({cis-3-[Methyl(7H-pyrrolo[2,3-d]pyrimidin-4-yl)amino]cyclobutyl}methyl) sulfonyl]pyridine-4-carbonitrile;

2-Methyl-N-{cis-3-[methyl(7H-pyrrolo[2,3-d]pyrimidin-4-yl)amino]cyclobutyl}-1,3-thiazole-5-sulfonamide;

N-{cis-3-[methyl(7H-pyrrolo[2,3-d]pyrimidin-4-yl)amino]cyclobutyl}-2,1,3-benzoxadiazole-4-sulfonamide;

1-(3-Methyloxetan-3-yl)-N-{cis-3-[methyl(7H-pyrrolo[2,3-d]pyrimidin-4-yl)amino]cyclobutyl}-methanesulfonamide;

(1S,2S)-trans-2-(cyanomethyl)-N-{cis-3-[methyl(7H-pyrrolo[2,3-d]pyrimidin-4-yl)amino]cyclobutyl}cyclopropanesulfonamide;

(1R,2R)-trans-2-(cyanomethyl)-N-{cis-3-[methyl(7H-pyrrolo[2,3-d]pyrimidin-4-yl)amino]cyclobutyl}cyclopropanesulfonamide;

3-Cyano-3-methyl-N-{cis-3-[methyl(7H-pyrrolo[2,3-d]pyrimidin-4-yl)amino]cyclobutyl}azet-idine-1-sulfonamide;

cis-3-Cyano-N-{cis-3-[methyl(7H-pyrrolo[2,3-d]pyrimidin-4-yl)amino]cyclobutyl}cyclopentanesulfonamide;

trans-3-Cyano-N-{cis-3-[methyl(7H-pyrrolo[2,3-d]pyrimidin-4-yl)amino]cyclobutyl}cyclopentanesulfonamide;

1-[({cis-3-[Methyl(7H-pyrrolo[2,3-d]pyrimidin-4-yl)amino]cyclobutyl}methyl)-sulfonyl]azetidine-3-carbonitrile;

cis-3-Cyano-N-{cis-3-[methyl(7H-pyrrolo[2,3-d]pyrimidin-4-yl)amino]cyclobutyl}-cyclobutanesulfonamide;

trans-3-Cyano-N-{cis-3-[methyl(7H-pyrrolo[2,3-d]pyrimidin-4-yl)amino]cyclobutyl}cyclobutane-sulfonamide;

cis-3-[({cis-3-[Methyl(7H-pyrrolo[2,3-d]pyrimidin-4-yl)amino]cyclobutyl}methyl)sulfonyl]cyclobutane-carbonitrile;

trans-3-[({cis-3-[Methyl(7H-pyrrolo[2,3-d]pyrimidin-4-yl)amino]cyclobutyl}methyl)sulfonyl]cyclobutane-carbonitrile;

N-Methyl-N-[cis-3-({[(3-methyloxetan-3-yl)methyl]sulfonyl}methyl)cyclobutyl]-7H-pyrrolo[2,3-d]pyrimidin-4-amine;

3-Methyl-1-[({cis-3-[methyl(7H-pyrrolo[2,3-d]pyrimidin-4-yl)amino]cyclobutyl}methyl)sulfon-yl]azetidine-3-carbonitrile;

(1R,5R)-3-[({cis-3-[Methyl(7H-pyrrolo[2,3-d]pyrimidin-4-yl)amino]cyclobutyl}methyl)-sulfonyl]-3-azabicyclo[3.1.0]hexane-1-carbonitrile;

cis-3-(Difluoromethyl)-N-{cis-3-[methyl(7H-pyrrolo[2,3-d]pyrimidin-4-yl)amino]cyclobutyl}cyclo-butanesulfonamide;

trans-3-(Difluoromethyl)-N-{cis-3-[methyl(7H-pyrrolo[2,3-d]pyrimidin-4-yl)amino]cyclobutyl}cyclo-butanesulfonamide;

cis-1-(3-Cyano-1-methylcyclobutyl)-N-{cis-3-[methyl(7H-pyrrolo[2,3-d]pyrimidin-4-yl)amino]cyclobutyl}methanesulfonamide;

trans-1-(3-Cyano-1-methylcyclobutyl)-N-{cis-3-[methyl(7H-pyrrolo[2,3-d]pyrimidin-4-yl)amino]-cyclobutyl}-methanesulfonamide;

N-[cis-3-({[3-(Difluoromethyl)azetidin-1-yl]sulfonyl}methyl)cyclobutyl]-N-methyl-7H-pyrrolo[2,3-d]pyrimidin-4-amine;

cis-3-Fluoro-N-{cis-3-[methyl(7H-pyrrolo[2,3-d]pyrimidin-4-yl)amino]cyclobutyl}cyclo-butanesulfonamide;

trans-3-Fluoro-N-{cis-3-[methyl(7H-pyrrolo[2,3-d]pyrimidin-4-yl)amino]cyclo-butyl}cyclobutane-sulfonamide;

3-(2,2-Difluoroethyl)-N-{cis-3-[methyl(7H-pyrrolo[2,3-d]pyrimidin-4-yl)amino]cyclobutyl}-azetidine-1-sulfonamide;

cis-3-[({cis-3-[Methyl(7H-pyrrolo[2,3-d]pyrimidin-4-yl)amino]cyclobutyl}methyl)sulfonyl]cyclobutane-carbonitrile;

trans-3-[({cis-3-[Methyl(7H-pyrrolo[2,3-d]pyrimidin-4-yl)amino]cyclobutyl}methyl)sulfonyl]cyclobutane-carbonitrile;

N-((1S,3S)-3-(((4-(Methoxymethyl)piperidin-1-yl)sulfonyl)methyl)cyclobutyl)-N-methyl-7H-pyrrolo[2,3-d]pyrimidin-4-amine;

N-((1S,3S)-3-(((1-(3-Methoxycyclobutyl)azetidin-3-yl)sulfonyl)methyl)cyclobutyl)-N-methyl-7H-pyrrolo[2,3-d]pyrimidin-4-amine;

N-Methyl-N-((1S,3S)-3-(((3,3,3-trifluoropropyl)sulfonyl)methyl)cyclobutyl)-7H-pyrrolo[2,3-d]pyrimidin-4-amine;

N-Methyl-N-[cis-3-({[3-(trifluoromethyl)pyrrolidin-1-yl]sulfonyl}methyl)cyclobutyl]-7H-pyrrolo[2,3-d]pyrimidin-4-amine;

N-[cis-3-({[3-(Difluoromethyl)pyrrolidin-1-yl]sulfonyl}methyl)cyclobutyl]-N-methyl-7H-pyrrolo[2,3-d]pyrimidin-4-amine;

N-(cis-3-{[(3,3-Difluoropyrrolidin-1-yl)sulfonyl]methyl}cyclobutyl)-N-methyl-7H-pyrrolo[2,3-d]pyrimidin-4-amine;

3-[({cis-3-[Methyl(7H-pyrrolo[2,3-d]pyrimidin-4-yl)amino]cyclobutyl}methyl)sulfonyl]cyclo-pentanecarbonitrile;

N-{cis-3-[(Benzylsulfonyl)methyl]cyclobutyl}-N-methyl-7H-pyrrolo[2,3-d]pyrimidin-4-amine;

N-(cis-3-{[(3-Chloroazetidin-1-yl)sulfonyl]methyl}cyclobutyl)-N-methyl-7H-pyrrolo[2,3-d]pyrimidin-4-amine;

1-methyl-3-{[({cis-3-[Methyl(7H-pyrrolo[2,3-d]pyrimidin-4-yl)amino]cyclobutyl}methyl)sulfon-yl]methyl}cyclobutanecarbonitrile;

N-[cis-3-({[3-(Difluoromethyl)cyclobutyl]sulfonyl}methyl)cyclobutyl]-N-methyl-7H-pyrrolo[2,3-d]pyrimidin-4-amine;

2-methyl-1-{3-[({cis-3-[Methyl(7H-pyrrolo[2,3-d]pyrimidin-4-yl)amino]cyclobutyl}methyl)sulfon-yl]azetidin-1-yl}propan-1-one;

cyclopropyl{3-[({cis-3-[Methyl(7H-pyrrolo[2,3-d]pyrimidin-4-yl)amino]cyclobutyl}methyl)sulfon-yl]azetidin-1-yl}methanone;

1-{3-[({cis-3-[Methyl(7H-pyrrolo[2,3-d]pyrimidin-4-yl)amino]cyclobutyl}methyl)sulfonyl]azetidin-1-yl}ethanone;

N-[cis-3-({[1-(Cyclopropylmethyl)azetidin-3-yl]sulfonyl}methyl)cyclobutyl]-N-methyl-7H-pyrrolo[2,3-d]pyrimidin-4-amine;

N-methyl-N-(cis-3-{[(4-Methylpiperazin-1-yl)sulfonyl]methyl}cyclobutyl)-7H-pyrrolo[2,3-d]pyrimidin-4-amine;

1-{4-[({cis-3-[Methyl(7H-pyrrolo[2,3-d]pyrimidin-4-yl)amino]cyclobutyl}methyl)sulfonyl]piperazin-1-yl}ethanone;

Cyclopropyl{4-[({cis-3-[methyl(7H-pyrrolo[2,3-d]pyrimidin-4-yl)amino]cyclobutyl}methyl)sulfon-yl]piperazin-1-yl}methanone;

N-[cis-3-({[1-(2,2-Difluoroethyl)azetidin-3-yl]sulfonyl}methyl)cyclobutyl]-N-methyl-7H-pyrrolo[2,3-d]pyrimidin-4-amine;

N-(cis-3-{[(1-Cyclopropylazetidin-3-yl)sulfonyl]methyl}cyclobutyl)-N-methyl-7H-pyrrolo[2,3-d]pyrimidin-4-amine;

(1R,3R)-3-[({cis-3-[Methyl(7H-pyrrolo[2,3-d]pyrimidin-4-yl)amino]cyclobutyl}methyl)sulfonyl]cyclo-pentanecarbonitrile;

N-Methyl-N-{cis-3-[(2-oxa-6-azaspiro[3.3]hept-6-ylsulfonyl)methyl]cyclobutyl}-7H-pyrrolo[2,3-d]pyrimidin-4-amine;

N-Methyl-N-(cis-3-{[(3-methylazetidin-1-yl)sulfonyl]methyl}cyclobutyl)-7H-pyrrolo[2,3-d]pyrimidin-4-amine;

N-(cis-3-{[(3-Methoxy-3-methylazetidin-1-yl)sulfonyl]methyl}cyclobutyl)-N-methyl-7H-pyrrolo[2,3-d]pyrimidin-4-amine;

3-Methyl-1-[({cis-3-[methyl(7H-pyrrolo[2,3-d]pyrimidin-4-yl)amino]cyclobutyl}methyl)sulfon-yl]azetidin-3-ol;

N-(cis-3-{[(3-Methoxyazetidin-1-yl)sulfonyl]methyl}cyclobutyl)-N-methyl-7H-pyrrolo[2,3-d]pyrimidin-4-amine;

N-(cis-3-{[(3-Fluoroazetidin-1-yl)sulfonyl]methyl}cyclobutyl)-N-methyl-7H-pyrrolo[2,3-d]pyrimidin-4-amine;

N-Methyl-N-(cis-3-{[1-(2,2,2-trifluoroethyl)azetidin-3-yl]sulfonyl}methyl)cyclobutyl]-7H-pyrrolo[2,3-d]pyrimidin-4-amine;

N-Methyl-N-{cis-3-[(1-oxa-6-azaspiro[3.3]hept-6-ylsulfonyl)methyl]cyclobutyl}-7H-pyrrolo[2,3-d]pyrimidin-4-amine;

(1R,3S)-3-[({cis-3-[Methyl(7H-pyrrolo[2,3-d]pyrimidin-4-yl)amino]cyclobutyl}methyl)sulfonyl]cyclo-pentanecarbonitrile;

N-(cis-3-{[(1-Cyclobutylazetidin-3-yl)sulfonyl]methyl}cyclobutyl)-N-methyl-7H-pyrrolo[2,3-d]pyrimidin-4-amine;

N-Methyl-N-{cis-3-[(pentan-3-ylsulfonyl)methyl]cyclobutyl}-7H-pyrrolo[2,3-d]pyrimidin-4-amine;

N-(cis-3-{[(3-Methoxypropyl)sulfonyl]methyl}cyclobutyl)-N-methyl-7H-pyrrolo[2,3-d]pyrimidin-4-amine;

N-(cis-3-{[(Cyclohexylmethyl)sulfonyl]methyl}cyclobutyl)-N-methyl-7H-pyrrolo[2,3-d]pyrimidin-4-amine;

N-(cis-3-{[(3-Fluoropropyl)sulfonyl]methyl}cyclobutyl)-N-methyl-7H-pyrrolo[2,3-d]pyrimidin-4-amine;

N-Methyl-N-{cis-3-[(oxetan-3-ylsulfonyl)methyl]cyclobutyl}-7H-pyrrolo[2,3-d]pyrimidin-4-amine;

N-Methyl-N-(cis-3-{[(3-methylbutyl)sulfonyl]methyl}cyclobutyl)-7H-pyrrolo[2,3-d]pyrimidin-4-amine;

N-(cis-3-{[(2-Ethylbutyl)sulfonyl]methyl}cyclobutyl)-N-methyl-7H-pyrrolo[2,3-d]pyrimidin-4-amine;

N-Methyl-N-(cis-3-{[(tetrahydrofuran-3-ylmethyl)sulfonyl]methyl}cyclobutyl)-7H-pyrrolo[2,3-d]pyrimidin-4-amine;

N-(cis-3-{[(2-Cyclopentylethyl)sulfonyl]methyl}cyclobutyl)-N-methyl-7H-pyrrolo[2,3-d]pyrimidin-4-amine;

N-Methyl-N-(cis-3-{[(2-methylbutyl)sulfonyl]methyl}cyclobutyl)-7H-pyrrolo[2,3-d]pyrimidin-4-amine;

N-[cis-3-({[1-(cis-3-Methoxycyclobutyl)azetidin-3-yl]sulfonyl}methyl)cyclobutyl]-N-methyl-7H-pyrrolo[2,3-d]pyrimidin-4-amine;

N-{cis-3-[({3-[(Difluoromethoxy)methyl]azetidin-1-yl}sulfonyl)methyl]cyclobutyl}-N-methyl-7H-pyrrolo[2,3-d]pyrimidin-4-amine;

N-(Bicyclo[1.1.1]pent-1-yl)-N-methyl-1-{cis-3-[methyl(7H-pyrrolo[2,3-d]pyrimidin-4-yl)amino]cyclobutyl}methanesulfonamide;

N-[cis-3-({[3-(Methoxymethyl)pyrrolidin-1-yl]sulfonyl}methyl)cyclobutyl]-N-methyl-7H-pyrrolo[2,3-d]pyrimidin-4-amine;

N-Methyl-N-[cis-3-({[6-(trifluoromethyl)-3-azabicyclo[3.1.0]hex-3-yl]sulfonyl}methyl)cyclobutyl]-7H-pyrrolo[2,3-d]pyrimidin-4-amine;

N-Methyl-N-[cis-3-({[(2R)-2-methylmorpholin-4-yl]sulfonyl}methyl)cyclobutyl]-7H-pyrrolo[2,3-d]pyrimidin-4-amine;

N-(cis-3-{[(4-Fluoropiperidin-1-yl)sulfonyl]methyl}cyclobutyl)-N-methyl-7H-pyrrolo[2,3-d]pyrimidin-4-amine;

N-[cis-3-({[2-(Methoxymethyl)morpholin-4-yl]sulfonyl}methyl)cyclobutyl]-N-methyl-7H-pyrrolo[2,3-d]pyrimidin-4-amine;

N-(cis-3-{[(4-Methoxypiperidin-1-yl)sulfonyl]methyl}cyclobutyl)-N-methyl-7H-pyrrolo[2,3-d]pyrimidin-4-amine;

N-{cis-3-[(6-Azaspiro[2.5]oct-6-ylsulfonyl)methyl]cyclobutyl}-N-methyl-7H-pyrrolo[2,3-d]pyrimidin-4-amine;

N-Methyl-1-{cis-3-[methyl(7H-pyrrolo[2,3-d]pyrimidin-4-yl)amino]cyclobutyl}-N-(pyridin-4-ylmethyl)methanesulfonamide;

N-[cis-3-({[(3R,4R)-3-Fluoro-4-methoxypyrrolidin-1-yl]sulfonyl}methyl)cyclobutyl]-N-methyl-7H-pyrrolo[2,3-d]pyrimidin-4-amine;

N-Methyl-N-[cis-3-({[(3R)-3-methylmorpholin-4-yl]sulfonyl}methyl)cyclobutyl]-7H-pyrrolo[2,3-d]pyrimidin-4-amine;

N-[cis-3-({[(3R)-3-Methoxypiperidin-1-yl]sulfonyl}methyl)cyclobutyl]-N-methyl-7H-pyrrolo[2,3-d]pyrimidin-4-amine;

N-[cis-3-({[(2R,5R)-2,5-Dimethylmorpholin-4-yl]sulfonyl}methyl)cyclobutyl]-N-methyl-7H-pyrrolo[2,3-d]pyrimidin-4-amine;

N-Methyl-1-{cis-3-[methyl(7H-pyrrolo[2,3-d]pyrimidin-4-yl)amino]cyclobutyl}-N-(tetrahydrofuran-2-ylmethyl)methanesulfonamide;

N-Methyl-1-{cis-3-[methyl(7H-pyrrolo[2,3-d]pyrimidin-4-yl)amino]cyclobutyl}-N-(tetrahydrofuran-3-yl)methanesulfonamide;

N-Methyl-N-{cis-3-[(morpholin-4-ylsulfonyl)methyl]cyclobutyl}-7H-pyrrolo[2,3-d]pyrimidin-4-amine;

N-Methyl-N-{cis-3-[(6-oxa-9-azaspiro[4.5]dec-9-ylsulfonyl)methyl]cyclobutyl}-7H-pyrrolo[2,3-d]pyrimidin-4-amine;

N-Methyl-1-{cis-3-[methyl(7H-pyrrolo[2,3-d]pyrimidin-4-yl)amino]cyclobutyl}-N-(pyrazin-2-ylmethyl)methanesulfonamide;

N-Methyl-1-{cis-3-[methyl(7H-pyrrolo[2,3-d]pyrimidin-4-yl)amino]cyclobutyl}-N-(pentan-2-yl)methanesulfonamide;

N-Butyl-N-methyl-1-{cis-3-[methyl(7H-pyrrolo[2,3-d]pyrimidin-4-yl)amino]cyclobutyl}methane-sulfonamide;

N-Methyl-N-{cis-3-[(2-oxa-6-azaspiro[3.5]non-6-ylsulfonyl)methyl]cyclobutyl}-7H-pyrrolo[2,3-d]pyrimidin-4-amine;

N-[cis-3-({[(3R)-3-Methoxypyrrolidin-1-yl]sulfonyl}methyl)cyclobutyl]-N-methyl-7H-pyrrolo[2,3-d]pyrimidin-4-amine;

N-Methyl-1-{cis-3-[methyl(7H-pyrrolo[2,3-d]pyrimidin-4-yl)amino]cyclobutyl}-N-(pyridin-3-ylmethyl)methanesulfonamide;

N-[cis-3-({[4-(2-Methoxyethoxy)piperidin-1-yl]sulfonyl}methyl)cyclobutyl]-N-methyl-7H-pyrrolo[2,3-d]pyrimidin-4-amine;

N-Methyl-N-{cis-3-[(8-oxa-2-azaspiro[4.5]dec-2-ylsulfonyl)methyl]cyclobutyl}-7H-pyrrolo[2,3-d]pyrimidin-4-amine;
N-(2-Methoxyethyl)-N-methyl-1-{cis-3-[methyl(7H-pyrrolo[2,3-d]pyrimidin-4-yl)amino]cyclobutyl}methanesulfonamide;
N-[cis-3-({[4-(Ethoxymethyl)-4-fluoropiperidin-1-yl]sulfonyl}methyl)cyclobutyl]-N-methyl-7H-pyrrolo[2,3-d]pyrimidin-4-amine;
N-Methyl-N-(cis-3-{[(3-methylpiperidin-1-yl)sulfonyl]methyl}cyclobutyl)-7H-pyrrolo[2,3-d]pyrimidin-4-amine;
N-Methyl-N-[cis-3-({[4-(trifluoromethyl)piperidin-1-yl]sulfonyl}methyl)cyclobutyl]-7H-pyrrolo[2,3-d]pyrimidin-4-amine;
N-Ethyl-N-methyl-1-{cis-3-[methyl(7H-pyrrolo[2,3-d]pyrimidin-4-yl)amino]cyclobutyl}methanesulfonamide;
N-[cis-3-({[(3S)-3-Fluoropyrrolidin-1-yl]sulfonyl}methyl)cyclobutyl]-N-methyl-7H-pyrrolo[2,3-d]pyrimidin-4-amine;
N-Methyl-N-[cis-3-({[(2S)-2-methylmorpholin-4-yl]sulfonyl}methyl)cyclobutyl]-7H-pyrrolo[2,3-d]pyrimidin-4-amine;
N-Methyl-N-(cis-3-{[(2-methylpiperidin-1-yl)sulfonyl]methyl}cyclobutyl)-7H-pyrrolo[2,3-d]pyrimidin-4-amine;
N-[cis-3-({[(3-exo)-3-Methoxy-8-azabicyclo[3.2.1]oct-8-yl]sulfonyl}methyl)cyclobutyl]-N-methyl-7H-pyrrolo[2,3-d]pyrimidin-4-amine;
N-Methyl-N-{cis-3-[(piperidin-1-ylsulfonyl)methyl]cyclobutyl}-7H-pyrrolo[2,3-d]pyrimidin-4-amine;
N-[cis-3-({[(3R)-3-Fluoropyrrolidin-1-yl]sulfonyl}methyl)cyclobutyl]-N-methyl-7H-pyrrolo[2,3-d]pyrimidin-4-amine;
N-Methyl-N-[cis-3-({[(2R)-2-methylpyrrolidin-1-yl]sulfonyl}methyl)cyclobutyl]-7H-pyrrolo[2,3-d]pyrimidin-4-amine;
N-(cis-3-{[(3-Fluoropyrrolidin-1-yl)sulfonyl]methyl}cyclobutyl)-N-methyl-7H-pyrrolo[2,3-d]pyrimidin-4-amine;
N-Cyclobutyl-N-methyl-1-{cis-3-[methyl(7H-pyrrolo[2,3-d]pyrimidin-4-yl)amino]cyclobutyl}meth-anesulfonamide;
2,5-Anhydro-1,3,4-trideoxy-3-{methyl[({cis-3-[methyl(7H-pyrrolo[2,3-d]pyrimidin-4-yl)amino]cyclobutyl}methyl)sulfonyl]amino}-L-threo-pentitol;
N-[cis-3-({[(2R,6S)-2,6-Dimethylmorpholin-4-yl]sulfonyl}methyl)cyclobutyl]-N-methyl-7H-pyrrolo[2,3-d]pyrimidin-4-amine;
N-[cis-3-({[3-(Methoxymethyl)piperidin-1-yl]sulfonyl}methyl)cyclobutyl]-N-methyl-7H-pyrrolo[2,3-d]pyrimidin-4-amine;
N-(cis-3-{[(3-Methoxypiperidin-1-yl)sulfonyl]methyl}cyclobutyl)-N-methyl-7H-pyrrolo[2,3-d]pyrimidin-4-amine;
N-(cis-3-{[(2-Ethylmorpholin-4-yl)sulfonyl]methyl}cyclobutyl)-N-methyl-7H-pyrrolo[2,3-d]pyrimidin-4-amine;
N-methyl-1-{cis-3-[Methyl(7H-pyrrolo[2,3-d]pyrimidin-4-yl)amino]cyclobutyl}-N-(tetrahydro-2H-pyran-3-yl)methanesulfonamide;
N-[cis-3-({[4-(ethoxymethyl)piperidin-1-yl]sulfonyl}methyl)cyclobutyl]-N-methyl-7H-pyrrolo[2,3-d]pyrimidin-4-amine;
N-methyl-1-{cis-3-[methyl(7H-pyrrolo[2,3-d]pyrimidin-4-yl)amino]cyclobutyl}-N-(2,2,2-trifluoroethyl)methanesulfonamide;
N-[cis-3-({[4-(methoxymethyl)piperidin-1-yl]sulfonyl}methyl)cyclobutyl]-N-methyl-7H-pyrrolo[2,3-d]pyrimidin-4-amine;
N-[cis-3-({[(3,3-difluoro-1-methylcyclobutyl)methyl]sulfonyl}methyl)cyclobutyl]-N-methyl-7H-pyrrolo[2,3-d]pyrimidin-4-amine;
N-[cis-3-({[1-(trans-3-methoxycyclobutyl)azetidin-3-yl]sulfonyl}methyl)cyclobutyl]-N-methyl-7H-pyrrolo[2,3-d]pyrimidin-4-amine;
N-methyl-N-[cis-3-({[3-(trifluoromethyl)azetidin-1-yl]sulfonyl}methyl)cyclobutyl]-7H-pyrrolo[2,3-d]pyrimidin-4-amine;
N-[cis-3-({[3-(difluoromethoxy)azetidin-1-yl]sulfonyl}methyl)cyclobutyl]-N-methyl-7H-pyrrolo[2,3-d]pyrimidin-4-amine;
N-methyl-N-(cis-3-{[(4,4,4-trifluorobutyl)sulfonyl]methyl}cyclobutyl)-7H-pyrrolo[2,3-d]pyrimidin-4-amine;
N-methyl-N-(cis-3-{[(3,3,3-trifluoropropyl)sulfonyl]methyl}cyclobutyl)-7H-pyrrolo[2,3-d]pyrimidin-4-amine;
N-[cis-3-({[3-(2,2-difluoroethyl)azetidin-1-yl]sulfonyl}methyl)cyclobutyl]-N-methyl-7H-pyrrolo[2,3-d]pyrimidin-4-amine; and,
N-(cis-3-{[(3,3-difluoroazetidin-1-yl)sulfonyl]methyl}cyclobutyl)-N-methyl-7H-pyrrolo[2,3-d]pyrimidin-4-amine;
or a pharmaceutically acceptable salt of any of the above listed compounds.

In other embodiments, the invention provides the compound selected from the group consisting of:
1-(3-methyloxetan-3-yl)-N-{cis-3-[methyl(7H-pyrrolo[2,3-d]pyrimidin-4-yl)amino]cyclobutyl}methanesulfonamide;
cis-3-cyano-N-{cis-3-[methyl(7H-pyrrolo[2,3-d]pyrimidin-4-yl)amino]cyclo-butyl}cyclobutanesulfonamide;
trans-3-cyano-N-{cis-3-[methyl(7H-pyrrolo[2,3-d]pyrimidin-4-yl)amino]cyclo-butyl}cyclobutanesulfonamide;
cis-3-(difluoromethyl)-N-{cis-3-[methyl(7H-pyrrolo[2,3-d]pyrimidin-4-yl)amino]cyclobut-yl}cyclobutanesulfonamide;
trans-3-(difluoromethyl)-N-{cis-3-[methyl(7H-pyrrolo[2,3-d]pyrimidin-4-yl)amino]cyclo-butyl}cyclobutanesulfonamide;
1-(cis-3-cyano-1-methylcyclobutyl)-N-{cis-3-[methyl(7H-pyrrolo[2,3-d]pyrimidin-4-yl)amino]cyclobutyl}methanesulfonamide;
1-(trans-3-cyano-1-methylcyclobutyl)-N-{cis-3-[methyl(7H-pyrrolo[2,3-d]pyrimidin-4-yl)amino]cyclobutyl}methanesulfonamide;
trans-3-fluoro-N-{cis-3-[methyl(7H-pyrrolo[2,3-d]pyrimidin-4-yl)amino]cyclobut-yl}cyclobutanesulfonamide;
cis-3-fluoro-N-{cis-3-[methyl(7H-pyrrolo[2,3-d]pyrimidin-4-yl)amino]cyclobutyl}cyclo-butanesulfonamide;
1-[({cis-3-[methyl(7H-pyrrolo[2,3-d]pyrimidin-4-yl)amino]cyclobutyl}methyl)sulfonyl]azetidine-3-carbonitrile;
3-methyl-1-[({cis-3-[methyl(7H-pyrrolo[2,3-d]pyrimidin-4-yl)amino]cyclobutyl}methyl)sulfonyl]azetidine-3-carbonitrile; and.
3-cyano-3-methyl-N-{cis-3-[methyl(7H-pyrrolo[2,3-d]pyrimidin-4-yl)amino]cyclobutyl}azetidine-1-sulfonamide;
or, pharmaceutically acceptable salts thereof.

The present invention also provides a pharmaceutical or a veterinary composition comprising a compound of formula I, or a pharmaceutically acceptable salt thereof, and a pharmaceutically acceptable carrier.

The present invention also provides a method of treating a disorder or condition related to dysregulation of JAK, and particularly of JAK1, in a subject, comprising administering to the subject a therapeutically effective amount of the compound having the structure of formula I, or a pharmaceutically acceptable salt thereof. In certain embodiments, the disorder or condition treated by the method is selected from among selected from rheumatoid arthritis, myositis, vasculitis, pemphigus, Crohn's disease, ulcerative colitis, Alzheimer's disease, lupus, nephritis, psoriasis, atopic dermatitis, autoimmune thyroid disorders, multiple sclerosis, major depression disorder, allergy, asthma, Sjogren's disease, dry eye syndrome, organ transplant rejection, xeno transplantation, Type I diabetes and complications from diabetes, cancer, leukemia, adult T cell leukemia activated B-cell like, diffuse large B cell lymphoma, inflammatory bowel disease, septic shock, cardiopulmonary dysfunction, chronic pulmonary obstructive disorder, acute respiratory disease, cachexia, acute myeloid leukemia, T cell acute lymphoblastic leukemia, multiple myeloma, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, chronic neuroinflammation associated with neurodegeneration including Alzheimer's disease, Parkinson's disease, Amyotophic Lateral Sclerosis, fronto-temporal lobe dementia, and with neuropsychiatric disorders including schizophrenia, bipolar disorder, treatment resistant depression, Post Traumatic Stress Disorder, anxiety, and auto-antibodies mediated encephalopathies, comprising the step of administering to a subject an effective amount of a composition comprising a compound of formula I.

As compounds of formula I noted above have the ability to cross the blood brain barrier, and therefore, will be useful in the treatment of a number of neurological conditions. These include, but are not limited to: vascular or infectious brain inflammation such as cerebral malaria, brain abscess, cerebral vasculitis, giant cell arteritis/temporal arteritis, and arachnoiditis meningitis; neurodegenerative diseases such as Pick's Disease, epilepsy, stroke; blood-occular barrier diseases such as uveitis, refractory uveitis, and age-related macular degeneration; immune-mediated, infectious (or vaccine-induced), or paraneoplastic encephalitides conditions including immune-mediated encephalomyelitis, Paraneoplastic syndromes with neurological manifestations (e.g., encephalomyelitis, limbic encephalitis, brainstem encephalitis), Rasmussen's encephalitis, HTLV-1 associated myelopathy, Transverse myelitis, Chronic inflammatory demyelinating polyneuropathy (CIDP) (AKA, Guillain-Barré syndrome) Acute disseminated encephalomyelitis (ADEM); and, HIV/AIDS Associated (Viral spread and inflammation suppression) including HIV-associated dementia, HIV-associated neurocognitive disorder (HAND) HIV suppression, standalone or in combination with antiviral treatment like HAART.

In the practice of the method, the compound of formula I is preferably selected from 1-(3-methyloxetan-3-yl)-N-{cis-3-[methyl(7H-pyrrolo[2,3-d]pyrimidin-4-yl)amino]cyclobutyl}methanesulfonamide;
cis-3-cyano-N-{cis-3-[methyl(7H-pyrrolo[2,3-d]pyrimidin-4-yl)amino]cyclo-butyl}cyclobutanesulfonamide;
trans-3-cyano-N-{cis-3-[methyl(7H-pyrrolo[2,3-d]pyrimidin-4-yl)amino]cyclo-butyl}cyclobutanesulfonamide;
cis-3-(difluoromethyl)-N-{cis-3-[methyl(7H-pyrrolo[2,3-d]pyrimidin-4-yl)amino]cyclobut-yl}cyclobutanesulfonamide;
trans-3-(difluoromethyl)-N-{cis-3-[methyl(7H-pyrrolo[2,3-d]pyrimidin-4-yl)amino]cyclo-butyl}cyclobutanesulfonamide;
1-(cis-3-cyano-1-methylcyclobutyl)-N-{cis-3-[methyl(7H-pyrrolo[2,3-d]pyrimidin-4-yl)amino]cyclobutyl}methanesulfonamide;
1-(trans-3-cyano-1-methylcyclobutyl)-N-{cis-3-[methyl(7H-pyrrolo[2,3-d]pyrimidin-4-yl)amino]cyclobutyl}methanesulfonamide;
trans-3-fluoro-N-{cis-3-[methyl(7H-pyrrolo[2,3-d]pyrimidin-4-yl)amino]cyclobut-yl}cyclobutanesulfonamide;
cis-3-fluoro-N-{cis-3-[methyl(7H-pyrrolo[2,3-d]pyrimidin-4-yl)amino]cyclobutyl}cyclo-butanesulfonamide;
1-[({cis-3-[methyl(7H-pyrrolo[2,3-d]pyrimidin-4-yl)amino]cyclobutyl}methyl)sulfonyl]azetidine-3-carbonitrile;
3-methyl-1-[({cis-3-[methyl(7H-pyrrolo[2,3-d]pyrimidin-4-yl)amino]cyclobutyl}methyl)sulfonyl]azetidine-3-carbonitrile; and.
3-cyano-3-methyl-N-{cis-3-[methyl(7H-pyrrolo[2,3-d]pyrimidin-4-yl)amino]cyclobutyl}azetidine-1-sulfonamide;
or, a pharmaceutically acceptable salt thereof.

The present invention further provides a method for treating or preventing a disorder or condition selected from atopic dermatitis, eczema, scleroderma, pruritus, other pruritic conditions, allergic reactions including allergic dermatitis in mammal, horse allergic diseases including bite hypersensitivity, summer eczema, sweet itch in horses, heaves, inflammatory airway disease, recurrent airway obstruction, and airway hyper-responsiveness, by administering to a mammal in need a therapeutically effective amount of a compound of formula I, or a pharmaceutically acceptable salt thereof.

In the practice of the method, the compound of formula I is preferably selected from:

1-(3-methyloxetan-3-yl)-N-{cis-3-[methyl(7H-pyrrolo[2,3-d]pyrimidin-4-yl)amino]cyclobutyl}methanesulfonamide;
cis-3-cyano-N-{cis-3-[methyl(7H-pyrrolo[2,3-d]pyrimidin-4-yl)amino]cyclo-butyl}cyclobutanesulfonamide;
trans-3-cyano-N-{cis-3-[methyl(7H-pyrrolo[2,3-d]pyrimidin-4-yl)amino]cyclo-butyl}cyclobutanesulfonamide;
cis-3-(difluoromethyl)-N-{cis-3-[methyl(7H-pyrrolo[2,3-d]pyrimidin-4-yl)amino]cyclobut-yl}cyclobutanesulfonamide;
trans-3-(difluoromethyl)-N-{cis-3-[methyl(7H-pyrrolo[2,3-d]pyrimidin-4-yl)amino]cyclo-butyl}cyclobutanesulfonamide;
1-(cis-3-cyano-1-methylcyclobutyl)-N-{cis-3-[methyl(7H-pyrrolo[2,3-d]pyrimidin-4-yl)amino]cyclobutyl}methanesulfonamide;
1-(trans-3-cyano-1-methylcyclobutyl)-N-{cis-3-[methyl(7H-pyrrolo[2,3-d]pyrimidin-4-yl)amino]cyclobutyl}methanesulfonamide;
trans-3-fluoro-N-{cis-3-[methyl(7H-pyrrolo[2,3-d]pyrimidin-4-yl)amino]cyclobut-yl}cyclobutanesulfonamide;
cis-3-fluoro-N-{cis-3-[methyl(7H-pyrrolo[2,3-d]pyrimidin-4-yl)amino]cyclobutyl}cyclo-butanesulfonamide;
1-[({cis-3-[methyl(7H-pyrrolo[2,3-d]pyrimidin-4-yl)amino]cyclobutyl}methyl)sulfonyl]azetidine-3-carbonitrile;
3-methyl-1-[({cis-3-[methyl(7H-pyrrolo[2,3-d]pyrimidin-4-yl)amino]cyclobutyl}methyl)sulfonyl]azetidine-3-carbonitrile; and.

3-cyano-3-methyl-N-{cis-3-[methyl(7H-pyrrolo[2,3-d]pyrimidin-4-yl)amino]cyclobutyl}azetidine-1-sulfonamide;
or, a pharmaceutically acceptable salt thereof.

The present invention also provides a method for treating or preventing a disorder or condition selected from acute myeloid leukemia, T cell acute lymphoblastic leukemia, multiple myeloma, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, Parkinson's disease, Amyotrophic Lateral Sclerosis, fronto-temporal lobe dementia, and with neuropsychiatric disorders including schizophrenia, bipolar disorder, depression, treatment resistant depression, Post Traumatic Stress Disorder, anxiety, and auto-antibodies mediated encephalopathies, comprising the step of administering to a subject an effective amount of a composition comprising a compound of formula I having the structure:

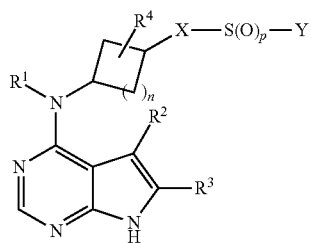

I or a pharmaceutically acceptable salt thereof, wherein $R^1$ is hydrogen or $C_1$-$C_4$ alkyl, wherein said alkyl is further optionally substituted with one or more substituents selected from the group consisting of halo, hydroxy, methoxy, amino, $CF_3$, and $C_3$-$C_6$ cycloalkyl;

$R^2$ and $R^3$ are each independently hydrogen, deuterium, $C_1$-$C_6$ linear or branched alkyl, $C_3$-$C_6$ cycloalkyl, $C_1$-$C_6$ linear or branched perfluoroalkyl, $C_1$-$C_6$ linear or branched alkoxy, $C_1$-$C_6$ linear or branched perfluoroalkoxy, halogen, cyano, hydroxyl, amino, carboxy, aminocarbonyl, aryl, heteroaryl, (aryl)$C_1$-$C_6$ linear or branched alkyl, (heteroaryl)$C_1$-$C_6$ linear or branched alkyl, (heterocyclic)$C_1$-$C_6$ linear or branched alkyl, ($C_1$-$C_6$ linear or branched alkyl)aryl, ($C_1$-$C_6$ linear or branched alkyl)heteroaryl, ($C_1$-$C_6$ linear or branched alkyl)heterocyclic, ($C_1$-$C_6$ linear or branched alkoxyl)carbonyl, ($C_1$-$C_6$ linear or branched alkyl)aminocarbonylamino, or ($C_1$-$C_6$ linear or branched alkyl)aminocarbonyl;

$R^4$ is selected from hydrogen, deuterium, $C_1$-$C_6$ linear or branched alkyl, $C_1$-$C_6$ linear or branched perfluoroalkyl, aryl, and alkylaryl;

X is selected from —NH— and —$CR_aR_b$—, where (a) $R_a$ and $R_b$ are independently hydrogen, deuterium, $C_1$-$C_6$ linear or branched alkyl, $C_3$-$C_6$ cycloalkyl, aryl, (aryl)$C_1$-$C_6$ linear or branched alkyl, heteroaryl, ($C_1$-$C_6$ linear or branched alkyl)heteroaryl, (heteroaryl)$C_1$-$C_6$ linear or branched alkyl, (heterocyclic)$C_1$-$C_6$ linear or branched alkyl, or (b) $R_a$ and $R_b$ together form a chain comprising —$(CR_cR_d)_j$—, where $R_c$ and $R_d$ are independently hydrogen, deuterium, $C_1$-$C_6$ linear or branched alkyl, aryl, ($C_1$-$C_6$ linear or branched alkyl)aryl, heteroaryl, ($C_1$-$C_6$ linear or branched alkyl)heteroaryl, halo, CN, $CF_3$, hydroxyl, $CONH_2$, or $SO_2CH_3$;

Y is A-$R^5$, where A is a bond, —$(CH_2)_k$— or —$(CD_2)_k$- and $R^5$ is $C_1$-$C_6$ linear or branched alkyl, $C_3$-$C_6$ cycloalkyl, aryl, or —$NR_{a'}R_{b'}$, or is an unsaturated, saturated or partially saturated monocyclic or bicyclic ring structure containing a total of four to eleven atoms having one to four heteroatoms independently selected from the group consisting of oxygen, nitrogen, and sulfur, wherein said alkyl, $C_3$-$C_6$ cycloalkyl, aryl, or monocyclic or bicyclic ring structure is further optionally substituted with one or more substituents selected from the group consisting of deuterium, halo, $C_1$-$C_6$ linear or branched alkyl, CN, hydroxyl, $CF_3$, —$OR_e$, —$NR_eR_f$, —$S(O)_pR_e$ and $C_3$-$C_6$ cycloalkyl, where said alkyl and cycloalkyl may be optionally substituted with one or more substituents selected from the group consisting of halo, CN, hydroxyl, $CONH_2$, and $SO_2CH_3$, where (a) $R_{a'}$ and $R_{b'}$ are independently hydrogen, deuterium, $C_1$-$C_6$ linear or branched alkyl, $C_3$-$C_6$ cycloalkyl, aryl, ($C_1$-$C_6$ linear or branched alkyl)aryl, heteroaryl, or ($C_1$-$C_6$ linear or branched alkyl)heteroaryl, where said alkyl and cycloalkyl may be optionally substituted with one or more $R_{c'}$, or (b) $R_{a'}$ and $R_{b'}$ together form a chain comprising —$(CR_{c'}R_{d'})_j$—, where $R_{c'}$ and $R_{d'}$ are independently hydrogen, deuterium, $C_1$-$C_6$ linear or branched alkyl, aryl, ($C_1$-$C_6$ linear or branched alkyl)aryl, heteroaryl, ($C_1$-$C_6$ linear or branched alkyl)heteroaryl, halo, CN, hydroxyl, $CF_3$, $CONH_2$, —$OR_e$, —$NR_eR_f$, or —$S(O)_pR_e$; where $R_e$ and $R_f$ are independently hydrogen, deuterium, $C_1$-$C_6$ linear or branched alkyl, or $C_3$-$C_6$ cycloalkyl, where said alkyl and cycloalkyl may be optionally substituted with one or more substituents selected from the group consisting of halo, CN, hydroxyl, $CF_3$, and $CONH_2$; j is 2, 3, 4 or 5; k is 1, 2; 3, or 4; p is 0, 1 or 2; and, n is 1 or 2. Compounds used in this method have been disclosed, along with methods of preparation thereof, in priority application U.S. Ser. No. 61/767,947, the contents of which are hereby incorporated by reference herein in their entirety.

In certain embodiments, the invention provides the method described above wherein the compound is a compound of formula IA having the structure:

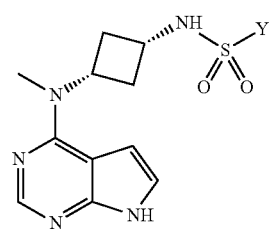

IA or a pharmaceutically acceptable salt thereof, wherein Y is A-$R^5$, where A is a bond, —$(CH_2)_k$— or —$(CD_2)_k$- and $R^5$ is $C_1$-$C_6$ linear or branched alkyl, $C_3$-$C_6$ cycloalkyl, aryl, or —$NR_{a'}R_{b'}$, or is an unsaturated, saturated or partially saturated monocyclic or bicyclic ring structure containing a total of four to eleven atoms having one to four heteroatoms independently selected from the group consisting of oxygen, nitrogen, and sulfur, wherein said alkyl, $C_3$-$C_6$ cycloalkyl, aryl, or monocyclic or bicyclic ring structure is further optionally substituted with one or more substituents selected from the group consisting of deuterium, halo, $C_1$-$C_6$ linear or branched alkyl, CN, hydroxyl, $CF_3$, —$OR_e$, —$NR_eR_f$, —$S(O)_pR_e$ and $C_3$-$C_6$ cycloalkyl, where said alkyl and cycloalkyl may be optionally substituted with one or more substituents selected from the group consisting of halo, CN, hydroxyl, $CONH_2$, and $SO_2CH_3$, where (a) $R_{a'}$ and $R_{b'}$ are independently hydrogen, deuterium, $C_1$-$C_6$ linear or branched alkyl, $C_3$-$C_6$ cycloalkyl, aryl, ($C_1$-$C_6$ linear or branched alkyl)aryl, heteroaryl, or ($C_1$-$C_6$ linear or branched alkyl)heteroaryl, where said alkyl and cycloalkyl may be optionally substituted with one or more $R_c$; or (b) $R_{a'}$ and $R_{b'}$ together form a chain comprising —($CR_c R_{d'}$)$_j$—, where $R_c$ and $R_{d'}$ are independently hydrogen, deuterium, $C_1$-$C_6$ linear or branched alkyl, aryl, ($C_1$-$C_6$ linear or branched alkyl)aryl, heteroaryl, ($C_1$-$C_6$ linear or branched alkyl)heteroaryl, halo, CN, hydroxyl, $CF_3$, $CONH_2$, —$OR_e$, —$NR_e R_f$, or —$S(O)_p R_e$; where $R_e$ and $R_f$ are independently hydrogen, deuterium, $C_1$-$C_6$ linear or branched alkyl, or $C_3$-$C_6$ cycloalkyl, where said alkyl and cycloalkyl may be optionally substituted with one or more substituents selected from the group consisting of halo, CN, hydroxyl, $CF_3$, and $CONH_2$; j is 2, 3, 4 or 5; k is 1, 2; 3, or 4; and, p is 0, 1 or 2. In particular embodiments, the invention provides the above method using a compound wherein A is a bond and $R^5$ is a $C_1$-$C_6$ linear or branched alkyl, $C_3$-$C_6$ cycloalkyl or aryl. In other particular embodiments, the invention provides the above method using a compound wherein A is a bond or —($CH_2$)$_k$—, and $R^5$ is $C_3$-$C_6$ cycloalkyl wherein said $C_3$-$C_6$ cycloalkyl is further optionally substituted with one or more substituents selected from the group consisting of halo, $C_1$-$C_6$ linear or branched alkyl, and CN where said alkyl and cycloalkyl may be optionally substituted with one or more substituents selected from the group consisting of halo, CN, hydroxyl, $CONH_2$, and $SO_2 CH_3$; where k is 1, 2, or 3.

In certain embodiments, the invention provides the method described above wherein the compound is a compound of formula IB having the structure:

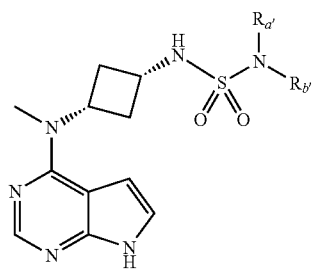

IB or a pharmaceutically acceptable salt thereof, wherein (a) $R_{a'}$ and $R_{b'}$ are independently hydrogen, deuterium, $C_1$-$C_6$ linear or branched alkyl, $C_3$-$C_6$ cycloalkyl, aryl, ($C_1$-$C_6$ linear or branched alkyl)aryl, heteroaryl, or ($C_1$-$C_6$ linear or branched alkyl)heteroaryl, where said alkyl and cycloalkyl may be optionally substituted with one or more $R_c$; (b) $R_{a'}$ and $R_{b'}$ together form a chain comprising —($CR_c R_{d'}$)$_j$—, where $R_c$ and $R_{d'}$ are independently hydrogen, deuterium, $C_1$-$C_6$ linear or branched alkyl, aryl, ($C_1$-$C_6$ linear or branched alkyl)aryl, heteroaryl, ($C_1$-$C_6$ linear or branched alkyl)heteroaryl, halo, CN, hydroxyl, $CF_3$, $CONH_2$, —$OR_e$, —$NR_e R_f$, or —$S(O)_p R_e$; where $R_e$ and $R_f$ are independently hydrogen, deuterium, $C_1$-$C_6$ linear or branched alkyl, or $C_3$-$C_6$ cycloalkyl, where said alkyl and cycloalkyl may be optionally substituted with one or more substituents selected from the group consisting of halo, CN, hydroxyl, $CF_3$, and $CONH_2$; or, (c) $R_{a'}$ and $R_{b'}$ together form an unsaturated, saturated or partially saturated monocyclic or bicyclic ring structure containing a total of five to eleven atoms having one to four heteroatoms independently selected from the group consisting of oxygen, nitrogen, and sulfur, wherein said monocyclic or bicyclic ring structure is further optionally substituted with one or more substituents selected from the group consisting of deuterium, halo, $C_1$-$C_6$ linear or branched alkyl, CN, hydroxyl, $CF_3$, —$NR_a R_b$, —$OR_e$, —$S(O)_p R_e$ and $C_3$-$C_6$ cycloalkyl; j is 2, 3, 4 or 5; and, p is 0, 1 or 2.

In certain embodiments, the invention provides the method described above wherein the compound is a compound of formula IC having the structure:

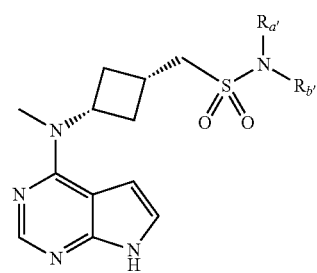

IC or a pharmaceutically acceptable salt thereof, wherein (a) $R_{a'}$ and $R_{b'}$ are independently hydrogen, deuterium, $C_1$-$C_6$ linear or branched alkyl, $C_3$-$C_6$ cycloalkyl, aryl, ($C_1$-$C_6$ linear or branched alkyl)aryl, heteroaryl, or ($C_1$-$C_6$ linear or branched alkyl)heteroaryl, where said alkyl and cycloalkyl may be optionally substituted with one or more $R_c$; (b) $R_{a'}$ and $R_{b'}$ together form a chain comprising —($CR_c R_{d'}$)$_j$—, where $R_c$ and $R_{d'}$ are independently hydrogen, deuterium, $C_1$-$C_6$ linear or branched alkyl, aryl, ($C_1$-$C_6$ linear or branched alkyl)aryl, heteroaryl, ($C_1$-$C_6$ linear or branched alkyl)heteroaryl, halo, CN, hydroxyl, $CF_3$, $CONH_2$, —$OR_e$, —$NR_e R_f$, or —$S(O)_p R_e$; where $R_e$ and $R_f$ are independently hydrogen, deuterium, $C_1$-$C_6$ linear or branched alkyl, or $C_3$-$C_6$ cycloalkyl, where said alkyl and cycloalkyl may be optionally substituted with one or more substituents selected from the group consisting of halo, CN, hydroxyl, $CF_3$, and $CONH_2$; or, (c) $R_{a'}$ and $R_{b'}$ together form an unsaturated, saturated or partially saturated monocyclic or bicyclic ring structure containing a total of five to eleven atoms having one to four heteroatoms independently selected from the group consisting of oxygen, nitrogen, and sulfur, wherein said monocyclic or bicyclic ring structure is further optionally substituted with one or more substituents selected from the group consisting of deuterium, halo, $C_1$-$C_6$ linear or branched alkyl, CN, hydroxyl, $CF_3$, —$NR_a R_b$, —$OR_e$, —$S(O)_p R_e$ and $C_3$-$C_6$ cycloalkyl; j is 2, 3, 4 or 5; and, p is 0, 1 or 2.

In certain other embodiments, the invention provides the method described above wherein the compound is a compound of formula ID having the structure:

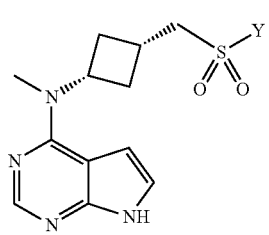

ID or a pharmaceutically acceptable salt thereof, wherein Y is $AR^5$, where A is a bond or —($CH_2$)$_k$—, and $R^5$ is $C_1$-$C_6$ linear or branched alkyl, $C_3$-$C_6$ cycloalkyl, aryl, or is an unsaturated, saturated or partially saturated monocyclic or bicyclic ring structure containing a total of four to eleven atoms having one to four heteroatoms independently selected from the group consisting of oxygen, nitrogen, and sulfur, wherein said alkyl, $C_3$-$C_6$ cycloalkyl, aryl, or monocyclic or bicyclic ring structure is further optionally substituted with one or more substituents selected from the group consisting of deuterium, halo, $C_1$-$C_6$ linear or branched alkyl, CN, hydroxyl, $CF_3$, —$NR_aR_{b'}$, —$OR_e$, —$S(O)_pR_e$ and $C_3$-$C_6$ cycloalkyl, where said alkyl and cycloalkyl may be optionally substituted with one or more substituents selected from the group consisting of halo, CN, hydroxyl, $CONH_2$, and $SO_2CH_3$, where (a) $R_{a'}$ and $R_{b'}$ are independently hydrogen, deuterium, $C_1$-$C_6$ linear or branched alkyl, $C_3$-$C_6$ cycloalkyl, aryl, (aryl)$C_1$-$C_6$ linear or branched alkyl, heteroaryl, ($C_1$-$C_6$ linear or branched alkyl)heteroaryl, (heteroaryl)$C_1$-$C_6$ linear or branched alkyl, (heterocyclic)$C_1$-$C_6$ linear or branched alkyl, where said alkyl and cycloalkyl may be optionally substituted with one or more $R_e$, or (b) $R_{a'}$ and $R_{b'}$ together form a chain comprising —$(CR_cR_{d'})_j$—, where $R_{c'}$ and $R_{d'}$ are independently hydrogen, deuterium, $C_1$-$C_6$ linear or branched alkyl, aryl, ($C_1$-$C_6$ linear or branched alkyl)aryl, heteroaryl, ($C_1$-$C_6$ linear or branched alkyl)heteroaryl, halo, CN, hydroxyl, $CF_3$, $CONH_2$, —$OR_e$, —$NR_eR_f$, or —$S(O)_pR_e$; where $R_e$ and $R_f$ where are independently hydrogen, deuterium, $C_1$-$C_6$ linear or branched alkyl, or $C_3$-$C_6$ cycloalkyl, where said alkyl and cycloalkyl may be optionally substituted with one or more substituents selected from the group consisting of halo, CN, hydroxyl, $CF_3$, and $CONH_2$; j is 2, 3, 4 or 5; k is 1, 2, or 3; and, p is 0, 1 or 2.

The present invention, in particular, provides the latter method wherein the compound is 2-methyl-N-{cis-3-[methyl(7H-pyrrolo[2,3-d]pyrimidin-4-yl)amino]cyclobutyl}-1,3-thiazole-5-sulfonamide, N-{cis-3-[methyl(7H-pyrrolo[2,3-d]pyrimidin-4-yl)amino]cyclobutyl}-propane-1-sulfonamide, trans-3-(cyano-methyl)-N-{cis-3-[methyl(7H-pyrrolo[2,3-d]pyrimidin-4-yl)amino]cyclobutyl}cyclobutanesulfonamide, 1-(3,3-difluorocyclobutyl)-N-{cis-3-[methyl(7H-pyrrolo[2,3-d]pyrimidin-4-yl)amino]cyclobutyl}methanesulfonamide, N-{cis-3-[methyl(7H-pyrrolo[2,3-d]pyrimidin-4-yl)amino]cyclobutyl}-1-(oxetan-3-yl)methanesulfonamide, (3R)-1-[({cis-3-[methyl(7H-pyrrolo[2,3-d]pyrimidin-4-yl)amino]cyclobutyl}methyl)sulfonyl]pyrrolidine-3-carbonitrile 3,3-difluoro-N-{cis-3-[methyl(7H-pyrrolo[2,3-d]pyrimidin-4-yl)amino]cyclobutane-sulfonamide, (1S,5S)-1-cyano-N-{cis-3-[methyl(7H-pyrrolo[2,3-d]pyrimidin-4-yl)amino]cyclobutyl}-3-azabicyclo[3.1.0]hexane-3-sulfonamide, 1-(3-methyloxetan-3-yl)-N-{cis-3-[methyl(7H-pyrrolo[2,3-d]pyrim-idin-4-yl)amino]cyclobutyl}methanesulfonamide, cis-3-cyano-N-{cis-3-[methyl(7H-pyrrolo[2,3-d]pyrimidin-4-yl)amino]cyclobutyl}cyclobutanesulfonamide, trans-3-cyano-N-{cis-3-[methyl(7H-pyrrolo[2,3-d]pyramid-in-4-yl)amino]cyclobutyl}cyclobutanesulfonamide, cis-3-(difluoromethyl)-N-{cis-3-[methyl(7H-pyrrolo[2,3-d]pyrimidin-4-yl)amino]cyclobut-yl}cyclobutanesulfonamide, trans-3-(difluoromethyl)-N-{cis-3-[methyl(7H-pyrrolo[2,3-d]pyrimidin-4-yl)amino]cyclo-butyl}cyclobutane-sulfonamide, 1-(3-cyano-1-methylcyclobut-yl)-N-{cis-3-[methyl(7H-pyrrolo[2,3-d]pyrimidin-4-yl)amino]cyclobutyl}methanesulfonamide, 1-(trans-3-cyano-1-methylcyclobutyl)-N-{cis-3-[methyl(7H-pyrrolo[2,3-d]pyrimidin-4-yl)amino]cyclobutyl}methane-sulfonamide, trans-3-fluoro-N-{cis-3-[methyl(7H-pyrrolo[2,3-d]pyrimidin-4-yl)amino]cyclobut-yl}cyclo-butanesulfonamide, cis-3-fluoro-N-{cis-3-[methyl(7H-pyrrolo[2,3-d]pyrimidin-4-yl)amino]cyclobutyl}cyclo-butanesulfonamide, 1-[({cis-3-[methyl(7H-pyrrolo[2,3-d]pyrimidin-4-yl)amino]cyclobutyl}methyl)sulfon-yl]azetidine-3-carbonitrile, 3-methyl-1-[({cis-3-[methyl(7H-pyrrolo[2,3-d]pyrimidin-4-yl)amino]cyclobutyl}methyl)sulfonyl]azetidine-3-carbonitrile, and 3-cyano-3-methyl-N-{cis-3-[methyl(7H-pyrrolo[2,3-d]pyrimidin-4-yl)amino]cyclobutyl}azetidine-1-sulfonamide; or, pharmaceutically acceptable salts thereof.

A further embodiment of the invention is directed to a sub-genus of compounds encompassed by formula IE, depicted below:

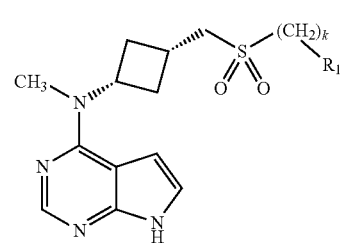

IE or a pharmaceutically acceptable salt thereof, wherein $R_1$ is represented by $C_1$-$C_6$ linear or branched alkyl, $C_3$-$C_6$ cycloalkyl, or —$NR_aR_b$, in which the alkyl or cycloalkyl moieties may be optionally substituted by one or more halo, haloalkyl, or haloalkoxy moieties;

$R_a$ and $R_b$ together form a chain comprising —$(CR_cR_d)_j$—, where $R_c$ and $R_d$ are independently represented by hydrogen, deuterium, $C_1$-$C_6$ linear or branched alkyl, $C_1$-$C_6$ alkoxy, —($C_1$-$C_6$ linear or branched alkyl)-O—($C_1$-$C_6$ linear or branched alkyl)-, —($C_1$-$C_6$ linear or branched alkoxy)-O—($C_1$-$C_6$ linear or branched alkyl)-, $C_3$-$C_6$ cycloakyl, halo, CN, hydroxyl, in which any alkyl, cycloalkyl or alkoxy moiety may be optionally substituted with one or more halogen atoms; k is represented by the integer 0 or 1; and, j is represented by the integer 3, 4, or 5. In a further embodiment the halogen atoms described in formula I E may be one or more fluorine atoms.

It has been discovered that the compounds of formula IE have the ability to cross the blood brain barrier and thus can be used in the treatment of a number of neurological conditions. Such conditions include stroke, epilepsy, Parkinson's Disease, Alzheimer's disease, Frontotemporal lobe dementia (FTD), Multiple sclerosis, and Pick's Disease.

A further embodiment of the invention is directed to a sub-genus of compounds encompassed by formula IE, or their pharmaceutically acceptable salts, selected from the group consisting of:

N-((1S,3S)-3-(((4-(methoxymethyl)piperidin-1-yl)sulfonyl)methyl)cyclobutyl)-N-methyl-7H-pyrrolo[2,3-d]pyrimidin-4-amine;

N-((1S,3S)-3-((((3,3-difluoro-1-methylcyclobutyl)methyl)sulfonyl)methyl)cyclobutyl)-N-methyl-7H-pyrrolo[2,3-d]pyrimidin-4-amine;

N-((1S,3S)-3-(((3-(difluoromethoxy)azetidin-1-yl)sulfonyl)methyl)cyclobutyl)-N-methyl-7H-pyrrolo[2,3-d]pyrimidin-4-amine;

N-methyl-N-((1S,3S)-3-(((3-(trifluoromethyl)azetidin-1-yl)sulfonyl)methyl)cyclobutyl)-7H-pyrrolo[2,3-d]pyrimidin-4-amine;

N-((1S,3S)-3-(((3,3-difluoroazetidin-1-yl)sulfonyl)methyl)cyclobutyl)-N-methyl-7H-pyrrolo[2,3-d]pyrimidin-4-amine; and, N-methyl-N-((1S,3S)-3-(((3,3,3-trifluoropropyl)sulfonyl)
methyl)cyclobutyl)-7H-pyrrolo[2,3-d]pyrimidin-4-
amine.

The invention also encompasses a compound selected from the group consisting of: N-(cis-3-{[(2-methoxy-7,8-dihydro-1,6-naphthyridin-6(5H)-yl)sulfonyl]
methyl}cyclobutyl)-N-methyl-7H-pyrrolo[2,3-d]pyrimidin-4-amine;
N-methyl-N-(cis-3-{[(2,7,7-trimethyl-2,4,6,7-tetrahydro-5H-pyrazolo[4,3-c]pyridin-5-yl)sulfonyl]
methyl}cyclobutyl)-7H-pyrrolo[2,3-d]pyrimidin-4-amine;
N-{cis-3-[(5,6-dihydroimidazo[1,5-a]pyrazin-7(8H)-ylsulfonyl)methyl]cyclobutyl}-N-methyl-7H-pyrrolo[2,3-d]pyrimidin-4-amine;
N-methyl-N-(cis-3-{[(1-methyl-4,6-dihydropyrrolo[3,4-c]pyrazol-5(1H)-yl)sulfonyl]methyl}cyclobutyl)-7H-pyrrolo[2,3-d]pyrimidin-4-amine;
N-methyl-N-[cis-3-({[3-(trifluoromethyl)piperidin-1-yl]sulfonyl}methyl)cyclobutyl]-7H-pyrrolo[2,3-d]pyrimidin-4-amine;
N-(cis-3-{[(1,3-dimethyl-1,4,6,7-tetrahydro-5H-pyrazolo[4,3-c]pyridin-5-yl)sulfonyl]methyl}cyclobutyl)-N-methyl-7H-pyrrolo[2,3-d]pyrimidin-4-amine;
N-(cis-3-{[(5-methoxy-1,3-dihydro-2H-isoindol-2-yl)sulfonyl]methyl}cyclobutyl)-N-methyl-7H-pyrrolo[2,3-d]pyrimidin-4-amine;
N-(cis-3-{[(4,4-difluoro-3,4-dihydroisoquinolin-2(1H)-yl)sulfonyl]methyl}cyclobutyl)-N-methyl-7H-pyrrolo[2,3-d]pyrimidin-4-amine;
N-{cis-3-[(3,4-dihydroisoquinolin-2(1H)-ylsulfonyl)methyl]cyclobutyl}-N-methyl-7H-pyrrolo[2,3-d]pyrimidin-4-amine;
N-{cis-3-[(3,4-dihydropyrrolo[1,2-a]pyrazin-2(1H)-ylsulfonyl)methyl]cyclobutyl}-N-methyl-7H-pyrrolo[2,3-d]pyrimidin-4-amine;
N-(cis-3-{[(3,3-difluorocyclobutyl)sulfonyl]methyl}cyclobutyl)-N-methyl-7H-pyrrolo[2,3-d]pyrimidin-4-amine;
N-[cis-3-({[6-methoxy-2-(trifluoromethyl)pyridin-3-yl]sulfonyl}methyl)cyclobutyl]-N-methyl-7H-pyrrolo[2,3-d]pyrimidin-4-amine;
N-methyl-N-{cis-3-[({[cis-4-(trifluoromethyl)cyclohexyl]methyl}sulfonyl)methyl]cyclobutyl}-7H-pyrrolo[2,3-d]pyrimidin-4-amine;
N-methyl-N-{cis-3-[({[trans-4-(trifluoromethyl)cyclohexyl]methyl}sulfonyl)methyl]cyclobutyl}-7H-pyrrolo[2,3-d]pyrimidin-4-amine;
4-[({cis-3-[methyl(7H-pyrrolo[2,3-d]pyrimidin-4-yl)amino]cyclobutyl}methyl)sulfonyl]butan-2-ol;
N-[cis-3-({[6-methoxy-4-(trifluoromethyl)pyridin-3-yl]sulfonyl}methyl)cyclobutyl]-N-methyl-7H-pyrrolo[2,3-d]pyrimidin-4-amine;
N-[cis-3-({[(4,4-difluorocyclohexyl)methyl]sulfonyl}methyl)cyclobutyl]-N-methyl-7H-pyrrolo[2,3-d]pyrimidin-4-amine;
N-methyl-N-[cis-3-({[4-(trifluoromethyl)pyridin-3-yl]sulfonyl}methyl)cyclobutyl]-7H-pyrrolo[2,3-d]pyrimidin-4-amine;
N-[cis-3-({[trans-4-(methoxymethyl)cyclohexyl]sulfonyl}methyl)cyclobutyl]-N-methyl-7H-pyrrolo[2,3-d]pyrimidin-4-amine;
N-(cis-3-{[(2-methoxy-5-methylpyridin-4-yl)sulfonyl]methyl}cyclobutyl)-N-methyl-7H-pyrrolo[2,3-d]pyrimidin-4-amine;
N-(cis-3-{[(2,3-dimethylpyridin-4-yl)sulfonyl]methyl}cyclobutyl)-N-methyl-7H-pyrrolo[2,3-d]pyrimidin-4-amine;
N-(cis-3-{[(5-methoxy-6-methylpyridin-3-yl)sulfonyl]methyl}cyclobutyl)-N-methyl-7H-pyrrolo[2,3-d]pyrimidin-4-amine;
N-(cis-3-{[(5-methoxy-2-methylpyridin-3-yl)sulfonyl]methyl}cyclobutyl)-N-methyl-7H-pyrrolo[2,3-d]pyrimidin-4-amine;
4-[({cis-3-[methyl(7H-pyrrolo[2,3-d]pyrimidin-4-yl)amino]cyclobutyl}methyl)sulfonyl]butan-1-ol;
N-methyl-N-[cis-3-({[(3S)-3-(methylsulfonyl)pyrrolidin-1-yl]sulfonyl}methyl)cyclobutyl]-7H-pyrrolo[2,3-d]pyrimidin-4-amine;
N-methyl-N-(cis-3-{[(4-methylpyridin-3-yl)sulfonyl]methyl}cyclobutyl)-7H-pyrrolo[2,3-d]pyrimidin-4-amine;
N-[cis-3-({[4-(difluoromethyl)piperidin-1-yl]sulfonyl}methyl)cyclobutyl]-N-methyl-7H-pyrrolo[2,3-d]pyrimidin-4-amine;
N-(cis-3-{[(2-methoxy-4-methylpyrimidin-5-yl)sulfonyl]methyl}cyclobutyl)-N-methyl-7H-pyrrolo[2,3-d]pyrimidin-4-amine;
N-(cis-3-{[(6-methoxy-4-methylpyridin-3-yl)sulfonyl]methyl}cyclobutyl)-N-methyl-7H-pyrrolo[2,3-d]pyrimidin-4-amine;
N-methyl-N-[cis-3-({[(2S)-2-methylbutyl]sulfonyl}methyl)cyclobutyl]-7H-pyrrolo[2,3-d]pyrimidin-4-amine;
N-methyl-N-[cis-3-({[(1-methylcyclobutyl)methyl]sulfonyl}methyl)cyclobutyl]-7H-pyrrolo[2,3-d]pyrimidin-4-amine;
N-(cis-3-{[(4,4-difluorobutyl)sulfonyl]methyl}cyclobutyl)-N-methyl-7H-pyrrolo[2,3-d]pyrimidin-4-amine;
N-methyl-N-[cis-3-({[(2R)-2-methylbutyl]sulfonyl}methyl)cyclobutyl]-7H-pyrrolo[2,3-d]pyrimidin-4-amine;
N-(cis-3-{[(1,1-dioxidothiomorpholin-4-yl)sulfonyl]methyl}cyclobutyl)-N-methyl-7H-pyrrolo[2,3-d]pyrimidin-4-amine;
N-(cis-3-{[(4,6-dimethylpyridin-3-yl)sulfonyl]methyl}cyclobutyl)-N-methyl-7H-pyrrolo[2,3-d]pyrimidin-4-amine;
1-methyl-5-[({cis-3-[methyl(7H-pyrrolo[2,3-d]pyrimidin-4-yl)amino]cyclobutyl}methyl)sulfonyl]pyridin-2(1H)-one;
N-methyl-N-(cis-3-{[(6-methylpyridin-3-yl)sulfonyl]methyl}cyclobutyl)-7H-pyrrolo[2,3-d]pyrimidin-4-amine;
1,6-dimethyl-5-[({cis-3-[methyl(7H-pyrrolo[2,3-d]pyrimidin-4-yl)amino]cyclobutyl}methyl)sulfonyl]pyridin-2(1H)-one;
1,4-dimethyl-5-[({cis-3-[methyl(7H-pyrrolo[2,3-d]pyrimidin-4-yl)amino]cyclobutyl}methyl)sulfonyl]pyridin-2(1H)-one;
1-methyl-4-[({cis-3-[methyl(7H-pyrrolo[2,3-d]pyrimidin-4-yl)amino]cyclobutyl}methyl)sulfonyl]piperazin-2-one;
N-methyl-N-[cis-3-({[4-(1,3-oxazol-5-yl)piperidin-1-yl]sulfonyl}methyl)cyclobutyl]-7H-pyrrolo[2,3-d]pyrimidin-4-amine;
N-methyl-N-[cis-3-({[4-(1,3-oxazol-2-yl)piperidin-1-yl]sulfonyl}methyl)cyclobutyl]-7H-pyrrolo[2,3-d]pyrimidin-4-amine;
N-methyl-N-[cis-3-({[4-(1-methyl-1H-pyrazol-3-yl)piperidin-1-yl]sulfonyl}methyl)cyclobutyl]-7H-pyrrolo[2,3-d]pyrimidin-4-amine;

N-(cis-3-{[(1-methoxy-6-azaspiro[2.5]oct-6-yl)sulfonyl]methyl}cyclobutyl)-N-methyl-7H-pyrrolo[2,3-d]pyrimidin-4-amine;

N-(cis-3-{[(4-fluorobutyl)sulfonyl]methyl}cyclobutyl)-N-methyl-7H-pyrrolo[2,3-d]pyrimidin-4-amine;

N-[cis-3-({[(3R)-3-(difluoromethoxy)pyrrolidin-1-yl]sulfonyl}methyl)cyclobutyl]-N-methyl-7H-pyrrolo[2,3-d]pyrimidin-4-amine;

N-{cis-3-[({4-[(1R)-1-methoxyethyl]piperidin-1-yl}sulfonyl)methyl]cyclobutyl}-N-methyl-7H-pyrrolo[2,3-d]pyrimidin-4-amine;

N-{cis-3-[({4-[(1S)-1-methoxyethyl]piperidin-1-yl}sulfonyl)methyl]cyclobutyl}-N-methyl-7H-pyrrolo[2,3-d]pyrimidin-4-amine;

N-{cis-3-[({4-[(difluoromethoxy)methyl]piperidin-1-yl}sulfonyl)methyl]cyclobutyl}-N-methyl-7H-pyrrolo[2,3-d]pyrimidin-4-amine;

N-[cis-3-({[4-(fluoromethyl)piperidin-1-yl]sulfonyl}methyl)cyclobutyl]-N-methyl-7H-pyrrolo[2,3-d]pyrimidin-4-amine;

N-[cis-3-({[4-(1-methoxyethyl)piperidin-1-yl]sulfonyl}methyl)cyclobutyl]-N-methyl-7H-pyrrolo[2,3-d]pyrimidin-4-amine;

N-(cis-3-{[(3,3-difluoropropyl)sulfonyl]methyl}cyclobutyl)-N-methyl-7H-pyrrolo[2,3-d]pyrimidin-4-amine;

N-(cis-3-{[(1,1-difluoro-6-azaspiro[2.5]oct-6-yl)sulfonyl]methyl}cyclobutyl)-N-methyl-7H-pyrrolo[2,3-d]pyrimidin-4-amine;

N-(cis-3-{[(3,3-difluorobutypsulfonyl]methyl}cyclobutyl)-N-methyl-7H-pyrrolo[2,3-d]pyrimidin-4-amine;

N-methyl-N-(cis-3-{[(2-methyl-1,3-thiazol-5-yl)sulfonyl]methyl}cyclobutyl)-7H-pyrrolo[2,3-d]pyrimidin-4-amine;

(3R,6S,9S,15S,20aS)-9-butyl-3-(cyclohexylmethyl)-6-(4-fluorobenzyl)-11-methyl-15-(3-phenylpropoxy)tetradecahydropyrrolo[1,2-a][1,4,7,10,13]pentaazacyclooctadecine-1,4,7,10,16(11H)-pentone;

N-methyl-N-(cis-3-{[(2-methyl-2H-indazol-5-yl)sulfonyl]methyl}cyclobutyl)-7H-pyrrolo[2,3-d]pyrimidin-4-amine;

N-(cis-3-{[(6-methoxypyridin-3-yl)sulfonyl]methyl}cyclobutyl)-N-methyl-7H-pyrrolo[2,3-d]pyrimidin-4-amine;

N-methyl-N-(cis-3-{[(1-methyl-1H-indazol-7-yl)sulfonyl]methyl}cyclobutyl)-7H-pyrrolo[2,3-d]pyrimidin-4-amine;

N-methyl-N-[cis-3-({[2-(trifluoromethoxy)phenyl]sulfonyl}methyl)cyclobutyl]-7H-pyrrolo[2,3-d]pyrimidin-4-amine;

N-(cis-3-{[(2-methoxypyridin-4-yl)sulfonyl]methyl}cyclobutyl)-N-methyl-7H-pyrrolo[2,3-d]pyrimidin-4-amine;

N-(cis-3-{[(2-ethoxypyridin-3-yl)sulfonyl]methyl}cyclobutyl)-N-methyl-7H-pyrrolo[2,3-d]pyrimidin-4-amine;

N-(cis-3-{[(5-fluoropyridin-3-yl)sulfonyl]methyl}cyclobutyl)-N-methyl-7H-pyrrolo[2,3-d]pyrimidin-4-amine;

N-(cis-3-{[(2-ethoxypyridin-4-yl)sulfonyl]methyl}cyclobutyl)-N-methyl-7H-pyrrolo[2,3-d]pyrimidin-4-amine;

N-methyl-N-[cis-3-({[4-(trifluoromethyl)phenyl]sulfonyl}methyl)cyclobutyl]-7H-pyrrolo[2,3-d]pyrimidin-4-amine;

N-(cis-3-{[(3-ethoxyphenyl)sulfonyl]methyl}cyclobutyl)-N-methyl-7H-pyrrolo[2,3-d]pyrimidin-4-amine;

N-(cis-3-{[(3-chloro-4-ethoxyphenyl)sulfonyl]methyl}cyclobutyl)-N-methyl-7H-pyrrolo[2,3-d]pyrimidin-4-amine;

N-methyl-N-[cis-3-({[6-(trifluoromethyl)pyridin-3-yl]sulfonyl}methyl)cyclobutyl]-7H-pyrrolo[2,3-d]pyrimidin-4-amine;

N-methyl-N-{cis-3-[(phenylsulfonyl)methyl]cyclobutyl}-7H-pyrrolo[2,3-d]pyrimidin-4-amine;

N-[cis-3-({[4-(1-methoxyethyl)phenyl]sulfonyl}methyl)cyclobutyl]-N-methyl-7H-pyrrolo[2,3-d]pyrimidin-4-amine;

N-(cis-3-{[(5-chloropyridin-2-yl)sulfonyl]methyl}cyclobutyl)-N-methyl-7H-pyrrolo[2,3-d]pyrimidin-4-amine;

N-methyl-N-(cis-3-{[(2-methylphenyl)sulfonyl]methyl}cyclobutyl)-7H-pyrrolo[2,3-d]pyrimidin-4-amine;

N-[cis-3-({[3-fluoro-4-(trifluoromethyl)phenyl]sulfonyl}methyl)cyclobutyl]-N-methyl-7H-pyrrolo[2,3-d]pyrimidin-4-amine;

N-{cis-3-[(isoquinolin-5-ylsulfonyl)methyl]cyclobutyl}-N-methyl-7H-pyrrolo[2,3-d]pyrimidin-4-amine;

N-methyl-N-[cis-3-({[3-(trifluoromethoxy)phenyl]sulfonyl}methyl)cyclobutyl]-7H-pyrrolo[2,3-d]pyrimidin-4-amine;

N-(cis-3-{[(6-methoxy-2-methylpyridin-3-yl)sulfonyl]methyl}cyclobutyl)-N-methyl-7H-pyrrolo[2,3-d]pyrimidin-4-amine;

N-methyl-N-[cis-3-({[3-(trifluoromethyl)phenyl]sulfonyl}methyl)cyclobutyl]-7H-pyrrolo[2,3-d]pyrimidin-4-amine;

N-(cis-3-{[(5-methoxypyridin-3-yl)sulfonyl]methyl}cyclobutyl)-N-methyl-7H-pyrrolo[2,3-d]pyrimidin-4-amine;

N-(cis-3-{[(5,6-dimethoxypyridin-3-yl)sulfonyl]methyl}cyclobutyl)-N-methyl-7H-pyrrolo[2,3-d]pyrimidin-4-amine;

N-(cis-3-{[(2-fluorophenyl)sulfonyl]methyl}cyclobutyl)-N-methyl-7H-pyrrolo[2,3-d]pyrimidin-4-amine;

N-methyl-N-{cis-3-[(quinolin-5-ylsulfonyl)methyl]cyclobutyl}-7H-pyrrolo[2,3-d]pyrimidin-4-amine;

N-(cis-3-{[(4-ethoxyphenyl)sulfonyl]methyl}cyclobutyl)-N-methyl-7H-pyrrolo[2,3-d]pyrimidin-4-amine;

N-(cis-3-{[(2-chloro-5-methoxyphenyl)sulfonyl]methyl}cyclobutyl)-N-methyl-7H-pyrrolo[2,3-d]pyrimidin-4-amine;

N-methyl-N-(cis-3-{[(1-methyl-1H-indazol-5-yl)sulfonyl]methyl}cyclobutyl)-7H-pyrrolo[2,3-d]pyrimidin-4-amine;

N-methyl-N-{cis-3-[(pyridin-4-ylsulfonyl)methyl]cyclobutyl}-7H-pyrrolo[2,3-d]pyrimidin-4-amine;

N-(cis-3-{[(4-methoxypyridin-3-yl)sulfonyl]methyl}cyclobutyl)-N-methyl-7H-pyrrolo[2,3-d]pyrimidin-4-amine;

N-(cis-3-{[(5-fluoro-2-methoxyphenyl)sulfonyl]methyl}cyclobutyl)-N-methyl-7H-pyrrolo[2,3-d]pyrimidin-4-amine;

N-methyl-N-{cis-3-[(quinolin-3-ylsulfonyl)methyl]cyclobutyl}-7H-pyrrolo[2,3-d]pyrimidin-4-amine;

N-methyl-N-[cis-3-({[2-(pyrrolidin-1-yl)pyrimidin-5-yl]sulfonyl}methyl)cyclobutyl]-7H-pyrrolo[2,3-d]pyrimidin-4-amine;

N-methyl-N-[cis-3-({[3-(propan-2-yloxy)phenyl]sulfonyl}methyl)cyclobutyl]-7H-pyrrolo[2,3-d]pyrimidin-4-amine;

N-[cis-3-({[2-chloro-5-(trifluoromethyl)phenyl]
sulfonyl}methyl)cyclobutyl]-N-methyl-7H-pyrrolo[2,3-
d]pyrimidin-4-amine;

N-(cis-3-{[(4-methoxyphenyl)sulfonyl]methyl}cyclobutyl)-
N-methyl-7H-pyrrolo[2,3-d]pyrimidin-4-amine;

N-methyl-N-(cis-3-{[(1,3,5-trimethyl-1H-pyrazol-4-yl)
sulfonyl]methyl}cyclobutyl)-7H-pyrrolo[2,3-d]pyrimi-
din-4-amine;

N-(cis-3-{[(3,5-dimethyl-1,2-oxazol-4-yl)sulfonyl]
methyl}cyclobutyl)-N-methyl-7H-pyrrolo[2,3-d]pyrimi-
din-4-amine;

N-(cis-3-{[(2-methoxypyrimidin-5-yl)sulfonyl]
methyl}cyclobutyl)-N-methyl-7H-pyrrolo[2,3-d]pyrimi-
din-4-amine;

N-methyl-N-(cis-3-{[(1-methyl-1H-indazol-6-yl)sulfonyl]
methyl}cyclobutyl)-7H-pyrrolo[2,3-d]pyrimidin-4-
amine;

N-(cis-3-{[(2-chlorophenyl)sulfonyl]methyl}cyclobutyl)-
N-methyl-7H-pyrrolo[2,3-d]pyrimidin-4-amine;

N-(cis-3-{[(6-ethoxypyridin-3-yl)sulfonyl]
methyl}cyclobutyl)-N-methyl-7H-pyrrolo[2,3-d]pyrimi-
din-4-amine;

N-(cis-3-{[(4-chloro-2-methoxyphenyl)sulfonyl]
methyl}cyclobutyl)-N-methyl-7H-pyrrolo[2,3-d]pyrimi-
din-4-amine;

N-methyl-N-{cis-3-[(pyridin-3-ylsulfonyl)methyl]cy-
clobutyl}-7H-pyrrolo[2,3-d]pyrimidin-4-amine;

N-(cis-3-{[(2,5-dimethylphenyl)sulfonyl]
methyl}cyclobutyl)-N-methyl-7H-pyrrolo[2,3-d]pyrimi-
din-4-amine;

N-{cis-3-[(furo[3,2-b]pyridin-6-ylsulfonyl)methyl]cy-
clobutyl}-N-methyl-7H-pyrrolo[2,3-d]pyrimidin-4-
amine;

N-(cis-3-{[(4-chloro-2-fluorophenyl)sulfonyl]
methyl}cyclobutyl)-N-methyl-7H-pyrrolo[2,3-d]pyrimi-
din-4-amine;

N-(cis-3-{[(2-fluoro-4-methoxyphenyl)sulfonyl]
methyl}cyclobutyl)-N-methyl-7H-pyrrolo[2,3-d]pyrimi-
din-4-amine;

N-methyl-N-{cis-3-[(quinolin-8-ylsulfonyl)methyl]cy-
clobutyl}-7H-pyrrolo[2,3-d]pyrimidin-4-amine;

N-[cis-3-({[3-(methoxymethyl)phenyl]sulfonyl}methyl)cy-
clobutyl]-N-methyl-7H-pyrrolo[2,3-d]pyrimidin-4-
amine;

N-(cis-3-{[(4-fluorophenyl)sulfonyl]methyl}cyclobutyl)-N-
methyl-7H-pyrrolo[2,3-d]pyrimidin-4-amine; and, N-(cis-3-{[(3-fluorophenyl)sulfonyl]methyl}cyclobutyl)-N-
methyl-7H-pyrrolo[2,3-d]pyrimidin-4-amine, or a phar-
maceutically acceptable salt thereof. The invention fur-
ther provides a method for treating a neurological
condition comprising administering an effective amount
of any of these compounds, or pharmaceutically accept-
able salt thereof, to a patient in need thereof. Said neu-
rological condition may be selected from the group con-
sisting of stroke, epilepsy, Parkinson's disease,
Alzheimer's disease, Frontotemporal lobe dementia, mul-
tiple sclerosis, and Pick's Disease.

Compounds that have the same molecular formula but differ in the nature or sequence of bonding of their atoms or the arrangement of their atoms in space are termed "isomers". Isomers that differ in the arrangement of their atoms in space are termed "stereoisomers". It will be appreciated by those skilled in the art that the compound of formula I can exist as cis- and trans-achiral diastereomers.

Included within the scope of the described compounds are all isomers (e.g. cis-, trans-, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds. Stereoisomeric mixtures, e.g., mixtures of diastereomers, can be separated into their corresponding isomers in a known manner by means of suitable separation methods. Diastereomeric mixtures for example may be separated into their individual diastereomers by means of fractionated crystallization, chromatography, solvent distribution and similar procedures. This separation may take place either at the level of one of the starting compounds or in a compound of formula I, IA, IB, IC, ID or IE itself. Enantiomers may be separated through the formation of diastereomeric salts, for example by salt formation with an enantiomer-pure chiral acid, or by means of chromatography, for example by HPLC, using chromatographic substrates with chiral ligands.

In therapeutic use for treating disorders in a mammal, a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Pharmaceutically acceptable salts of the compounds of formula I include the acid addition and base salts thereof. Suitable acid addition salts are formed from acids which form non-toxic salts. Examples include the acetate, adipate, aspartate, benzoate, besylate, bicarbonate/carbonate, bisulphate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of formula I, may be prepared, respectively, by one or more of three methods: (i) by reacting the compound of formula I, IA, IB, IC ID, or IE with the desired acid or base; (ii) by removing an acid- or base-labile protecting group from a suitable precursor of the compound of formula I or by ring-opening a suitable cyclic precursor, for example, a lactone or lactam, using the desired acid or base; or (iii) by converting one salt of the compound of formula I to another by reaction with an appropriate acid or base or by means of a suitable ion exchange column. All three reactions are typically carried out in solution. The resulting salt may precipitate out and be collected by filtration or may be recovered by evaporation of the solvent. The degree of ionization in the resulting salt may vary from completely ionized to almost non-ionized.

Pharmaceutical compositions of the present invention may be manufactured by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remington's Pharmaceutical Sciences" Mack Pub. Co., New Jersey (1991). The formulations of the invention can be designed to be short-acting, fast-releasing, long-acting, and sustained-releasing. Thus, the pharmaceutical formulations can also be formulated for controlled release or for slow release.

Pharmaceutical compositions suitable for use in the present invention include compositions wherein the active ingredients are contained in an amount sufficient to achieve the intended purpose, i.e., control or the treatment of disorders or diseases. More specifically, a therapeutically effective amount means an amount of compound effective to prevent, alleviate or ameliorate symptoms/signs of disease or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 to about 100 mg/kg of body weight/day, preferably about 0.1 to about 10 mg/kg of body weight/day, more preferably about 0.3 to 3 mg/kg of body weight/day, even more preferably about 0.3 to 1.5 mg/kg of body weight/day It is to be understood that the dosages may vary depending upon the requirements of each subject and the severity of the disorders or diseases being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Compounds of the present invention are directed to pyrrolo[2,3-d]pyrimidine compounds useful as Janus Kinase inhibitors (JAK-i). They are useful as therapeutic agents in connection with the treating or preventing a disorder or condition selected from rheumatoid arthritis, myositis, vasculitis, pemphigus, Crohn's disease, ulcerative colitis, Alzheimer's disease, lupus, nephritis, psoriasis, atopic dermatitis, autoimmune thyroid disorders, multiple sclerosis, major depression disorder, allergy, asthma, Sjogren's disease, dry eye syndrome, organ transplant rejection, xeno transplantation, Type I diabetes and complications from diabetes, cancer, leukemia, T cell acute lymphoblastic leukemia, adult T cell leukemia activated B-cell like, diffuse large B cell lymphoma, inflammatory bowel disease, septic shock, cardiopulmonary dysfunction, chronic pulmonary obstructive disorder, acute respiratory disease, cachexia, and other indications where immunosuppression/immunomodulation would be desirable, comprising the step of administering to a subject an effective amount of a compound of the invention.

There are substantial needs for safe and efficacious agents to control disorders related to JAK, such as atopic dermatitis, both in human and animals. The market for treating atopic dermatitis in animals is currently dominated by corticosteroids, which cause distressing and undesirable side effects in animals, specifically in companion animals such as dogs. Antihistamines are also used, but are poorly effective. A canine formulation of cyclosporine (ATOPICA™) is currently being marketed for atopic dermatitis, but is expensive and has a slow onset of efficacy. In addition, there are GI toleration issues with ATOPICA™. Compounds of the present invention are JAK inhibitors with selective efficacy against JAK1. These compounds are expected to provide an alternative to steroid usage and provide resolution of chronic pruritus and inflammation that would either persist in atopic dermatitis or slowly regress following removal of allergen or causative agent, such as fleas in flea-allergic dermatitis.

Compounds of the present invention may be administered in a pharmaceutically acceptable form either alone or in combination with one or more additional agents which modulate a mammalian immune system or with anti-inflammatory agents. These agents may include but are not limited to cyclosporin A (e.g., Sandimmune™ or Neoral™, rapamycin, FK-506 (tacrolimus), leflunomide, deoxyspergualin, mycophenolate (e.g., Cellcept™, azathioprine (e.g., Imuran™), daclizumab (e.g., Zenapax™), OKT3 (e.g., Orthocolone™), AtGam, aspirin, acetaminophen, ibuprofen, naproxen, piroxicam, and anti-inflammatory steroids (e.g., prednisolone or dexamethasone). These agents may be administered as part of the same or separate dosage forms, via the same or different routes of administration, and on the same or different administration schedules according to standard pharmaceutical practice known to one skilled in the art.

The present invention also provides any of the uses, methods or compositions as defined above wherein the compound of formula I, or pharmaceutically acceptable salt thereof, or pharmaceutically acceptable solvate of said compound or salt, is used in combination with another pharmacologically active compound, particularly one of the functionally-defined classes or specific compounds listed below. These agents may be administered as part of the same or separate dosage forms, via the same or different routes of administration, and on the same or different administration schedules according to standard pharmaceutical practice known to one skilled in the art.

Suitable agents for use in combination therapy with a compound of formula I, or pharmaceutically acceptable salt thereof, or pharmaceutically acceptable solvate of said compound or salt, particularly in the treatment of respiratory disease, include: a 5-lipoxygenase activating protein (FLAP) antagonist; a leukotriene antagonist (LTRA) such as an antagonist of $LTB_4$, $LTC_4$, $LTD_4$, $LTE_4$, $CysLT_1$ or $CysLT_2$, e.g., montelukast or zafirlukast; a histamine receptor antagonist, such as a histamine type 1 receptor antagonist or a histamine type 2 receptor antagonist, e.g., loratidine, fexofenadine, desloratidine, levocetirizine, methapyrilene or cetirizine; an α1-adrenoceptor agonist or an α2-adrenoceptor agonist, e.g., phenylephrine, methoxamine, oxymetazoline or methylnorephrine; a muscarinic M3 receptor antagonist, e.g., tiotropium or ipratropium; a dual muscarinic M3 receptor antagononist/β2 agonist; a PDE inhibitor, such as a PDE3 inhibitor, a PDE4 inhibitor or a PDE5 inhibitor, e.g., theophylline, sildenafil, vardenafil, tadalafil, ibudilast, cilomilast or roflumilast; sodium cromoglycate or sodium nedocromil; a cyclooxygenase (COX) inhibitor, such as a non-selective inhibitor (e.g., aspirin or ibuprofen) or a selective inhibitor (e.g., celecoxib or valdecoxib); a glucocorticosteroid, e.g., fluticasone, mometasone, dexamethasone, prednisolone, budesonide, ciclesonide or beclamethasone; an anti-inflammatory monoclonal antibody, e.g., infliximab, adalimumab, tanezumab, ranibizumab, bevacizumab or mepolizumab; a β2 agonist, e.g., salmeterol, albuterol, salbutamol, fenoterol or formoterol, particularly a long-acting β2 agonist; an intigrin antagonist, e.g., natalizumab; an adhesion molecule inhibitor, such as a VLA-4 antagonist; a kinin $B_1$ or $B_2$ receptor antagonist; an immunosuppressive agent, such as an inhibitor of the IgE pathway (e.g., omalizumab) or cyclosporine; a matrix metalloprotease (MMP) inhibitor, such as an inhibitor of MMP-9 or MMP-12; a tachykinin $NK_1$, $NK_2$ or $NK_3$ receptor antagonist; a protease inhibitor, such as an inhibitor of elastase, chymase or catheopsin G; an adenosine $A_{2a}$ receptor agonist; an adenosine $A_{2b}$ receptor antagonist; a urokinase inhibitor; a dopamine receptor agonist (e.g., ropinirole), particularly a dopamine D2 receptor agonist (e.g., bromocriptine); a modulator of the NFκB pathway, such as an IKK inhibitor; a further modulator of a cytokine signalling pathway such as an inhibitor of JAK kinase, syk kinase, p38 kinase, SPHK-1 kinase, Rho kinase, EGF-R or MK-2; a mucolytic, mucokinetic or anti-tussive agent; an antibiotic; an antiviral agent; a vaccine; a chemokine; an epithelial sodium channel (ENaC) blocker or Epithelial sodium channel (ENaC) inhibitor; a nucleotide receptor agonist, such as a P2Y2 agonist; a thromboxane inhibitor; niacin; a 5-lipoxygenase (5-LO) inhibitor, e.g., Zileuton; an adhesion factor, such as VLAM, ICAM or ELAM; a CRTH2 receptor ($DP_2$) antagonist; a prostaglandin $D_2$ receptor ($DP_1$) antagonist; a haematopoietic prostaglandin D2 synthase (HPGDS) inhibitor; interferon-G3; a soluble human TNF receptor, e.g., Etanercept; a HDAC inhibitor; a phosphoinositotide 3-kinase gamma (PI3Kγ) inhibitor; a phosphoinositide 3-kinase delta (PI3Kδ) inhibitor; a CXCR-1 or a CXCR-2 receptor antagonist; an IRAK-4 inhibitor; and, a TLR-4 or TLR-9 inhibitor, including the pharmaceutically acceptable salts of the specifically named compounds and the pharmaceutically acceptable solvates of said specifically named compounds and salts.

As noted above, the compounds of formula I are useful in the treatment of a number of neurological conditions. They can be used as mono-therapy to treat these conditions, or they can be combined with other pharmaceutically active agents that are routinely used for neurological conditions. Examples of such pharmaceutically agents include, without limitation:

(i) acetylcholinesterase inhibitors such as donepezil hydrochloride (ARICEPT, MEMAC); or Adenosine $A_{2A}$ receptor antagonists such as Preladenant (SCH 420814) or SCH 412348;

(ii) amyloid-β (or fragments thereof), such as $Aβ_{1-15}$ conjugated to pan HLA DR-binding epitope (PADRE) and ACC-001 (Elan/Wyeth);

(iii) antibodies to amyloid-R (or fragments thereof), such as bapineuzumab (also known as AAB-001) and AAB-002 (Wyeth/Elan);

(iv) amyloid-lowering or -inhibiting agents (including those that reduce amyloid production, accumulation and fibrillization) such as colostrinin and bisnorcymserine (also known as BNC);

(v) alpha-adrenergic receptor agonists such as clonidine (CATAPRES);

(vi) beta-adrenergic receptor blocking agents (beta blockers) such as carteolol;

(vii) anticholinergics such as amitriptyline (ELAVIL, ENDEP);

(viii) anticonvulsants such as carbamazepine (TEGRETOL, CARBATROL);

(ix) antipsychotics, such as lurasidone (also known as SM-13496; Dainippon Sumitomo);

(x) calcium channel blockers such as nilvadipine (ESCOR, NIVADIL);

(xi) catechol O-methyltransferase (COMT) inhibitors such as tolcapone (TASMAR);

(xii) central nervous system stimulants such as caffeine;

(xiii) corticosteroids such as prednisone (STERAPRED, DELTASONE);

(xiv) dopamine receptor agonists such as apomorphine (APOKYN);

(xv) dopamine receptor antagonists such as tetrabenazine (NITOMAN, XENAZINE, dopamine D2 antagonist such as Quetiapine);

(xvi) dopamine reuptake inhibitors such as nomifensine maleate (MERITAL);

(xvii) gamma-aminobutyric acid (GABA) receptor agonists such as baclofen (LIORESAL, KEMSTRO);

(xviii) histamine 3 ($H_3$) antagonists such as ciproxifan;

(xix) immunomodulators such as glatiramer acetate (also known as copolymer-1; COPAXONE);

(xx) immunosuppressants such as methotrexate (TREXALL, RHEUMATREX);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA));

(xxiii) N-methyl-D-aspartate (NMDA) receptor antagonists such as memantine (NAMENDA, AXURA, EBIXA);

(xxiv) monoamine oxidase (MAO) inhibitors such as selegiline (EMSAM);

(xxv) muscarinic receptor (particularly M1 subtype) agonists such as bethanechol chloride (DUVOID, URECHOLINE);

(xxvi) neuroprotective drugs such as 2,3,4,9-tetrahydro-1H-carbazol-3-one oxime;

(xxvii) nicotinic receptor agonists such as epibatidine;

(xxviii) norepinephrine (noradrenaline) reuptake inhibitors such as atomoxetine (STRATTERA);

(xxix) phosphodiesterase (PDE) inhibitors, for example, PDE9 inhibitors such as BAY 73-6691 (Bayer AG) and PDE 10 (e.g. PDE10A) inhibitors such as papaverine;
(xxx) other PDE inhibitors including (a) PDE1 inhibitors (e.g., vinpocetine), (b) PDE2 inhibitors (e.g., erythro-9-(2-hydroxy-3-nonyl)adenine (EHNA)), (c) PDE4 inhibitors (e.g., rolipram), and (d) PDE5 inhibitors (e.g., sildenafil (VIAGRA, REVATIO));
(xxxi) quinolines such as quinine (including its hydrochloride, dihydrochloride, sulfate, bisulfate and gluconate salts);
(xxxii) β-secretase inhibitors such as WY-25105;
(xxxiii) γ-secretase inhibitors such as LY-411575 (Lilly);
(xxxiv) serotonin (5-hydroxytryptamine) 1A (5-HT$_{1A}$) receptor antagonists such as spiperone;
(xxxv) serotonin (5-hydroxytryptamine) 4 (5-HT$_4$) receptor agonists such as PRX-03140 (Epix);
(xxxvi) serotonin (5-hydroxytryptamine) 6 (5-HT$_6$) receptor antagonists such as mianserin (TORVOL, BOLVI DON, NORVAL);
(xxxvii) serotonin (5-HT) reuptake inhibitors such as alaproclate, citalopram (CELEXA, CIPRAMIL);
(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline;
and the like.

Accordingly, the invention provides methods of treating or preventing a disease, condition or disorder associated with JAK in a subject, such as a human or non-human mammal, comprising administering an effective amount of one or more compounds described herein to the subject. Suitable subjects that can be treated include domestic or wild animals, companion animals, such as dogs, cats, horses and the like; livestock including, cows and other ruminants, pigs, poultry, rabbits and the like; primates, for example monkeys, such as rhesus monkeys and cynomolgus (also known as crab-eating or long-tailed) monkeys, marmosets, tamarins, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier.

Conditions in which selective targeting of the JAK pathway or modulation of the JAK kinases, particularly JAK1, are contemplated to be therapeutically useful include, arthritis, asthma, autoimmune diseases, cancers or tumors, diabetes, certain eye diseases, disorders or conditions, inflammation, intestinal inflammations, allergies or conditions, neurodegenerative diseases, psoriasis, and transplant rejection. Conditions which can benefit from selective inhibition of JAK1 are discussed in greater detail below.

Accordingly, the compound of formula I, IA, IB, IC, ID or IE, or its pharmaceutically acceptable salts, and pharmaceutical compositions thereof can be used to treat a variety of conditions or diseases such as the following:

Arthritis, including rheumatoid arthritis, juvenile arthritis, and psoriatic arthritis; Autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be O-cell (humoral) based or T-cell based, including Cogan's syndrome, ankylosing spondylitis, Wegener's granulomatosis, autoimmune alopecia, Type I or juvenile onset diabetes, or thyroiditis;

Cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, or angiogenic-associated disorders including solid tumors;

Diabetes, including Type I diabetes or complications from diabetes; Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, or ocular neovascularization;

Intestinal inflammations, allergies or conditions including Crohn's disease and/or ulcerative colitis, inflammatory bowel disease, celiac diseases, proctitis, eosinophilic gastroenteritis, or mastocytosis;

Neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, or platelet aggregation;

Skin diseases, conditions or disorders including atopic dermatitis, eczema, psoriasis, scleroderma, pruritus or other pruritic conditions;

Allergic reactions including allergic dermatitis in mammal (including horse allergic diseases such as bite hypersensitivity), summer eczema, sweet itch in horses, heaves, inflammatory airway disease, recurrent airway obstruction, airway hyper-responsiveness, or chronic obstruction pulmonary disease;

Asthma and other obstructive airways diseases, including chronic or inveterate asthma, late asthma, bronchitis, bronchial asthma, allergic asthma, intrinsic asthma, extrinsic asthma, or dust asthma;

Transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation; and Another embodiment provides a method of selectively inhibiting a JAK1 enzyme, which includes contacting the JAK enzyme with either a non-therapeutic amount or a therapeutically effective amount of one or more of the presently taught compounds. Such methods can occur in vivo or in vitro. In vitro contact can involve a screening assay to determine the efficacy of the one or more compounds against a selected enzyme at various amounts or concentrations. In vivo contact with a therapeutically effective amount of the one or more compounds can involve treatment of a described disease, disorder or condition or prophylaxis of organ transplant rejection in the animal in which the contact occurs. The effect of the one or more compounds on the JAK enzyme and/or host animal can also be determined or measured. Methods for determining JAK activity include those described in the Examples as well as those disclosed in WO99/65908, WO 99/65909, WO01/42246, WO02/00661, WO02/096909, WO2004/046112 and WO2007/012953.

Chemical Synthesis

The following schemes and written descriptions provide general details regarding the preparation of the compounds of the invention.

Compounds of formula I, wherein p is 2, X is NH, Y is $AR^5$, and A is a bond, may be prepared according to Scheme 1.

deprotected during the synthesis of a compound of the invention. Protection and deprotection may be achieved by conventional methods, as described, for example, in "Protective Groups in Organic Synthesis" by T. W. Greene and P. G. M. Wuts, John Wiley & Sons Inc. (1999), and references therein. Thus, in Scheme 1, Step 1, a compound of formula II, wherein $Q^1$ is halogen, is treated with a protecting agent to provide a compound of formula III, wherein $PG^1$ is an arylsulfonyl protecting group such as benzenesulfonyl, or preferably para-toluenesulfonyl ("tosyl"). The protecting group may be installed by reaction of the compound of formula II with an arylsulfonyl chloride, preferably tosyl chloride, in the presence of a base such as aqueous sodium hydroxide solution and an organic solvent such as acetone. The reaction is typically run at 0° C. to about 50° C., preferably at about 23° C. (room temperature). Alternatively, bases such as sodium hydride and potassium tert-butoxide may be used, employing a suitable solvent such as N,N-dimethylformamide or tetrahydrofuran. Several compounds of formula II are known in the literature and have been prepared by the methods above. For example, the synthesis of compound of formula II, wherein $Q^1$ is Cl and $R^2$ and $R^3$ are hydrogen has been reported previously, for example in WO 2007 012953.

In Scheme 1, Step 2, the protected compound of formula III is combined with 1-2 equivalents of an amine of formula Scheme 1

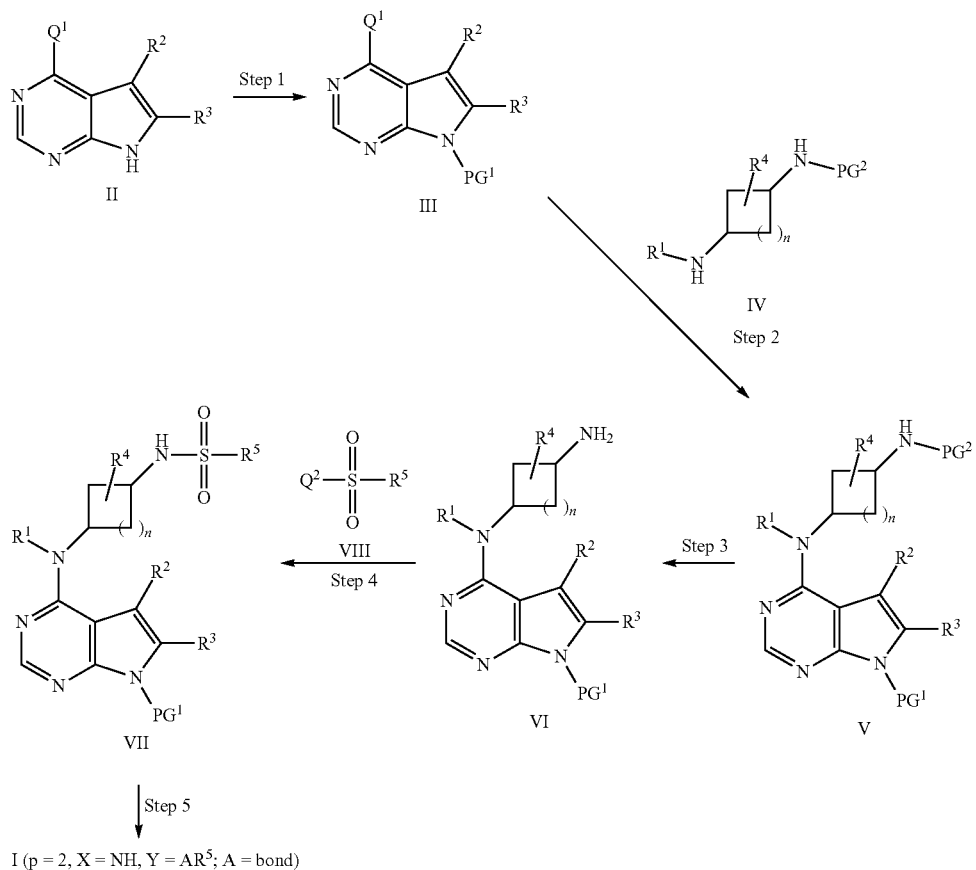

It will be apparent to those skilled in the art that sensitive functional groups (PG) may need to be protected and IV in the presence of a 1-3 equivalents of a base and a protic solvent to afford a compound of formula V. Suitable bases include triethylamine, diisopropylethylamine, and potassium carbonate while suitable solvents include methanol, ethanol, diisopropyl alcohol and water or mixtures thereof. The reaction is typically run at about 23° C. to about 150° C., preferably about 75° C. It will be noted that the amine of formula IV contains a second amino group that is protected with a protecting group PG$^2$ that can be removed under conditions that do not lead to loss of PG$^1$. Suitable protecting groups PG$^2$ include t-butoxycarbonyl ("Boc") and ("Cbz"), preferably benzyloxycarbonyl.

In Scheme 1, Step 3, the protecting group PG$^2$ is removed from the compound of formula V under conditions that do not lead to loss of PG$^1$ to give a primary amine (or a salt thereof) of formula VI. When PG$^2$ is benzyloxycarbonyl, the benzyloxycarbonyl protecting group may be removed by hydrogenolysis wherein the compound of formula V is exposed to hydrogen or a hydrogen transfer reagent such as cyclohexene in the presence of a hydrogenation catalyst such as palladium hydroxide using a solvent such as methanol, acetic acid or, preferably, ethanol. Alternatively, when PG$^2$ is benzyloxycarbonyl, the benzyloxycarbonyl protecting group may be removed by treatment of the compound of formula V with a solution of hydrogen bromide (about 6 equivalents) in acetic acid optionally in the presence of a suitable solvent such as ethyl acetate at a temperature from about minus 20° C. to about 40° C., preferably less than 25° C. This latter deprotection method is preferred wherein n is 1, R$^2$, R$^3$ and R$^4$ are hydrogen, R$^1$ is methyl, PG$^1$ is tosyl and PG$^2$ is benzyloxycarbonyl and provides the amine of formula VI as the dihydrobromide salt. When PG$^2$ is t-butoxycarbonyl, the t-butoxycarbonyl protecting group may be removed by treatment with an excess of an acid such as hydrochloric acid or trifluoroacetic acid in a solvent such as dichloromethane or 1,4-dioxane.

In Scheme 1, Step 4, the primary amine of formula VI (or salt thereof) is converted to a sulfonamide derivative of formula VII by treatment with an activated sulfonic acid derivative of formula VIII, wherein Q$^2$ is halogen, O-alkyl or O-aryl in the presence of a base. Most commonly, VIII is a sulfonyl chloride derivative wherein Q$^2$ is Cl. Many sulfonyl chlorides may be obtained from commercial sources. Also, several methods exist for the preparation of sulfonyl chlorides, which are well known to those skilled in the art and have been described in texts such as "Advanced Organic Chemistry" by J. March, John Wiley & Sons (1985). Typically, the amine of formula VI is treated with a sulfonyl chloride derivative of formula VIII wherein Q$^2$ is Cl in the presence of at least one equivalent of a base such as triethylamine or diisopropylamine in a suitable solvent such as dichloromethane, tetrahydrofuran or acetonitrile. When a salt form of the amine is used, an additional equivalent of base is used for each equivalent of acid forming the salt. For example, using a dihydrobromide salt, two extra equivalents of base are used. The reaction may be run from about minus 20° C. to about 50° C., preferably starting the reaction at about 0° C. and then allowing it to warm to about 23° C. (room temperature).

Finally, in Scheme 1, Step 5, the sulfonamide derivative of formula VII is deprotected to afford a compound of formula 1, wherein p is 2, X is NH, Y is AR$^5$ and A is a bond. Two methods are typically employed, the choice of which is determined by the compatibility of the conditions with other functional groups on the molecule. The first method involves exposure of the compound of formula VII to an excess (about 4 equivalents) of a base such as lithium hydroxide or sodium hydroxide. The reaction is run in a solvent mixture containing water and an alcohol such as methanol or ethanol. It may also be run in a mixture of water and tetrahydrofuran, and, optionally an alcohol such as methanol or ethanol. The reaction may be run at a temperature of about 23° C. to about 100° C., typically about 60° C. The second method, which is preferred in instances where there is hydroxide-sensitive functionality such as nitrile present in the molecule, involves reaction of the compound of formula VII with an excess of tetrabutylammonium fluoride (4-25 equivalents) in a solvent such as 1,2-dimethoxyethane or, preferably tetrahydrofuran, The deprotection is conducted at a temperature of about 0° C. to about 60° C., preferably about 23° C.

Compounds of formula II, wherein Q$^1$ is halogen, are commercially available or are known in the chemical literature. For example, 4-chloro-7H-pyrrolo[2,3-d]pyrimidine, wherein Q$^1$ is Cl and R$^2$ and R$^3$ are both hydrogen, is a readily available commercial compound.

Compounds of formula IV are known in the chemical literature or may be prepared by standard chemical reactions well known to one skilled in the art.

An alternative method of preparing compounds of the invention wherein p is 2, X is NH, Y is AR$^5$, A is a bond is shown in Scheme 2.

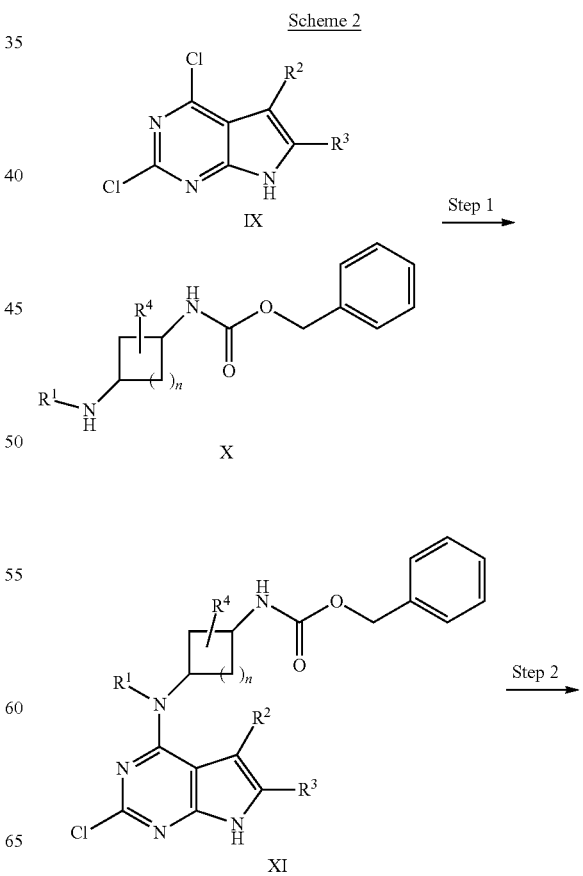

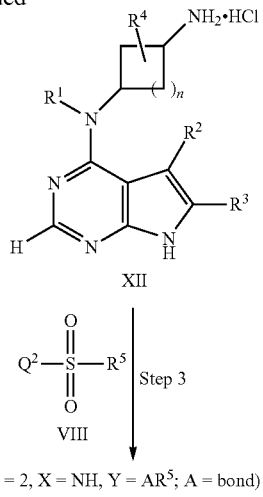

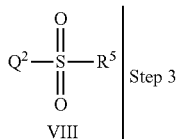

I (p = 2, X = NH, Y = AR⁵; A = bond)

In Scheme 2, Step 1, a compound of formula IX is combined with a benzyloxycarbamate derivative of formula X in the presence of a base (1-5 equivalents) to provide a benzyloxycarbamate derivative of formula XI. The reaction is carried out in a solvent such as water or an alcohol such as ethanol, optionally with addition of a miscible co-solvent such as tetrahydrofuran. Suitable bases include potassium carbonate, cesium carbonate, triethylamine and diisopropylethylamine. The reaction is run at about 23° C. to about 100° C. When n is 1, $R^2$, $R^3$ and $R^4$ are hydrogen, and $R^1$ is methyl, the preferred conditions are to run the reaction in water, using potassium carbonate (3 equivalents) as base, starting the reaction at about 23° C. and then heating to about 95° C.

In Scheme 2, Step 2, the benzyloxycarbamate derivative of formula XI is deprotected by exposure to hydrogen or a hydrogen transfer reagent such as cyclohexene in the presence of a hydrogenation catalyst such as palladium hydroxide. At the same time, under the conditions of the deprotection, the chlorine atom at the 2-position of 7H-pyrrolo[2,3-d]pyrimidine ring is replaced with hydrogen to provide an amine hydrochloride salt of formula XII. The reaction is run in a solvent such as methanol or ethanol at a temperature of about 50° C. to about 80° C. When $R^2$, $R^3$ and $R^4$ are hydrogen, and $R^1$ is methyl, the preferred conditions are to run the reaction in ethanol at about 78° C. using palladium hydroxide as catalyst, and cyclohexene (about 20 equivalents) as a hydrogen transfer reagent.

Finally, in Scheme 2, Step 3, the amine hydrochloride of formula XII is converted to a sulfonamide of formula I, wherein p is 2, X is NH, Y is AR⁵, A is a bond by reaction with an activated sulfonic acid derivative of formula VIII, wherein $Q^2$ is halogen, O-alkyl or O-aryl in the presence of at least two equivalents of a base. Most commonly, VIII is a sulfonyl chloride derivative wherein $Q^2$ is Cl. Suitable bases include triethylamine, diisopropylethylamine and potassium carbonate. Suitable solvents include N,N-dimethylformamide, and a mixture of tetrahydrofuran and water. The reaction may be run at a temperature of about minus 20° C. to about 50° C. preferably at about 23° C. Alternatively, the amine hydrochloride of formula XII is first treated with about 2 equivalents of trimethylchlorosilane in the presence of about 2-3 equivalents of a base such as lithium bis(dimethylsilyl)amide or sodium bis(dimethylsilyl)amide in an suitable aprotic solvent such as tetrahydrofuran. Then, after about 1 hour, about 1.2 equivalents of the sulfonyl chloride of formula VIII, $Q^2$ is Cl is added to provide, after workup, the sulfonamide of formula I, wherein p is 2, X is NH, Y is AR⁵, A is a bond The reaction may be run at a temperature of about minus 20° C. to about 50° C., preferably at about 23° C.

Compounds of formula IX, are commercially available or are known in the chemical literature. For example, 2,4-dichloro-7H-pyrrolo[2,3-d]pyrimidine, wherein $R^2$ and $R^3$ are both hydrogen, is commercially available. Its synthesis is described in PCT International Publication No. WO2007/012953.

Compounds of formula I, wherein p is 2, X is NH, and Y is $NR_aR_b$, may be prepared according to Scheme 3.

Scheme 3

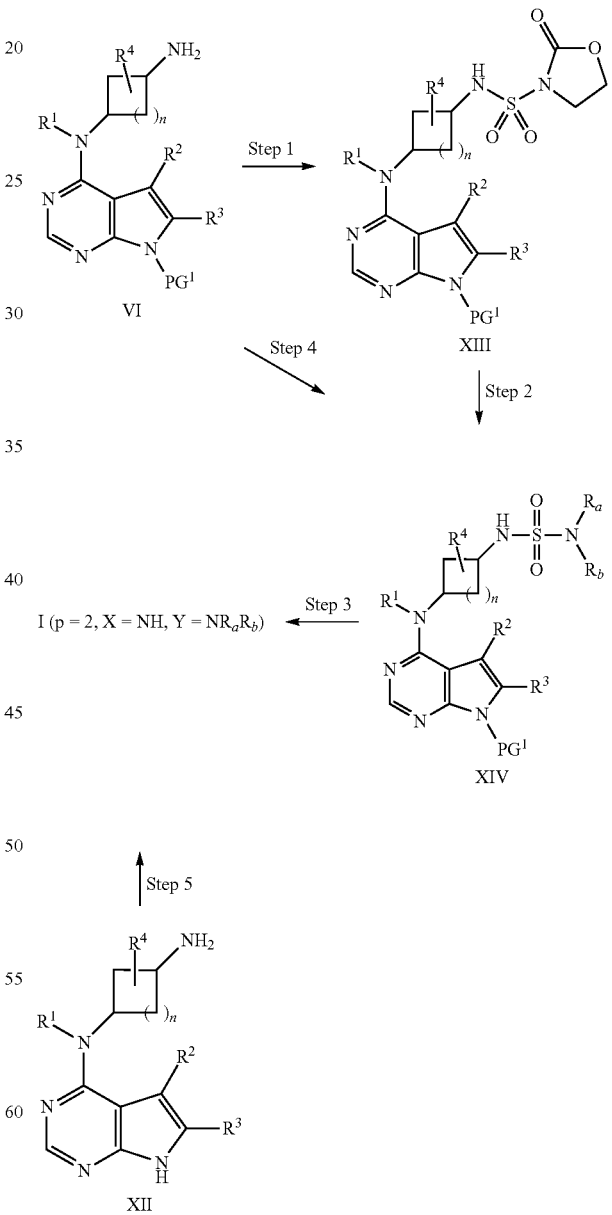

In Scheme 3, Step 1, an amine of formula VI (or salt thereof), wherein PG¹ is an arylsulfonyl protecting group such benzenesulfonyl, or preferably tosyl, is converted to oxazolidinone derivative of formula XIII. First, a solution of N-chlorosulfonylisocyanate (1 equivalent) is slowly added to a solution of 2-bromoethanol (1 equivalent) at a temperature of about −40° C. to about 10° C., preferably about 0° C. Subsequently, after 0.5 to 2 hours, a solution of the amine of formula VI (1 equivalent) and a base such as triethylamine or diisopropylethylamine (about 3 equivalents, plus one equivalent for each mole of acid forming a salt) is added slowly and the reaction is allowed to warm to about 23° C. over a period of about 10 to 24 hours. Suitable solvents for the reaction include chloroform or preferably dichloromethane.

In Scheme 3, Step 2, the oxazolidinone derivative of formula XIII is reacted with 1-3 equivalents of an amine of the formula $HNR_aR_b$, in the presence of a base (2-5 equivalents), to afford a sulfamide derivative of formula XIV. Suitable bases include triethylamine and diisopropylethylamine. The reaction is preferably carried out by heating to about 90° C. to about 150° C. in a pressure vessel using a suitable solvent such a N,N-dimethylformamide or acetonitrile.

In Scheme 3, Step 3, the compound of formula XIV is deprotected, removing the arylsulfonyl protecting group $PG^1$ to provide a sulfamide derivative of formula 1, wherein p is 2, X is NH, and Y is $NR_aR_b$. The reaction may be carried out by one of the two general methods described for Scheme 1, Step 5. Again, the choice of deprotection method is determined by the compatibility of the conditions with other functional groups on the molecule. Alternatively, the sulfamides of the formula XIV may be obtained directly from an amine of formula VI (or salt thereof). Thus, in Scheme 3, Step 4, the amine of formula VI (or salt thereof) is treated with a sulfamoyl chloride of the formula $Cl-SO_2NR_aR_b$ and a base such as triethylamine or diisopropylethylamine as described for Scheme 1, Step 4. Sulfamoyl chlorides of the formula $Cl-SO_2NR_aR_b$ may be prepared, in turn, from amines of the formula $HNR_aR_b$ according to the procedures reviewed by W. R. Bowman and R. J. Marmon in "Comprehensive Organic Functional Group Transformations, Volume 2", Pergamon (1995).

The compounds of formula I, wherein p is 2, X is NH, and Y is $NR_aR_b$ may also be obtained directly from an amine of formula XII (or salt thereof). Thus, in Scheme 3, Step 5, the amine of formula XII (or salt thereof) is treated with a sulfamoyl chloride of the formula $Cl-SO_2NR_aR_b$ and a base such as triethylamine or diisopropylethylamine as described for Scheme 1, Step 4. Amines of formula XII are obtained as described for Scheme 2. Amines of formula XII (or salts thereof) may be obtained by the removal of the arylsulfonyl protecting group $PG^1$ from a compound of the formula VI (refer to Scheme 1). The deprotection may be carried out by one of the two general deprotection methods described for Scheme 1, Step 5. The choice of deprotection method is determined by the compatibility of the conditions with other functional groups on the molecule.

Compounds of formula I, wherein p is 2, X is $CH_2$, and Y is $NR_aR_b$, may be prepared according to Scheme 4, Scheme 4a, and Scheme 4b.

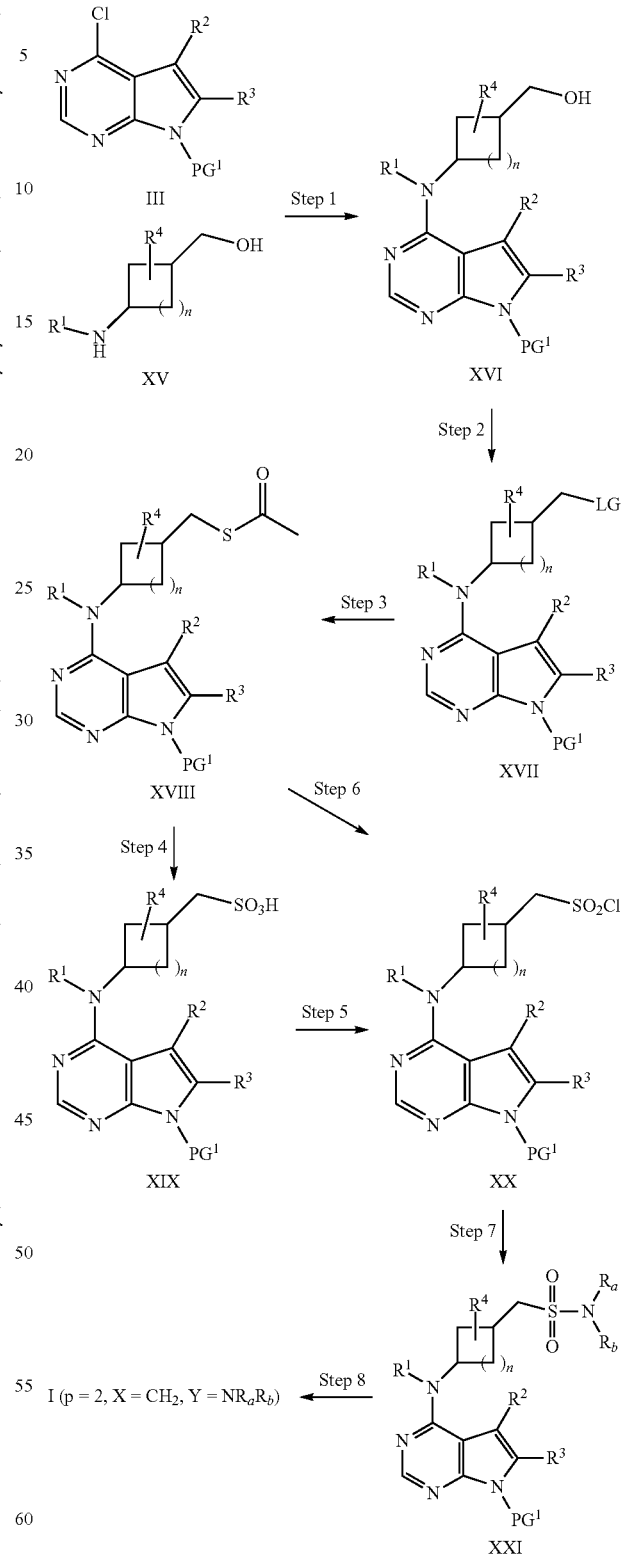

Scheme 4

In Scheme 4, Step 1, a compound of formula III (refer to Scheme 1), is combined with an amino alcohol of formula XV in the presence of a base and a polar solvent to afford a compound of formula XVI. Suitable bases include triethylamine and diisopropylethylamine while suitable solvents include methanol, diisopropyl alcohol and acetone. The reaction is typically run at about 23° C. to about 70° C. Preferably, a catalytic amount (about 1 mole %) of potassium iodide is added to the reaction.

In Scheme 4, Step 2, the compound of formula XVI is converted to a compound of formula XVII, wherein LG is a leaving group such as bromo, iodo, methanesulfonate or, preferably, para-toluenesulfonate. Methods for installing such leaving groups are well-known to those skilled in the art and have been described in texts such as "Advanced Organic Chemistry" by J. March, John Wiley & Sons (1985). In the case where LG is para-toluenesulfonate, the compound of formula XVI is treated with para-toluenesulfonyl chloride in the presence of a base such as triethylamine, diisopropylethylamine or N,N-dimethylaminopyridine in an aprotic solvent such as dichloromethane or tetrahydrofuran. The reaction is run at a temperature of about −10° C. to about 40° C., preferably beginning at around 0° C. and allowing the reaction to warm to about 23° C.

In Scheme 4, Step 3, the compound of formula XVII is combined with a salt of thioacetic acid, preferably potassium thioacetate to yield a thioester derivative of formula XVIII. The reaction is carried out in a polar solvent such as N,N-dimethylformamide or N-methylpyrrolidine, at a temperature of about 23° C. to about 80° C., preferably at about 55° C.

In Scheme 4, Step 4, the thioester derivative of formula XVIII is converted to a sulfonic acid derivative of formula XIX by reaction with an aqueous solution of hydrogen peroxide, typically 30% by weight. The reaction is carried out in an acidic solvent such as formic or acetic acid at a temperature from about 0° C. to about 40° C., preferably at about 23° C.

In Scheme 4, Step 5, the sulfonic acid derivative of formula XIX is converted to a sulfonyl chloride derivative of formula XX. Several methods for carrying out this functional group transformation are known in the literature. The preferred method is to treat the compound of formula XIX with an excess (3-15 equivalents) of thionyl chloride in the presence of a catalytic amount of N,N-dimethylformamide in an aprotic solvent such as dichloromethane or chloroform. The reaction may be run from about minus 20° C. to about 100° C., preferably beginning the reaction at about 0° C., and then warming to about 75° C.

Alternatively, in Scheme 4, Step 6, the thioester derivative of formula XVIII may be directly converted to the sulfonyl chloride derivative of formula XX by treatment with a chlorinating agent. Several methods for carrying out this functional group transformation are known in the literature. Chlorinating agents include chlorine gas and N-chlorosuccinimide, and the reaction is commonly run in the presence of an acid such as hydrochloric acid or acetic acid. Mixed aqueous solvents systems are often used, such as water and dichloromethane and water and acetonitrile.

In Scheme 4, Step 7, the sulfonyl chloride derivative of formula XX is combined with 1-3 equivalents of an amine of the formula $HNR_aR_b$ to form a sulfonamide derivative of formula XXI. The reaction is run in the presence of at least one equivalent of a base such as triethylamine or diiosopropylethylamine at a temperature from about minus 20° C. to about 50° C., preferably starting the reaction at about 0° C. and allowing the reaction to warm to about 23° C. The reaction is run in an aprotic solvent such as tetrahydrofuran or dichloromethane.

Finally in Scheme 4, Step 8, the arylsulfonyl protecting group $PG^1$ is removed to provide a compound of the formula I, wherein p is 2, X is $CH_2$, and Y is $NR_aR_b$. The reaction may be carried out by one of the two general deprotection methods described for Scheme 1, Step 5. The choice of deprotection method is determined by the compatibility of the conditions with other functional groups on the molecule. Amino alcohols of formula XV are known in the chemical literature or may be prepared by methods well known to one skilled in the art.

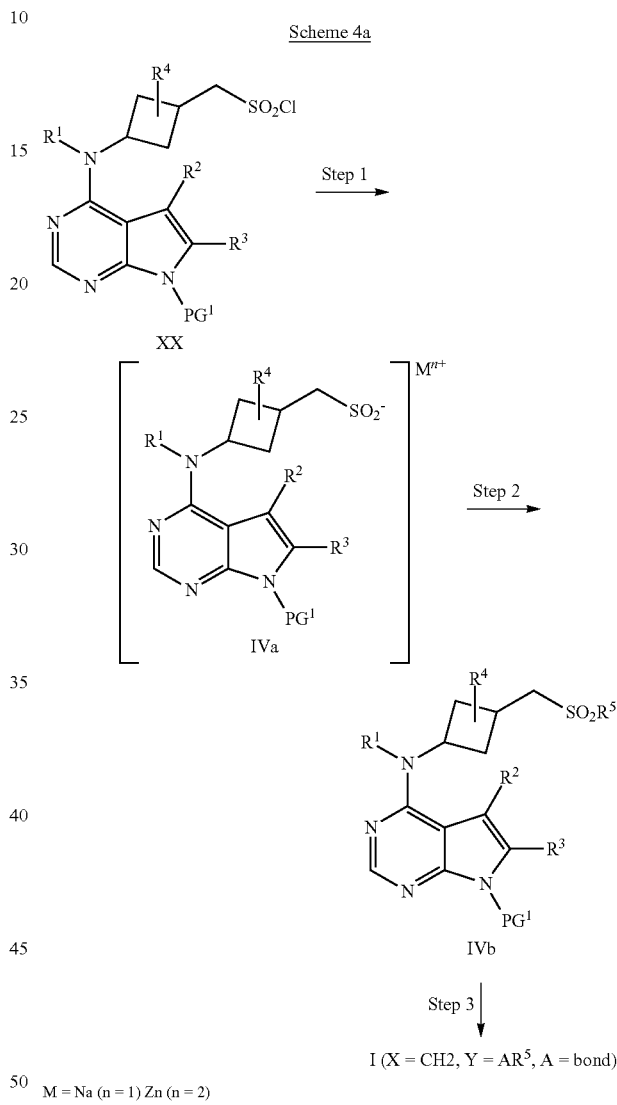

In Scheme 4a, Step 1, the compound of formula XX is reacted with 1-2 equivalents of zinc dust to give zinc sulfinate intermediate Iva (M=Zn). The reaction is carried out in a suitable solvent such as ethanol at a temperature from about 30° C. to reflux, preferably 70° C. Alternately the compound of formula XX is reacted with 2 or more equivalents of sodium bisulfite to give the sodium sulfinate intermediate IVa (M=Na). The reaction is conducted in the presence of 1-2 equivalents of a suitable base, such as sodium bicarbonate, using water as a solvent, or a mixture of water and a solvent such as acetone or dioxane, at a temperature from about 10° C. to about 60° C., preferably about 25° C.

In Scheme 4a, Step 2, sulfinates of formula IVa are treated with 2 equivalents of an alkyl halide to give a sulfone of formula IVb. Suitable halides include chloro, bromo and iodo derivatives and the reaction is carried out in a solvent such as DMSO at a temperature from about 20° C. to 110° C., depending on the halide. Alternatively, intermediate IVa can be treated with 2-5 eq. of a suitably substituted aryl or heteroaryl derivative. Examples of such derivatives include iodo, boronate ester, boronic acids, and $BF_3K$ salts. The reaction is carried out in the presence of a copper source such as copper (I) triflate or copper (II) acetate with or without a suitable diamine such as N, $N^1$ dimethylethylene diamine in the presence of a suitable base, including potassium carbonate or triethylamine. The reaction is conducted in a solvent such as dimethyl sulfoxide alone, or as a mixture with dioxane, at a temperature from about 25° C. to 75° C., preferably 60° C.

Compounds of formula I, wherein p is 0, X is $CH_2$, Y is $AR^5$ and A is a bond are prepared in Scheme 4a Step 3, by removing the arylsulfonyl protecting group $PG^1$ from a compound of formula XXV. The reaction may be carried out by one of the two general deprotection methods described from Scheme 1, Step 5. The choice of deprotection method is determined by the compatibility of the conditions with other functional groups on the molecule.

Scheme 4b

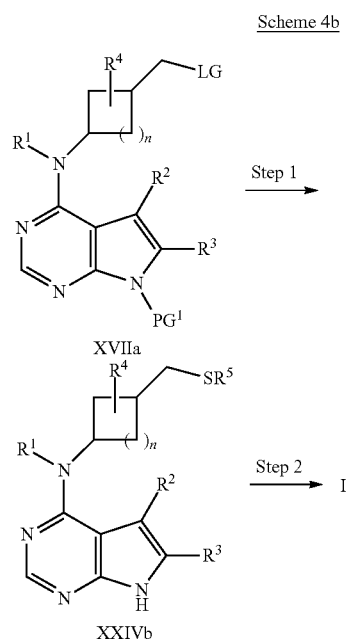

As shown above in Scheme 4b, Step 1, the order of reaction in Scheme 4 can be modified. Starting with the product of Step 2, compounds off formula XVIIa where LG can be a suitable leaving group, such as a tosylate, can be reacted with a suitably substituted thioacetate derivative in the presence of a base, such as $K_2CO_3$, and a polar solvent, such as MeOH, with heating, typically 60-65° C. to provide thioethers of formula XXIVb.

In Scheme 4b, Step 2, a sulfide of formula XXIVa is oxidized to yield a sulfone of formula I, wherein p is 2, X is $CH_2$, Y is $AR^5$ and A is a bond. Several methods are known in the literature and all involve the use of an oxidant such as meta-chloroperbenzoic acid, hydrogen peroxide, or potassium peroxymonosulfate (Oxone®). A preferred method is to treat the compound of formula XXIV with 2 equivalents of potassium peroxymonosulfate (Oxone®) in a solvent mixture of tetrahydrofuran, ethanol and water at a temperature of about 23° C. The sulfide of formula XXIVb may also be oxidized under milder conditions, for example using 1 equivalent of meta-chlorobenzoic acid in a solvent such as dichloromethane at about 0° C. to produce a sulfoxide of formula I, wherein p is 1, X is $CH_2$, Y is $AR^5$ and A is a bond.

It is noted that in some cases, the sulfide XXIVb may optionally retain $PG^1$ after Step 1 and will require a deprotection step to provide compounds of Formula I. The reaction may be carried out by one of the two general deprotection methods described from Scheme 1, Step 5. The choice of deprotection method is determined by the compatibility of the conditions with other functional groups on the molecule.

Compounds of formula I, wherein p is 0, 1, or 2, X is $CH_2$, Y is $AR^5$ and A is a bond, may be prepared according to Scheme 5.

Scheme 5

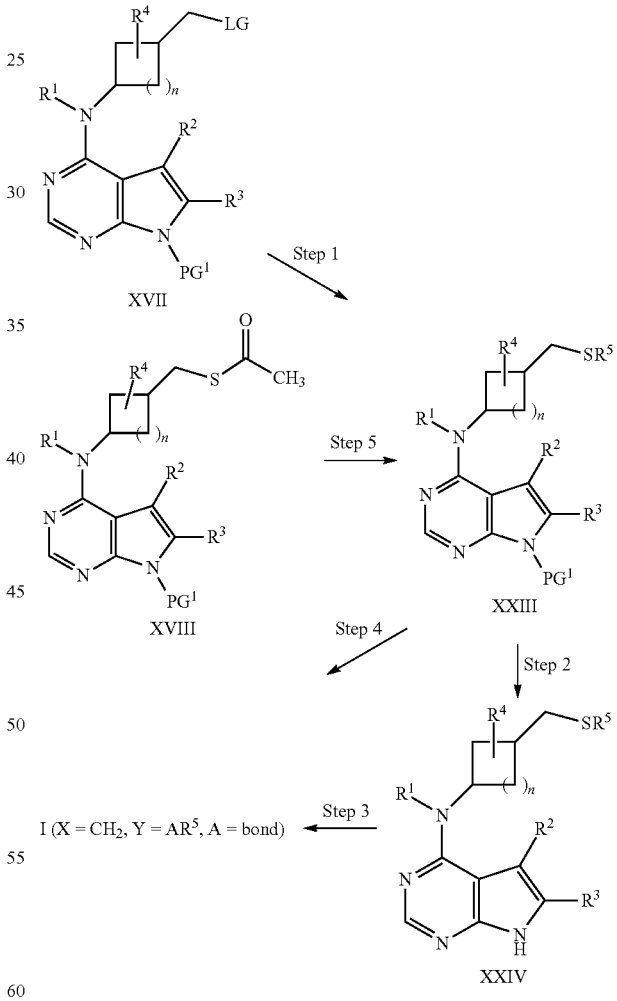

In Scheme 5, Step 1, a compound of formula XVII (refer to Scheme 4) is treated with 1-2 equivalents of a thiol of the formula $R^5SH$ in the presence of 1-2 equivalents of a base to give a sulfide of the formula XXIII. Suitable bases include sodium hydride, sodium bis(trimethylsilyl)amide, 1,5-diazabicyclo[4.3.0]non-5-ene (DBN) and preferably, 1,8-diazabicyclo[5.4.0]undec-7-ene (DBU). The reaction is carried out in a solvent such as N,N-dimethylformamide or N-methylpyrrolidinone at a temperature from about 0° C. to about 50° C., preferably at about 23° C.

In Scheme 5, Step 2, the compound of formula XXIII is deprotected, removing the arylsulfonyl protecting group $PG^1$ to provide a compound of formula XXIV. The reaction may be carried out by one of the two general deprotection methods described for Scheme 1, Step 5. The choice of deprotection method is determined by the compatibility of the conditions with other functional groups on the molecule.

In Scheme 5, Step 3, a sulfide of formula XXIV is oxidized to yield a sulfone of formula I, wherein p is 2, X is $CH_2$, Y is $AR^5$ and A is a bond. Several methods are known in the literature and all involve the use of an oxidant such as meta-chloroperbenzoic acid, hydrogen peroxide, or potassium peroxymonosulfate (Oxone®). A preferred method is to treat the compound of formula XXIV with 2 equivalents of potassium peroxymonosulfate (Oxone®) in a solvent mixture of tetrahydrofuran, ethanol and water at a temperature of about 23° C. The sulfide of formula XXIV may also be oxidized under milder conditions, for example using 1 equivalent of meta-chlorobenzoic acid in a solvent such as dichloromethane at about 0° C. to produce a sulfoxide of formula I, wherein p is 1, X is $CH_2$, Y is $AR^5$ and A is a bond It is noted that the order of Steps 2 and 3 in Scheme 5, may optionally be reversed such that the oxidation step is carried out prior to the deprotection step.

Compounds of the formula I, wherein p is 0, X is $CH_2$, Y is $AR^5$ and A is a bond are prepared in Scheme 5, Step 4 by removing the arylsulfonyl protecting group $PG^1$ from a compound of formula XXIII. The reaction may be carried out by one of the two general deprotection methods described for Scheme 1, Step 5. Again, the choice of deprotection method is determined by the compatibility of the conditions with other functional groups on the molecule.

In Scheme 5, Step 5, compounds of the formula XXIII are alternatively prepared from a thioacetate derivative of formula XVIII. First, the thioacetate of formula XVIII is dissolved in a solvent such as ethanol, methanol, or water (or a mixture thereof). A suitable base such as potassium carbonate or cesium carbonate (about 2 equivalents) is added and nitrogen is bubbled through the solution to remove oxygen. An alkylating agent of the formula $R^5$-LG is then added, wherein LG is a leaving group such as bromo, iodo, methanesulfonate or, para-toluene-sulfonate. The reaction is conducted at a temperature from about minus 20° C. to about 30° C. Preferably, the reaction is started at about 0° C. and then allowed to warm to about 23° C.

Many thiols of the formula $R^5SH$ and alkylating agents of the formula $R^5$-LG may be obtained from commercial sources. Also, several methods exist for the preparation of such compounds, which are well known to those skilled in the art and have been described in texts such as "Advanced Organic Chemistry" by J. March, John Wiley & Sons (1985).

It is noted that certain compounds of the invention can be obtained by functional group transformations at a late stage of the synthesis, for example, by chemical modification of the groups $R^4$ or $R^5$ after carrying out Steps 4 or 5 in Scheme 1, Step 3 in Scheme 2, Steps 2, 3 or 4 in Scheme 3, Steps 7 or 8 Scheme 4 and Steps 2, 3, 4 or 5 in Scheme 5. Such functional group transformations may include one step or multiple steps, for example, reduction of an ester to an alcohol, reoxidation to an aldehyde, addition of an organomagnesium reagent to form a secondary alcohol, reoxidation to a ketone and, finally, addition of an organomagesium reagent to yield a tertiary alcohol.

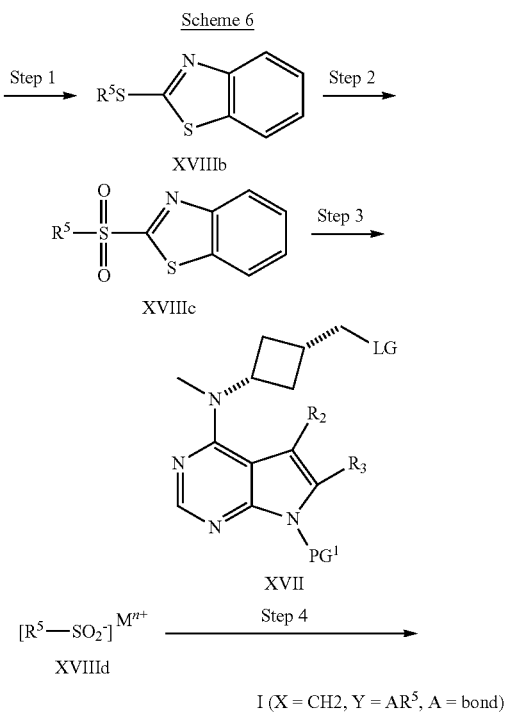

Scheme 6

In Scheme 6, Step 1, the compounds of formula XVIIIa, where $R^5$ can be alkyl, cycloalkyl, or heterocycloalkyl, are reacted with 1 equivalent of 2,2'-dibenzothiazolyl disulfide in the presence of 1-2 equivalents of an activating reagent such as triphenylphosphine. The reaction is carried out in a suitable solvent such as THF at 0° C. to 60° C., preferably at room temperature.

In Scheme 6, Step 2, thioethers of formula XVIIIb are reacted with 2-3 equivalents of an oxidizing agent, such as m-chloroperbenzoic acid. The reaction is carried out in a suitable solvent such as dichloromethane at room temperature.

In Scheme 6, Step 3, compounds of formula XVIIIc are reacted with 1-2 equivalents of a suitable base such as sodium methoxide or a reducing agent, such as sodium borohydride. The reaction is carried out in a suitable solvent such as MeOH preferably at room temperature.

In Scheme 6, Step 4, 1-2 equivalents of crude sulfinates of the formula XVIIId are reacted with an alkyl halide, such as XVII, in the presence of 2-3 equivalents of a base such as potassium carbonate. Suitable halides include chloro, bromo, and iodo derivatives and the reaction is carried out in a solvent such as DMSO at a temperature from 10° C. to 100° C., preferably 50° C. For alkyl halides such as XVII protecting groups, for example tosylates, can be subsequently removed in situ after completion of the sulfonylation reaction to provide the final compounds.

In executing the synthesis of the compounds of the invention, one skilled in the art will recognize the need to sample and assay reaction mixtures prior to work up in order to monitor the progress of reactions and decide whether the reaction should be continued or whether it is ready to be worked up to obtain the desired product. Common methods for assaying reaction mixtures include thin-layer chromatography (TLC), liquid chromatography/mass spectroscopy (LCMS), and nuclear magnetic resonance (NMR).

One skilled in the art will also recognize that the compounds of the invention may be prepared as mixtures of diastereomers or geometric isomers (e.g., cis and trans substitution on a cycloalkane ring). These isomers can be separated by standard chromatographic techniques, such as normal phase chromatography on silica gel, reverse phase preparative high pressure liquid chromatography or supercritical fluid chromatography. One skilled in the art will also recognize that some compounds of the invention are chiral and thus may be prepared as racemic or scalemic mixtures of enantiomers. Several methods are available and are well known to those skilled in the art for the separation of enantiomers. A preferred method for the routine separation enantiomers is supercritical fluid chromatography employing a chiral stationary phase.

Experimental Section

Except where otherwise noted, reactions were run under an atmosphere of nitrogen. Chromatography on silica gel was carried out using 250-400 mesh silica gel using pressurized nitrogen (~10-15 psi) to drive solvent through the column ("flash chromatography"). Where indicated, solutions and reaction mixtures were concentrated by rotary evaporation under vacuum.

Example 1

2,2,2-Trifluoro-N-{cis-3[methyl(7H-pyrrolo[2,3-d]pyrimidin-4-yl)amino]cyclobutyl}ethanesulfonamide Step 1: Benzyl[cis-3-(methylamino)cyclobutyl]carbamate and benzyl[trans-3-(methylamino)cyclobutyl]carbamate A 33% solution of methylamine (1000 mL, 9.13 mol) in absolute ethanol was added to a mixture of benzyl(3-oxocyclobutyl)carbamate (WO2012/75381 A1 and WO2012/09678 A1) (200 g, 0.913 mol) and acetic acid (88 mL) stirring in ethanol (1000 mL) at 0° C. The reaction mixture stirred for at 0° C. for 1.5 hours and then stirred at room temperature for 2 hours. Lithium borohydride (41 g, 2.05 mol) was added in portions to the reaction mixture at −70° C. After addition was complete, the reaction mixture was stirred at −70° C. for 1 hour and then allowed to warm to room temperature over 12 hours. The reaction mixture was quenched with water (400 mL), and concentrated under vacuum to remove ethanol. The aqueous layer was acidified with concentrated hydrochloric acid to pH 2, washed with ethyl acetate (2×1000 mL), basified with 10% sodium hydroxide to pH 9-10 and then extracted with dichloromethane (3×1000 mL). The combined organic layers were washed with brine (1000 mL), dried over sodium sulfate, and concentrated to obtain the crude product as a pale brown liquid. This was dissolved in dichloromethane (400 mL) and cooled to 0° C. To the resulting solution was added a solution of 4M HCl in dioxane (300 mL). The mixture was stirred at 0° C. for 30 minutes, and then at room temperature for 12 hours. The reaction mixture was filtered and the remaining solid was recrystallized from a mixture of methanol and methyl tert-butyl ether to afford the cis-isomer as a white solid (111.09 g, 52%). $^1$H NMR: (400 MHz, D$_2$O): δ 7.33-7.38 (m, 5H); 5.02 (s, 2H), 3.83-3.87 (m, 1H), 3.89-3.41 (m, 1H), 2.66-2.70 (m, 2H), 2.56 (s, 3H), 2.03-2.05 (m, 2H). LC/MS (exact mass) calculated for $C_{13}H_{18}N_2O_2$; 234.137. found (M+H$^+$); 235.1.

The trans isomer was isolated from the mother liquor using supercritical fluid chromatography.

Step 2: Benzyl {cis-3-[(2-chloro-7H-pyrrolo[2,3-d]pyrimidin-4-yl)(methyl)amino]-cyclobutyl}carbamate To a solution of potassium carbonate (20.47 g, 148 mmol) in water (180 mL) was added benzyl[cis-3-(methylamino)cyclobutyl]carbamate (13.57 g, 50.2 mmol), followed by 2,4-dichloro-7H-pyrrolo(2,3-d)pyrimidine (9.0 g, 47.9 mmol) at room temperature. After addition was complete, the reaction mixture was stirred at 95° C. overnight. The mixture was filtered to collect the solid. The filter cake was washed with water and dried under vacuum to afford the title compound (16.5 g, 89.7%) as a yellow solid. $^1$H NMR (400 MHz, DMSO-d$_6$): δ 11.81 (sm 1H), 7.65 (d, 1H), 7.38 (m, 5H), 7.16 (m, 1H), 6.67 (d, 1H), 5.02 (s, 2H), 4.81 (m, 1H), 3.85 (m, 1H), 3.25 (s, 3H), 2.53 (m, 2H), 2.25 (m, 2H). LC/MS (exact mass) calculated for $C_{19}H_{20}ClN_5O_2$; 385.131. found (M+H$^+$); 386.1.

Step 3: cis-N-Methyl-N-7H-pyrrolo[2,3-d]pyrimidin-4-ylcyclobutane-1,3-diamine hydrochloride A mixture of {cis-3-[(2-chloro-7H-pyrrolo[2,3-d]pyrimidin-4-yl)(methyl)-amino]cyclobutyl}carbamate (13.0 g, 34.0 mmol), Pd(OH)$_2$ (40.3 g, 40.8 mmol) and cyclohexene (72.5 mL, 0.71 mol) in ethanol (300 mL) was stirred at reflux for 3 hours. The reaction mixture was
filtered through a pad of Celite® and the pad was washed with methanol. The filtrate was concentrated under vacuum to afford the title compound (4.8 g, 66%) as a white solid. $^1$H NMR (400 MHz, DMSO-d$_6$): δ 11.68 (br, 1H), 8.11 (s, 1H), 7.67 (br, 2H), 7.17 (d, 1H), 6.65 (d, 1H), 5.08 (m, 1H), 3.45 (m, 1H), 3.26 (s, 3H), 2.31 (m, 4H). LC/MS (exact mass) calculated for $C_{11}H_{15}N_5$; 217.133. found (M+H$^+$); 218.1.

Step 4: 2, 2,2-Trifluoro-N-{cis-3-[methyl(7H-pyrrolo[2,3-d]pyrimidin-4-yl)amino]-cyclobutyl}ethanesulfonamide To a solution of cis-N-methyl-N-7H-pyrrolo[2,3-d]pyrimidin-4-ylcyclobutane-1,3-diamine hydrochloride (100 mg, 0.39 mmol) in tetrahydrofuran (0.8 mL) was added lithium bis(trimethylsilyl)amide (1M solution in tetrahydrofuran) (0.9 mL, 0.9 mmol) and chlorotrimethylsilane (94 mg, 0.88 mmol) at room temperature. The reaction mixture was stirred for 45 minutes and then 2,2,2-trifluoroethanesulfonyl chloride (86 mg, 0.47 mmol) was added slowly. The mixture was stirred at room temperature for 18 hours and then partitioned between dichloromethane and water. The aqueous layer was and extracted twice with dichloromethane and the combined organic layers were concentrated to afford the crude product as a tan solid. The crude material was purified by chromatography on silica gel eluting with a mixture of dichloromethane and methanol (93:7) to afford the title compound as a white solid (93 mg, 65%). $^1$H NMR (400 MHz, DMSO-d$_6$): δ 11.61 (br. s., 1H), 8.20 (d, 1H), 8.08 (s, 1H), 7.13 (d, 1H), 6.60 (d, 1H), 4.80-4.94 (m, 1H), 4.34 (q, 2H), 3.58-3.71 (m, 1H), 3.23 (s, 3H), 2.55-2.67 (m, 2H), 2.17-2.30 (m, 2H). LC/MS (exact mass) calculated for $C_{13}H_{16}F_3N_5O_2S$; 363.098. found (M+H$^+$); 363.9.

The following compounds, Examples 2-7, were prepared from cis-N-methyl-N-7H-pyrrolo[2,3-d]pyrimidin-4-ylcyclobutane-1,3-diamine hydrochloride (Example 1, Step 3) in a similar manner to that described in Example 1, Step 4, substituting the indicated sulfonyl chloride for 2,2,2-trifluoroethanesulfonyl chloride.

Example 2

N-{cis-3-[Methyl(7H-pyrrolo[2,3-d]pyrimidin-4-yl)amino]cyclobutyl}-propane-1-sulfonamide This compound was prepared using 1-propanesulfonyl chloride. The crude compound was purified by chromatography on silica gel eluting with a mixture of dichloromethane and methanol (93:7) to afford the title compound as a tan solid (78% yield). $^1$H NMR (400 MHz, DMSO-$d_6$): δ 11.60 (br s, 1H), 8.08 (s, 1H), 7.46 (d, 1H), 7.12 (d, 1H), 6.61 (d, 1H), 4.81-4.94 (m, 1H), 3.47-3.62 (m, 1H), 3.23 (s, 3H), 2.87-2.96 (m, 2H), 2.52-2.63 (m, 2H), 2.14-2.27 (m, 2H) 1.60-1.73 (m, 2H) 0.96 (t, 3H). LC/MS (exact mass) calculated for $C_{14}H_{21}N_6O_2S$; 323.142. found (M+H$^+$); 324.1.

Example 3

2-Methyl-N-{cis-3[methyl(7H-pyrrolo[2,3-d]pyrimidin-4-yl)amino]-cyclobutyl}propane-1-sulfonamide This compound was prepared using 2-methyl-1 propanesulfonyl chloride. The crude compound was purified by chromatography on silica gel eluting with a mixture of dichloromethane and methanol (93:7) to afford the title compound as a white solid (52%). $^1$H NMR (400 MHz, DMSO-$d_6$): δ 11.64 (br s, 1H), 8.12 (s, 1H), 7.51 (d, 1H), 7.03-7.26 (m, 1H), 6.65 (d, 1H), 4.82-5.02 (m, 1H), 3.52-3.70 (m, 1H), 3.26 (s, 3H), 2.87 (d, 2H), 2.55-2.67 (m, 2H), 2.18-2.30 (m, 2H), 2.11 (dt, 1H), 1.04 (d, 6H). LC/MS (exact mass) calculated for $C_{16}H_{23}N_5O_2S$; 337.157. found (M+H$^+$); 338.0.

Example 4A and Example 4B cis and trans-3-(Cyanomethyl)-N-{cis-3-[methyl(7H-pyrrolo[2,3-d]pyrimidin-4-yl)amino]cyclobutyl}cyclobutanesulfonamide These compounds were prepared using a mixture (~1:1) of cis- and trans-3-(cyanomethyl)cyclo-butanesulfonyl chloride. The crude mixture of cis and trans isomers was purified by chromatography on silica gel eluting with a gradient of dichloromethane and methanol (100:0 to 10:1) to afford a mixture (420 mg) of the title compounds as a white solid (67%). The cis and trans isomers were separated by supercritical fluid chromatography.
cis-isomer 4A: 160 mg (21%). $^1$H NMR (400 MHz, methanol-$d_4$): δ 8.12 (s, 1H), 7.13-7.12 (d, 1H), 6.69-6.69 (d, 1H), 4.92-4.89 (m, 1H), 3.84-3.78 (m, 1H), 3.76-3.67 (m, 1H), 3.36 (s, 3H), 2.79-2.73 (m, 2H), 2.65-2.64 (m, 3H), 2.58-2.52 (m, 2H), 2.32-2.19 (m, 4H). LC/MS (exact mass) calculated for $C_{17}H_{22}N_6O_2S$; 374.152. found (M+H$^+$); 375.3.
trans-isomer 4B: 155 mg (20%). $^1$H NMR (400 MHz, methanol-$d_4$): δ 8.13 (s, 1H), 7.13 (d, 1H), 6.70 (d, 1H), 4.94-4.89 (m, 1H), 3.89-3.85 (m, 1H), 3.72-3.69 (m, 1H), 3.36 (s, 3H), 2.85-2.62 (m, 7H), 2.31-2.23 (m, 4H). LC/MS (exact mass) calculated for $C_{17}H_{22}N_6O_2S$; 374.152. found (M+H$^+$); 374.9.

The mixture of cis- and trans-3-(cyanomethyl)cyclobutanesulfonyl chlorides was prepared as follows:

Step 1: [3-(Benzyloxy)cyclobutylidene]acetonitrile

To a cold suspension of sodium hydride (125 mg, 3.12 mmol) in tetrahydrofuran (12 mL) at 0° C. was added diethyl cyanomethylphosphonate (1.21 g, 3.40 mmol). The mixture was stirred at room temperature for 1 hour before adding a solution of 3-(benzyloxy)cyclobutanone (500 mg, 2.84 mmol) in tetrahydrofuran (8 mL). The mixture was stirred at room temperature overnight, and was then quenched with water. The mixture was extracted with ethyl acetate (3×25 mL) and the combined organic layers were dried over sodium sulfate and concentrated. The residue was chromatographed on silica gel eluting with a gradient of petroleum ether and ethyl acetate (100:0 to 85:15) to afford the title compound (450 mg, 80%) as a yellow oil.

Step 2: [3-(Benzyloxy)cyclobutyl]acetonitrile

A mixture of [3-(benzyloxy)cyclobutylidene]acetonitrile (10.2 g, 51 mmol) and 10% Pd/C (2.0 g) in dry tetrahydrofuran was pressurized to 50 psi with hydrogen and stirred at room temperature for 3 days. The mixture was then filtered and concentrated under vacuum. The residue was chromatographed on silica gel eluting with a gradient of petroleum ether and ethyl acetate (100:0 to 80:20) to give the title compound (7 g, 70%) as a colorless oil. $^1$H NMR (400 MHz, CDCl$_3$): δ 7.36-7.28 (m, 5H), 4.44-4.43 (m, 2H), 4.30-4.09 (m, 1H), 3.98-3.95 (m, 1H), 2.64-2.45 (m, 4H), 1.81-1.759 (m, 2H).

Step 3: (3-Hydroxycyclobutyl)acetonitrile

To a solution of [3-(benzyloxy)cyclobutyl]acetonitrile (1 g, 5.00 mmol) in acetonitrile (15 mL) was added dropwise iodotrimethylsilane (1.5 g, 7.50 mmol) at 0° C. The mixture was stirred at room temperature overnight. The mixture was quenched with triethylamine, concentrated and then purified by chromatography on silica gel eluting with a gradient of petroleum ether and ethyl acetate (1:0 to 1:1) to afford the title compound (340 mg, 62%) as yellow oil. $^1$H NMR (400 MHz, CDCl$_3$): δ 4.55-4.15 (m, 1H), 2.49-2.46 (m, 2H), 2.25-2.21 (m, 2H), 2.14-2.08 (m, 1H), 1.79-1.72 (m, 2H).

Step 4: 3-(Cyanomethyl)cyclobutyl-4-methylbenzenesulfonate

To a solution of (3-hydroxycyclobutyl)acetonitrile (333 mg, 3.0 mmol) in dry dichloromethane (25 mL) was added 4-dimethylaminopyridine (732 mg, 6.0 mmol). The mixture stirred at room temperature for 5 minutes and then p-toluenesulfonyl chloride (859 mg, 4.5 mmol) was added. The resulting mixture was stirred at room temperature overnight. The mixture was washed with water (2×15 mL). The organic layer was dried over sodium sulfate and concentrated. The residue was purified by chromatography on silica gel eluting with a gradient of petroleum ether and ethyl acetate (10:0 to 7:3) to afford the title compound (520 mg, 65% yield) as colorless oil.

Step 5: S-[3-(Cyanomethyl)cyclobutyl]ethanethioate

The mixture of 3-(cyanomethyl)cyclobutyl 4-methylbenzenesulfonate (1.5 g, 5.7 mmol) and potassium thioacetate (1.29 g, 3.00 mmol) in N,N-dimethylformamide (8 mL) was heated at 80° C. overnight. The mixture was diluted with ethyl acetate (15 mL), washed with water (30 mL) and brine (2×30 mL), dried over sodium sulfate and concentrated. The residue was purified by preparative thin layer chromatography eluting with a mixture of petroleum ether and ethyl acetate (3:1) to afford the title compound (750 mg, 78%) as colorless oil. $^1$H NMR (400 MHz, CDCl$_3$): δ 4.12-3.92 (m, 1H), 2.86-2.77 (m, 2H), 2.71-2.47 (m, 2H), 2.42-2.37 (m, 2H), 2.30-2.29 (m, 3H), 1.97-1.90 (m, 1H).

Step 6: 3-(Cyanomethyl)cyclobutanesulfonyl chloride

A mixture of N-chlorosuccinimide (1.6 g, 12.0 mmol) in concentrated HCl (3 mL) and acetonitrile (12 mL) was stirred at room temperature for 10 minutes. S-[3-(cyanomethyl)cyclobutyl]ethanethioate (507 mg, 3.0 mmol) in acetonitrile (3 mL) was added at 0° C. and stirred for 10 minutes. The mixture was diluted with aqueous sodium bicarbonate (50 mL), and extracted with methyl tert-butyl ether (3×50 mL). The combined dried organic layers were dried over anhydrous sodium sulfate and concentrated. The crude product was purified by chromatography on silica gel eluting with a mixture of petroleum ether and ethyl acetate (100:0 to 50:50) to afford the title compound (400 mg, 69%) as a yellow oil. $^1$H NMR (400 MHz, CDCl$_3$): δ 4.45-4.40 (m, 1H), 3.06-2.71 (m, 3H), 2.61-2.49 (m, 4H).

Example 5

1-[3-(Cyanomethyl)oxetan-3-yl]-N-{cis-3-[methyl (7H-pyrrolo[2,3-d]pyrimidin-4-yl)amino] cyclobutyl}methanesulfonamide This compound was prepared from [3-(cyanomethyl) oxetan-3-yl]methanesulfonyl chloride. The crude compound was purified using preparative thin layer chromatography eluting with ethyl acetate to afford the title compound as a white solid (32%). $^1$H NMR (400 MHz, methanol-d$_4$): δ 8.13 (s, 1H), 7.14-7.13 (m, 1H), 6.71-6.70 (m, 1H), 5.06-5.05 (m, 1H), 4.85-4.81 (m, 2H), 4.52-4.50 (m, 2H), 3.77-3.75 (m, 1H), 3.63 (m, 2H), 3.39 (s, 3H), 3.29-3.26 (m, 2H), 2.85-2.78 (m, 2H), 2.38-2.30 (m, 2H). LC/MS (exact mass) calculated for C$_{17}$H$_{22}$N$_6$O$_3$S; 390.147. found (M+H$^+$); 391.0.

[3-(Cyanomethyl)oxetan-3-yl]methanesulfonyl chloride

Step 1: [3-(Cyanomethyl)oxetan-3-yl]methyl 4-methylbenzenesulfonate

This compound was prepared following the procedure of Example 4 Step 4, substituting [3-(Hydroxymethyl)-3-oxetanyl]acetonitrile for (3-hydroxycyclobutyl)acetonitrile. The crude compound was purified by chromatography on silica gel eluting with a mixture of petroleum ether and ethyl acetate (1:0 to 1:1) to afford the title compound as a white solid (10%). $^1$H NMR (400 MHz, CDCl$_3$): δ 7.82-7.80 (m, 2H), 7.41-7.39 (m, 2H), 4.54-4.35 (m, 4H), 4.31 (s, 2H), 2.79 (s, 2H), 2.45 (s, 3H).

Step 2: [3-(Cyanomethyl)oxetan-3-yl]methyl thiocyanate

A solution of [3-(cyanomethyl)oxetan-3-yl]methyl 4-methylbenzenesulfonate (150 mg, 0.53 mmol) and potassium thiocyanate (104 mg, 1.07 mmol) was stirred in ethanol (10 mL). The reaction was heated to 85° C. and stirred for 16 hours. The solvent was evaporated to afford the crude title compound as a white solid.

Step 3: [3-(Cyanomethyl)oxetan-3-yl]methanesulfonyl chloride

Chlorine gas was bubbled through a solution of [3-(cyanomethyl)oxetan-3-yl]methyl thiocyanate (0.53 mmol, crude) in water (10 mL) at 0° C. for 30 minutes. The reaction mixture was extracted with methyl tert-butyl ether (2×20 mL). The combined organic layers were dried over sodium sulfate and concentrated to afford the title compound (20 mg, 18%).

Example 6

N-{cis-3-[methyl(7H-pyrrolo[2,3-d]pyrimidin-4-yl) amino]cyclobutyl}-1-oxetan-3-ylmethanesulfonamide This compound was prepared using oxetan-3-ylmethanesulfonyl chloride. The crude compound was purified by chromatography on silica gel eluting with a mixture of dichloromethane and methanol (85:15) to afford the title compound as a white solid (23%). $^1$H NMR (400 MHz, methanol-d$_4$): δ 8.13 (m, 1H), 7.13 (d, J=4 Hz, 1H), 6.70-6.69 (m, J=4 Hz, 1H), 4.93-4.91 (m, 1H), 4.84-4.83 (m, 2H), 4.63-4.59 (m, 2H), 3.74-3.68 (m, 1H), 3.58-3.56 (m, 1H), 3.47-3.45 (m, 2H), 3.37 (s, 3H), 2.79-2.77 (m, 2H), 2.32-2.29 (m, 2H). LC/MS (exact mass) calculated for C$_{15}$H$_{21}$N5O$_3$S; 351.136. found (M+H$^+$); 352.1.

Oxetan-3-ylmethanesulfonyl chloride

Step 1: Oxetan-3-ylmethyl thiocyanate

This compound was prepared according to the procedure of Example 5, Step 2, substituting oxetan-3-ylmethyl 4-methylbenzenesulfonate (WO2012/117000A1) for [3-(cyanomethyl)oxetan-3-yl]methyl 4-methylbenzenesulfonate to afford the crude title compound as a white solid. (100%).

Step 2: Oxetan-3-ylmethanesulfonyl chloride

This compound was prepared in crude form (25% yield) following the procedure of Example 5 Step 3, substituting oxetan-3-ylmethyl thiocyanate for [3-(cyanomethyl)oxetan-3-yl]methyl thiocyanate.

Example 7A and 7B cis- and trans-3-(Cyanomethyl)-3-methyl-N-{cis-3-[methyl(7H-pyrrolo[2,3-d]pyrimidin-4-yl)amino] cyclobutyl}cyclobutanesulfonamide These compounds were prepared using a mixture (~1:1) of cis- and trans-3-(cyanomethyl)-3-methylcyclobutanesulfonyl chloride. The crude mixture of cis- and trans isomers was purified by chromatography on silica gel eluting with a gradient of petroleum ether:ethyl acetate (10:1 to 1:15) to afford a mixture (70 mg) of the title compounds as a light brown solid (28%). The cis and trans isomers were then separated by supercritical fluid chromatography (SFC).

cis-isomer (7A): 26 mg (10%); SFC retention time=7.11 minutes; $^1$H NMR (400 MHz, methanol-d$_4$): δ 8.13 (s, 1H), 7.13-7.13 (d, 1H), 6.69 (d, 1H), 4.93-4.86 (m, 1H), 3.91-3.87 (m, 1H), 3.71-3.65 (m, 1H), 3.37-3.33 (m, 3H), 2.77-2.75 (m, 2H), 2.68 (s, 2H), 2.41-2.36 (m, 2H), 2.26-2.21 (m, 2H), 1.34 (m, 3H). LC/MS (exact mass) calculated for C$_{18}$H$_{24}$N$_6$O$_2$S; 388.168. found (M+H$^+$); 389.1.

trans-isomer (7B) 24 mg (10%); SFC retention time=11.35 minutes; $^1$H NMR (400 MHz, methanol-d$_4$): δ 8.13 (s, 1H), 7.14 (d, 1H), 6.69 (d, 1H), 4.93-4.86 (m, 1H), 3.96-3.86 (m, 1H), 3.72-3.65 (m, 1H), 3.36-3.31 (m, 3H), 2.77-2.75 (m, 2H), 2.71 (s, 2H), 2.34-2.26 (m, 6H), 1.33 (m, 3H). LC/MS (exact mass) calculated for C$_{18}$H$_{24}$N$_6$O$_2$S; 388.168. found (M+H$^+$); 389.0.

The mixture of cis- and trans-3-(cyanomethyl)-3-methyl-cyclobutanesulfonyl chlorides was prepared as follows:

Step 1: 1-Methyl-3-methylenecyclobutanecarbonitrile

To a solution of 3-methylenecyclobutanecarbonitrile (35.0 g, 373.0 mmol) in tetrahydrofuran (200 mL) was added dropwise lithium bis(trimethylsilyl)amide (450 mL, 1M) at −78° C. The solution was stirred for 1 hour at −78° C. and iodomethane (30 mL, 448 mmol) was added to the reaction. After 1 hour, the mixture was warmed to room temperature and stirred overnight. The reaction mixture was quenched with aqueous ammonium chloride (380 mL) and extracted with methyl tert-butyl ether (3×400 mL). The combined organic layers were dried over sodium sulfate and concentrated. The crude product was purified by distillation under reduced pressure to afford the title compound (20 g, 50%) as clear oil. $^1$H NMR (400 MHz, CDCl$_3$): δ 4.90-4.89 (m, 2H), 3.24-3.20 (m, 2H), 2.67-2.62 (m, 2H), 1.50 (s, 3H).

Step 2: 1-Methyl-3-methylenecyclobutanecarboxylic acid

To a solution of 1-methyl-3-methylenecyclobutanecarbonitrile (10.0 g, 93.3 mmol) in water (50 mL) and ethanol (50 mL) was added potassium hydroxide (25.6 g, 466.6 mmol). The reaction mixture was heated to reflux and stirred overnight. The ethanol was removed under reduced pressure, and the solution was cooled to below 10° C., acidified with concentrated hydrochloric acid to pH 1. The aqueous phase was extracted with ethyl acetate (3×150 mL). The combined organic layers were dried over sodium sulfate and concentrated to afford the title compound (9 g, 77%). $^1$H NMR (400 MHz, CDCl$_3$): δ 11.90 (s, 1H), 4.88-4.85 (m, 2H), 3.23-3.17 (m, 2H), 2.53-2.41 (m, 2H), 1.45 (s, 3H).

Step 3: Ethyl 1-methyl-3-methylenecyclobutanecarboxylate

To a solution of 1-methyl-3-methylenecyclobutanecarboxylic acid (6 g, 47.6 mmol) in dichloromethane (30 mL) at 0° C. was added dropwise thionyl chloride (11.0 mL, 143 mmol). The solution was stirred at 0° C. for 1 hour. Three drops of N,N-dimethylformamide were added to the solution. The solution was stirred at 0° C. for 30 minutes. The solvent was evaporated and dichloromethane (20 mL) and ethanol (125 mL) were added to the residue. The resulting solution was stirred for 16 hours at room temperature. The solvent was evaporated and water (20 mL) was added to the residue. The aqueous layer was extracted with dichloromethane (4×20 mL). The combined organic layers were dried over sodium sulfate and concentrated. The crude product was purified by chromatography on silica gel eluting with a gradient of petroleum ether and ethyl acetate (20:1 to 10:1) to afford the title compound (5 g, 68%). $^1$H NMR (400 MHz, CDCl$_3$): δ 4.85-4.83 (m, 2H), 4.17-4.12 (m, 2H), 3.18-3.12 (m, 2H), 2.48-2.42 (m, 2H), 1.41 (s, 3H), 1.27-1.23 (m, 3H).

Step 4: (1-Methyl-3-methylenecyclobutyl)methanol

A mixture of ethyl 1-methyl-3-methylenecyclobutanecarboxylate (4.55 g, 29.5 mmol) lithium aluminum hydride (2.8 g, 72 mmol) in tetrahydrofuran (50 mL) was stirred overnight at room temperature. To the reaction mixture was added Na$_2$SO$_4$.10H$_2$O (3.7 g, 11.5 mmol) and the resulting mixture was stirred for 1 hour at room temperature. The solids were removed by filtration and the filtrate was concentrated under vacuum. The residue was extracted with dichloromethane (3×50 mL). The combined organic extracts were dried over sodium sulfate and concentrated to afford the title compound (2.6 g, 79%) as a colorless oil. $^1$H NMR (400 MHz, CDCl$_3$): δ 4.79-4.78 (m, 2H), 3.48 (s, 2H), 2.53-2.48 (m, 2H), 2.36-2.27 (m, 2H), 1.16 (s, 3H).

Step 5: (1-Methyl-3-methylenecyclobutyl)methyl 4-methylbenzenesulfonate

This compound was prepared following Example 4, Step 4, substituting (1-methyl-3-methylenecyclobutyl)methanol for (3-hydroxycyclobutyl)acetonitrile. The crude compound was purified by chromatography on silica gel eluting with a gradient of petroleum ether and ethyl acetate (20:1 to 4:1) to afford the title compound (70%). $^1$H NMR (400 MHz, CDCl$_3$): δ 7.79 (d, 2H), 7.34 (d, 2H), 4.79-4.78 (m, 2H), 3.90 (s, 2H), 2.51-2.47 (m, 2H), 2.44 (s, 3H), 2.35-2.31 (m, 2H), 1.15 (s, 3H).

Step 6: (1-Methyl-3-methylenecyclobutyl)acetonitrile

A mixture of (1-methyl-3-methylenecyclobutyl)methyl 4-methylbenzenesulfonate (2.5 g, 9.4 mmol), potassium cyanide (1.3 g, 19 mmol) and N,N-dimethylformamide (8 mL) was stirred overnight at 70° C. Water (10 mL) and methyl tert-butyl ether (20 mL) were added to the mixture and the organic layer was separated. The aqueous phase was extracted with methyl tert-butyl ether (3×30 mL). The combined organic layers were washed with an aqueous saturated sodium bicarbonate solution (15 mL), dried over sodium sulfate, and concentrated. The crude product was purified by chromatography on silica gel eluting with a gradient of petroleum ether and ethyl acetate (10:1 to 5:1) to afford the title compound (1.1 g, 97%) as light brown oil. $^1$H NMR (400 MHz, CDCl$_3$): δ 4.88-4.87 (m, 2H), 2.62-2.54 (m, 2H), 2.50 (s, 2H), 1.33 (s, 3H).

Step 7: (1-Methyl-3-oxocyclobutyl)acetonitrile

Ozone gas was bubbled through a solution of (1-methyl-3-methylenecyclo-butyl)acetonitrile (1.08 g, 8.91 mmol) in dichloromethane (30 mL) −78° C. for 10 minutes. After purging the solution with nitrogen gas, dimethylsulfide (10 mL) was added dropwise to the solution at −78° C. The solution was stirred for 30 minutes at −78° C. and the solvent was removed under reduced pressure. The crude product was purified by chromatography on silica gel eluting with a gradient of petroleum ether and ethyl acetate (20:1 to 8:1) to afford the title compound (920 mg, 84%) as a colorless oil.

¹H NMR (400 MHz, CDCl₃): δ 3.11-3.06 (m, 2H), 2.96-2.91 (m, 2H), 2.69 (s, 2H), 1.53 (s, 3H).

Step 8: (3-Hydroxy-1-methylcyclobutyl)acetonitrile

To a solution of (1-methyl-3-oxocyclobutyl)acetonitrile (400 mg, 3.25 mmol) in tetrahydrofuran (15 mL) was added sodium borohydride (246 mg, 6.5 mmol). The mixture was stirred for 3 hours at room temperature. Acetone (2 mL) was added and then the solvent was evaporated. Water (10 mL) was added to the residue and the aqueous phase was extracted with dichloromethane (4×15 mL). The combined organic layers were dried over sodium sulfate and concentrated. The crude product was purified by chromatography on silica gel eluting with a gradient of petroleum ether and ethyl acetate (10:1 to 1:1) to afford the title compound (300 mg, 74%) as a colorless oil.
¹H NMR (400 MHz, CDCl₃): δ 4.38-4.34 (m, 2H), 2.46-2.27 (m, 4H), 1.94-1.86 (m, 2H), 1.33-1.12 (m, 3H).

Step 9: 3-(Cyanomethyl)-3-methylcyclobutyl 4-methylbenzenesulfonate

This compound was prepared following Example 7, Step 5, substituting (3-hydroxy-1-methylcyclobutyl)acetonitrile for (1-methyl-3-methylenecyclo-butyl)methanol. The crude compound was purified by chromatography on silica gel eluting with a gradient of petroleum ether and ethyl acetate (20:1 to 4:1) to afford the title compound (36%). ¹H NMR (400 MHz, CDCl₃): δ 7.77 (d, 2H), 7.35 (d, 2H), 4.89-4.81 (m, 1H), 2.45 (s, 3H), 2.43-2.34 (m, 3H), 2.26-2.21 (m, 1H), 2.15-2.11 (m, 2H), 1.33 (s, 3H).

Step 10: S-[3-(Cyanomethyl)-3-methylcyclobutyl] ethanethioate

This compound was prepared in 89% yield (crude) following the procedure of Example 4, Step 5, substituting 3-(cyanomethyl)-3-methylcyclobutyl 4-methylbenzenesulfonate for 3-(cyanomethyl)cyclobutyl 4-methylbenzenesulfonate. ¹H NMR (400 MHz, CDCl₃): δ 3.12 (s, 1H), 2.46-2.30 (m, 4H), 2.19 (s, 2H), 1.29 (s, 1H) 1.26-1.24 (m, 1H), 1.18-1.14 (m, 1H), 1.13 (s, 3H).

Step 11: 3-(Cyanomethyl)-3-methylcyclobutanesulfonyl chloride

This compound was prepared following Example 4 Step 6, substituting S-[3-(cyanomethyl)-3-methylcyclobutyl]ethanethioate for S-[3-(cyanomethyl)-cyclobutyl]ethanethioate. The crude compound was purified using chromatography on silica gel eluting with a gradient of petroleum ether and ethyl acetate (90:10 to 30:70) to afford the title compound as a yellow liquid (66%). ¹H NMR (400 MHz, CDCl₃): δ 4.45-4.38 (m, 1H), 2.67-2.55 (m, 4H), 2.46-2.40 (m, 2H), 1.42-1.40 (m, 3H).

Example 8

4-Cyano-N-{cis-3-[methyl(7H-pyrrolo[2,3-d]pyrimidin-4-yl)amino]-cyclobutyl}pyridine-2-sulfonamide Step 1: 2-(Benzylthio)isonicotinonitrile A 60% suspension of sodium hydride in mineral oil (8.36 g, 210.0 mmol) was suspended in tetrahydrofuran (100 mL). A solution of benzyl mercaptan (21.5 g, 173 mmol) in tetrahydrofuran (50 mL) was then added dropwise. A thick slurry formed during the addition. 4-Cyano-2-chloropyridine (12.5 g, 90.2 mmol) was added and the resulting mixture was stirred for 3 hours at room temperature. After carefully quenching with water, the mixture was partitioned between water and diethyl ether. The ether layer was washed with saturated aqueous sodium bicarbonate solution, dried over magnesium sulfate and concentrated under reduced pressure. Heptane was added to the residue with solids forming rapidly. The solids were collected by filtration, washed with heptane, and dried to give (33.02 g, 84%) of the title compound as an off-white solid. ¹H NMR (400 MHz, CDCl₃): δ 8.61 (d, 1H), 7.25-7.46 (m, 6H), 7.16-7.22 (m, 1H), 4.47 (s, 2H). LC/MS (exact mass) calculated for $C_{13}H_{10}N_2S$; 226.056. found (M+H⁺); 227.1.

Step 2: 4-cyanopyridine-2-sulfonyl chloride

To a mechanically-stirred mixture of 2-(benzylthio)isonicotinonitrile (8.92 g, 39.4 mmol) in dichloromethane (139 mL) and water (31 mL) was added dropwise sulfuryl chloride (22.5 mL, 278 mmol), keeping the temperature of the mixture below 3° C. After addition was complete, the mixture was stirred for 30 minutes with continued cooling in an ice bath. A slurry of water (50 mL) and ice (20 g) was added. The aqueous phase was extracted twice with dichloromethane. The combined extracts were dried over magnesium sulfate and concentrated under reduced pressure to afford the crude title compound.

Step 3: 4-Cyano-N-{cis-3[methyl(7H-pyrrolo[2,3-d]pyrimidin-4-yl)amino]cyclobutyl}pyr-idine-2-sulfonamide A solution of 4-cyanopyridine-2-sulfonyl chloride (9.7 g, 47.9 mmol) in N,N-dimethylformamide (10 mL) was added to a solution of cis-N-methyl-N-7H-pyrrolo[2,3-d]pyrimidin-4-ylcyclobutane-1,3-diamine hydrochloride (8.0 g, 36.8 mmol) and 4-dimethylaminopyridine (150 mg, 0.03 mmol) in N,N-dimethylformamide (90 mL) at room temperature. Diisopropylethylamine (13 mL, 77 mmol) was added and the resulting mixture was stirred at room temperature for 2 hours. The mixture was diluted with ethyl acetate (200 mL) and aqueous saturated sodium bicarbonate solution was added. Water was added to dissolve the precipitated solids. The aqueous phase was extracted three times with ethyl acetate. The combined organic extracts were washed four times with brine, dried over anhydrous magnesium sulfate and concentrated under reduced pressure. A 1:1 mixture of ethyl acetate and hexanes was added to the residue. The solids were collected by filtration and then dissolved in dichloromethane and a minimum amount of methanol. The resulting solution was passed through a silica gel plug eluting with a 5% solution of methanol in dichloromethane. The solvents were evaporated to afford a solid to which was added a solution of 10% methanol in dichloromethane. The mixture was briefly stirred and then let stand overnight. The solids were filtered, washed with dichloromethane and dried to afford the title compound (5.58 g, 39%) as an off-white solid. ¹H NMR (400 MHz, DMSO-d₆): δ 11.62 (br. s., 1H), 9.02 (d, 1H), 8.52 (d, 1H), 8.38 (s, 1H), 8.17 (dd, 1H), 8.07 (s, 1H), 7.10-7.15 (m, 1H), 6.59 (dd, 3.41 Hz, 1H), 4.80-4.91 (m, 1H), 3.58-3.71 (m, 1H), 3.19 (s, 3H), 2.25-2.36 (m, 2H), 2.10 (m, 2H). LC/MS (exact mass) calculated for $C_{17}H_{17}N_7O_2S$; 383.116. found (M+H⁺); 384.1.

Example 9

3-(1-Hydroxy-1-methylethyl)-N-{cis-3-[methyl(7H-pyrrolo[2,3-d]pyrimidin-4-yl)amino]cyclobutyl}benzenesulfonamide

Step 1: Methyl 3-[({cis-3-[methyl(7H-pyrrolo[2,3-d]pyrimidin-4-yl)amino]-cyclobutyl}amino)-sulfonyl]benzoate To a suspension of cis-N-methyl-N-7H-pyrrolo[2,3-d]pyrimidin-4-ylcyclobutane-1,3-diamine hydrochloride (1.8 g, 8.29 mmol) in N,N-dimethylformamide (100 mL) was added portionwise triethylamine (6.7 mL, 49 mmol) at 0° C. Methyl 3-(chlorosulfonyl)benzoate (2.3 g, 9.9 mmol) was added at 0° C. The resulting mixture was stirred at room temperature for 3 hours. The solvent was removed under vacuum. The residue was chromatographed on silica gel eluting with a gradient of methanol in dichloromethane (3% to 10%) to afford the title compound (1.6 g, 47%) as a yellow solid.

Step 2: 3-(Hydroxymethyl)-N-{cis-3-[methyl(7H-pyrrolo[2,3-d]pyrimidin-4-yl)amino]cyclobutyl}benzenesulfonamide To a solution of methyl 3-[({cis-3-[methyl(7H-pyrrolo[2,3-d]pyrimidin-4-yl)amino]cyclobutyl}amino)sulfonyl]benzoate (800 mg, 1.92 mmol) in tetrahydrofuran (120 mL) was added lithium aluminum hydride (0.25 g, 6.7 mmol) at 0° C. The reaction was warmed to 25° C. and stirred for 3 hours. The reaction was quenched with water (2 mL) and stirred for 15 minutes. The reaction mixture was filtered. The filter cake was stirred in tetrahydrofuran (50 mL) and filtered again. The combined filtrate was concentrated to dryness to afford the title compound (430 mg, 58%) as a yellow solid.

Step 3: 3-Formyl-N-{cis-3-[methyl(7H-pyrrolo[2,3-d]pyrimidin-4-yl)amino]-cyclobutyl}benzenesulfonamide To a solution of 3-(hydroxymethyl)-N-{cis-3-[methyl(7H-pyrrolo[2,3-d]pyrimidin-4-yl)amino]cyclobutyl}benzenesulfonamide (400 mg, 1.03 mmol) in chloroform (50 mL) and methanol (5 mL) was added manganese dioxide (0.89 g, 10.0 mmol). The reaction mixture was stirred at 25° C. overnight. The reaction mixture was filtered and the filter cake was washed with chloroform (3×25 mL). The combined filtrates were concentrated. The residue was chromatographed on silica gel eluting with a gradient of methanol in dichloromethane (2% to 8%) to afford the title compound (240 mg, 60%) as an oil.

Step 4: 3-(1-Hydroxyethyl)-N-{cis-3-[methyl(7H-pyrrolo[2,3-d]pyrimidin-4-yl)amino]cyclobutyl}benzenesulfonamide To a solution of 3-formyl-N-{cis-3-[methyl(7H-pyrrolo[2,3-d]pyrimidin-4-yl)amino]cyclobutyl}benzenesulfonamide (260 mg, 0.68 mmol) in tetrahydrofuran (20 mL) was added methylmagnesium bromide (1.8 mL, 5.4 mmol) at 0° C. under nitrogen. The reaction was stirred at 25° C. overnight and was then quenched with aqueous ammonium chloride (10 mL). The reaction mixture was extracted with ethyl acetate (3×25 mL). The combined organic layers were dried over sodium sulfate and concentrated. The residue was purified by preparative high performance liquid chromatography to afford the title compound (60 mg, 22%) as a white solid. $^1$H NMR (400 MHz, DMSO-$d_6$): δ 11.6 (s, 1H), 8.08 (s, 1H), 8.03 (d, 1H), 7.86 (s, 1H), 7.70 (m, 1H), 7.55 (m, 2H), 7.15 (m, 1H), 6.61 (m, 1H), 5.44 (m, 1H), 4.85 (m, 1H), 3.56 (m, 1H), 3.18 (s, 3H), 2.18 (m, 2H), 2.04 (m, 2H), 1.32 (d, 3H). LC/MS (exact mass) calculated for $C_{16}H_{23}N_6O_3S$; 401.152. found (M+H$^+$); 402.2.

Step 5: 3-Acetyl-N-{cis-3-[methyl(7H-pyrrolo[2,3-d]pyrimidin-4-yl)amino]-cyclobutyl}benzenesulfonamide To a solution of 3-(1-hydroxyethyl)-N-{cis-3-[methyl(7H-pyrrolo[2,3-d]pyrimidin-4-yl)amino]cyclobutyl}benzenesulfonamide (60 mg, 0.15 mmol) in chloroform (30 mL) and methanol (5 mL) was added manganese dioxide (190 mg, 2.2 mmol). The reaction mixture was stirred at 45° C. overnight. Then the reaction mixture was filtered and the filter cake was washed with chloroform (3×25 mL). The combined filtrates were concentrated. The residue was purified by preparative high performance liquid chromatography to afford the title compound (15 mg, 25%) as a white solid. $^1$H NMR (400 MHz, DMSO-$d_6$): δ 11.58 (s, 1H), 8.31 (s, 1H), 8.21 (m, 2H), 8.16 (m, 2H), 7.76 (m, 1H), 7.09 (d, 1H), 6.56 (s, 1H), 4.82 (m, 1H), 3.54 (m, 1H), 3.14 (s, 3H), 2.81 (m, 3H), 2.26 (m, 2H), 1.98 (m, 2H). LC/MS (exact mass) calculated for $C_{19}H_{21}N_5O_3S$; 399.136. found (M+H$^+$); 400.1.

Step 6: 3-(1-Hydroxy-1-methylethyl)-N-{cis-3-[methyl(7H-pyrrolo[2,3-d]pyrimidin-4-yl)amino]cyclobutyl}benzenesulfonamide To a solution of 3-acetyl-N-{cis-3-[methyl(7H-pyrrolo[2,3-d]pyrimidin-4-yl)amino]cyclobutyl}benzenesulfonamide (240 mg, 0.58 mmol) in tetrahydrofuran (20 mL) was added methylmagnesium bromide (2.4 mL, 7.2 mmol) at 0° C. under nitrogen. The reaction was stirred at 25° C. for 2 hours and was quenched with aqueous ammonium chloride solution (10 mL). The reaction mixture was extracted with ethyl acetate (3×25 mL). The combined organic layers were dried over sodium sulfate and concentrated. The residue was purified by preparative high performance liquid chromatography to afford the title compound (101 mg, 42%) as a white solid. $^1$H NMR (400 MHz, DMSO-$d_6$): δ 11.6 (s, 1H), 8.05 (s, 1H), 7.97 (m, 2H), 7.67 (m, 2H), 7.52 (m, 1H), 7.12 (m, 1H), 6.57 (m, 1H), 5.29 (s, 1H), 4.85 (m, 1H), 3.53 (m, 1H), 3.15 (s, 3H), 2.24 (m, 2H), 1.98 (m, 2H), 1.44 (s, 6H). LC/MS (exact mass) calculated for $C_{20}H_{25}N_5O_3S$; 415.168. found (M+H$^+$); 416.0.

Example 10

1-Cyclopropyl-N-{trans-3-[methyl(7H-pyrrolo[2,3-d]pyrimidin-4-yl)amino]cyclobutyl}methanesulfonamide

This compound was synthesized starting from benzyl [trans-3-(methylamino)-cyclobutyl]carbamate (Example 1, Step 1), following procedures similar to those described for Example 1, Steps 2 and 3 to obtain trans-N-methyl-N-7H-pyrrolo[2,3-d]pyrimidin-4-ylcyclobutane-1,3-diamine hydrochloride. To the resulting hydrochloride (60 mg, 0.28 mmol) in THF (10 mL) was added potassium carbonate (76 mg, 0.55 mmol), H2O (5 mL) and cyclopropylmethanesulfonyl chloride (52 mg, 0.33 mmol). The mixture stirred for two hours, was diluted with dichloromethane, washed with brine, dried over sodium sulfate, filtered, and concentrated. The crude product was purified by preparative high performance liquid chromatography to afford the title compound as a white solid (7 mg; 8%). $^1$H NMR (400 MHz, methanol-d$_4$): δ 8.14 (s, 1H), 7.16 (d, 1H), 6.72 (d, 1H), 5.44-5.40 (m, 1H), 4.07-4.06 (m, 1H), 3.41 (s, 3H), 3.01-2.99 (m, 2H), 2.81-2.74 (m, 2H), 2.54-2.49 (m, 2H), 1.15-1.13 (m, 1H), 0.720-0.69 (m, 2H), 0.42-0.41 (m, 2H). LC/MS (exact mass) calculated for C$_{15}$H$_{21}$N$_5$O$_2$S; 335.142. found (M+H$^+$); 336.1.

Example 11

N-{(1S,3R)-3-[Methyl(7H-pyrrolo[2,3-d]pyrimidin-4-yl)amino]cyclopentyl}propane-1-sulfonamide This compound was prepared following Example 10 substituting (1S,3R)—N-benzyl-N'-methylcyclopentane-1,3-diamine for benzyl[trans-3-(methylamino)-cyclobutyl]carbamate, (1R,3S)—N-methyl-N-7H-pyrrolo[2,3-d]pyrimidin-4-ylcyclopentane-1,3-diamine hydrochloride for trans-N-methyl-N-7H-pyrrolo[2,3-d]pyrimidin-4-ylcyclobutane-1,3-diamine hydrochloride, and propane-1-sulfonyl chloride for cyclopropylmethanesulfonyl chloride to afford the title compound as an off-white solid (11%). The crude compound was purified using preparative high performance liquid chromatography. $^1$H NMR (400 MHz, methanol-d$_4$): δ 8.08 (s, 1H), 7.08 (s, 1H), 6.65 (s, 1H), 5.27-5.23 (m, 1H), 3.81-3.76 (m, 1H), 3.31 (s, 3H), 2.33-2.29 (m, 1H), 2.13-2.04 (m, 1H), 1.98-1.92 (m, 2H), 1.82-1.75 (m, 4H), 1.06 (t, 3H), 0.42-0.41 (m, 2H). LC/MS (exact mass) calculated for C$_{15}$H$_{23}$N$_5$O$_2$S; 337.157. found (M+H$^+$); 337.8.

(1S,3R)—N-benzyl-N'-methylcyclopentane-1,3-diamine was prepared as follows

Step 1: Benzyl[(1R,3S)-3-aminocyclopentyl]carbamate

Trifluoroacetic acid (15 mL, 190 mmol) was added to a solution of benzyl tert-butyl(1R,3S)-cyclopentane-1,3-diyl-biscarbamate (prepared as described in WO2011/086053A1) (5.02 g, 15.0 mmol) in dichloromethane (75 mL) at room temperature. The reaction was stirred for 2 hours and was then concentrated to afford the title compound as a light brown oil (6.70 g, crude)

Step 2: Benzyl[(1R,3S)-3-(benzylamino)cyclopentyl]carbamate

Sodium triacetoxyhydroborate (4.38 g, 20.0 mmol) was added to a solution of benzyl[(1R,3S)-3-aminocyclopentyl]carbamate (5.23 g, 15.0 mmol) and benzaldehyde (1.7 mL, 16.0 mmol) in dichloromethane (75 mL) at room temperature. The mixture was stirred for 21 hours and then aqueous 1 M sodium hydroxide solution (75 mL) was added to make the solution basic. The aqueous layer was extracted with dichloromethane (2×25 mL). The combined organic layers were washed with brine (50 mL), dried over sodium sulfate and concentrated. The crude material was chromatographed on silica gel eluting with a mixture of dichloromethane and methanol (100:0 to 88:12) to afford the title compound as a yellow oil (3.47 g, 71%). $^1$H NMR (400 MHz, CDCl$_3$): δ 7.35-7.31 (m, 5H), 7.30-7.26 (m, 5H), 5.07 (s, 2H), 4.17-4.07 (m, 1H) 3.76-3.68 (m, 2H), 3.27-3.20 (m, 1H), 2.02-1.51 (m, 6H).

Step 3: (1S,3R)—N—Benzyl-N'-methylcyclopentane-1,3-diamine

Lithium aluminum hydride (1.02 g, 26.9 mmol) was added in portions to a solution of benzyl[(1R,3S)-3-(benzylamino)cyclopentyl]carbamate (3.47 g, 10.7 mmol) in tetrahydrofuran (70 mL) at room temperature. The reaction was heated to reflux for 3.5 hours. The mixture was then cooled in an ice bath and sequentially quenched with water (1.0 mL), aqueous 15% sodium hydroxide solution (1.0 mL) and water (3.0 mL). The suspension was diluted with ethyl acetate and filtered through Celite. The filtrate was concentrated and the residue was taken up in aqueous 0.5 M hydrochloric acid solution. The mixture was washed with diethyl ether (2×20 mL) and the aqueous solution was made basic (pH-11) with sodium hydroxide. The resulting mixture was extracted with dichloromethane (3×25 mL). The combined organic layers were dried over sodium sulfate and concentrated. The crude material was chromatographed on silica gel eluting with a mixture of dichloromethane and methanol (90:10) to afford the title compound as a yellow oil (204 mg, 9%). $^1$H NMR (400 MHz, CDCl$_3$): δ 7.33-7.20 (m, 5H), 3.74 (s, 2H), 3.19-3.13 (m, 1H), 3.08-3.02 (m, 1H) 2.39 (s, 3H), 2.09-2.03 (m, 1H), 1.87-1.81 (m, 2H), 1.67-1.54 (m, 2H), 1.46-1.39 (m, 1H). LC/MS (exact mass) calculated for C$_{13}$H$_{20}$N$_2$; 204.163. found (M+H$^+$); 205.1.

Example 12

1-(3,3-Difluorocyclobutyl)-N-{cis-3-[methyl(7H-pyrrolo[2,3-d]pyrimidin-4-yl)amino]cyclobutyl}methanesulfonamide Step 1: Benzyl[cis-3-(methyl{7-[(4-methylphenyl)sulfonyl]-7H-pyrrolo[2,3-d]pyrimidin-4-yl}amino)cyclobutyl]carbamate 4-Chloro-7-[(4-methylphenyl)sulfonyl]-7H-pyrrolo[2,3-d]pyrimidine (15 g, 48.7 mmol) and benzyl[cis-3-(methylamino)cyclobutyl]carbamate (17.2 g, 63.5 mmol) were mixed with isopropyl alcohol (180 mL) and diisopropylethylamine (28 mL, 161 mmol). The resulting slurry was heated at 75° C. for 6 hours. The reaction was cooled to room temperature, filtered, washed with isopropyl alcohol (150 mL) and dried in an oven at 50° C. to give the title compound (23.5 g, 95%) as a white solid. $^1$H NMR (400 MHz, DMSO-d$_6$): δ 8.38 (s, 1H), 8.03 (d, 2H), 7.45 (d, 1H), 7.38-7.28 (m, 4H), 7.26 (s, 1H), 7.25 (d, 1H), 6.61 (d, 1H), 5.08 (s, 2H), 4.96 (d, 1H), 4.77 (m, 1H), 3.88 (m, 1H), 3.23 (s, 3H), 2.71 (m, 2H), 2.36 (s, 3H), 2.18 (m, 2H).

Step 2: cis-N-Methyl-N-{7-[(4-methylphenyl)sulfonyl]-7H-pyrrolo[2,3-d]pyrimidin-4-yl}cyclobutane-1,3-diamine dihydrobromide Benzyl[cis-3-(methyl{7-[(4-methylphenyl)sulfonyl]-7H-pyrrolo[2,3-d]pyrimidin-4-yl}amino)cyclobutyl]carbamate (15.2 g, 30.1 mmol) was suspended in ethyl acetate (45 mL) and acetic acid (45 mL). To the slurry was slowly added a 4M solution of HBr in acetic acid (45 mL, 180 mmol), maintaining the temperature below 25° C. The resulting slurry was stirred at room temperature for 2 hours. The solids were collected by filtration, washed with ethyl acetate (450 mL), and dried at 40° C. to afford the title compound (16 g; 100%) as a white solid. $^1$H NMR (400 MHz, DMSO-d$_6$): δ 8.31 (s, 1H), 8.20 (s, 2H), 7.97 (d, 2H), 7.72 (d, 1H), 7.44 (d, 2H), 7.08 (d, 1H), 4.93 (m, 1H), 3.54 (m, 1H), 3.30 (s, 3H), 2.50 (m, 4H), 2.35 (s, 3H). LC/MS (exact mass) calculated for C$_{18}$H$_{21}$N$_6$O$_2$S; 371.142. found (M+H$^+$); 372.1.

Step 3: ({[(3,3-Difluorocyclobutyl)methyl]thio}methyl)benzene

A mixture of (3,3-difluorocyclobutyl)methyl 4-methylbenzenesulfonate (see WO2010/032200A1) (4 g, 14.5 mmol), benzyl imidothiocarbamate (3.53 g, 17.4 mmol), sodium hydroxide solution (1.45 g, 36.2 mmol, dissolved in 16 mL water) and N,N-dimethylformamide (16 mL) was stirred at 60° C. for 16 hours. Water (40 mL) and ethyl acetate (150 mL) were added. The organic layer was washed with water (40 mL), separated, dried over sodium sulfate and concentrated. The residue was chromatographed on silica gel eluting with a gradient of petroleum ether and ethyl acetate (100:0 to 95:5) to afford the title compound as colorless oil (3.2 g, 81%). $^1$H NMR (400 MHz, CDCl$_3$): δ 7.34-7.24 (m, 5H), 5.71 (s, 2H), 2.71-2.61 (m, 2H), 2.57-2.55 (m, 2H), 2.30-2.14 (m, 3H).

Step 4: (3,3-Difluorocyclobutyl)methanesulfonyl chloride

This compound was prepared following the procedure of Example 8 Step 2, substituting S-[3-(cyanomethyl)-3-methylcyclobutyl]ethanethioate for 2-(benzylthio)isonicotinonitrile to afford the title compound as a colorless oil (93%). $^1$H NMR (400 MHz, CDCl$_3$): δ 3.88-3.86 (m, 2H), 3.03-2.94 (m, 3H), 2.61-2.49 (m, 2H).

Step 5: 1-(3,3-Difluorocyclobutyl)-N-[cis-3-(methyl{7-[(4-methylphenyl)sulfonyl]-7H-pyrrolo[2,3-d]pyrimidin-4-yl}amino)cyclobutyl]methanesulfonamide A solution of (3,3-difluorocyclobutyl)methanesulfonyl chloride (2.5 g, 12.19 mmol) in 10 mL dichloromethane was added dropwise to a solution of cis-N-methyl-N-{7-[(4-methylphenyl)sulfonyl]-7H-pyrrolo[2,3-d]pyrimidin-4-yl}cyclobutane-1,3-diamine dihydrobromide (3.25 g, 6.10 mmol) and triethylamine (3.08 g, 30.49 mmol) in dichloromethane (150 mL) at 0° C. over 15 minutes. The reaction was stirred at room temperature for 4 hours. Water (50 mL) was added and the organic layer was separated. The aqueous layer was extracted with dichloromethane (2×150 mL), and the combined organic layers were separated dried over sodium sulfate. The crude compound was purified by chromatography on silica gel eluting with a gradient of dichloromethane and methanol (100:0 to 90:10) to afford the title compound as a white solid (2.0 g, 61%). LC/MS (exact mass) calculated for C$_{23}$H$_{27}$F$_2$N$_5$O$_4$S$_2$; 539.147. found (M+H$^+$); 540.1.

Step 6: 1-(3,3-Difluorocyclobutyl)-N-{cis-3-[methyl(7H-pyrrolo[2,3-d]pyrimidin-4-yl)amino]cyclobutyl}methanesulfonamide A solution of 1-(3,3-difluorocyclobutyl)-N-[cis-3-(methyl{7-[(4-methylphenyl)-sulfonyl]-7H-pyrrolo[2,3-d]pyrimidin-4-yl}amino)cyclobutyl]methanesulfonamide (2 g, 3.71 mmol) and lithium hydroxide monohydrate (780 mg, 18.6 mmol) in ethanol (40 mL) and water (20 mL) was stirred at 60° C. for 4 hours. The ethanol was evaporated and the remaining aqueous layer was neutralized to pH 7 with hydrochloric acid and subsequently extracted with dichloromethane (2×200 mL). The combined organic layers was dried over sodium sulfate, filtered, concentrated, and purified by preparative high performance liquid chromatography to afford the title compound (800 mg, 56%) as a white solid. $^1$H NMR (400 MHz, methanol-d$_4$): δ 8.15 (s, 1H), 8.13 (s, 1H), 7.16-7.15 (m, 1H), 6.73-6.62 (m, 1H), 4.95-4.88 (m, 1H), 3.73-3.71 (m, 1H), 3.38 (s, 3H), 3.28-3.26 (m, 2H), 2.87-2.78 (m, 4H), 2.63-2.61 (m, 1H), 2.56-2.48 (m, 2H), 2.35-2.28 (m, 2H). LC/MS (exact mass) calculated for C$_{16}$H$_{21}$F$_2$N$_6$O$_2$S; 385.138. found (M+H$^+$); 386.1.

The following compounds, Examples 13-14, were prepared from cis-N-methyl-N-{7-[(4-methylphenyl)sulfonyl]-7H-pyrrolo[2,3-d]pyrimidin-4-yl}cyclobutane-1,3-diamine dihydrobromide (Example 12, Step 2) in a similar manner to that described in Example 12, Step 5, substituting the indicated sulfonyl chloride for (3,3-difluorocyclobutyl)methanesulfonyl chloride and using the deprotection method illustrated in Example 12, Step 6.

Example 13

3,3-Difluoro-N-{cis-3-[methyl(7H-pyrrolo[2,3-d]pyrimidin-4-yl)amino]cyclobutyl}cyclobutanesulfonamide This compound was prepared using 3,3-difluorocyclobutanesulfonyl chloride using the procedure in PCT Publication No. WO2011/068881. The crude compound was purified by chromatography on silica gel eluting with a gradient of petroleum ether and ethyl acetate (80:20 to 10:90) to afford the title compound as an off-white solid (22% over 2 steps). $^1$H NMR (400 MHz, methanol-d$_4$): δ 8.13 (s, 1H), 7.13 (d, 1H), 6.70 (d, 1H), 4.86-4.81 (m, 1H), 3.78-3.72 (m, 2H), 3.35 (s, 3H), 3.01-2.93 (m, 4H), 2.78-2.76 (m, 2H), 2.32-2.25 (m, 2H). LC/MS (exact mass) calculated for C$_{16}$H$_{16}$F$_2$N$_6$O$_2$S; 371.123. found (M+H$^+$); 372.1.

Example 14

1-Cyclopropyl-N-{cis-3-[methyl(7H-pyrrolo[2,3-d]pyrimidin-4-yl)amino]cyclobutyl}methanesulfonamide This compound was prepared as a white solid using cyclopropylmethanesulfonyl chloride (73% over 2 steps). $^1$H NMR (400 MHz, DMSO-d$_6$): δ 11.64 (br. s., 1H), 8.11 (s, 1H), 7.53 (d, 1H), 7.12-7.19 (m, 1H), 6.64 (m, 1H), 4.84-4.97 (m, 1H), 3.54-3.70 (m, 1H), 3.26 (s, 3H), 2.93 (d, 2H), 2.55-2.66 (m, 2H), 2.29-2.22 (m, 2H), 0.96-1.09 (m, 1H), 0.53-0.64 (m, 2H), 0.29-0.39 (m, 2H). LC/MS (exact mass) calculated for C$_{15}$H$_{19}$F$_2$N$_5$O$_2$S; 335.142. found (M+H$^+$); 336.0.

Example 15

1-Cyclopropyl-N-{cis-3-[methyl(7H-pyrrolo[2,3-d]pyrimidin-4-yl)amino]cyclobutyl}azetidine-3-sulfonamide

Step 1: tert-Butyl 3-({[cis-3-(methyl{7-[(4-methylphenyl)sulfonyl]-7H-pyrrolo[2,3-d]pyrimidin-4-yl}amino)cyclobutyl]amino}sulfonyl)azetidine-1-carboxylate cis-N-Methyl-N-{7-[(4-methylphenyl)sulfonyl]-7H-pyrrolo[2,3-d]pyrimidin-4-yl}cyclobutane-1,3-diamine dihydrobromide (7.0 g, 18.8 mmol) was free-based by stirring in excess aqueous 1N sodium hydroxide solution for 3 minutes and then extracting into dichloromethane. The organic layer was dried over sodium sulfate and concentrated. The remaining free base was taken up in dichloromethane (200 mL), cooled to 0° C. and treated with and triethylamine (13 mL, 94 mmol) and tert-butyl 3-(chlorosulfonyl)azetidine-1-carboxylate. The reaction was allowed to stir at room temperature for 10 minutes. The crude mixture was washed with water and brine, then dried over sodium sulfate and concentrated to afford the crude product as a white solid. The solid was crystallized using a mixture of dichloromethane and diethyl ether to afford the title compound as a white solid (9.61 g, 90%). $^1$H NMR (400 MHz, methanol-d$_4$): δ 8.19 (s, 1H), 7.92-8.01 (m, 2H), 7.54 (d, 1H), 7.35 (d, 2H), 6.86 (d, 1H), 4.76-4.65 (m, 1H), 4.18 (br. s., 2H), 3.99-4.10 (m, 3H), 3.66-3.78 (m, 1H), 3.25 (s, 3H), 2.64-2.78 (m, 2H), 2.37 (s, 3H), 2.10-2.25 (m, 2H), 1.41 (s, 9H). LC/MS (exact mass) calculated for $C_{26}H_{34}N_6O_6S_2$; 590.198. found (M+H$^+$); 591.45.

Step 2: N-[cis-3-(Methyl{7-[(4-methylphenyl)sulfonyl]-7H-pyrrolo[2,3-c]pyrimidin-4-yl}amino)cyclobutyl]azetidine-3-sulfonamide Acetyl chloride (0.20 mL, 2.8 mmol) was added to a solution of tert-butyl 3-({[cis-3-(methyl{7-[(4-methylphenyl)sulfonyl]-7H-pyrrolo[2,3-d]pyrimidin-4-yl}amino)cyclobutyl]amino}sulfonyl)azetidine-1-carboxylate (1.64 g, 2.78 mmol) in anhydrous dichloromethane (18 mL) and methanol (7 mL) at 0° C. The reaction mixture was stirred at room temperature for 16 hours. The white precipitate was filtered off and taken up in saturated aqueous sodium bicarbonate solution (20 mL). The resulting solution was extracted with dichloromethane (3×20 mL) and the combined organic layers were dried over sodium sulfate and concentrated to afford the title compound (810 mg, 60%) as a white solid. LC/MS (exact mass) calculated for $C_{21}H_{26}N_6O_4S_2$; 490.146. found (M+H$^+$); 491.0.

Step 3: 1-Cyclopropyl-N-[bis-3-(methyl{7-[(4-methylphenyl)sulfonyl]-7H-pyrrolo[2,3-d]pyrimidin-4-yl}amino)cyclobutyl]azetidine-3-sulfonamide N-[cis-3-(Methyl{7-[(4-methylphenyl)sulfonyl]-7H-pyrrolo[2,3-d]pyrimidin-4-yl}amino)cyclobutyl]azetidine-3-sulfonamide (810 mg, 1.65 mmol), methanol (10 mL), molecular sieves, and [(1-ethoxycyclopropyl)oxy](trimethyl)silane (0.53 mL, 2.64 mmol) were combined in a sealable reaction vessel. The vessel was purged with nitrogen and acetic acid (1.28 mL, 8.26 mmol) was added. The vessel was sealed and then heated at 80° C. for 2 hours. After the mixture was cooled to room temperature, sodium cyanoborohydride (273 mg, 4.13 mmol) was added. The vessel was resealed and heated slowly to 40° C. for 1.5 hours. The crude mixture was filtered over a bed of Celite, rinsing with methanol. The filtrate was concentrated and the residue was taken up an aqueous saturated sodium bicarbonate solution. The resulting solution was extracted with dichloromethane (5×20 mL), and the combined organic layers were dried over sodium sulfate and concentrated to afford the title compound (576 mg, 74%) as a white solid. $^1$H NMR (400 MHz, methanol-d$_4$): δ 8.23 (s, 1H), 7.95-8.05 (m, 2H), 7.58 (d, 1H), 7.39 (d, 2H), 6.90 (d, 1H), 4.69-4.83 (m, 1H), 3.94-4.09 (m, 1H), 3.65-3.75 (m, 3H), 3.54-3.64 (m, 2H), 3.29 (s, 3H), 2.67-2.79 (m, 2H), 2.41 (s, 3H), 2.15-2.29 (m, 2H), 2.02-2.15 (m, 1H), 0.43-0.51 (m, 2H), 0.29-0.39 (m, 2H). LC/MS (exact mass) calculated for $C_{24}H_{30}N_6O_4S_2$; 530.177. found (M+H$^+$); 531.0.

Step 4: 1-Cyclopropyl-N-{cis-3-[methyl(7H-pyrrolo[2,3-d]pyrimidin-4-yl)amino]cyclobutyl}azetidine-3-sulfonamide A solution of cesium carbonate (976 mg, 3.0 mmol) in water (5 mL) was added to a solution of 1-cyclopropyl-N-[cis-3-(methyl{7-[(4-methylphenyl)sulfonyl]-7H-pyrrolo[2,3-d]pyrimidin-4-yl}amino)cyclobutyl]azetidine-3-sulfonamide (530 mg, 1.0 mmol) in ethanol (10 mL). The reaction mixture was heated to reflux for 16 hours. After the solvent was removed, remaining material was taken up in water and extracted with a mixture of dichloromethane and methanol (96:4; 3×10 mL). The combined organic layers were dried over sodium sulfate and concentrated. The crude solid was crystallized from methanol to afford the title compound (225 mg, 59%) as a white solid. $^1$H NMR (400 MHz, methanol-d$_4$): δ 8.10 (s, 1H), 7.09 (d, 1H), 6.66 (d, 1H), 4.88-4.80 (m, 1H), 4.03-3.96 (m, 1H), 3.73-3.65 (m, 3H), 3.61-3.57 (m, 2H), 3.32 (s, 3H), 2.77-2.68 (m, 2H), 2.28-2.19 (m, 2H), 2.08-2.03 (m, 1H), 0.46-0.41 (m, 2H), 0.34-0.31 (m, 2H). LC/MS (exact mass) calculated for $C_{17}H_{24}N_6O_2S$; 376.168. found (M+H$^+$); 377.0.

Example 16

N-(Cyclopropylmethyl)-N'-{cis-3-[methyl(7H-pyrrolo[2,3-d]pyrimidin-4-yl)amino]cyclobutyl}sulfamide Step 1: N-[cis-3-(Methyl{7-[(4-methylphenyl)sulfonyl]-7H-pyrrolo[2,3-d]pyrimidin-4-yl}amino)cyclobutyl]-2-oxo-1,3-oxazolidine-3-sulfonamide To a solution of chlorosulfonyl isocyanate (1.76 mL, 20.6 mmol) in dichloromethane (150 mL) was added dropwise a solution of 2-bromoethanol (1.43 mL, 20.6 mmol) in dichloromethane (80 mL) at 0° C. After 30 minutes at 0° C., a solution of cis-N-methyl-N-{7-[(4-methylphenyl)sulfonyl]-7H-pyrrolo[2,3-d]pyrimidin-4-yl}cyclobutane-1,3-diamine dihydrobromide (11.0 g, 20.6 mmol) and triethylamine (10.42 g, 103.2 mmol) in dry dichloromethane (80 mL) was added dropwise, and the reaction mixture was allowed to warm to room temperature overnight. The reaction solution was dissolved in dichloromethane (1 L), washed with aqueous 1M hydrochloric acid solution (2×800 mL) and brine (500 mL). The solution was dried over sodium sulfate and concentrated to afford the title compound as white solid (8.5 g, 79%). $^1$H NMR (400 MHz, CD$_3$OD): δ 8.22 (s, 1H), 8.00 (d, 2H), 7.58 (d, 1H), 7.38 (d, 2H), 6.91 (d, 1H), 4.88 (m, 1H), 4.45-4.41 (m, 2H), 4.06-4.02 (m, 2H), 3.75 (m, 1H), 3.29 (s, 3H), 2.72-2.69 (m, 2H), 2.40 (s, 3H); 2.30-3.27 (m, 2H). LC/MS (exact mass) calculated for $C_{21}H_{24}N_6O_6S_2$; 520.120. found (M+H$^+$); 521.4.

Step 2: N-(Cyclopropylmethyl)-N'-[cis-3-(methyl{7-[(4-methylphenyl)sulfonyl]-7H-pyrrolo[2,3-d]pyrimidin-4-yl}amino)cyclobutyl]sulfamide A solution of N-[cis-3-(methyl{7-[(4-methylphenyl)sulfonyl]-7H-pyrrolo[2,3-d]pyrimidin-4-yl}amino)cyclobutyl]-2-oxo-1,3-oxazolidine-3-sulfonamide (150 mg, 0.29 mmol), cyclopropanemethylamine (51 mg, 0.72 mmol) and triethylamine (116 mg, 1.15 mmol) in acetonitrile (3 mL) was stirred for 15 minutes at 100° C. using microwave heating. The reaction mixture was concentrated to afford the crude title compound (146 mg, 100% crude yield) as a yellow oil. LC/MS (exact mass) calculated for $C_{22}H_{28}N_6O_4S_2$; 504.161. found (M+H$^+$); 505.2.

Step 3: N-(Cyclopropylmethyl)-N'-{cis-3-[methyl (7H-pyrrolo[2,3-d]pyrimidin-4-yl)amino] cyclobutyl}sulfamide A solution of N-(cyclopropylmethyl)-N'-[cis-3-(methyl{7-[(4-methylphenyl)sulfonyl]-7H-pyrrolo[2,3-d]pyrimidin-4-yl}amino)cyclobutyl]sulfamide (146 mg, 0.29 mmol), lithium hydroxide monohydrate (48 mg, 1.15 mmol) in ethanol (5 mL) and water (2.5 mL) was stirred at 100° C. for 1 h. The reaction mixture was concentrated under vacuum and the crude product was purified by preparative high performance liquid chromatography to afford the title compound (14 mg, 14%) as a white solid. $^1$H NMR (400 MHz, methanol-d$_4$): δ 8.12 (s, 1H), 7.13 (d, 1H), 6.90 (d, 1H), 4.90-4.86 (m, 1H), 3.63-3.59 (m, 1H), 3.37 (s, 3H), 2.85-2.83 (m, 2H), 2.78-2.71 (m, 2H), 2.33-2.26 (m, 2H), 1.05-1.03 (m, 1H), 0.57-0.52 (m, 2H); 0.30-0.25 (m, 2H). LC/MS (exact mass) calculated for $C_{15}H_{22}N_6O_2S$; 350.152. found (M+H$^+$); 351.2.

The following compounds, Examples 17-18, were prepared from N-[cis-3-(methyl{7-[(4-methylphenyl)sulfonyl]-7H-pyrrolo[2,3-d]pyrimidin-4-yl}amino)cyclobutyl]-2-oxo-1,3-oxazolidine-3-sulfonamide (Example 16, Step 1) in a similar manner to that described in Example 16, Step 2, substituting the indicated amine for cyclopropanemethylamine, and using the deprotection method illustrated in Example 16, Step 3.

Example 17A and 17B (R)- and (S)-3-Cyano-N-{cis-3-[methyl(7H-pyrrolo [2,3-d]pyrimidin-4-yl)amino]cyclobutyl}pyrrolidine-1-sulfonamide These compounds were prepared using racemic pyrrolidine-3-carbonitrile hydrochloride. The crude racemic mixture was purified by high performance liquid chromatography to afford a white solid (60 mg, 52% over 2 steps). The enantiomers were separated by supercritical fluid chromatography.

Enantiomer A (17A): 24 mg (21%): $^1$H NMR (400 MHz, CD$_3$OD): δ 8.13 (s, 1H), 7.13 (d, J=3.2 Hz, 1H), 6.69 (d, 1H, J=3.6 Hz, 1H), 4.87-4.84 (m, 1H), 3.73-3.67 (m, 1H), 3.65-3.57 (m, 1H), 3.53-3.50 (m, 2H), 3.48-3.44 (m, 2H), 3.405 (s, 3H), 2.77-2.75 (m, 2H), 2.42-2.20 (m, 4H). LC/MS (exact mass) calculated for $C_{16}H_{21}N_7O_2S$; 375.148. found (M+H$^+$); 376.1. Chiral HPLC retention time=5.97 minutes.

Enantiomer B (17B): 25 mg (21%). $^1$H NMR (400 MHz, CD$_3$OD): δ 8.13 (s, 1H), 7.13 (d, J=3.2 Hz, 1H), 6.69 (d, 1H, J=3.6 Hz, 1H), 4.87-4.84 (m, 1H), 3.73-3.67 (m, 1H), 3.65-3.57 (m, 1H), 3.53-3.50 (m, 2H), 3.48-3.44 (m, 2H), 3.405 (s, 3H), 2.77-2.75 (m, 2H), 2.42-2.20 (m, 4H). LC/MS (exact mass) calculated for $C_{16}H_{21}N_7O_2S$; 375.148. found (M+H$^+$); 376.1. Chiral HPLC retention time=5.16 minutes.

Example 18

2-Methyl-N-{cis-3-[methyl(7H-pyrrolo[2,3-d]pyrimidin-4-yl)amino]cyclobutyl}2,6-dihydropyrrolo [3,4-c]pyrazole-5(4H)-sulfonamide This compound was prepared using 2-methyl-2,4,5,6-tetrahydropyrrolo[3,4-c]pyrazole hydrochloride. The crude compound was purified by high performance liquid chromatography to afford the title compound as an off-white solid (24% over 2 steps). $^1$H NMR (400 MHz, methanol-d$_4$): δ 8.08 (s, 1H), 7.38 (s, 1H), 7.10 (d, 1H), 6.66 (d, 1H), 4.87-4.86 (m, 1H), 4.42-4.41 (m, 4H), 3.87 (s, 3H), 3.71-3.67 (m, 1H), 3.31 (s, 3H), 2.68-2.61 (m, 2H), 2.27-2.22 (m, 3H). LC/MS (exact mass) calculated for $C_{17}H_{22}N_8O_2S$; 402.159. found (M+H$^+$); 403.2 and (M+Na); 425.1.

Example 19

N-{cis-3-[Methyl(7H-pyrrolo[2,3-d]pyrimidin-4-yl) amino]cyclobutyl}-6-oxa-3-azabicyclo[3.1.1]heptane-3-sulfonamide Step 1: N-[cis-3-(Methyl{7-[(4-methylphenyl)sulfonyl]-7H-pyrrolo[2,3-d]pyrimidin-4-yl}amino)cyclobutyl]-6-oxa-3-azabicyclo[3.1.1]heptane-3-sulfonamide A mixture of N-[cis-3-(Methyl{7-[(4-methylphenyl) sulfonyl]-7H-pyrrolo[2,3-d]pyrimidin-4-yl}amino)cyclobutyl]-2-oxo-1,3-oxazolidine-3-sulfonamide (208 mg, 0.40 mmol), 6-oxa-3-azabicyclo[3.1.1]heptane (50 mg, 0.50 mmol), triethylamine (220 µL, 1.58 mmol) in acetonitrile (15 mL), was heated in a 20 mL microwave vial in a microwave reactor for 1 hour at 120° C. Excess solvent was evaporated and the resulting oil was taken up in dichloromethane. The solution was washed with aqueous ammonium chloride and brine. The crude material was dried over sodium sulfate and concentrated to give an oil. This was chromatographed on silica gel eluting with a gradient methanol in dichloromethane (0:100 to 5:100) to afford the title compound as a foam (82 mg, 30%). $^1$H NMR (CDCl$_3$): δ 8.38 (s, 1H), 8.04 (d, 2H), 7.48 (d, 1H), 7.28 (d, 2H), 6.63 (d, 1H), 4.78-4.69 (m, 1H), 4.62 (d, 1H), 4.47 (d, 1H), 3.69-3.61 (m, 1H), 3.58 (d, 3H), 3.26-3.17 (m, 1H), 3.24 (s, 3H), 2.83-0.275 (m, 2H), 2.37 (s, 3H), 2.18-2.11 (m, 2H), 2.04 (d, 1H), 1.18 (t, 1H). LC/MS (exact mass) calculated for $C_{23}H_{28}N_6O_5S_2$; 532.156. found (M+H$^+$); 533.

Step 2: N-{cis-3-[Methyl(7H-pyrrolo[2,3-d]pyrimidin-4-yl)amino]cyclobutyl}-6-oxa-3-azabicyclo [3.1.1]heptane-3-sulfonamide N-[cis-3-(Methyl{7-[(4-methylphenyl)sulfonyl]-7H-pyrrolo[2,3-d]pyrimidin-4-yl}amino)cyclobutyl]-6-oxa-3-azabicyclo[3.1.1]heptane-3-sulfonamide (229 mg, 0.43 mmol) was added to a solution of in 1M tetrabutylammonium fluoride in tetrahydrofuran (6.5 mL, 6.4 mmol). The reaction was stirred at room temperature for 10 hours. The mixture was concentrated and the remaining material was chromatographed on silica gel eluting with a mixture of methanol in ethyl acetate (1:9). A yellow oil was isolated that was triturated with a mixture of ethyl acetate and hept-ane to give a yellow solid. The solid was partitioned between ethyl acetate and water. The aqueous layer was extracted with ethyl acetate and the combined organic layers were washed with brine, dried over sodium sulfate and concentrated to afford an off-white solid. This was triturated with diethyl ether and then isopropyl alcohol to afford the title compound as a white solid (14 mg, 9%). $^1$H NMR (CD$_3$OD) δ 8.08 (s, 1H), 7.09 (d, 1H), 6.66 (s, 1H), 4.90-4.81 (m, 1H), 4.62 (d, 2H), 3.86-8.84 (m, 1H), 3.66 (t, 1H), 3.56-3.49 (m, 3H), 3.33 (s, 3H), 3.19-3.13 (m, 1H), 2.75-2.70 (m, 2H), 2.32-2.24 (m, 2H), 2.05-2.03 (d, 1H). LC/MS (exact mass) calculated for $C_{16}H_{22}N_6O_3S$; 378.147. found (M+H$^+$); 379.5.

The following compounds, Examples 20-24, were prepared from N-[cis-3-(methyl{7-[(4-methylphenyl)sulfonyl]-7H-pyrrolo[2,3-d]pyrimidin-4-yl}amino)cyclobutyl]-2-oxo-1,3-oxazolidine-3-sulfonamide (Example 16, Step 1) in a similar manner to that described in Example 16, Step 2, substituting the indicated amine for cyclopropanemethylamine, and using the deprotection method illustrated in Example 19, Step 2.

Example 20

3-Cyano-N-{cis-3-[methyl(7H-pyrrolo[2,3-d]pyrimidin-4-yl)amino]-cyclobutyl}azetidine-1-sulfonamide This compound was prepared using azetidine-3-carbonitrile. The crude compound was purified by high performance liquid chromatography to afford the title compound as a white solid (23% over 2 steps). $^1$H NMR (400 MHz, CD$_3$OD): δ 8.10 (s, 1H), 7.11 (d, 1H), 6.68 (d, 1H), 4.80 (m, 1H), 4.02 (m, 2H), 3.90 (m, 2H), 3.58 (m, 2H), 3.32 (s, 3H), 2.72 (m, 2H), 2.25 (m, 2H). LC/MS (exact mass) calculated for $C_{15}H_{19}N_7O_2S$; 361.132. found (M+H$^+$); 362.1.

Example 21

N-{cis-3-[Methyl(7H-pyrrolo[2,3-d]pyrimidin-4-yl)amino]cyclobutyl}-4-(1H-pyrazol-3-yl)piperidine-1-sulfonamide This compound was prepared using 4-(1H-pyrazol-3-yl)piperidine. The crude compound was purified by chromatography on silica gel eluting with a mixture of dichloromethane and methanol (9:1). The isolated material was triturated with diethyl ether and then ethyl acetate to afford the title compound as a white solid (10% over 2 steps). $^1$H NMR (300 MHz, CD$_3$OD): δ 8.09 (s, 1H), 7.48 (s, 1H), 7.12-7.05 (m, 1H), 6.71-6.60 (m, 1H), 6.22-6.08 (m, 1H), 4.92-4.73 (m, 1H), 3.80-3.55 (m, 3H), 3.41 (s, 3H), 2.90-2.65 (m, 5H), 2.38-2.19 (m, 2H), 2.09-1.90 (m, 2H) and 1.83-1.65 (m, 2H). LC/MS (exact mass) calculated for $C_{19}H_{26}N_8O_2S$; 430.190. found (M+H$^+$); 431.1.

Example 22

N-(2-Cyanoethyl)-N-methyl-N'-{cis-3-[methyl(7H-pyrrolo[2,3-d]pyrimidin-4-yl)amino]cyclobutyl}sulfamide This compound was prepared using 3-methylaminopropionitrile. The crude compound was purified by high performance liquid chromatography to afford the title compound (7% over 2 steps). LC/MS (exact mass) calculated for $C_{15}H_{21}N_7O_2S$; 363.148. found (M+H$^+$); 364.0.

Example 23 and 27

(1S,5S)-1-Cyano-N-{cis-3-[methyl(7H-pyrrolo[2,3-d]pyrimidin-4-yl)amino]cyclobutyl}-3-azabicyclo[3.1.0]hexane-3-sulfonamide and (1R,5R)-1-Cyano-N-{cis-3-[methyl(7H-pyrrolo[2,3-d]pyrimidin-4-yl)amino]cyclobutyl}-3-azabicyclo[3.1.0]hexane-3-sulfonamide These compounds were prepared using racemic 3-azabicyclo[3.1.0]hexane-1-carbonitrile. The crude racemic compound was purified as a white solid (92 mg, 21% over 2 steps) by chromatography on silica gel eluting with a gradient of dichloromethane and methanol (30:1 to 5:1). The title enantiomers were separated by supercritical fluid chromatography.

Enantiomer 23: 41 mg (9%); SFC retention time=4.28 minutes; $^1$H NMR (400 MHz, methanol-d$_4$): δ 8.13 (s, 1H), 7.13 (d, 1H), 6.70 (d, 1H), 4.61 (s, 1H), 3.57-3.72 (m, 2H), 3.43-3.51 (m, 3H), 3.36 (s, 3H), 2.70-2.77 (m, 2H), 2.24-2.38 (m, 3H), 1.41-1.48 (m, 1H), 1.32 (t, 1H). LC/MS (exact mass) calculated for $C_{17}H_{21}N_7O_2S$; 387.148. found (M+H$^+$); 388.1.

Enantiomer 27: 40 mg (9%); SFC retention time=4.84 minutes $^1$H NMR (400 MHz, methanol-d$_4$): δ 8.13 (s, 1H), 7.13 (d, 1H), 6.70 (d, 1H), 4.61 (s, 1H), 3.57-3.72 (m, 2H), 3.43-3.51 (m, 3H), 3.36 (s, 3H), 2.70-2.77 (m, 2H), 2.24-2.38 (m, 3H), 1.41-1.48 (m, 1H), 1.32 (t, 1H). LC/MS (exact mass) calculated for $C_{17}H_{21}N_7O_2S$; 387.148. found (M+H$^+$); 388.1.

Racemic 3-azabicyclo[3.1.0]hexane-1-carbonitrile was prepared as follows.

Step 1: Racemic tert-butyl rac-1-formyl-3-azabicyclo[3.1.0]hexane-3-carboxylate 1,1,1-Triacetoxy-1,1-dihydro-1,2-benziodoxol-3(1H)-one (6.5 g, 15.2 mmol) was added to a solution of racemic tert-butyl-1-(hydroxymethyl)-3-azabicyclo[3.1.0]hexane-3-carboxylate (Synlett 2009, 921) (2.5 g, 11.7 mmol) in anhydrous dichloromethane (60 mL). The reaction mixture stirred for 2 hours at room temperature. The mixture was diluted with dichloromethane (60 mL), washed with a saturated aqueous solution of sodium sulfite, saturated sodium bicarbonate (30 mL) and brine (50 mL). The organic layer was dried over sodium sulfate and concentrated to give afford the title compound as a colorless oil (1.7 g, 68%). $^1$H NMR (400 MHz, CDCl$_3$): δ 9.01 (d, 1H), 3.83 (d, 1H), 3.68 (t, 1H), 3.59 (dd, 1H), 3.50-3.36 (m, 1H), 2.25-2.09 (m, 1H), 1.63 (t, 1H), 1.43 (s, 9H), 1.19-1.06 (m, 1H).

Step 2: Racemic tert-butyl-1-[(hydroxyimino)methyl]-3-azabicyclo[3.1.0]hexane-3-carboxylate Potassium carbonate (3.89 g, 28.2 mmol) and hydroxylamine hydrochloride (671 mg, 9.7 mmol) were added to a solution of tert-butyl racemic 1-formyl-3-azabicyclo[3.1.0]hexane-3-carboxylate (1.7 g, 8.05 mmol) in anhydrous dichloromethane (40 mL) at room temperature and then stirred for 16 hours. The mixture was diluted with ethyl acetate (80 mL), and washed with water (30 mL) and brine (30 mL). The organic layer was dried over sodium sulfate and concentrated. The residue was chromatographed on silica gel eluting with a gradient of petroleum ether and ethyl acetate (0:100 to 83:17) to afford the title compound as a yellow oil (1.6 g, 88%). $^1$H NMR (400 MHz, CDCl$_3$): δ 7.18 (s, 1H), 3.74-3.55 (m, 3H), 3.44-3.40 (m, 1H), 1.74-1.72 (m, 1H), 1.44 (s, 9H), 1.10 (t, 1H), 0.86-0.83 (m, 1H).

Step 3: Racemic tert-butyl-1-cyano-3-azabicyclo[3.1.0]hexane-3-carboxylate

To a solution of racemic tert-butyl-1-[(hydroxyimino)methyl]-3-azabicyclo[3.1.0]hexane-3-carboxylate (925 mg, 4.09 mmol) in anhydrous tetrahydrofuran (100 mL) was added methyl N-(triethylammonium sulfonyl)carbamate (2.92 g, 12.3 mmol). The reaction mixture was heated to reflux for 3 hours. After evaporation of the solvent, the residue was chromatographed on silica gel eluting with a mixture of petroleum ether and ethyl acetate (5:1) to afford the title compound as a colorless oil (570 mg, 67%). $^1$H NMR (400 MHz, CDCl$_3$): δ 3.84 (dd, 1H), 3.64 (dd, 1H), 3.50 (d, 1H), 3.46 (dd, 1H), 2.21-2.12 (m, 1H), 1.44 (s, 9H), 0.96 (t, 1H).

Step 4: Racemic 3-azabicyclo[3.1.0]hexane-1-carbonitrile

A solution of racemic tert-butyl-1-cyano-3-azabicyclo [3.1.0]hexane-3-carboxylate in trifluoroacetic acid (1 mL) and dichloromethane (10 mL) was stirred at room temperature for 1 hour. The solvent was removed to afford the title compound (205 mg, 100%) as a brown oil.

Example 24

Racemic 3-cyano-N-{trans-3-[methyl(7H-pyrrolo[2,3-d]pyrimidin-4-yl)amino]cyclobutyl}pyrrolidine-1-sulfonamide This compound was synthesized following the procedure of Example 10, substituting 3-cyanopyrrolidine-1-sulfonyl chloride for cyclopropylmethanesulfonyl chloride. The crude product was purified using preparative high performance liquid chromatography to afford the title compound as an off-white solid (5%). $^1$H NMR (400 MHz, CD$_3$OD): δ 8.13 (s, 1H), 7.14 (d, 1H), 6.67 (d, 1H), 5.45-5.41 (m, 1H), 4.00-3.64 (m, 1H), 3.62-3.52 (m, 1H), 3.51-3.47 (m, 2H), 3.45-3.39 (m, 2H), 3.369 (s, 3H), 2.78-2.70 (m, 2H), 2.53-2.47 (m, 2H); 2.39-2.36 (m, 1H); 2.27-2.24 (m, 1H). LC/MS (exact mass) calculated for C$_{16}$H$_{21}$N$_7$O$_2$S; 375.148. found (M+H$^+$); 375.9.

Racemic 3-cyanopyrrolidine-1-sulfonyl chloride

A solution of racemic pyrrolidine-3-carbonitrile (53 mg, 0.4 mmol) and triethylamine (101 g, 1 mmol) in dry dichloromethane (1.0 mL) was added dropwise to a stirred solution of sulfuryl chloride (64.8 mg, 0.48 mmol) in dichloromethane (3.0 mL) was added at −78° C. The reaction was stirred at −78° C. for 30 minutes, and then allowed to warm to room temperature over 1 hour. The reaction solution was washed with aqueous 1M hydrochloric acid (5 mL) and brine (5 mL), dried over sodium sulfate and concentrated to afford the title compound as colorless oil (68 mg, crude).

Example 25

N-(cis-3-{[(4,4-Difluoropiperidin-1-yl)sulfonyl] methyl}cyclobutyl)-N-methyl-7H-pyrrolo[2,3-d] pyrimidin-4-amine Step 1: cis/trans-Ethyl 3-[(tert-butoxycarbonyl) amino]cyclobutanecarboxylate To a solution of a mixture of cis- and trans-ethyl 3-aminocyclobutanecarboxylate hydrochloride (cis/trans=10:1) (WO2009/60278) (10 g, 55.7 mmol) and triethylamine (19.4 mL, 139.1 mmol.) in dichloromethane (370 mL) at 0° C. was added dropwise di-tert-butyl dicarbonate (15.8 g, 72.3 mmol). After addition was complete, the mixture was stirred at room temperature overnight. The solvent was evaporated under reduced pressure and the resulting residue was chromatographed on silica gel eluting with a gradient of petroleum ether and ethyl acetate (10:1 to 3:1) to afford the title mixture as a white solid (19 g, 92%). $^1$H NMR (400 MHz, CDCl$_3$): δ 4.77 (s, 1H), 4.13 (q, 3H), 2.68-2.82 (m, 1H), 2.60 (d, 2H), 1.99-2.17 (m, 2H), 1.43 (s, 9H), 1.25 (t, 3H).

Step 2: cis/trans-[3-(Methylamino)cyclobutyl] methanol

Lithium aluminum hydride (9.14 g, 240.4 mmol) was suspended in dry tetrahydrofuran (350 mL). The mixture was cooled to 0° C. and a solution of cis/trans ethyl 3-[(tert-butoxycarbonyl)amino]cyclobutanecarboxylate (cis/trans=10:1) (11.7 g, 48.1 mmol) in dry tetrahydrofuran (170 mL) was added drop wise. After addition was complete, the resulting mixture was heated to reflux overnight. After it was cooled to room temperature, the reaction was diluted with tetrahydrofuran (1.5 L) and then cooled to 0-5° C. Small portions of Na$_2$SO$_4$.10H$_2$O were added until gas evolution had ceased. The mixture was filtered to remove the solids, which were washed with more tetrahydrofuran (500 mL). The filtrate was concentrated to dryness affording the title mixture (cis/trans=10:1) as an oil (10 g, >100%). $^1$H NMR (400 MHz, CDCl$_3$): δ 3.58 (d, J=3.8 Hz, 2H), 3.06-3.17 (m, 1H), 2.34-2.43 (m, 3H), 2.32 (s, 3H), 1.48-1.57 (m, 2H).

Step 3: cis/trans-[3-(Methyl{7-[(4-methylphenyl) sulfonyl]-7H-pyrrolo[2,3-d]pyrimidin-4-yl}amino) cyclobutyl]methanol Potassium iodide (173 mg) and triethylamine (13 mL, 93.8 mmol) were added to a solution of cis/trans-[3-(methylamino)cyclobutyl]methanol (6.0 g, 52.1 mmol) in acetone (250 mL). 4-Chloro-7-[(4-methylphenyl)sulfonyl]-7H-pyrrolo[2,3-d]pyrimidine (14.4 g, 46.9 mmol) was then added and the resulting mixture was heated to reflux overnight. After evaporation of the solvent under reduced pressure, the residue was diluted with dichloromethane (500 mL). The solution was washed sequentially with water (300 mL), 2% aqueous citric acid (300 mL) and brine (300 mL), and then dried over sodium sulfate. After filtration, the solution was filtered and concentrated to afford the title mixture as a light solid (15.3 g, 85%). A portion (5.0 g) of the cis/trans-[3-(methyl{7-[(4-methylphenyl)sulfonyl]-7H-pyrrolo[2,3-d] pyrimidin-4-yl}amino)-cyclobutyl]methanol mixture was separated by supercritical fluid chromatography using a Chiralpak-AD column:

cis isomer, 4.6 g: $^1$H NMR (400 MHz, methanol-d$_4$): δ 8.20 (s, 1H), 7.98 (d, 2H), 7.53 (d, 1H), 7.34 (d, 2H), 6.83 (d, 2H), 4.99-4.95 (m, 1H), 3.56 (d, J=5.6 Hz, 1H), 3.24 (s, 3H), 2.36 (s, 3H), 2.34-2.28 (m, 2H), 2.24-2.19 (m, 1H), 2.11-2.03 (m, 2H). LC/MS (exact mass) calculated for C$_{19}$H$_{22}$N$_4$O$_3$S: 386.14. found (M+H$^+$): 387.3.

trans isomer, 0.4 g: $^1$H NMR (400 MHz, methanol-d$_4$): δ 8.20 (s, 1H), 7.98 (d, 2H), 7.55 (d, 1H), 7.35 (d, 2H), 6.84 (d, 2H), 5.26-5.22 (m, 1H), 3.69 (d, 1H), 3.30 (s, 3H), 2.46-2.41 (m, 3H), 2.39 (s, 3H), 2.19-2.14 (m, 2H). LC/MS (exact mass) calculated for C$_{19}$H$_{22}$N$_4$O$_3$S: 386.14. found (M+H$^+$): 387.3.

Step 4: cis-[3-(Methyl{7[(4-methylphenyl)sulfonyl]-7H-pyrrolo[2,3-d]pyrimidin-4-yl}amino)cyclobutyl] methyl 4-methylbenzenesulfonate To a solution of cis-[3-(methyl{7-[(4-methylphenyl) sulfonyl]-7H-pyrrolo[2,3-d]pyrimidin-4-yl}amino)cyclobutyl]methanol (20 g, 51.8 mmol) and N,N-dimethylaminopyridine (12.6 g, 103.6 mmol) in dichloromethane (500 mL) at 0° C. was added p-toluenesulfonyl chloride (14.8 g, 77.7 mmol). The reaction mixture was stirred at room temperature for 16 hours and then washed with water (500 mL). The combined aqueous washes were extracted with dichloromethane (2×800 mL). The combined organic layers were dried, filtered and concentrated under vacuum. The residue was chromatographed on silica gel eluting with a gradient of dichloromethane and methanol (100:0 to 95:5) to afford the title compound (23 g, 82%) as a white solid. LC/MS (exact mass) calculated for $C_{26}H_{28}N_4O_5S_2$: 540.150. found (M+H$^+$): 541.3.

Step 5: S-{[cis-3-(Methyl{7[(4-methylphenyl)sulfonyl]-7H-pyrrolo[2,3-d]pyrimidin-4-yl}amino)cyclobutyl]methyl}ethanethioate To a solution of potassium thioacetate (678 mg, 5.93 mmol) in N,N-dimethylformamide (5 mL) was added a solution of [cis-3-(methyl{7-[(4-methylphenyl)sulfonyl]-7H-pyrrolo[2,3-d]pyrimidin-4-yl}amino)cyclobutyl]methyl 4-methylbenzenesulfonate (2.0 g, 3.70 mmol) in N,N-dimethylformamide (6 mL) dropwise over 5 minutes at room temperature. The mixture was then heated to at 50-55° C. overnight. The mixture was cooled to room temperature and quenched by pouring into aqueous saturated sodium bicarbonate solution (60 mL). The mixture was extracted with ethyl acetate (3×30 mL) and the combined organic layers were washed with water (3×30 mL), brine (30 mL). After drying over $Na_2SO_4$ the solution was concentrated. The residue was chromatographed on silica gel eluting with a gradient of dichloromethane and methanol (100:0 to 80:20) to afford the title compound (1.2 g, 73%) as a yellow solid. $^1$H NMR (400 MHz, CDCl$_3$): δ 8.39 (s, 1H), 8.04 (d, 2H), 7.45 (d, 1H), 7.27 (d, 2H), 6.63 (d, 1H), 4.98-4.88 (m, 1H) 3.22 (s, 3H) 3.02-3.00 (m, 2H) 2.45-2.44 (m, 2H), 2.47 (m, 3H) 2.22 (m, 3H) 2.21-2.24 (m, 1H) 1.92-1.87 (m, 2H). LC/MS (exact mass) calculated for $C_{21}H_{24}N_4O_3S_2$: 444.129. found (M+H$^+$): 445.1.

Step 6: [cis-3-(Methyl{7[(4-methylphenyl)sulfonyl]-7H-pyrrolo[2,3-d]pyrimidin-4-yl}amino)cyclobutyl]methanesulfonic acid To a solution of S-{[cis-3-(methyl{7-[(4-methylphenyl)sulfonyl]-7H-pyrrolo[2,3-d]pyrimidin-4-yl}amino)cyclobutyl]methyl}ethanethioate (580 mg, 1.31 mmol), in formic acid (10 mL) at room temperature was added 30% aqueous hydrogen peroxide solution (0.7 mL, 6.92 mmol). The resulting mixture was stirred at room temperature overnight. The reaction was poured into an aqueous 33% aqueous sodium bisulfate solution (1.12 mL) and then stirred for 10 minutes. Aqueous 33% sodium hydroxide solution (1.8 mL) was then added to adjust the pH to 5. The resulting mixture was stirred at room temperature for 1 hour. The solid was collected solid by filtration, washed with water (10 mL) and vacuum dried at about 60° C. to afford the title compound (634 mg, crude) as a white solid. LC/MS (exact mass) calculated for $C_{19}H_{22}N_4O_5S_2$; 450.103. found (M+H$^+$); 451.3.

Step 7: cis-[3-(Methyl{7-[(4-methylphenyl)sulfonyl]-7H-pyrrolo[2,3-d]pyrimidin-4-yl}amino)cyclobutyl]methanesulfonyl chloride Thionyl chloride (0.3 ml, 3.33 mmol) was added dropwise over 5 minutes to a solution of cis-[3-(methyl{7-[(4-methylphenyl)sulfonyl]-7H-pyrrolo[2,3-d]pyrimidin-4-yl}amino)cyclobutyl]methanesulfonic acid (150 mg, 0.33 mmol) in dichloromethane (20 mL) at 0° C. Two drops of N,N-dimethylformamide were added to the solution, which was then heated at 75° C. for 2 hours. The mixture was cooled and the solvent was evaporated. The residue was washed with anhydrous dichloromethane (3×10 mL) to afford the crude title compound (170 mg) as a yellow solid. LC/MS (exact mass) calculated for $C_{19}H_{21}ClN_4O_4S_2$; 468.069. found (M+H$^+$); 469.2.

Step 8: N-(cis-3-{[(4,4-Difluoropiperidin-1-yl)sulfonyl]methyl}cyclobutyl)-N-methyl-7-[(4-methylphenyl)sulfonyl]-7H-pyrrolo[2,3-d]pyrimidin-4-amine To a mixture of 4,4-difluoropiperidine (77 mg, 0.64 mmol) and triethylamine (97 mg, 0.96 mmol) in tetrahydrofuran (20 mL) at 0° C. was added dropwise a solution of cis-[3-(methyl{7-[(4-methylphenyl)sulfonyl]-7H-pyrrolo[2,3-d]pyrimidin-4-yl}amino)cyclobutyl]methanesulfonyl chloride (150 mg, 0.320 mmol) in tetrahydrofuran (10 mL). The mixture was allowed to warm to room temperature overnight. The solvent was evaporated and the residue was taken up in ethyl acetate (80 mL). The solution was washed with brine (30 mL), dried over sodium sulfate and concentrated to afford the crude title compound (134 mg) as a white solid. LC/MS (exact mass) calculated for $C_{24}H_{29}F_2N_5O_4S_2$; 553.651. found (M+H$^+$); 554.3.

Step 9: N-(cis-3-{[(4,4-difluoropiperidin-1-yl)sulfonyl]methyl}cyclobutyl)-N-methyl-7H-pyrrolo[2,3-d]pyrimidin-4-amine N-(cis-3-{[(4,4-Difluoropiperidin-1-yl)sulfonyl]methyl}cyclobutyl)-N-methyl-7-[(4-methylphenyl)sulfonyl]-7H-pyrrolo[2,3-d]pyrimidin-4-amine (134 mg, 0.24 mmol) and lithium hydroxide monohydrate (51 mg, 1.21 mmol) were combined in a mixture of ethanol (14 mL) and water (7 mL) and then heated at 50° C. overnight. The reaction was concentrated under vacuum and diluted with ethyl acetate (100 mL). The resulting solution was washed with brine (30 mL), dried over sodium sulfate and concentrated. The residue was chromatographed using preparative thin layer chromatography eluting with a mixture of ethyl acetate and methanol (20:1) to afford the title compound (31 mg, 32.3%) as a white solid. $^1$H NMR (400 MHz, methanol-d$_4$): δ 8.13 (s, 1H), 7.13 (d, J=3.6, 1H), 6.70 (d, J=3.6, 1H), 5.12 (m, 1H), 3.49-3.47 (m, 4H), 3.46 (m, 3H), 3.33 (m, 2H), 2.62-2.54 (m, 3H), 2.25-2.20 (m, 1H), 2.11-2.05 (m, 2H). LC/MS (exact mass) calculated for $C_{17}H_{23}F_2N_5O_2S$; 399.154. found (M+H$^+$); 400.3.

Examples 26 to 29

The following compounds were made starting from cis-[3-(methyl{7-[(4-methylphenyl)sulfonyl]-7H-pyrrolo[2,3-d]pyrimidin-4-yl}amino)cyclobutyl]methanesulfonyl chloride (Example 25, Step 7), according to the procedures of Example 25, Step 8 (sulfonylation) and step 9 (deprotection), substituting the appropriate amine for 4,4-difluoropiperidine in Step 8.

Example 26

1-[({cis-3-[Methyl(7H-pyrrolo[2,3-d]pyrimidin-4-yl)amino]cyclobutyl}-methyl)sulfonyl]-4-(trifluoromethyl)piperidin-4-ol The title compound (31 mg) was prepared using 4-(trifluoromethyl)piperidin-4-ol in the sulfonylation step and was deprotected using the method from Example 25, Step 9. The compound was purified using preparative thin layer chromatography eluting with eluting with a mixture of ethyl acetate and methanol (20:1). $^1$H NMR (400 MHz, methanol-d$_4$): δ 8.13 (s, 1H), 7.13 (d, J=3.6, 1 H), 6.70 (d, J=3.6, 1H), 5.10-5.08 (m, 1H), 3.74-3.71 (m, 2H), 3.36 (m, 3H), 3.32-3.27 (m, 2H), 3.19-3.13 (m, 2H), 2.62-2.54 (m, 3H), 2.25-2.21 (m, 2H), 1.86-1.84 (m, 4H). LC/MS (exact mass) calculated for C$_{18}$H$_{24}$F$_3$N$_5$O$_3$S; 447.155. found (M+H$^+$); 448.3.

Example 28 and 29

(3R) and (3S)-1-[({cis-3-[Methyl(7H-pyrrolo[2,3-d]pyrimidin-4-yl)amino]cyclobutyl}methyl)sulfonyl]pyrrolidine-3-carbonitrile The title compounds (330 mg total) were prepared using pyrrolidine-3-carbonitrile enriched as an 80:20 scalemic mixture of (3R)-pyrrolidine-3-carbonitrile and (3S)-pyrrolidine-3-carbonitrile enantiomers in the sulfonylation step and was de-protected using the method from Example 19, Step 2. The compound was purified by chromatography on silica gel eluting with gradient of petroleum ether and ethyl acetate (10:1 to 1:10). LC/MS m/z=375.2 (M+1). The enantiomers were separated by preparative supercritical fluid chromatography:

3R-enantiomer (28): 178 mg. $^1$H NMR (400 MHz, CDCl$_3$): δ 8.31 (s, 1H), 7.06 (d, 1H), 6.58 (d, 1H), 5.19-5.10 (m, 1H), 3.77-3.75 (m, 1H), 3.61-3.54 (m, 3H), 3.33 (s, 3H), 3.21-3.19 (m, 3H), 2.69-2.66 (m, 3H), 2.36-2.31 (m, 2H), 2.14-2.11 (m, 2H). LC/MS (exact mass) calculated for C$_{17}$H$_{22}$N$_6$O$_2$S; 374.15. found (M+H$^+$); 375.2. Chiral HPLC retention time=2.65 minutes 3S-enantiomer (29): 31 mg. $^1$H NMR (400 MHz, CDCl$_3$): δ 8.31 (s, 1H), 7.06 (d, 1H), 6.58 (d, 1H), 5.19-5.10 (m, 1H), 3.77-3.75 (m, 1H), 3.61-3.54 (m, 3H), 3.33 (s, 3H), 3.21-3.19 (m, 3H), 2.69-2.66 (m, 3H), 2.36-2.31 (m, 2H), 2.14-2.11 (m, 2H). LC/MS (exact mass) calculated for C$_{17}$H$_{22}$N$_6$O$_2$S; 374.15. found (M+H$^+$); 375.2 Chiral HPLC retention time=2.53 minutes Example 30

N-{cis-3-[(Butylsulfonyl)methyl]cyclobutyl}-N-methyl-7H-pyrrolo[2,3-d]pyrimidin-4-amine Step 1: N-{cis-3-[(Butylthio)methyl]cyclobutyl}-N-methyl-7H-pyrrolo[2,3-d]pyrimidin-4-amine A solution of cis-[3-(methyl{7-[(4-methylphenyl)sulfonyl]-7H-pyrrolo[2,3-d]pyrimidin-4-yl}amino)cyclobutyl]methyl 4-methylbenzenesulfonate from Example 25, Step 4 (23 g, 42.6 mmol) was stirred in N-methylpyrrolidine (100 mL). Then 1,8-diazabicycloundec-7-ene (12.8 g, 85.2 mmol) and 1-butanethiol (7.8 g, 85.2 mmol) was added to the reaction mixture. The reaction was stirred at room temperature for 16 hours. Water (200 mL) and ethyl acetate (500 mL) were added. The aqueous layer was extracted with ethyl acetate (2×500 mL) and the combined organic layers were dried and concentrated. The residue was chromatographed on silica gel eluting with a gradient of dichloromethane and methanol (100:0 to 90:10) to afford the title compound (11.8 g, 91%). LC/MS (exact mass) calculated for C$_{16}$H$_{24}$N$_4$S; 304.172. found (M+H$^+$); 305.3.

Step 2: N-{cis-3-[(Butylsulfonyl)methyl]cyclobutyl}-N-methyl-7H-pyrrolo[2,3-d]pyrimidin-4-amine N-{cis-3-[(Butylthio)methyl]cyclobutyl}-N-methyl-7H-pyrrolo[2,3-d]pyrimidin-4-amine (12 g, 39.5 mmol) was dissolved in a mixture of tetrahydrofuran (200 mL), ethanol (200 mL) and water (200 mL). Potassium peroxomonosulfate (48.6 g, 79.0 mmol) was added and the reaction was stirred at room temperature for 1 hour. The mixture was then filtered; the solids were washed with a mixture of tetrahydrofuran (40 mL), ethanol (40 mL) and water (20 mL). The filtrate was treated with aqueous 10% sodium bisulfite solution (200 mL) and stirred at room temperature for 20 minutes. A saturated solution of aqueous sodium bicarbonate was added to adjust the pH to 7. The mixture was extracted with dichloromethane (3×800 mL) and the combined organic layers were dried and concentrated under vacuum. The crude residue was chromatographed on silica gel eluting with a gradient of dichloromethane and methanol (100:0 to 95:5) to obtain the title compound (11.4 g, 86%). $^1$H NMR (400 MHz, methanol-d$_4$): δ 8.13 (s, 1H), 7.13-7.12 (m, 1H), 6.70-6.69 (m, 1H), 5.13-5.10 (m, 1H), 3.42 (s, 3H), 3.33 (m, 2H), 3.11-3.07 (m, 2H), 2.65-2.63 (m, 3H), 2.29-2.25 (m, 2H), 1.86-1.78 (m, 2H), 1.55-1.50 (m, 2H), 1.03-0.99 (m, 3H). LC/MS (exact mass) calculated for C$_{16}$H$_{24}$N$_4$O$_2$S; 336.162. found (M+H$^+$); 337.3.

Example 31

N-Methyl-N-(trans-3-((propylsulfonyl)methyl)cyclobutyl)-7H-pyrrolo[2,3-d]pyrimidin-4-amine The title compounds were made as a mixture of cis and trans isomers (50 mg) starting from cis and trans-[3-(methyl{7-[(4-methylphenyl)sulfonyl]-7H-pyrrolo[2,3-d]pyrimidin-4-yl}amino)cyclobutyl]methyl 4-methylbenzenesulfonate (cis/trans=10:1) (Example 25, Step 4), according to procedures similar to those of Example 30, Steps 1 and 2, using propane-1-thiol instead of butane-1-thiol in Step 2. The mixture of cis and trans isomers was purified by reverse phase high performance liquid chromatography eluting with gradient of water and acetonitrile (95:5 to 5:95). LC/MS (exact mass) calculated for C$_{15}$H$_{22}$N$_4$O$_2$S; 322.15. found (M+H$^+$); 323.2.

The cis and trans isomers were then separated by preparative supercritical fluid chromatography.

trans isomer (31), 12 mg: $^1$H NMR (400 MHz, methanol-d$_4$): δ 8.12 (s, 1H), 7.13-7.12 (m, 1H), 6.69-6.66 (m, 1H), 5.45-5.41 (m, 1H), 3.46-3.44 (m, 2H), 3.36 (s, 3H), 3.11-3.09 (m, 2H), 2.88-2.86 (m, 1H), 2.75-2.67 (m, 2H), 2.40-2.38 (m, 2H), 1.91-1.86 (m, 2H), 1.12-1.10 (m, 3H). LC/MS (exact mass) calculated for C$_{15}$H$_{22}$N$_4$O$_2$S; 322.15. found (M+H$^+$); 323.2.

cis isomer, 36 mg: $^1$H NMR (400 MHz, methanol-d$_4$): δ 8.12 (s, 1H), 7.13-7.12 (m, 1H), 6.70-6.69 (m, 1H), 5.10-5.20 (m, 1H), 3.36 (s, 3H), 3.33-3.32 (m, 2H), 3.08-3.04 (m, 2H), 2.64-2.61 (m, 3H), 2.24-2.22 (m, 2H), 1.90-1.84 (m, 2H), 1.13-1.09 (m, 3H). LC/MS (exact mass) calculated for C$_{15}$H$_{22}$N$_4$O$_2$S; 322.15. found (M+H$^+$); 323.2.

Example 32

N-(cis-3-{[(2-Cyclopropylethyl)sulfonyl]methyl}cyclobutyl)-N-methyl-7H-pyrrolo[2,3-d]pyrimidin-4-amine

Step 1: N-(cis-3-{[(2-Cyclopropylethyl)sulfanyl]methyl}cyclobutyl)-N-methyl-7-[(4-methylphenyl)sulfonyl]-7H-pyrrolo[2,3-d]pyrimidin-4-amine Nitrogen was bubbled through a mixture of S-{[cis-3-(methyl{7-[(4-methylphenyl)sulfonyl]-7H-pyrrolo[2,3-d]pyrimidin-4-yl}amino)cyclobutyl]methyl}ethanethioate Example 25, Step 5 (190 mg, 0.43 mmol) and potassium carbonate (129 mg, 0.94 mmol) in methanol (10 mL) at 0° C. for 2 minutes. 2-Cyclopropylethyl 4-methylbenzenesulfonate (159 mg, 1.53 mmol) was then added and the solution was stirred for 6 hours at room temperature. Dichloromethane (30 mL) and water (20 mL) were added and the aqueous layer was extracted with dichloromethane (2×20 mL). The combined organic layers were washed with brine, dried over sodium sulfate and concentrated. The crude product was purified by preparative thin layer chromatography using ethyl acetate-petroleum ether (1:2) to give the title compound as a white solid (62 mg, 31%). LC/MS (exact mass) calculated for $C_{24}H_{30}N_4O_2S_2$; 470.18. found (M+H$^+$); 471.1.

Step 2: N-(cis-3-{[(2-Cyclopropylethyl)sulfonyl]methyl}cyclobutyl)-N-methyl-7-[(4-methylphenyl)sulfonyl]-7H-pyrrolo[2,3-d]pyrimidin-4-amine The mixture of N-(cis-3-{[(2-cyclopropylethyl)sulfanyl]-methyl}cyclobutyl)-N-methyl-7-[(4-methylphenyl)-sulfonyl]-7H-pyrrolo[2,3-d]pyrimidin-4-amine (24 mg, 0.051 mmol) and potassium peroxomonosulfate (49 mg, 0.079 mmol) in tetrahydrofuran (1.2 mL), water (0.6 mL) and ethanol (1.2 mL) was stirred at room temperature for 20 minutes. Aqueous sodium bisulfite was added, followed by dichloromethane (20 mL). The aqueous layer was extracted with dichloromethane (2×20 mL) and the combined organic layers were extracted with brine, dried over sodium sulfate and concentrated. The crude material was used directly in next step. LC/MS (exact mass) calculated for $C_{24}H_{30}N_4O_4S_2$; 502.17. found (M+H$^+$); 503.3.

Step 3: N-(cis-3-{[(2-Cyclopropylethyl)sulfonyl]methyl}cyclobutyl)-N-methyl-7H-pyrrolo[2,3-d]pyrimidin-4-amine The mixture of N-(cis-3-{[(2-cyclopropylethyl)sulfonyl]methyl}cyclobutyl)-N-methyl-7-[(4-methylphenyl)sulfonyl]-7H-pyrrolo[2,3-d]pyrimidin-4-amine (49 mg, 0.097 mmol) and lithium hydroxide (30 mg, 1.3 mmol) in water (5 mL) and ethanol (10 mL) was stirred at 50° C. for 2 hours. Then, dichloromethane (20 mL) was added and the aqueous layer was extracted with dichloromethane. The combined organic layers were washed with brine, dried over sodium sulfate and concentrated. The crude product was purified by reverse phase high performance liquid chromatography using a gradient of water and acetonitrile gradient (95:5 to 5:95) to give the title compound (14 mg, 40%) as white solid. $^1$H NMR (400 MHz, methanol-d$_4$): δ 8.12 (s, 1H), 7.13 (d, 2H), 6.70 (d, 2H), 5.12-5.09 (m, 1H), 3.34 (s, 3H), 3.34-3.33 (m, 2H), 3.20-3.17 (m, 2H), 2.64-2.61 (m, 3H), 2.26-2.22 (m, 2H), 1.75-1.69 (m, 2H), 0.89-0.86 (m, 2H), 0.56-0.52 (m, 2H), 0.18-0.17 (m, 2H). LC/MS (exact mass) calculated for $C_{17}H_{24}N_4O_2S$; 348.16. found (M+H$^+$); 349.1.

Example 33

N-[cis-3-({[(3,3-Difluorocyclobutyl)methyl]sulfonyl}-methyl)cyclobutyl]-N-methyl-7H-pyrrolo[2,3-d]pyrimidin-4-amine

Step 1: N-[cis-3-({[(3,3-Difluorocyclobutyl)methyl]sulfanyl}methyl)cyclobutyl]-N-methyl-7H-pyrrolo[2,3-d]pyrimidin-4-amine Nitrogen was bubbled through a mixture of S-{[cis-3-(methyl{7-[(4-methylphenyl)-sulfonyl]-7H-pyrrolo[2,3-d]pyrimidin-4-yl}amino)cyclobutyl]methyl}ethanethioate, Example 25, Step 5 (250 mg, 0.56 mmol) and potassium carbonate (194 mg, 1.41 mmol) in methanol (100 mL) for two minutes at 0° C. followed by addition of (3,3-difluorocyclobutyl)methyl 4-methylbenzenesulfonate (prepared as described in WO2004/032834) (310 mg, 1.12 mmol). The mixture stirred for 6 hours at room temperature, filtered, and concentrated to give the title compound (270 mg, crude) as white solid. LC/MS (exact mass) calculated for $C_{17}H_{22}F_2N_4S$; 352.15. found (M+H$^+$); 353.2.

Step 2: N-[cis-3-({[(3,3-Difluorocyclobutyl)methyl]sulfonyl}methyl)cyclobutyl]-N-methyl-7H-pyrrolo[2,3-d]pyrimidin-4-amine The mixture of N-[cis-3-({[(3,3-difluorocyclobutyl)methyl]sulfanyl}-methyl)cyclobutyl]-N-methyl-7H-pyrrolo[2,3-d]pyrimidin-4-amine (45 mg, 0.13 mmol) and potassium peroxomonosulfate (157 mg, 0.26 mmol) in a mixture of tetrahydrofuran (20 mL), water (10 mL) and ethanol (20 mL) was stirred at room temperature for 20 minutes. Aqueous sodium bisulfite was then added, followed by dichloromethane (20 mL). The aqueous layer was extracted with dichloromethane (2×20 mL) and the combined organic layers were extracted with brine, dried over sodium sulfate, and concentrated. The crude product was purified by reverse phase high performance liquid chromatography using water-acetonitrile gradient (95:5 to 5:95) to give the title compound as white solid (34 mg, 39%). $^1$H NMR (400 MHz, methanol-d$_4$): δ 8.29 (s, 1H), 7.42 (d, 1H), 7.03 (d, 1H), 4.86 (m, 1H), 3.51 (s, 3H), 3.39-3.33 (m, 4H), 2.84 (m, 1H), 2.76-2.71 (m, 4H), 2.53 (m, 2H), 2.37-2.34 (m, 2H). LC/MS (exact mass) calculated for $C_{17}H_{22}F_2N_4O_2S$; 384.14. found (M+H$^+$); 385.1.

Example 34A and 34B

(1R,3R) and (1S,3S)-[({cis-3-[methyl(7H-pyrrolo[2,3-d]pyrimidin-4-yl)amino]cyclobutyl}methyl)sulfonyl]cyclopentanecarbonitrile The title compound mixture of (1R,3R) and (1S,3S)-3-[({cis-3-[methyl(7H-pyrrolo[2,3-d]pyrimidin-4-yl)amino]cyclobutyl}-methyl)sulfonyl]cyclopentane-carbonitrile was prepared from S-{[cis-3-(methyl{7-[(4-methylphenyl)sulfonyl]-7H-pyrrolo[2,3-d]pyrimidin-4-yl}amino)cyclobutyl]methyl}ethanethioate Example 25, Step 5, according to the procedure of Example 30, steps 1 and 2.

The title compound (180 mg) was separated by preparative supercritical fluid chromatography using a Chiralpak AS column:

(1R,3R) enantiomer 34A: 60 mg, $^1$H NMR (400 MHz, methanol-d$_4$): δ 8.12 (s, 1H), 7.13-7.12 (d, 1H), 6.70-6.69 (d, 1H), 5.17-5.11 (m, 1H), 3.86-3.78 (m, 1H), 3.41-3.36 (m, 5H), 3.15-3.11 (m, 1H), 2.63-2.53 (m, 4H), 2.37-2.13 (m, 6H), 2.03-1.91 (m, 1H). LC/MS (exact mass) calculated for $C_{17}H_{22}F_2N_4O_2S$; 373.16. found (M+H$^+$); 374.1.

(1S,3S) enantiomer 34B: 27 mg, LC/MS (exact mass) calculated for $C_{17}H_{22}F_2N_4O_2S$; 373.16. found (M+H$^+$); 374.1.

The intermediate 3-cyanocyclopentyl 4-methylbenzenesulfonate used in step-1 was prepared as shown below:

3-Cyanocyclopentyl 4-methylbenzenesulfonate

4-Methylbenzene-1-sulfonyl chloride (6.9 g, 36 mmol) and N,N-dimethylpyridin-4-amine (100 mg) were added to a solution of compound 3-hydroxycyclopentane-carbonitrile (*J. Org. Chem.* 2007, 72, 7423) (2 g, 18 mmol) and triethylamine (5.5 g, 54 mmol) in dichloromethane (100 mL). The reaction was stirred at room temperature for 15 hours and then quenched mixture was quenched by addition of saturated aqueous sodium bicarbonate solution (20 mL). The mixture was extracted with dichloromethane (4×50 mL). The combined organic layers were dried over magnesium sulfate and concentrated. The residue was chromatographed on silica gel by eluting with a mixture of petroleum ether and ethyl acetate (1:1) to give the title compound as yellow oil (0.5 g, 11% yield). LC/MS (exact mass) calculated for $C_{13}H_{15}NO_3S$; 265.08. found (M+23); 287.9.

Example 35

Racemic N-methyl-N-[cis-3-({[1-(propan-2-yl)pyrrolidin-3-yl]sulfonyl}methyl)cyclobutyl]-7H-pyrrolo[2,3-d]pyrimidin-4-amine

Step 1: tert-Butyl 3-({[cis-3-(methyl{7[(4-methylphenyl)sulfonyl]-7H-pyrrolo[2,3-d]pyrimidin-4-yl}amino)cyclobutyl]methyl}sulfanyl)pyrrolidine-1-carboxylate The solution of cis-[3-(methyl{7-[(4-methylphenyl)sulfonyl]-7H-pyrrolo[2,3-d]pyrimidin-4-yl}amino)cyclobutyl] methyl 4-methylbenzenesulfonate from Example 25, Step 4 (2 g, 3.7 mmol) was stirred in N-methylpyrrolidine (40 mL). 1,8-Diazabicycloundec-7-ene (1.13 g, 7.4 mmol) and 3-mercapto-pyrrolidine-1-carboxylic acid tert-butyl ester (1.13 g, 5.6 mmol) were then added to the reaction mixture. The reaction was stirred at room temperature for 16 hours. Water (200 mL) and ethyl acetate (500 mL) were added. The aqueous layer was extracted with ethyl acetate (2×500 mL). and the combined organic layers were dried and concentrated under vacuum to give the title compound as a white solid (2.6 g, 118%). LC/MS (exact mass) calculated for $C_{28}H_{37}N_5O_4S_2$; 571.23. found (M+H$^+$): 572.1.

Step 2: N-Methyl-7-[(4-methylphenyl)sulfonyl]-N-{cis-3-[(pyrrolidin-3-ylsulfanyl)methyl]cyclobutyl}-7H-pyrrolo[2,3-d]pyrimidin-4-amine To a solution of tert-butyl 3-({[cis-3-(methyl{7-[(4-methylphenyl)sulfonyl]-7H-pyrrolo[2,3-d]pyrimidin-4-yl}amino)cyclobutyl]methyl}sulfanyl)pyrrolidine-1-carboxylate (2.6 g, 4.5 mmol) in methanol (15 mL) was added 3M hydrochloric acid solution in methanol (40 mL). The resulting solution was stirred at room temperature for 1 hour. The solution was concentrated to give the crude product, which was purified by chromatography on silica gel eluting with a gradient of dichloromethane and methanol (100:0 to 85:15) to give the title compound as colorless oil (1.7 g, 52%). $^1$H NMR (400 MHz, methanol-d$_4$): δ 8.21 (s, 1H), 7.99 (d, 2H), 7.56 (d, 1H), 7.37 (d, 2H), 6.88 (d, 1H), 4.95-4.87 (m, 1H), 3.29 (s, 1H), 3.27 (s, 3H), 3.21-3.17 (m, 1H), 3.04-3.96 (m, 1H), 2.92-29 (m, 1H), 2.72-2.01 (m, 3H), 2.50-2.43 (m, 2H), 2.39 (s, 3H), 2.29-2.15 (m, 2H), 2.03-2.01 (m, 2H), 1.98-1.65 (m, 1H). LC/MS (exact mass) calculated for $C_{23}H_{29}N_5O_2S_2$; 471.18. found (M+23): 494.

Step 3: N-Methyl-7-[(4-methylphenyl)sulfonyl]-N-[cis-3-({[1-(propan-2-yl)pyrrolidin-3-yl]sulfanyl}methyl)cyclobutyl]-7H-pyrrolo[2,3-d]pyrimidin-4-amine To a solution of N-methyl-7-[(4-methylphenyl)sulfonyl]-N-{cis-3-[(pyrrolidin-3-ylsulfanyl)methyl]cyclobutyl}-7H-pyrrolo[2,3-d]pyrimidin-4-amine (472 mg, 1 mmol) in dichloromethane (50 mL) was added acetone (174 mg, 3 mmol), 4A molecular sieves (40 mg) and sodium cyanoborohydride (189 mg, 3 mmol). The resulting solution was stirred at room temperature for 1 hour, then diluted with dichloromethane (70 mL) and water (70 mL). The aqueous layer was extracted with dichloromethane (2×50 mL) and the combined organic layers were washed with brine (100 mL). The organic layer was dried over anhydrous sodium sulfate and concentrated to give title compound (500 mg, 97% yield) as colorless oil. LC/MS (exact mass) calculated for $C_{26}H_{35}N_5O_2S_2$; 513.22. found (M+H$^+$); 514.1.

Step 4: N-Methyl-7-[(4-methylphenyl)sulfonyl]-N-[cis-3-({[1-(propan-2-yl)pyrrolidin-3-yl]sulfonyl}methyl)cyclobutyl]-7H-pyrrolo[2,3-d]pyrimidin-4-amine The mixture of N-methyl-7-[(4-methylphenyl)sulfonyl]-N-[cis-3-({[1-(propan-2-yl)pyrrolidin-3-yl]sulfanyl}methyl)cyclobutyl]-7H-pyrrolo[2,3-d]pyrimidin-4-amine (500 mg, 1.0 mmol) and potassium peroxomonosulfate (1.23 g, 2.0 mmol) in tetrahydrofuran (20 mL), water (10 mL), and ethanol (20 mL) was stirred at room temperature for 30 minutes. The reaction solution was diluted with ethyl acetate (100 mL) and water (50 mL). The aqueous layer was extracted with ethyl acetate (3×50 mL) and the combined organic layers were washed with brine (100 mL), dried over sodium sulfate and concentrated to give title compound as colorless oil (420 mg, 90%). LC/MS (exact mass) calculated for $C_{26}H_{35}N_5O_4S_2$; 545.21. found (M+H$^+$): 546.3.

Step 5: N-Methyl-N-[cis-3-({[1-(propan-2-yl)pyrrolidin-3-yl]sulfonyl}methyl)-cyclobutyl]-7H-pyrrolo[2,3-d]pyrimidin-4-amine The mixture of N-methyl-7-[(4-methylphenyl)sulfonyl]-N-[cis-3-({[1-(propan-2-yl)pyrrolidin-3-yl]sulfonyl}methyl)cyclobutyl]-7H-pyrrolo[2,3-d]pyrimidin-4-amine (330 mg, 0.6 mmol) and lithium hydroxide (126 mg, 3 mmol) in a mixture of water (5 mL) and ethanol (10 mL) was stirred at 50° C. for 2 hours. The mixture was then concentrated and the residue was taken up in ethyl acetate. The organic layer was washed with brine, dried over sodium sulfate and concentrated. The crude product was purified by reverse phase high performance liquid chromatography using a gradient of water and acetonitrile (95:5 to 5:95) to give the title compound (89 mg, 38%) as white solid. $^1$H NMR (400 MHz, CDCl$_3$): δ 8.32 (s, 1H), 7.07 (d, 1H), 6.57 (d, 1H), 5.13 (m, 1H), 3.57 (m, 1H), 3.33 (s, 3H) 3.05-3.22 (m, 3H), 2.92 (m, 1H), 2.78-2.87 (m, 1H), 2.58-2.77 (m, 4H), 2.50 (m, 1H), 2.19-2.34 (m, 2H), 2.06-2.19 (m, 2H), 1.12 (d, 6H). LC/MS (exact mass) calculated for C$_{19}$H$_{29}$N$_5$O$_2$S; 391.20. found (M+H$^+$); 392.3.

Example 36

N-(cis-3-{[(3-Chloro-4-fluorophenyl)sulfonyl]methyl}cyclobutyl)-N-methyl-7H-pyrrolo[2,3-d]pyrimidin-4-amine Step 1: N-(cis-3-{[(3-Chloro-4-fluorophenyl)sulfanyl]methyl}cyclobutyl)-N-methyl-7H-pyrrolo[2,3-d]pyrimidin-4-amine To a solution of 3-chloro-4-fluorothiophenol (93 mg, 0.55 mmol) in tetrahydrofuran (1.5 mL) was added 50% aqueous sodium hydroxide (44 mg, 0.55 mmol) and ethanol (1.5 mL). The mixture was stirred at room temperature for 1 hour. A solution of cis-[3-(methyl{7-[(4-methylphenyl)sulfonyl]-7H-pyrrolo[2,3-d]pyrimidin-4-yl}amino)cyclobutyl]methyl 4-methylbenzenesulfonate from Example 25, Step 4 (200 mg, 0.37 mmol) in tetrahydrofuran (1.5 mL) was added to the reaction mixture. The combined mixture was heated at 40° C. overnight. The reaction was concentrated and purified by silica column eluting with a gradient of heptanes and ethyl acetate (90:10 to 0:100) to afford the title compound (69 mg, 49.6%). $^1$H NMR (400 MHz, CDCl$_3$): δ 8.18 (s, 1H), 7.39 (dd, 1H), 7.28 (s, 1H), 7.03-7.08 (m, 1H), 7.00 (d, 1H), 6.52 (d, 1H), 4.97-5.07 (m, 1H), 3.35 (m, 2H), 3.23 (s, 3H), 2.89 (s, 1H), 2.43-2.52 (m, 2H), 2.19-2.30 (m, 2H).

Step 2: N-(cis-3-{[(3-Chloro-4-fluorophenyl)sulfonyl]methyl}cyclobutyl)-N-methyl-7H-pyrrolo[2,3-d]pyrimidin-4-amine To a solution of N-(cis-3-{[(3-chloro-4-fluorophenyl)sulfanyl]methyl}cyclobutyl)-N-methyl-7H-pyrrolo[2,3-d]pyrimidin-4-amine (75 mg, 0.2 mmol) in dichloromethane (10 mL) was added 3-chlorobenzoperoxoic acid (107 mg). The reaction was stirred at room temperature overnight and then concentrated. The crude residue was chromatographed on silica gel eluting with a gradient of dichloromethane and 2M ammonia in methanol (80:20) to obtain the title compound (48 mg, 59.2%). $^1$H NMR (400 MHz, methanol-d$_4$): δ 8.31 (s, 1H), 8.02 (m, 1H), 7.81-7.83 (m, 1H) 7.37-7.27 (m, 1H), 7.09 (d, 1H), 6.65 (s, 1H), 5.18-5.10 (m, 1H), 4.15-4.09 (m, 1H), 3.32 (m, 5H), 2.59-2.54 (m, 2H), 2.44-2.42 (m, 2H). LC/MS (exact mass) calculated for C$_{18}$H$_{18}$ClFN$_4$O$_2$S; 408.08. found (M+H$^+$); 409.

Example 37

2-[({cis-3-[Methyl(7H-pyrrolo[2,3-d]pyrimidin-4-yl)amino]cyclobutyl}methyl) sulfonyl]pyridine-4-carbonitrile Step 1: 2-({[cis-3-(Methyl{7[(4-methylphenyl)sulfonyl]-7H-pyrrolo[2,3-d]pyrimidin-4-yl}amino)cyclobutyl]methyl}sulfanyl)pyridine-4-carbonitrile 1,8-Diazabicycloundec-7-ene (24.6 g, 161 mmol) and 2-mercapto-isonicotinonitrile (16.1 g, 118 mmol) were added to a solution of [cis-3-(methyl{7-[(4-methylphenyl)sulfonyl]-7H-pyrrolo[2,3-d]pyrimidin-4-yl}amino)cyclobutyl]-methyl methanesulfonate (50 g, 110 mmol) in N-methylpyrrolidine (250 mL). The reaction was heated at 50° C. overnight. Additional 2-mercaptoisonicotinonitrile (8.1 g, 59 mmol) was added to drive the reaction to completion. The mixture was cooled to about 0° C. and then the reaction was quenched by dropwise addition of water. The solids were collected by filtration, washed with water, and dried under vacuum at 50° C. to give the title compound as a bright yellow solid (45.8 g, 82.8%). LC/MS (exact mass) calculated for C$_{25}$H$_{24}$N$_6$O$_2$S$_2$; 504.14. found (M+H$^+$); 505.1.

Step 2: 2-[({cis-3-[Methyl(7H-pyrrolo[2,3-d]pyrimidin-4-yl)amino]cyclobutyl}methyl)sulfanyl]pyridine-4-carbonitrile To a solution of 2-({[cis-3-(methyl{7-[(4-methylphenyl)sulfonyl]-7H-pyrrolo[2,3-d]pyrimidin-4-yl}amino)cyclobutyl]methyl}sulfanyl)pyridine-4-carbonitrile (45.3 g, 89.8 mmol) in tetrahydrofuran (180 mL) was added a solution of 1M tetrabutylammonium fluoride in tetrahydrofuran (269 mL). The reaction mixture was heated to reflux for 6 hours and then cooled to room temperature. Water was added dropwise over 45 minutes. The solids were collected by filtration and washed with a mixture of 20% tetrahydrofuran (33 mL) and water (97 mL). The wet cake was dried under vacuum at 50° C. to give the title compound as a tan solid (25 g, 79%). LC/MS (exact mass) calculated for C$_{18}$H$_{18}$N$_6$S$_2$; 350.13. found (M+H$^+$); 351.1.

Step 3: 2-[({cis-3-[Methyl(7H-pyrrolo[2,3-d]pyrimidin-4-yl)amino]cyclobutyl}methyl)sulfonyl]pyridine-4-carbonitrile Potassium peroxomonosulfate (236.8 g, 385.2 mmol) was added slowly to a mixture of 2-[({cis-3-[methyl(7H-pyrrolo[2,3-d]pyrimidin-4-yl)amino]cyclobutyl}-methyl)sulfanyl]pyridine-4-carbonitrile (22.5 g, 64.2 mmol) in methanol (337 mL) and water (56 mL) at 0° C. The reaction was stirred at 3° C. for 20 hours. The reaction was quenched using 10% aqueous sodium bisulfate solution (40 mL). and the resulting slurry was stirred at room temperature for 2 hours. Aqueous 10% potassium carbonate solution was added until the pH was 4 to 5. The material was filtered and rinsed with water. The wet filter cake was dried under vacuum at 40° C. to give an off-white solid. This material was taken up in tetrahydrofuran (50 mL) and heated to reflux for 3 hours. The mixture was cooled to room temperature and filtered to collect the solid, which was dried under vacuum at 40° C. to the title compound as a light tan powder (17.3 g, 70.46%). $^1$H NMR (400 MHz, CDCl$_3$): δ 11.97 (s, 1H), 8.95 (d, 1H), 8.33-8.28 (m, 2H), 7.81 (d, 1H) 7.1 (d, 1H), 6.54 (d, 1H), 5.13-5.08 (m, 1H), 3.63 (m, 2H), 3.30 (s, 3H), 2.54-2.48 (m, 3H), 2.09-2.07 (m, 2H). LC/MS (exact mass) calculated for C$_{18}$H$_{18}$N$_6$O$_2$S$_2$; 382.12. found (M+H$^+$); 383.1.

Example 38

2-Methyl-N-{cis-3-[methyl(7H-pyrrolo[2,3-d]pyrimidin-4-yl)amino]cyclobutyl}-1,3-thiazole-5-sulfonamide Step 1: 2-Methyl-N-[cis-3-(methyl{7-[(4-methylphenyl)sulfonyl]-7H-pyrrolo[2,3-d]pyrimidin-4-yl}amino)cyclobutyl]-1,3-thiazole-5-sulfonamide Triethylamine (62.0 g, 0.613 mol) is added to a solution of cis-N-methyl-N-7H-pyrrolo[2,3-d]pyrimidin-4-ylcyclobutane-1,3-diamine hydrochloride (22.2. g, 0.102 mol) in dichloromethane (250 mL). 2-Methylthiazole-5-sulfonyl chloride (28.0 g, 0.142 mol) in dichloromethane (250 mL) is added over 30 minutes at room temperature to the reaction mixture. After 1.5 hours the solvent is removed under reduced pressure and the resultant solid dissolved in 4:1 ethyacetate:dichloromethane (400 mL). The solution is filtered through a 40 g silica plug, rinsing with ethylacetate (800 mL) and dichloromethane (100 mL). The solvent from the filtrate is removed under reduced pressure to give solid (59 g). The solid is purified using silica gel column chromatography eluting from 1:1 dichloromethane:ethylacetate to neat ethylacetate to give the title compound (44.4 g, 81%); m/z (Cl) 533 [M+H]$^+$.

Step 2: 2-Methyl-N-{cis-3-[methyl(7H-pyrrolo[2,3-d]pyrimidin-4-yl)amino]cyclobutyl}-1,3-thiazole-5-sulfonamide Lithium hydroxide (12.1 g, 0.505 mol) in water (290 mL) is added to 2-methyl-N-[cis-3-(methyl{7-[(4-methylphenyl)sulfonyl]-7H-pyrrolo[2,3-d]pyrimidin-4-yl}amino)cyclobutyl]-1,3-thiazole-5-sulfonamide (43.8 g, 82.2 mmol) in isopropyl alcohol (435 mL) and the mixture heated to 60° C. overnight. After cooling to room temperature the reaction mixture is filtered rinsing with water (145 mL). The filtrate is pH is adjusted to 6-7 using 6M aqueous hydrochloric acid. The reaction slurry is concentrated under reduced pressure. Water (370 mL) is added and the mixture cooled to 0° C. The solved is collected by filtration, washed with cold water (150 ml) then vacuum dried at 60° C. overnight to give the title compound (25.0 g, 80%); $^1$H NMR (DMSO-d6): δ 11.66-11.71 (1H), 8.44-8.47 (1H), 8.11-8.08 (2H), 7.16-7.17 (1H), 6.63-6.65 (1H), 4.86-4.94 (1H), 3.58-3.68 (1H), 3.22 (3H), 2.74 (3H), 2.40-2.46 (2H), 2.10-2.18 (2H). m/z (Cl) 379 [M+H]$^+$.

Example 39

N-{cis-3-[methyl(7H-pyrrolo[2,3-d]pyrimidin-4-yl)amino]cyclobutyl}-2,1,3-benzoxadiazole-4-sulfonamide Step 1: Benzyl[cis-3-(methylamino)cyclobutyl]carbamate and benzyl[trans-3-(methylamino)-cyclobutyl]carbamate A 33% solution of methylamine (1000 mL, 9.13 mol) in absolute ethanol was added to a mixture of benzyl(3-oxocyclobutyl)carbamate (WO2012/75381 and WO2012/09678) (200 g, 0.913 mol) and acetic acid (88 mL) stirring in ethanol (1000 mL) at 0° C. The reaction mixture stirred for at 0° C. for 1.5 hours and then stirred at room temperature for 2 hours. Lithium borohydride (41 g, 2.05 mol) was added in portions to the reaction mixture at −70° C. After addition was complete, the reaction mixture was stirred at −70° C. for 1 hour and then allowed to warm to room temperature over 12 hours. The reaction mixture was quenched with water (400 mL), and concentrated under vacuum to remove ethanol. The aqueous layer was acidified with concentrated hydrochloric acid to pH 2, washed with ethyl acetate (2×1000 mL), basified with 10% sodium hydroxide to pH 9-10 and then extracted with dichloromethane (3×1000 mL). The combined organic layers were washed with brine (1000 mL), dried over sodium sulfate, and concentrated to obtain the crude product as a pale brown liquid. This was dissolved in dichloromethane (400 mL) and cooled to 0° C. To the resulting solution was added a solution of 4M hydrochloric acid in dioxane (300 mL). The mixture was stirred at 0° C. for 30 minutes, and then at room temperature for 12 hours. The reaction mixture was filtered and the remaining solid was recrystallized from a mixture of methanol and methyl tert-butyl ether to afford the cis-isomer as a white solid (111.09 g, 52%). $^1$H NMR: (400 MHz, D$_2$O): δ 7.33-7.38 (m, 5H); 5.02 (s, 2H), 3.83-3.87 (m, 1H), 3.89-3.41 (m, 1H), 2.66-2.70 (m, 2H), 2.56 (s, 3H), 2.03-2.05 (m, 2H). LC/MS (exact mass) calculated for C$_{13}$H$_{18}$N$_2$O$_2$; 234.137. found (M+H$^+$); 235.1. The trans isomer was isolated from the mother liquor using supercritical fluid chromatography.

Step 2: Benzyl{cis-3-[(2-chloro-7H-pyrrolo[2,3-d]pyrimidin-4-yl)(methyl)amino]-cyclobutyl}carbamate To a solution of potassium carbonate (20.47 g, 148 mmol) in water (180 mL) was added benzyl[cis-3-(methylamino)cyclobutyl]carbamate (13.57 g, 50.2 mmol), followed by 2,4-dichloro-7H-pyrrolo(2,3-d)pyrimidine (9.0 g, 47.9 mmol) at room temperature. After addition was complete, the reaction mixture was stirred at 95° C. overnight. The mixture was filtered to collect the solid. The filter cake was washed with water and dried under vacuum to afford the title compound (16.5 g, 89.7%) as a yellow solid. $^1$H NMR (400 MHz, DMSO-d$_6$): δ 11.81 (s, 1H), 7.65 (d, 1H), 7.38 (m, 5H), 7.16 (m, 1H), 6.67 (d, 1H), 5.02 (s, 2H), 4.81 (m, 1H), 3.85 (m, 1H), 3.25 (s, 3H), 2.53 (m, 2H), 2.25 (m, 2H). LC/MS (exact mass) calculated for C$_{19}$H$_{20}$ClN$_5$O$_2$; 385.131. found (M+H$^+$); 386.1.

Step 3: cis-N-Methyl-N-7H-pyrrolo[2,3-d]pyrimidin-4-ylcyclobutane-1,3-diamine hydrochloride A mixture of {cis-3-[(2-chloro-7H-pyrrolo[2,3-d]pyrimidin-4-yl)(methyl)-amino]cyclobutyl}carbamate (13.0 g, 34.0 mmol), Pd(OH)$_2$ (40.3 g, 40.8 mmol) and cyclohexene (72.5 mL, 0.71 mol) in ethanol (300 mL) was stirred at reflux for 3 hours. The reaction mixture was filtered through a pad of Celite™ and the pad was washed with methanol. The filtrate was concentrated under vacuum to afford the title compound (4.8 g, 66%) as a white solid. $^1$H NMR (400 MHz, DMSO-d$_6$): δ 11.68 (br, 1H), 8.11 (s, 1H), 7.67 (br, 2H), 7.17 (d, 1H), 6.65 (d, 1H), 5.08 (m, 1H), 3.45 (m, 1H), 3.26 (s, 3H), 2.31 (m, 4H). LC/MS (exact mass) calculated for C$_{11}$H$_{15}$N$_5$; 217.133. found (M+H$^+$); 218.1.

Step 4: N-{cis-3-[Methyl(7H-pyrrolo[2,3-d]pyrimidin-4-yl)amino]cyclobutyl}-2,1,3-benzoxadiazole-4-sulfon-amide To a solution of cis-N-methyl-N-7H-pyrrolo[2,3-d]pyrimidin-4-ylcyclobutane-1,3-diamine hydrochloride (141 mg, 0.5 mmol) in tetrahydrofuran (5.0 mL) was added lithium bis(trimethylsilyl)amide (1M solution in tetrahydrofuran) (1.4 mL, 1.375 mmol) and chlorotrimethylsilane (108 mg, 1.01 mmol) at room temperature. The reaction mixture was stirred for 1 h at room temperature and then 2,1,3-benzoxadiazole-4-sulfonyl chloride (109 mg, 0.5 mmol) was added slowly. The mixture was stirred at room temperature for 4 h and then partitioned between dichloromethane and aqueous ammonium chloride. The aqueous layer was and extracted twice with dichloromethane and the combined organic layers were concentrated to afford the crude product as a tan solid. The crude material was purified by chromatography on silica gel eluting with a mixture of dichloromethane and methanol (95:5) to afford the title compound as a orange solid (130 mg, 65%). $^1$H NMR (400 MHz, CH$_3$OH-d$_4$): δ 8.15 (d, 1H), 8.08 (s, 1H), 7.72 (m, 1H), 7.10-7.09 (m, 2H), 6.62 (m, 1H), 3.84 (m, 1H), 3.26 (s, 4H), 2.55-2.47 (m, 2H), 2.17-2.30 (m, 2H); LC/MS (exact mass) calculated for C$_{17}$H$_{17}$N$_7$O$_3$S; 399.43. found (M+H$^+$); 400.9.

The following compounds, Examples 40-45, were prepared from cis-N-methyl-N-7H-pyrrolo[2,3-d]pyrimidin-4-ylcyclobutane-1,3-diamine hydrochloride (Example 39, Step 3) in a similar manner to that described in Example 39, Step 4, substituting the indicated sulfonyl chloride for 2,1,3-benzoxadiazole-4-sulfonyl chloride

Example 40

1-(3-Methyloxetan-3-yl)-N-{cis-3-[methyl(7H-pyrrolo[2,3-c]pyrimidin-4-yl)amino]cyclobutyl}-methanesulfonamide This compound was prepared using (3-methyloxetan-3-yl)methanesulfonyl chloride. The crude compound was purified by chromatography on silica gel eluting with a mixture of dichloromethane and methanol (90:10) to afford the title compound as a white solid (48%). $^1$H NMR (400 MHz, DMSO-d$_6$) δ 11.65 (br. s., 1H), 8.12 (s, 1H), 7.62 (d, 1H), 7.07-7.28 (m, 1H), 6.66 (dd, 1H), 4.82-5.05 (m, 1H), 4.59 (d, 2H), 4.20 (d, 2H), 3.55-3.71 (m, 1H), 3.41 (s, 2H), 3.27 (s, 3H), 2.56-2.70 (m, 2H), 2.15-2.34 (m, 2H), 1.53 (s, 3H); LC/MS (exact mass) calculated for C$_{16}$H$_{23}$N$_6$O$_3$S; 365.46. found (M+H$^+$); 366.2.

Example 41A (1S,2S) and 41B (1R,2R)

Racemic trans-2-(cyanomethyl)-N-{cis-3-[methyl(7H-pyrrolo[2,3-c]pyrimidin-4-yl)amino]cyclobutyl}cyclopropanesulfonamide(cis),(trans)

These compounds were prepared using a mixture (~1:1) of racemic trans-2-(cyanomethyl)-N-{cis-3-[methyl(7H-pyrrolo[2,3-d]pyrimidin-4 yl)amino]cyclobutyl}cyclopropane sulfonamide. The crude mixture of racemic trans isomers was purified by chromatography on silica gel eluting with a gradient of ethyl acetate and methanol (90:10) to afford a mixture (215 mg) of the title compounds as a white solid (58%). The trans isomers were then chirally separated by supercritical fluid chromatography (SFC) using (Chiral Pak IC, 21×250 mm col, 65/35 CO$_2$/methanol with 0.2% isopropyl amine, 65 mL/min) column conditions. Absolute stereochemistry of trans-isomers was arbitrarily assigned.

(1S,2S)-2-(Cyanomethyl)-N-((1s,3R)-3-(methyl(7H-pyrrolo[2,3-d]pyrimidin-4-yl)amino)cyclobutyl)cyclopropane-1-sulfonamide Isolation of the first eluting isomer afforded the title compound; Peak 1, trans-isomer: 35 mg (9.5%); SFC retention time=4.99 minutes; $^1$H NMR (400 MHz, DMSO-d$_6$) δ 11.6 (br, s, 1H), 8.08 (s, 1H), 7.59 (d, 1H), 7.13 (dd, 1H), 6.62 (dd, 1H), 4.93-4.89 (m, 1H), 3.63-3.60 (m, 1H), 3.33 (s, 3H), 2.51-2.72 (m, 4H), 2.16-2.34 (m, 2H), 1.55-1.72 (m, 1H), 1.10-1.21 (m, 2H), 1.02 (dt, 1H); LC/MS (exact mass) calculated for C$_{16}$H$_{20}$N$_6$O$_2$S; 360.44. found (M+H); 361.1.

(1R,2R)-2-(Cyanomethyl)-N-((1s,3S)-3-(methyl(7H-pyrrolo[2,3-d]pyrimidin-4-yl)amino)cyclobutyl)cyclopropane-1-sulfonamide Isolation of the second eluting isomer afforded the title compound; Peak 2, trans-isomer: 32 mg (8.7%); SFC retention time=5.38 minutes; $^1$H NMR (400 MHz, DMSO-d$_6$) δ 11.6 (br, s, 1H), 8.08 (s, 1H), 7.59 (d, 1H), 7.13 (dd, 1H), 6.62 (dd, 1H), 4.93-4.89 (m, 1H), 3.60-3.63 (m, 1H), 3.33 (s, 3H), 2.51-2.72 (m, 4H), 2.16-2.34 (m, 2H), 1.55-1.72 (m, 1H), 1.10-1.21 (m, 2H), 1.02 (dt, 1H); LC/MS (exact mass) calculated for C$_{16}$H$_{20}$N$_6$O$_2$S; 360.44. found (M+H); 361.1

The mixture of racemic trans-2-(cyanomethyl)-N-{cis-3-[methyl(7H-pyrrolo[2,3-d]pyrimidin-4-yl)amino]-cyclobutyl}cyclopropanesulfonamide was prepared as follows:

Step 1: Benzyl[cis-3-(methyl{7-[(4-methylphenyl)sulfonyl]-7H-pyrrolo[2,3-d]pyrimidin-4-yl}amino)cyclo-butyl]carbamate 4-Chloro-7-[(4-methylphenyl)sulfonyl]-7H-pyrrolo[2,3-d]pyrimidine (15 g, 48.7 mmol) and benzyl[cis-3-(methylamino)cyclobutyl]carbamate (17.2 g, 63.5 mmol) were mixed with isopropyl alcohol (180 mL) and diisopropylethylamine (28 mL, 161 mmol). The resulting slurry was heated at 75° C. for 6 hours. The reaction was cooled to room temperature, filtered, washed with isopropyl alcohol (150 mL) and dried in an oven at 50° C. to give the title compound (23.5 g, 95%) as a white solid.

$^1$H NMR (400 MHz, DMSO-d$_6$): δ 8.38 (s, 1H), 8.03 (d, 2H), 7.45 (d, 1H), 7.38-7.28 (m, 4H), 7.26 (s, 1H), 7.25 (d, 1H), 6.61 (d, 1H), 5.08 (s, 2H), 4.96 (d, 1H), 4.77 (m, 1H), 3.88 (m, 1H), 3.23 (s, 3H), 2.71 (m, 2H), 2.36 (s, 3H), 2.18 (m, 2H).

Step 2: cis-N-Methyl-N-{7[(4-methylphenyl)sulfonyl]-7H-pyrrolo[2,3-d]pyrimidin-4-yl}cyclobutane-1,3-diamine dihydrobromide Benzyl[cis-3-(methyl{7-[(4-methylphenyl)sulfonyl]-7H-pyrrolo[2,3-d]pyrimidin-4-yl}amino)cyclobutyl]carb-amate (15.2 g, 30.1 mmol) was suspended in ethyl acetate (45 mL) and acetic acid (45 mL). To the slurry was slowly added a 4M solution of hydrobromic acid in acetic acid (45 mL, 180 mmol), maintaining the temperature below 25° C. The resulting slurry was stirred at room temperature for 2 hours. The solids were collected by filtration, washed with ethyl acetate (450 mL), and dried at 40° C. to afford the title compound (16 g; 100%) as a white solid. $^1$H NMR (400 MHz, DMSO-d$_6$): δ 8.31 (s, 1H), 8.20 (s, 2H), 7.97 (d, 2H), 7.72 (d, 1H), 7.44 (d, 2H), 7.08 (d, 1H), 4.93 (m, 1H), 3.54 (m, 1H), 3.30 (s, 3H), 2.50 (m, 4H), 2.35 (s, 3H); LC/MS (exact mass) calculated for C$_{18}$H$_{21}$N$_6$O$_2$S; 371.142. found (M+H$^+$); 372.1.

Step 3: Sodium but-3-ene-1-sulfonate

To a suspension of 4-bromobut-1-ene (10 g, 74 mmol) in water (70 mL) was added sodium sulphite (11.2 g, 89 mmol). The reaction mixture was heated at 90° C. for 16 hours and then concentrated under reduce pressure to give desired compound in quantitative yield. $^1$H NMR (400 MHz, D$_2$O) δ 5.80-5.87 (m, 1H), 4.94-5.13 (m, 2H), 2.78-3.03 (m, 2H), 2.32-2.48 (m, 2H)

Step 4: But-3-ene-1-sulfonyl chloride

To a flask containing sodium but-3-ene-1-sulfonate (3 g, 22.2 mmol) at 0° C. was added oxalyl chloride (18 mL, 200 mmol) in dropwise manner followed by N,N-dimethylformamide (150 µL). The reaction was stirred at room temperature for 2 hours and concentrated under reduced pressure. The residue was diluted with ether and filtered, the organic layer washed with water, brine, dried over sodium sulfate and concentrated to give title compound (0.45 g, 13%) as oil. $^1$H NMR (400 MHz, CDCl3) δ 5.80-5.85 (m, 1H), 5.0-5.2 (m, 2H), 2.90-3.03 (m, 2H), 2.42-2.58 (m, 2H)

Step 5: Ethyl but-3-ene-1-sulfonate

To a solution of but-3-ene-1-sulfonyl chloride (6.2 g, 40 mmol) in ethanol (70 mL) was added triethylamine (5.69 mL, 40 mmol) at 0° C. The reaction was stirred at room temperature for 2 hours and then concentrated under reduced pressure. The residue was diluted with ethyl acetate, the organic layer washed with water, brine, dried over sodium sulfate and concentrated to give title compound (6.58 g, 71%) as oil. $^1$H NMR (400 MHz, CDCl$_3$) δ 5.82 (m, 1H), 5.01-5.21 (m, 2H), 4.19-4.41 (q, 2H), 3.08-3.24 (m, 2H), 2.46-2.70 (m, 2H), 1.34-1.46 (t, 3H)

Step 6: Ethyl 2-(oxiran-2-yl)ethane-1-sulfonate

To a solution of ethyl but-3-ene-1-sulfonate (4.5 g, 27.4 mmol) in dichloromethane (46 mL) was added meta-chloroperoxybenzoic acid (6.76 g, 30.1 mmol) at room temperature. The reaction was stirred over the weekend and quenched with aqueous sodium thiosulfate. The organic layer was extracted, washed with brined, dried over sodium sulfate, filtered and concentrated. The crude compound was purified by chromatography on silica gel eluting with a gradient of heptane and ethyl acetate (0-50%) to afford the title compound (3.1 g, 63%) as oil. $^1$H NMR (400 MHz, CDCl$_3$) δ 4.32 (q, 2H), 3.24 (t, 2H), 2.99-3.13 (m, 1H), 2.78-2.90 (m, 1H), 2.57 (dd, 1H), 2.20-2.39 (m, 1H), 1.79-2.03 (m, 1H), 1.42 (t, 3H)

Step 7: Ethyl 2-(hydroxymethyl)cyclopropane-1-sulfonate

To a solution of ethyl 2-(oxiran-2-yl)ethane-1-sulfonate (2.3 g, 12.76 mmol) in tetrahydrofuran (40 mL) between −30° C. and −40° C. was added 1M solution of lithium hexamethyl disilazane in toluene (15.3 mL, 15.3 mmol). The reaction mixture was allowed to stir at −30° C. and −40° C. for 2 hours and then warmed up to −10° C. over 30 minutes. The reaction was quenched with aqueous dilute 1M hydrochloric acid (25 mL) till pH=2-3. The reaction was diluted with ethyl acetate, extracted, washed with brine, dried over sodium sulfate and concentrated. The crude compound was purified by chromatography on silica gel eluting with a gradient of heptane and ethyl acetate (0-70%) to afford the title compound (1.45 g, 63%) as oil. $^1$H NMR (400 MHz, CDCl$_3$) δ 4.33 (q, 2H), 3.81 (dd, 1H), 3.58 (dd, 1H), 2.39-2.53 (m, 1H), 1.84-2.00 (m, 1H), 1.33-1.48 (m, 4H), 1.06-1.20 (m, 1H)

Step 8: Ethyl 2-(cyanomethyl)cyclopropane-1-sulfonate

To a stirred suspension of triphenylphosphine (0.3 g, 1.16 mmol) in tetrahydrofuran (3.0 mL) was added diisopropyl azodicarboxylate (0.157 g, 0.77 mmol) at 0° C. After stirring for 15 minutes, a solution of ethyl 2-(hydroxymethyl)cyclopropane-1-sulfonate (0.14 g, 0.77 mmol) in tetrahydrofuran (3 mL) was added dropwise and reaction stirred for 20 minutes. Acetone cyanohydrin (0.1 g, 1.16 mmol) was added dropwise and reaction gradually warmed to room temperature overnight. The reaction mixture was concentrated under reduced pressure. The crude compound was purified by chromatography on silica gel eluting with a gradient of heptane and ethyl acetate (0-70%) to afford the title compound (0.035 g, 24%) as oil. $^1$H NMR (400 MHz, CDCl$_3$) δ 4.33 (q, 2H), 3.79 (dd, 1H), 3.52 (dd, 1H), 2.38-2.52 (m, 1H), 1.81-1.97 (m, 1H), 1.33-1.48 (m, 4H), 1.05-1.18 (m, 1H)

Step 9: Sodium 2-(cyanomethyl)cyclopropane-1-sulfonate

To a solution of ethyl 2-(cyanomethyl)cyclopropane-1-sulfonate (0.65 g, 3.44 mmol) in acetone (5 mL) was added sodium iodide (0.52 g, 3.47 mmol). The reaction mixture was stirred at room temperature overnight. The residue was triturated with dichloromethane followed by pentane and ether. The solid was dried under high vacuum to afford the title compound (0.6 g, 100%) as white solid.
$^1$H NMR (400 MHz, DMSO-d$_6$) δ 3.79 (dd, 1H), 3.52 (dd, 1H), 2.38-2.52 (m, 1H), 1.81-1.97 (m, 1H), 1.33-1.48 (m, 1H), 1.05-1.18 (m, 1H)

Step 10: 2-(Cyanomethyl)cyclopropane-1-sulfonyl chloride

To a mixture of sodium 2-(cyanomethyl)cyclopropane-1-sulfonate (0.6 g, 3.17 mmol) at 0° C. was added oxalyl chloride (6.5 g, 50 mmol) followed by 2 drops of N,N'-dimethylformamide. The reaction mixture was warmed up to room temperature and stirred for 1 hour. The reaction was diluted with dichloromethane and water, the organic layer extracted, washed with brine, dried over sodium sulfate, filtered and concentrated to give title compound (0.56 g, 98.3%) as oil, used directly in next step.

Step 11: 2-(Cyanomethyl)-N-[cis-3-(methyl{7-[(4-methylphenyl)sulfonyl]-7H-pyrrolo[2,3-d]pyrimidin-4-yl}amino)cyclobutyl]cyclopropanesulfonamide A solution of 2-(cyanomethyl)cyclopropane-1-sulfonyl chloride (0.25 g, 1.39 mmol) in 2 mL dichloromethane was added dropwise to a solution of cis-N-methyl-N-{7-[(4-methylphenyl)sulfonyl]-7H-pyrrolo[2,3-d]pyrimidin-4-yl}cyclobutane-1,3-diamine (0.517 g, 1.39 mmol) and N'N-diethyl isopropyl amine (0.27 g, 2.09 mmol) in dichloromethane (5 mL) at 0° C. over 15 minutes. The reaction was stirred at room temperature for 4 hours. Water (50 mL) was added and the organic layer was separated. The aqueous layer was extracted with dichloromethane (2×150 mL), and the combined organic layers were separated dried over sodium sulfate. The crude compound was purified by chromatography on silica gel eluting with a gradient of heptanes and ethyl acetate (0-100%) to afford the title compound as a yellow solid (0.716 g, 74%); LC/MS (exact mass) calculated for $C_{23}H_{26}N_6O_4S_2$; 514.15. found (M+H$^+$); 515.1.

Step 12: racemic-trans-2-(Cyanomethyl)-N-{cis-3-[methyl(7H-pyrrolo[2,3-d]pyrimidin-4-yl)amino] cyclo-butyl}cyclopropanesulfonamide To a solution of 2-(cyanomethyl)-N-[cis-3-(methyl{7-[(4-methylphenyl)sulfonyl]-7H-pyrrolo[2,3-d]pyrimidin-4-yl}amino)cyclobutyl]cyclopropanesulfonamide (0.525 g, 1.02 mmol) in tetrahydrofuran (10 mL) and was added 1M solution of tetrabutylammonium fluoride in tetrahydrofuran (5.1 mL, 5.1 mmol). The reaction was heated at 50° C. for 5 hours. The reaction mixture was concentrated and diluted with ethyl acetate. The organic layer was washed with brine, dried over sodium sulfate, filtered and concentrated. The crude compound was purified by chromatography on silica gel eluting with a gradient of ethyl acetate and methanol (0-20%) to afford the title compound as a yellow solid (0.216 g, 58%). LC/MS (exact mass) calculated for $C_{16}H_{20}N_6O_2S$; 360.44. found (M+H$^+$); 361.1.

Example 42

3-Cyano-3-methyl-N-{cis-3-[methyl(7H-pyrrolo[2,3-d]pyrimidin-4-yl)amino]cyclobutyl}azet-idine-1-sulfonamide Step 1: N-[cis-3-(Methyl{7-[(4-methylphenyl)sulfonyl]-7H-pyrrolo[2,3-d]pyrimidin-4-yl}amino)cyclobutyl]-2-oxo-1,3-oxazolidine-3-sulfonamide To a solution of chlorosulfonyl isocyanate (1.76 mL, 20.6 mmol) in dichloromethane (150 mL) was added dropwise a solution of 2-bromoethanol (1.43 mL, 20.6 mmol) in dichloromethane (80 mL) at 0° C. After 30 minutes at 0° C., a solution of cis-N-methyl-N-{7-[(4-methylphenyl)sulfonyl]-7H-pyrrolo[2,3-d]pyrimidin-4-yl}cyclobutane-1,3-diamine dihydrobromide (11.0 g, 20.6 mmol) and triethylamine (10.42 g, 103.2 mmol) in dry dichloromethane (80 mL) was added dropwise, and the reaction mixture was allowed to warm to room temperature overnight. The reaction solution was dissolved in dichloromethane (1 L), washed with aqueous 1M hydrochloric acid solution (2×800 mL) and brine (500 mL). The solution was dried over sodium sulfate and concentrated to afford the title compound as white solid (8.5 g, 79%). $^1$H NMR (400 MHz, CD$_3$OD): δ 8.22 (s, 1H), 8.00 (d, 2H), 7.58 (d, 1H), 7.38 (d, 2H), 6.91 (d, 1H), 4.88 (m, 1H), 4.45-4.41 (m, 2H), 4.06-4.02 (m, 2H), 3.75 (m, 1H), 3.29 (s, 3H), 2.72-2.69 (m, 2H), 2.40 (s, 3H); 2.30-3.27 (m, 2H). LC/MS (exact mass) calculated for $C_{21}H_{24}N_6O_6S_2$; 520.120. found (M+H$^+$); 521.4.

Step 2: N-(Cyclopropylmethyl)-N'-[cis-3-(methyl{7-[(4-methylphenyl)sulfonyl]-7H-pyrrolo[2,3-d]pyrimidin-4-yl}amino)cyclobutyl]sulfamide A solution of N-[cis-3-(methyl{7-[(4-methylphenyl)sulfonyl]-7H-pyrrolo[2,3-d]pyrimidin-4-yl}amino)-cyclobutyl]-2-oxo-1,3-oxazolidine-3-sulfonamide (2.87 g, 5.53 mmol), 3-methylazetidine-3-carbonitrile hydrochloride (1.09 g, 8.27 mmol) and triethylamine (1.674 g, 16.6 mmol) in acetonitrile (35 mL) was stirred for 60 minutes at 120° C. using microwave heating. The reaction mixture was concentrated, extracted with ethyl acetate, washed with water; organic layer was dried over magnesium sulfate, filtered and concentrated. The residue was purified by silica gel chromatography using gradient of petroleum ether and ethyl acetate (45:55) to afford the title compound (1.66 g, 56%) as a white solid. LC/MS (exact mass) calculated for $C_{23}H_{27}N_7O_4S_2$; 529.63. found (M+H$^+$); 530.3.

Step 3: N-(Cyclopropylmethyl)-N'-{cis-3-[methyl(7H-pyrrolo[2,3-d]pyrimidin-4-yl)amino]cyclobutyl}-sulfamide To a solution of N-(cyclopropylmethyl)-N'-[cis-3-(methyl{7-[(4-methylphenyl)sulfonyl]-7H-pyrrolo[2,3-d]pyrimidin-4-yl}amino)cyclobutyl]sulfamide (1.66 g, 3.14 mmol) in tetrahydrofuran (40 mL) was added a solution of 1M tetrabutylammonium fluoride in tetrahydrofuran (2.45 g, 9.42 mmol). The reaction mixture was heated at 50° C. for 6 hours and then cooled to room temperature. The reaction was concentrated under vacuum and diluted with ethyl acetate (100 mL). The resulting solution was washed with brine (30 mL), dried over sodium sulfate and concentrated. The residue was purified using preparative reverse phase high performance liquid chromatography using gradient of water and acetonitrile (90:10 to 10:90) to afford the title compound (0.5 g, 43%) as a white solid. $^1$H NMR (400 MHz, methanol-d$_4$): δ 8.12 (s, 1H), 7.14-7.13 (d, 1H), 6.70-6.69 (d, 1H), 4.93-4.90 (m, 1H), 4.13-4.11 (m, 2H), 3.78-3.74 (m, 2H), 3.72-3.66 (m, 1H), 3.37 (s, 3H), 2.80-2.74 (m, 2H), 2.36-2.29 (m, 2H) 1.68 (s, 3H); LC/MS (exact mass) calculated for $C_{16}H_{21}N_7O_2S$; 375.45. found (M+H$^+$); 376.1.

Examples 43A, 43B, 43C, and 43D cis- and trans-3-Cyano-N-{cis-3-[methyl(7H-pyrrolo[2,3-d]pyrimidin-4-yl)amino]cyclobutyl}-cyclopentanesulfonamide Cis Diastereomers
Trans Diastereomers These compounds were prepared using a mixture (~1:1) of cis- and trans-3-cyanocyclopentane-1-sulfonyl chloride. The crude mixture of cis- and trans-isomers was purified by chromatography on silica gel eluting with a gradient of petroleum ether and ethyl acetate (10:1 to 1:15) to afford a mixture (1920 mg) of the title compounds as a light brown solid (25.5%). The cis and trans isomers were then chirally separated by supercritical fluid chromatography (SFC) using (OD-H 20×250 mm col, 30% propanol, 60 mL/min) column conditions. Absolute stereochemistry for cis and trans isomers were arbitrarily assigned.

(1S,3S)-3-Cyano-N-((1 s,3R)-3-(methyl(7H-pyrrolo[2,3-d]pyrimidin-4-yl)amino)cyclobutyl)cyclopentane-1-sulfonamide Isolation of the first eluting isomer afforded the title compound; Peak 1, trans-isomer: 326 mg (17%); SFC retention time=7.79 minutes; $^1$H NMR (400 MHz, CH$_3$OH-d$_4$): δ 8.12 (s, 1H), 7.13-7.12 (d, 1H), 6.70-6.69 (d, 1H), 4.91-4.88 (m, 1H), 3.80-3.70 (m, 2H), 3.36 (s, 3H), 3.20-3.10 (m, 1H), 2.79-2.76 (m, 2H), 2.52-2.45 (m, 1H), 2.35-2.29 (m, 5H) 2.18-2.05 (m, 1H), 2.03-1.95 (m, 1H); LC/MS (exact mass) calculated for $C_{17}H_{22}N_6O_2S$; 374.46. found (M+H$^+$); 375.1.

(1R,3S)-3-Cyano-N-((1 s,3S)-3-(methyl(7H-pyrrolo[2,3-d]pyrimidin-4-yl)amino)cyclobutyl)cyclopentane-1-sulfonamide Isolation of second eluting isomer afforded the title compound; Peak 2 (PF-06652734), cis-isomer: 300 mg (15.6%); SFC retention time=8.12 minutes; $^1$H NMR (400 MHz, CH$_3$OH-d$_4$): δ 8.10 (s, 1H), 7.10 (d, 1H), 6.66 (d, 1H), 4.83-4.87 (m, 1H), 3.67-3.78 (m, 1H), 3.63 (dd, 1H), 3.36 (s, 3H), 2.96-3.08 (m, 1H), 2.69-2.80 (m, 2H), 2.47-2.59 (m, 1H), 2.11-2.33 (m, 5H), 2.01-2.09 (m, 2H); LC/MS (exact mass) calculated for $C_{17}H_{22}N_6O_2S$; 374.46. found (M+H$^+$); 375.2.

(1S,3R)-3-Cyano-N-((1s,3R)-3-(methyl(7H-pyrrolo [2,3-d]pyrimidin-4-yl)amino)cyclobutyl)cyclopentane-1-sulfonamide Isolation of third eluting isomer afforded the title compound; Peak 3 (PF-06652735), cis-isomer: 222 mg (11.5%); SFC retention time=8.33 minutes; $^1$H NMR (400 MHz, CH$_3$OH-d$_4$): δ 8.10 (s, 1H), 7.10 (d, 1H), 6.66 (d, 1H), 4.83-4.87 (m, 1H), 3.67-3.78 (m, 1H), 3.63 (dd, 1H), 3.36 (s, 3H), 2.96-3.08 (m, 1H), 2.69-2.80 (m, 2H), 2.47-2.59 (m, 1H), 2.11-2.33 (m, 5H), 2.01-2.09 (m, 2H); LC/MS (exact mass) calculated for C$_{17}$H$_{22}$N$_6$O$_2$S; 374.46. found (M+H$^+$); 375.2.

(1R,3R)-3-Cyano-N-((1S,3S)-3-(methyl(7H-pyrrolo [2,3-d]pyrimidin-4-yl)amino)cyclobutyl)cyclopentane-1-sulfonamide Isolation of fourth eluting isomer afforded the title compound; Peak 4 (PF-06609710), trans-isomer: 230 mg (12%); SFC retention time=9.19 minutes; $^1$H NMR (400 MHz, methanol-d$_4$): δ 8.127 (s, 1H), 7.13-7.12 (d, 1H), 6.70-6.69 (d, 1H), 4.90-4.85 (m, 1H), 3.78-3.71 (m, 2H), 3.36 (s, 3H) 3.17-3.13 (m, 1H), 2.81-2.74 (m, 2H), 2.51-2.46 (m, 1H), 2.35-2.31 (m, 5H) 2.29-2.11 (m, 1H), 2.03-1.90 (m, 1H); LC/MS (exact mass) calculated for C$_{17}$H$_{22}$N$_6$O$_2$S; 374.46. found (M+H$^+$); 375.2.

The mixture of cis- and trans-3-cyanocyclopentane-1-sulfonyl chloride was prepared as follows:

Step 1: 3-Oxocyclopentane-1-carbonitrile

To a solution of triethylamine hydrochloride (117.4 g, 854 mmol), potassium cyanide (35.9 g, 630 mmol) in mixture of water (150 mL) and methanol (150 mL) was added dropwise solution of cyclopent-2-en-1-one (50 g, 610 mmol) in methanol (60 mL). The mixture was stirred at room temperature overnight. The organic solvent was concentrated and the remaining aqueous phase extracted with dichloromethane (3×500 mL). The combined organic layers were dried over magnesium sulfate and crude product was purified by chromatography on silica gel eluting with a gradient of petroleum ether and ethyl acetate (1:1) to afford the title compound as yellow oil (35 g, 53%). $^1$H NMR (400 MHz, CDCl$_3$): δ 3.25-3.15 (m, 1H), 2.62-2.52 (m, 2H), 2.52-2.40 (m, 2H), 2.40-2.20 (m, 2H).

Step 2: 3-Hydroxycyclopentane-1-carbonitrile

A solution of 3-oxocyclopentane-1-carbonitrile (20 g, 183 mmol) in methanol (150 mL) was cooled at 0° C. and treated with sodium borohydride (7 g, 183 mmol) in small portions. The mixture was then warmed to room temperature; reaction stirred for few hours and quenched using 2 equivalents of acetic acid. The organic solvent was concentrated and the aqueous phase was diluted using saturated aqueous sodium bicarbonate. The mixture was extracted using ethyl acetate; organic layers were combined and dried over magnesium sulfate. The crude product was purified by chromatography on silica gel eluting with a gradient of petroleum ether and ethyl acetate (1:1) to afford the title compound as yellow oil (18 g, 88%). $^1$H NMR (400 MHz, CDCl$_3$): δ 4.48-4.35 (m, 1H), 3.10-2.72 (m, 1H), 2.65-2.45 (br, 1H), 2.30-1.65 (m, 6H).

Step 3: 3-Cyanocyclopentyl 4-methylbenzenesulfonate

To a solution of 3-hydroxycyclopentane-1-carbonitrile (18 g, 162 mmol) in dry dichloromethane (200 mL) was added 4-dimethylaminopyridine (500 mg, 4.1 mmol) and triethylamine (34 mL, 243 mmol). The mixture stirred at room temperature for 5 minutes and then p-toluenesulfonyl chloride (46.3 g, 243 mmol) was added. The resulting mixture was stirred at room temperature overnight. The mixture was washed with saturated aqueous sodium bicarbonate. The dichloromethane layer was extracted, dried over magnesium sulfate and concentrated. The residue was purified by chromatography on silica gel eluting with a gradient of petroleum ether and ethyl acetate (9:1 to 2:3) to afford the title compound as colorless oil (20 g, 46.5%). $^1$H NMR (400 MHz, CDCl$_3$): δ 7.78-7.76 (d, 2H), 7.35-7.33 (d, 2H), 4.98 (m, 1H), 2.81-2.73 (m, 1H), 2.43 (s, 3H), 2.31-2.34 (m, 1H), 2.10-2.03 (m, 4H), 1.84-1.70 (m, 1H).

Step 4: S-(3-Cyanocyclopentyl) ethanethioate

The mixture of 3-cyanocyclopentyl 4-methylbenzenesulfonate (20 g, 75 mmol) and potassium thioacetate (12.9 g, 113 mmol) in N,N-dimethylformamide (180 mL) was heated at 60° C. for 5 hours. The mixture was diluted with methyl tert-butyl ether (3×400 mL), washed with water (50 mL), dried over magnesium sulfate and concentrated to afford the title compound as yellow oil (18 g, >100%).
$^1$H NMR (400 MHz, CDCl$_3$): δ 3.93-3.86 (m, 1H), 2.96-2.90 (m, 1H), 2.45-2.41 (m, 1H), 2.37-2.22 (m, 4H), 2.10-1.90 (m, 2H), 1.70-1.60 (m, 1H).

Step 5: 3-Cyanocyclopentane-1-sulfonyl chloride

A mixture of N-chlorosuccinimide (40.3 g, 300.2 mmol) in concentrated hydrochloric acid (82 mL) and acetonitrile (409 mL) was stirred at room temperature for 15 minutes. A solution of S-(3-cyanocyclopentyl) ethanethioate (12 g, 75.5 mmol) in acetonitrile (82 mL) was added dropwise at 0° C. and stirred for 1 hour. The mixture was diluted with aqueous sodium bicarbonate (50 mL), and extracted with methyl tert-butyl ether (3×300 mL). The combined organic layers were dried over anhydrous sodium sulfate and concentrated. The crude product was purified by chromatography on silica gel eluting with a mixture of petroleum ether and ethyl acetate (100:0 to 80:20) to afford the title compound as a yellow oil (8.2 g, 60%). $^1$H NMR (400 MHz, CDCl$_3$): δ 4.38-4.25 (m, 1H), 3.20-3.10 (m, 1H), 2.75-2.62 (m, 1H), 2.58-2.00 (m, 5H).

Example 44

1-[({cis-3-[Methyl(7H-pyrrolo[2,3-d]pyrimidin-4-yl) amino]cyclobutyl}methyl)-sulfonyl]azetidine-3-carbonitrile

Step 1: cis/trans-Ethyl 3-[(tert-butoxycarbonyl) amino]cyclobutanecarboxylate To a solution of a mixture of cis- and trans-ethyl 3-aminocyclobutanecarboxylate hydrochloride (cis/trans=10:1) (WO 2009 60278 A1) (10 g, 55.7 mmol) and triethylamine (19.4 mL, 139.1 mmol) in dichloromethane (370 mL) at 0° C. was added dropwise di-tert-butyl dicarbonate (15.8 g, 72.3 mmol). After addition was complete, the mixture was stirred at room temperature overnight. The solvent was evaporated under reduced pressure and the resulting residue was chromatographed on silica gel eluting with a gradient of petroleum ether and ethyl acetate (10:1 to 3:1) to afford the title mixture as a white solid (19 g, 92%). $^1$H NMR (400

MHz, CDCl$_3$): δ 4.77 (s, 1H), 4.13 (q, 3H), 2.68-2.82 (m, 1H), 2.60 (d, 2H), 1.99-2.17 (m, 2H), 1.43 (s, 9H), 1.25 (t, 3H).

Step 2: cis/trans-[3-(Methylamino)cyclobutyl] methanol

Lithium aluminum hydride (9.14 g, 240.4 mmol) was suspended in dry tetrahydrofuran (350 mL). The mixture was cooled to 0° C. and a solution of cis/trans ethyl 3-[(tert-butoxycarbonyl)amino]cyclobutanecarb-oxylate (cis/trans=10:1) (11.7 g, 48.1 mmol) in dry tetrahydrofuran (170 mL) was added drop wise. After addition was complete, the resulting mixture was heated to reflux overnight. After it was cooled to room temperature, the reaction was diluted with tetrahydrofuran (1.5 L) and then cooled to 0-5° C. Small portions of Na$_2$SO$_4$.10H$_2$O were added until gas evolution had ceased. The mixture was filtered to remove the solids, which were washed with more tetrahydrofuran (500 mL). The filtrate was concentrated to dryness affording the title mixture (cis/trans=10:1) as an oil (10 g, >100%). $^1$H NMR (400 MHz, CD$_3$OD) δ 3.52 (d, 2H) 3.15 (t, 1H) 2.29-2.44 (m, 5H) 2.06-2.29 (m, 1H) 1.43-1.69 (m, 2H).

Step 3: cis/trans-[3-(Methyl{7[(4-methylphenyl) sulfonyl]-7H-pyrrolo[2,3-d]pyrimidin-4-yl}amino) cyclobutyl]-methanol Potassium iodide (173 mg) and triethylamine (13 mL, 93.8 mmol) were added to a solution of cis/trans-[3-(methylamino)cyclobutyl]methanol (6.0 g, 52.1 mmol) in acetone (250 mL). 4-Chloro-7-[(4-methylphenyl)sulfonyl]-7H-pyrrolo[2,3-d]pyrimidine (14.4 g, 46.9 mmol) was then added and the resulting mixture was heated to reflux overnight. After evaporation of the solvent under reduced pressure, the residue was diluted with dichloromethane (500 mL). The solution was washed sequentially with water (300 mL), 2% aqueous citric acid (300 mL) and brine (300 mL), and then dried over sodium sulfate. After filtration, the solution was filtered and concentrated to afford the title mixture as a light solid (15.3 g, 85%). A portion (5.0 g) of the cis/trans-[3-(methyl{7-[(4-methylphenyl)sulfonyl]-7H-pyrrolo[2,3-d]pyrimidin-4-yl}amino)cyclobutyl]methanol mixture was separated by supercritical fluid chromatography using a Chiralpak-AD column:
cis isomer, 4.6 g: $^1$H NMR (400 MHz, CH$_3$OH-d$_4$): δ 8.20 (s, 1H), 7.98 (d, 2H), 7.53 (d, 1H), 7.34 (d, 2H), 6.83 (d, 2H), 4.99-4.95 (m, 1H), 3.56 (d, 1H), 3.24 (s, 3H), 2.36 (s, 3H), 2.34-2.28 (m, 2H), 2.24-2.19 (m, 1H), 2.11-2.03 (m, 2H). LC/MS (exact mass) calculated for C$_{19}$H$_{22}$N$_4$O$_3$S: 386.14. found (M+H$^+$): 387.3.
trans isomer, 0.4 g: $^1$H NMR (400 MHz, CH$_3$OH-d$_4$): δ 8.20 (s, 1H), 7.98 (d, 2H), 7.55 (d, 1H), 7.35 (d, 2H), 6.84 (d, 2H), 5.26-5.22 (m, 1H), 3.69 (d, 1H), 3.30 (s, 3H), 2.46-2.41 (m, 3H), 2.39 (s, 3H), 2.19-2.14 (m, 2H). LC/MS (exact mass) calculated for C$_{19}$H$_{22}$N$_4$O$_3$S: 386.14. found (M+H$^+$): 387.3.

Step 4: cis-[3-(Methyl{7-[(4-methylphenyl)sulfonyl]-7H-pyrrolo[2,3-d]pyrimidin-4-yl}amino)cyclobutyl]-methyl 4-methylbenzenesulfonate To a solution of cis-[3-(methyl{7-[(4-methylphenyl) sulfonyl]-7H-pyrrolo[2,3-d]pyrimidin-4-yl}amino)cyclobutyl]methanol (20 g, 51.8 mmol) and N,N-dimethylamino-pyridine (12.6 g, 103.6 mmol) in dichloromethane (500 mL) at 0° C. was added p-toluenesulfonyl chloride (14.8 g, 77.7 mmol). The reaction mixture was stirred at room temperature for 16 hours and then washed with water (500 mL). The combined aqueous washes were extracted with dichloromethane (2×800 mL). The combined organic layers were dried, filtered and concentrated under vacuum. The residue was chromatographed on silica gel eluting with a gradient of dichloromethane and methanol (100:0 to 95:5) to afford the title compound (23 g, 82%) as a white solid. LC/MS (exact mass) calculated for C$_{26}$H$_{28}$N$_4$O$_5$S$_2$: 540.150. found (M+H$^+$): 541.3.

Step 5: S-{[cis-3-(Methyl{7[(4-methylphenyl)sulfonyl]-7H-pyrrolo[2,3-d]pyrimidin-4-yl}amino)cyclobutyl]-methyl}ethanethioate To a solution of potassium thioacetate (678 mg, 5.93 mmol) in N,N-dimethylformamide (5 mL) was added a solution of [cis-3-(methyl{7-[(4-methylphenyl)sulfonyl]-7H-pyrrolo[2,3-d]pyrimidin-4-yl}amino)-cyclobutyl] methyl 4-methylbenzenesulfonate (2.0 g, 3.70 mmol) in N,N-dimethylformamide (6 mL) dropwise over 5 minutes at room temperature. The mixture was then heated to at 50-55° C. overnight. The mixture was cooled to room temperature and quenched by pouring into aqueous saturated sodium bicarbonate solution (60 mL). The mixture was extracted with ethyl acetate (3×30 mL) and the combined organic layers was washed with water (3×30 mL), brine (30 mL). After drying over Na$_2$SO$_4$ the solution was concentrated. The residue was chromatographed on silica gel eluting with a gradient of dichloromethane and methanol (100:0 to 80:20) to afford the title compound (1.2 g, 73%) as a yellow solid. $^1$H NMR (400 MHz, CDCl$_3$): δ 8.39 (s, 1H), 8.04 (d, 2H), 7.45 (d, 1H), 7.27 (d, 2H), 6.63 (d, 1H), 4.98-4.88 (m, 1H) 3.22 (s, 3H) 3.02-3.00 (m, 2H) 2.45-2.44 (m, 2H), 2.47 (m, 3H) 2.22 (m, 3H) 2.21-2.24 (m, 1H) 1.92-1.87 (m, 2H); LC/MS (exact mass) calculated for C$_{21}$H$_{24}$N$_4$O$_3$S$_2$: 444.129. found (M+H$^+$): 445.1.

Step 6: [cis-3-(Methyl{7[(4-methylphenyl)sulfonyl]-7H-pyrrolo[2,3-d]pyrimidin-4-yl}amino)cyclobutyl] meth-anesulfonic acid To a solution of S-{[cis-3-(methyl{7-[(4-methylphenyl) sulfonyl]-7H-pyrrolo[2,3-d]pyrimidin-4-yl}amino)cyclobutyl]methyl}ethanethioate (580 mg, 1.31 mmol), in formic acid (10 mL) at room temperature was added 30% aqueous hydrogen peroxide solution (0.7 mL, 6.92 mmol). The resulting mixture was stirred at room temperature overnight. The reaction was poured into an aqueous 33% aqueous sodium bisulfate solution (1.12 mL) and then stirred for 10 minutes. Aqueous 33% sodium hydroxide solution (1.8 mL) was then added to adjust the pH to 5. The resulting mixture was stirred at room temperature for 1 hour. The solid was collected solid by filtration, washed with water (10 mL) and vacuum dried at about 60° C. to afford the title compound (634 mg, crude) as a white solid. LC/MS (exact mass) calculated for C$_{19}$H$_{22}$N$_4$O$_5$S$_2$; 450.103. found (M+H$^+$); 451.3.

Step 7: cis-[3-(Methyl{7[(4-methylphenyl)sulfonyl]-7H-pyrrolo[2,3-d]pyrimidin-4-yl}amino)cyclobutyl]-methanesulfonyl chloride Thionyl chloride (0.3 ml, 3.33 mmol) was added dropwise over 5 minutes to a solution of cis-[3-(methyl{7-[(4-methylphenyl)sulfonyl]-7H-pyrrolo[2,3-d]pyrimidin-4-yl}amino)cyclobutyl]methanesulfonic acid (150 mg, 0.33 mmol) in dichloromethane (20 mL) at 0° C. Two drops of N,N-dimethylformamide were added to the solution, which was then heated at 75° C. for 2 hours. The mixture was cooled and the solvent was evaporated. The residue was washed with anhydrous dichloromethane (3×10 mL) to afford the crude title compound (170 mg) as a yellow solid; LC/MS (exact mass) calculated for $C_{19}H_{21}ClN_4O_4S_2$; 468.069. found (M+H$^+$); 469.2.

Step 8: 1-({[cis-3-(Methyl{7-[(4-methylphenyl) sulfonyl]-7H-pyrrolo[2,3-d]pyrimidin-4-yl}amino) cyclobutyl]-methyl}sulfonyl)azetidine-3-carbonitrile To a mixture of azetidine-3-carbonitrile 2,2,2-trifluoroacetate (20 mg, 0.246 mmol) and N,N-diisopropylethylamine (79 mg, 0.528 mmol) in tetrahydrofuran (20 mL) at 0° C. was added dropwise a solution of cis-[3-(methyl{7-[(4-methylphenyl)sulfonyl]-7H-pyrrolo[2,3-d]pyrimidin-4-yl}amino)-cyclobutyl]meth-anesulfonyl chloride (20 mg, 0.164 mmol) in tetrahydrofuran (5 mL). The mixture was allowed to warm to room temperature and stirred for 4 hours. The solution was washed with brine, dried over sodium sulfate and concentrated to afford the crude title compound (10 mg, 11%) as a white solid. LC/MS (exact mass) calculated for $C_{23}H_{26}N_6O_4S_2$; 514.62. found (M+H$^+$); 515.1.

Step 9: 1-[({cis-3-[Methyl(7H-pyrrolo[2,3-d]pyrimidin-4-yl)amino]cyclobutyl}methyl)sulfonyl]azetidine-3-carbonitrile 1-({[cis-3-(Methyl{7-[(4-methylphenyl)sulfonyl]-7H-pyrrolo[2,3-d]pyrimidin-4-yl}amino)cyclobutyl]-methyl}sulfonyl)azetidine-3-carbonitrile (30 mg, 0.58 mmol) in tetrahydrofuran (5 mL) was added a solution of 1M tetrabutylammonium fluoride in tetrahydrofuran (78 mg, 0.3 mmol). The reaction mixture was heated at 50° C. for 4 hours and then cooled to room temperature. The reaction was concentrated under vacuum and diluted with ethyl acetate (100 mL). The resulting solution was washed with brine (30 mL), dried over sodium sulfate and concentrated. The residue was chromatographed using preparative thin layer chromatography eluting with a mixture of ethyl acetate and methanol (20:1) to afford the title compound (11 mg, 52.6%) as a white solid. $^1$H NMR (400 MHz, CH$_3$OH-d$_4$): δ 8.12 (s, 1H), 7.13-7.12 (d, 1H), 6.70-6.69 (d, 1H), 5.13-5.08 (m, 2H), 4.88-4.81 (m, 1H), 4.26-4.22 (m, 2H), 4.14-4.10 (m, 2H), 3.74-3.68 (m, 1H), 3.36-3.32 (s, 3H), 2.64-2.53 (m, 3H), 2.25-2.17 (m, 2H); LC/MS (exact mass) calculated for $C_{16}H_{20}N_6O_2S$; 360.44. found (M+H$^+$); 361.1.

Example 45 (Cis) and 46 (Trans)

cis- and trans-3-Cyano-N-{cis-3-[methyl(7H-pyrrolo[2,3-d]pyrimidin-4-yl)amino]cyclobutyl}-cyclobutanesulfonamide These compounds were prepared using a mixture (~1:1) of cis and trans-3-cyanocyclobutane-1-sulfonyl chloride. The crude mixture of cis and trans isomers was purified by chromatography on silica gel eluting with a gradient of dichloromethane and methanol (10:0 to 10:1) to afford a mixture (1.1 g) of the title compounds as a white solid (61%). The cis- and trans-isomers were then chirally separated by supercritical fluid chromatography (SFC)

cis-3-Cyano-N-{cis-3-[methyl(7H-pyrrolo[2,3-d] pyrimidin-4-yl)amino] cyclobutyl}cyclobutanesulfonamide Isolation of the first eluting isomer afforded the title compound; Peak 1, cis-isomer: 337 mg (33%);
$^1$H NMR (400 MHz, DMSO-d$_6$) δ 11.61 (br. s., 1H), 8.08 (s, 1H), 7.66 (d, 1H), 7.13 (dd, 1H), 6.62 (dd, 1H), 4.86 (s, 1H), 3.84 (t, 1H), 3.57 (d, 1H), 3.26-3.41 (m, 2H), 3.22 (s, 3H), 2.41-2.70 (m, 6H), 2.09-2.23 (m, 1H); LC/MS (exact mass) calculated for $C_{16}H_{20}N_6O_2S$; 360.44. found (M+H$^+$); 361.2.

trans-3-cyano-N-{cis-3-[methyl(7H-pyrrolo[2,3-d] pyrimidin-4-yl)amino] cyclobutyl}cyclobutanesulfonamide Isolation of the second eluting isomer afforded the title compound; Peak 2, trans-isomer: 361 mg (36%); $^1$H NMR (400 MHz, DMSO-d$_6$) δ 11.60 (br. s., 1H), 8.08 (s, 1H), 7.68 (d, 1H), 7.12 (dd, 1H), 6.61 (dd, 1H), 4.70-4.99 (m, 1H), 3.81-3.95 (m, 1H), 3.51-3.63 (m, 2H), 3.36-3.51 (m, 2H), 3.22 (s, 3H), 2.59-2.77 (m, 2H), 2.50-2.59 (m, 2H), 2.09-2.24 (m, 2H); LC/MS (exact mass) calculated for $C_{16}H_{20}N_6O_2S$; 360.44. found (M+H$^+$); 361.2 The mixture of cis- and trans-3-cyanocyclobutane-1-sulfonyl chlorides was prepared as follows:

Step 1: 3-Oxocyclobutane-1-carbonitrile

Ozone gas was bubbled through a solution of 3-methylenecyclobutanel-carbonitrile (5 g, 53.73 mmol) in dichloromethane (225 mL) at −78° C. for 10 minutes until solution turned blue. The solution was then purged with nitrogen gas until the blue color disappeared, and quenched with dropwise addition of dimethylsulfide (1.5 mL) at −78° C. The resulting solution was used directly in next step.

Step 2: 3-Hydroxycyclobutane-1-carbonitrile

To a solution of 3-oxocyclobutane-1-carbonitrile in methanol (150 mL) was added sodium borohydride (4.44 g, 116.84 mmol) at room temperature. The reaction mixture was stirred overnight and quenched using saturate aqueous ammonium chloride (100 mL). The organic layer was removed using a rotary evaporator and aqueous phase was extracted with dichloromethane (2×100 mL).

The combined organic layers were washed with brine, dried over sodium sulfate and concentrated to give title compound (6.5 g, 100%) as oil. $^1$H NMR (400 MHz, CDCl$_3$): δ 4.25-4.17 (m, 1H), 2.67-2.78 (m, 2H), 2.50-2.61 (m, 1H), 2.24-2.38 (m, 2H).

Step 4: 3-(Cyanomethyl)-3-methylcyclobutyl 4-methylbenzenesulfonate

To a solution of 3-hydroxycyclobutane-1-carbonitrile (6.5 g, 67 mmol) in dry dichloromethane (125 mL) was added 4-dimethylaminopyridine (1.50 g, 12.22 mmol) and triethylamine (20 mL, 140 mmol). The mixture stirred at room temperature for 5 minutes and then p-toluenesulfonyl chloride (19.62 g, 102.91 mmol) was added. The resulting mixture was stirred at room temperature overnight. The mixture was washed with saturated aqueous sodium bicarbonate. The dichloromethane layer was extracted, washed with brine, dried over magnesium sulfate and concentrated. The residue was purified by chromatography on silica gel eluting with a gradient of petroleum ether and ethyl acetate (0-50%) to afford the title compound (9.5 g, 65.7%) as yellow solid. $^1$H NMR (400 MHz, CDCl$_3$): δ 7.71 (d, 2H), 7.296 (d, 2H), 4.56-4.77 (m, 1H), 2.54-2.67 (m, 3H), 2.43-2.52 (m, 2H), 2.4 (s, 3H).

Step 5: S-(3-Cyanocyclobutyl) ethanethioate

The mixture of 3-(cyanomethyl)-3-methylcyclobutyl 4-methylbenzenesulfonate (9.39 g, 37.4 mmol) and potassium thioacetate (8.60 g, 75.49 mmol) in N,N-dimethylformamide (125 mL) was heated at 80° C. for 2 hours and then poured into water (200 mL). The mixture was diluted with methyl tert-butyl ether (2×150 mL), dried over sodium sulfate and concentrated to afford the title compound (3.52 g, 61%) as yellow oil. $^1$H NMR (400 MHz, CDCl$_3$): δ 4.22 (m, 1H), 2.99-3.34 (m, 1H), 2.82-2.92 (m, 2H), 2.40-2.49 (m, 2H), 2.26-2.32 (s, 3H).

Step 5: 3-Cyanocyclobutane-1-sulfonyl chloride

A mixture of N-chlorosuccinimide (7.98 g, 60 mmol) in concentrated hydrochloric acid (15 mL) and acetonitrile (60 mL) was stirred at room temperature for 30 minutes. A solution of S-(3-cyanocyclobutyl) ethanethioate (2.33 g, 15 mmol) in acetonitrile (15 mL) was added dropwise at 0° C. and stirred for 30 minutes. The mixture was diluted with saturated aqueous sodium bicarbonate (200 mL) and extracted with methyl tert-butyl ether (3×200 mL). The combined organic layers were dried over anhydrous sodium sulfate and concentrated. The crude product was purified by chromatography on silica gel eluting with a mixture of petroleum ether and ethyl acetate (1:0 to 1:1) to afford the title compound (2.22 g, 83%). as a white solid $^1$H NMR (400 MHz, CDCl$_3$): δ 4.53-4.47 (m, 1H), 3.52-3.45 (m, 1H), 3.14-3.06 (m, 2H), 3.03-2.95 (m, 2H).

Example 47 (Cis) and 50 (Trans)

cis- and trans-3-[({cis-3-[Methyl(7H-pyrrolo[2,3-d]pyrimidin-4-yl)amino]cyclobutyl}methyl)-sulfonyl]cyclobutanecarbonitrile These compounds were prepared using a mixture (~1:1) of cis- and trans-3-[({cis-3-[methyl(7H-pyrrolo[2,3-d]pyrimidin-4-yl)amino]cyclobutyl}methyl)sulfonyl]cyclobutanecarbonitrile. The crude mixture of cis- and trans isomers was purified by reverse phase high performance liquid chromatography using a gradient of water and acetonitrile (95:5 to 5:95) to afford a mixture of the title compounds (80 mg, 45.5%) as a light brown solid. The cis and trans isomers were then chirally analyzed by supercritical fluid chromatography (SFC) using (AD-3 4.6×50 mm col, 60% ethanol, 3 mL/min) column conditions.

cis-3-[({cis-3-[methyl(7H-pyrrolo[2,3-c]pyrimidin-4-yl)amino]cyclobutyl}methyl)sulfonyl]cyclobutanecarbonitrile Isolation of the first eluting isomer afforded the title compound; Peak 1 cis isomer: 17.3 mg (21%); SFC retention time=0.992 minutes; $^1$H NMR (400 MHz, CH$_3$OH-d4): δ 8.12 (s, 1H), 7.13 (d, 1H), 6.69 (d, 1H), 5.12 (m, 1H), 4.02 (m, 1H), 3.45 (m, 1H), 3.43 (s, 3H), 3.27 (m, 2H), 2.77 (m, 3H), 2.58 (m, 3H), 2.21 (m, 2H); LC/MS (exact mass) calculated for C$_{17}$H$_{21}$N$_5$O$_2$S; 359.452. found (M+H$^+$); 360.1.

trans-3-[({cis-3-[Methyl(7H-pyrrolo[2,3-d]pyrimidin-4-yl)amino]cyclobutyl}methyl)sulfonyl]cyclobutane-carbonitrile Isolation of the second eluting isomer afforded the title compound; Peak 2 trans isomer: 17.3 mg (21%); SFC retention time=2.007 minutes. $^1$H NMR (400 MHz, DMSO-d$_6$): δ 11.6 (s, 1H), 8.11 (s, 1H), 7.15 (d, 1H), 6.63 (d, 1H), 5.13 (m, 1H), 4.07 (m, 1H), 3.51 (m, 1H), 3.46 (m, 1H), 3.44 (m, 1H), 3.26 (s, 3H), 2.75 (m, 4H), 2.40 (m, 3H), 2.12 (m, 2H); LC/MS (exact mass) calculated for C$_{17}$H$_{21}$N$_5$O$_2$S; 359.452. found (M+H$^+$); 360.1.

The mixture of cis- and trans-3-[({cis-3-[methyl(7H-pyrrolo[2,3-d]pyrimidin-4-yl)amino]cyclobutyl}methyl)-sulfonyl]cyclobutanecarbonitrile was prepared as follows Step 1: 3-Mercaptocyclobutane-1-carbonitrile The solution of S-(3-cyanocyclobutyl) ethanethioate from Example 42, step 5 (2.0 g, 12.9 mmol) in methanol (40 mL) was added potassium carbonate (4.45 g, 32.3 mmol) and reaction mixture stirred at 50° C. for 2 hours. The reaction was then cooled to room temperature and 2N aqueous hydrochloric acid was added till pH<4. The resulting solution was extracted with tert-butyl methyl ether (3×25 mL) and then the combined organic layers were washed by water (2×20 mL) and brine (40 mL), dried over sodium sulfate, filtered and removed the excess solvent to obtain the crude product as yellow oil. The crude product was purified by silica gel chromatography using gradient of petroleum ether and ethyl acetate (100:0 to 90:10) to obtain the title compound (650 mg, 44.6%) as colorless oil.

Step 2: 3-({[cis-3-(Methyl{7[(4-methylphenyl)sulfonyl]-7H-pyrrolo[2,3-d]pyrimidin-4-yl}amino) cyclobutyl]-methyl}sulfanyl)cyclobutanecarbonitrile A solution of cis-[3-(methyl{7-[(4-methylphenyl)sulfonyl]-7H-pyrrolo[2,3-d]pyrimidin-4-yl}amino)cyclo-butyl] methyl 4-methylbenzenesulfonate from Example 47, Step 4 (400 mg, 0.741 mmol) was stirred in N-methylpyrrolidine (5 mL). Then 1,8-diazabicycloundec-7-ene (225 mg, 1.482 mmol) and 3-mercaptocyclobutane-1-carbonitrile (167 mg, 1.482 mmol) was added to the reaction mixture. The reaction was stirred at room temperature for 16 hours. Water (200 mL) and ethyl acetate (500 mL) were added. The aqueous layer was extracted with ethyl acetate (2×500 mL) and the combined organic layers were dried and concentrated. The residue was chromatographed on silica gel eluting with a gradient of petroleum ether and ethyl acetate (100:0 to 50:50) to afford the title compound (340 mg, 95%). LC/MS (exact mass) calculated for C$_{24}$H$_{27}$N$_5$O$_2$S$_2$; 481.63. found (M+H$^+$); 482.3.

Step 3: 3-({[cis-3-(Methyl{7-[(4-methylphenyl)sulfonyl]-7H-pyrrolo[2,3-d]pyrimidin-4-yl}amino) cyclobutyl]-methyl}sulfonyl)cyclobutanecarbonitrile 3-({[cis-3-(Methyl{7-[(4-methylphenyl)sulfonyl]-7H-pyrrolo[2,3-d]pyrimidin-4-yl}amino)cyclobutyl]methyl}-sulfanyl)cyclobutanecarbonitrile (340 mg, 0.706 mmol) was dissolved in a mixture of tetrahydrofuran (8 mL), ethanol (8 mL) and water (4 mL) at 0° C. Potassium peroxomonosulfate (3.04 g, 4.94 mmol) was added and the reaction was made in portions over 1 hour at 0° C. The reaction was warmed to room temperature, the mixture was then filtered, and washing the solids with a mixture of tetrahydrofuran (8 mL), ethanol (8 mL) and water (4 mL), the filtrate was treated with aqueous 10% sodium bisulfite solution (20 mL) and stirred at room temperature for 20 minutes. A saturated solution of aqueous sodium bicarbonate was added to adjust the pH to 7. The mixture was extracted with dichloromethane (3×30 mL) and the combined organic layers were dried and concentrated under vacuum. The crude residue was chromatographed on silica gel eluting with a gradient of petroleum ether and ethyl acetate (100:0 to 10:90) to obtain the title compound (250 mg, 69%) as solid. LC/MS (exact mass) calculated for $C_{24}H_{27}N_5O_4S_2$; 513.63. found (M+H$^+$); 514.0.

Step 4: cis and trans-3-[({cis-3-[Methyl(7H-pyrrolo [2,3-d]pyrimidin-4-yl)amino]cyclobutyl}methyl)-sulfonyl]cyclobutanecarbonitrile To a solution of 3-({[cis-3-(methyl{7-[(4-methylphenyl)sulfonyl]-7H-pyrrolo[2,3-d]pyrimidin-4-yl}amino)-cyclobutyl]methyl}sulfonyl)cyclobutanecarbonitrile (250 mg, 2.76 mmol) in tetrahydrofuran (4 mL) was added a solution of 1M tetrabutylammonium fluoride in tetrahydrofuran (636 mg, 13.8 mmol). The reaction mixture was heated at 50° C. for 6 hours and then cooled to room temperature. The reaction was concentrated under vacuum and diluted with ethyl acetate (50 mL). The resulting solution was washed with brine (30 mL), dried over sodium sulfate and concentrated. The residue was purified using preparative reverse phase high performance liquid chromatography using gradient of water and acetonitrile (90:10 to 10:90) to afford the title compound (80 mg, 45%) as a white solid. $^1$H NMR (400 MHz, CH$_3$OH-d$_4$): δ 8.13 (s, 1H), 7.13 (d, 1H), 6.69 (d, 1H), 5.11 (m, 1H), 4.07 (m, 1H), 3.49 (m, 1H), 3.47 (m, 1H), 3.36 (s, 3H), 2.92 (m, 2H), 2.82 (m, 2H), 2.62 (m, 3H), 2.26 (m, 2H); LC/MS (exact mass) calculated for $C_{17}H_{21}N_5O_2S$; 359.452. found (M+H$^+$); 360.2.

Example 48

N-Methyl-N-[cis-3-({[(3-methyloxetan-3-yl)methyl] sulfonyl}methyl)cyclobutyl]-7H-pyrrolo[2,3-d]pyrimidin-4-amine Step 1: N-methyl-N-[cis-3-({[(3-methyloxetan-3-yl) methyl]sulfanyl}methyl)cyclobutyl]-7-[(4-methylphenyl)-sulfonyl]-7H-pyrrolo[2,3-d]pyrimidin-4-amine Nitrogen was bubbled through a mixture of S-{[cis-3-(methyl{7-[(4-methylphenyl)-sulfonyl]-7H-pyrrolo[2,3-d] pyrimidin-4-yl}amino)cyclobutyl]methyl}ethanethioate (Example 47, Step 5; 539 mg, 1.21 mmol) and potassium carbonate (209 mg, 1.51 mmol) in methanol (30 mL) for two minutes at 0° C. followed by addition of 3-(bromomethyl)-3-methyloxetane (100 mg, 0.60 mmol). The mixture gradually warmed and stirred at room temperature for 6 hours. The reaction was concentrated and diluted with ethyl acetate (200 mL), washed with water, brine, dried over sodium sulfate, filtered, and concentrated to give the title compound (170 mg, crude) as white solid. LC/MS (exact mass) calculated for $C_{24}H_{30}N_4O_3S_2$; 486.65. found (M+H$^+$); 487.1.

Step 2: N-methyl-N-[cis-3-({[(3-methyloxetan-3-yl) methyl]sulfonyl}methyl)cyclobutyl]-7-[(4-methylphenyl)-sulfonyl]-7H-pyrrolo[2,3-d]pyrimidin-4-amine To a solution of N-methyl-N-[cis-3-({[(3-methyloxetan-3-yl)methyl]sulfanyl}methyl)cyclobutyl]-7-[(4-methylphenyl)sulfonyl]-7H-pyrrolo[2,3-d]pyrimidin-4-amine (170 mg, 0.35 mmol) in tetrahydrofuran (20 mL), water (10 mL) and ethanol (20 mL) was added potassium peroxomonosulfate (645 mg, 1.049 mmol) in portions at 0° C. over 1 hour. The mixture was warmed to room temperature for 30 minutes. Aqueous sodium bisulfite was then added, followed by dichloromethane (20 mL). The aqueous layer was extracted with ethyl acetate (2×20 mL) and the combined organic layers were washed with brine, dried over sodium sulfate, and concentrated to give the title compound as white solid (152 mg, crude). LC/MS (exact mass) calculated for $C_{24}H_{30}N_4O_5S_2$; 518.65. found (M+H$^+$); 519.2.

Step 3: N-Methyl-N-[cis-3-({[(3-methyloxetan-3-yl) methyl]sulfonyl}methyl)cyclobutyl]-7H-pyrrolo[2,3-d]pyrimidin-4-amine The mixture of N-methyl-N-[cis-3-({[(3-methyloxetan-3-yl)methyl]sulfonyl}methyl)cyclobutyl]-7-[(4-methylphenyl)sulfonyl]-7H-pyrrolo[2,3-d]pyrimidin-4-amine (152 mg, 0.293 mmol) and lithium hydroxide (62 mg, 1.47 mmol) in a mixture of water (10 mL) and ethanol (20 mL) was stirred at 50° C. for 2 hours. The mixture was then concentrated and the residue was taken up in ethyl acetate. The organic layer was washed with brine, dried over sodium sulfate and concentrated. The crude product was purified by reverse phase high performance liquid chromatography using a gradient of water and acetonitrile (95:5 to 5:95) to give the title compound (17.6 mg, 16%) as white solid. $^1$H NMR (400 MHz, CH$_3$OH-d$_4$): δ 8.13 (s, 1H), 7.13-7.12 (d, 1H), 6.70-6.69 (d, 1H), 5.16-5.13 (m, 1H), 4.77-4.76 (m, 2H), 4.40-4.39 (m, 2H), 3.56 (s, 2H), 3.36 (m, 3H), 3.31 (m, 2H), 2.65-2.62 (m, 2H), 2.26-2.23 (m, 2H), 1.67 (s, 3H); LC/MS (exact mass) calculated for $C_{17}H_{24}N_4O_3S$; 364.48. found (M+H$^+$); 365.1.

Examples 49, 51, and 55

The following compounds were made starting from cis-[3-(methyl{7-[(4-methylphenyl)sulfonyl]-7H-pyrrolo[2,3-d]pyrimidin-4-yl}amino)cyclobutyl]methanesulfonyl chloride, according to the procedures of Example 44, Step 8 (sulfonylation) and step 9 (deprotection), substituting the appropriate amine for azetidine-3-carbonitrile 2,2,2-trifluoroacetate in Step 8.

Example 49

3-Methyl-1-[({cis-3-[methyl(7H-pyrrolo[2,3-c]pyrimidin-4-yl)amino]cyclobutyl}methyl)sulfon-yl] azetidine-3-carbonitrile The title compound (68 mg) was prepared using 3-methylazetidine-3-carbonitrile hydrochloride in the sulfonylation step and was deprotected using the method from Example 44, Step 9. The compound was purified using preparative thin layer chromatography eluting with ethyl acetate (100%).

$^1$H NMR (400 MHz, CH$_3$OH-d$_4$): δ 8.12 (s, 1H), 7.13-7.13 (d, 1H), 6.70-6.69 (d, 1H), 5.06-5.17 (m, 1H), 4.27-4.25 (d, 2H), 3.92-3.90 (d, 2H), 3.36 (s, 3H), 3.33 (s, 2H), 2.61-2.58 (m, 3H), 2.23-2.21 (m, 1H), 1.695 (s, 3H). LC/MS (exact mass) calculated for $C_{17}H_{22}N_6O_2S$; 374.467. found (M+H$^+$); 375.1.

Example 51

(1R,5R)-3-[({cis-3-[Methyl(7H-pyrrolo[2,3-c]pyrimidin-4-yl)amino]cyclobutyl}methyl)-sulfonyl]-3-azabicyclo[3.1.0]hexane-1-carbonitrile The title compound (120 mg) was prepared using (1R, 5R)-3-azabicyclo[3.1.0]hexane-1-carbonitrile 2,2,2-trifluoroacetate in the sulfonylation step and was de-protected using the method from Example 44, Step 9. The residue was chromatographed on silica gel eluting with a gradient of dichloromethane and ethyl acetate (100:0 to 95:5). $^1$H NMR (400 MHz, $CH_3OH$-$d_4$): δ 8.107 (s, 1H), 7.15 (s, 1H), 6.63 (s, 1H), 5.14 (m, 1H), 3.69-3.67 (d, 1H), 3.58-3.56 (d, 1H) 3.50 (m, 1H) 3.45 (m, 1H) 3.33 (m, 1H) 3.26 (s, 3H) 2.44 (m, 2H) 2.42-2.38 (m, 3H) 2.11-2.09 (m, 1H) 1.51-1.48 (m, 1H) 1.11-1.09 (m, 1H); LC/MS (exact mass) calculated for $C_{18}H_{22}N_6O_2S$; 386.47. found (M+H$^+$); 387.0 (1R,5R)-3-Azabicyclo[3.1.0]hexane-1-carbonitrile 2,2,2-trifluoroacetate was prepared as follows:

Step 1: racemic-tert-Butyl rac-1-formyl-3-azabicyclo[3.1.0]hexane-3-carboxylate 1,1,1-Triacetoxy-1,1-dihydro-1,2-benziodoxol-3(1H)-one (6.5 g, 15.2 mmol) was added to a solution of racemic tert-butyl-1-(hydroxymethyl)-3-azabicyclo[3.1.0]hexane-3-carboxylate (Synlett 2009, 921) (2.5 g, 11.7 mmol) in anhydrous dichloromethane (60 mL). The reaction mixture stirred for 2 hours at room temperature. The mixture was diluted with dichloromethane (60 mL), washed with a saturated aqueous solution of sodium sulfite, saturated sodium bicarbonate (30 mL) and brine (50 mL). The organic layer was dried over sodium sulfate and concentrated to give afford the title compound as a colorless oil (1.7 g, 68%). $^1$H NMR (400 MHz, $CDCl_3$): δ 9.01 (d, 1H), 3.83 (d, 1H), 3.68 (t, 1H), 3.59 (dd, 1H), 3.50-3.36 (m, 1H), 2.25-2.09 (m, 1H), 1.63 (t, 1H), 1.43 (s, 9H), 1.19-1.06 (m, 1H).

Step 2: Racemic-tert-butyl-1-[(hydroxyimino)methyl]-3-azabicyclo[3.1.0]hexane-3-carboxylate Potassium carbonate (3.89 g, 28.2 mmol) and hydroxylamine hydrochloride (671 mg, 9.7 mmol) were added to a solution of tert-butyl racemic 1-formyl-3-azabicyclo[3.1.0] hexane-3-carboxylate (1.7 g, 8.05 mmol) in anhydrous dichloromethane (40 mL) at room temperature and then stirred for 16 hours. The mixture was diluted with ethyl acetate (80 mL), and washed with water (30 mL) and brine (30 mL). The organic layer was dried over sodium sulfate and concentrated. The residue was chromatographed on silica gel eluting with a gradient of petroleum ether and ethyl acetate (0:100 to 83:17) to afford the title compound as a yellow oil (1.6 g, 88%). $^1$H NMR (400 MHz, $CDCl_3$): δ 7.18 (s, 1H), 3.74-3.55 (m, 3H), 3.44-3.40 (m, 1H), 1.74-1.72 (m, 1H), 1.44 (s, 9H), 1.10 (t, 1H), 0.86-0.83 (m, 1H).

Step 3: racemic-tert-Butyl-1-cyano-3-azabicyclo[3.1.0]hexane-3-carboxylate

To a solution of racemic tert-butyl-1-[(hydroxyimino)methyl]-3-azabicyclo[3.1.0]hexane-3-carboxylate (925 mg, 4.09 mmol) in anhydrous tetrahydrofuran (100 mL) was added methyl N-(triethylammoniumsulfonyl)carbamate (2.92 g, 12.3 mmol). The reaction mixture was heated to reflux for 3 hours. After evaporation of the solvent, the residue was chromatographed on silica gel eluting with a mixture of petroleum ether and ethyl acetate (5:1) to afford the title compound as a colorless oil (570 mg, 67%). $^1$H NMR (400 MHz, $CDCl_3$): δ 3.84 (dd, 1H), 3.64 (dd, 1H), 3.50 (d, 1H), 3.46 (dd, 1H), 2.21-2.12 (m, 1H), 1.44 (s, 9H), 0.96 (t, 1H).

The racemic mixture (1 g) was chirally separated by supercritical fluid chromatography (SFC) using (Chiral Pak AD-H, 21×250 mm col, 20% ethanol (0.05% formic acid), 20 mL/min) column conditions.

tert-Butyl(1R,5R)-1-Cyano-3-azabicyclo[3.1.0]hexane-3-carboxylate

Isolation of the first eluting isomer afforded the title compound; Peak 1 (PF-06689475), 450 mg (45%); SFC retention time=3.674 minutes; $^1$H NMR (400 MHz, $CDCl_3$): δ 3.84 (dd, 1H), 3.64 (dd, 1H), 3.50 (d, 1H), 3.46 (dd, 1H), 2.21-2.12 (m, 2H), 1.44 (s, 9H), 0.96 (t, 1H)

tert-butyl(1S,5S)-1-Cyano-3-azabicyclo[3.1.0]hexane-3-carboxylate

Isolation of the second eluting isomer afforded the title compound; Peak 2 (PF-06689473), 420 mg (42%); SFC retention time=5.118 minutes; $^1$H NMR (400 MHz, $CDCl_3$): δ 3.84 (dd, 1H), 3.64 (dd, 1H), 3.50 (d, 1H), 3.46 (dd, 1H), 2.21-2.12 (m, 2H), 1.44 (s, 9H), 0.96 (t, 1H).

Step 4: (1R,5R)-3-Azabicyclo[3.1.0]hexane-1-carbonitrile 2,2,2-trifluoroacetate To a solution of tert-butyl(1R,5R)-1-cyano-3-azabicyclo[3.1.0]hexane-3-carboxylate (150 mg, 0.725 mmol) in dichloromethane (3 mL) was added a 1:1 mixture of dichloromethane (1 mL) and trifluoroacetic acid (1 mL) dropwise at 0° C. The reaction mixture was stirred at room temperature for 3 hours. The mixture was concentrated and washed with dichloromethane (2×10 ml) to give title compound (120 mg, >100%) as yellow oil.

Example 52 (Cis) and 53 (Trans)

cis- and trans-3-(Difluoromethyl)-N-{cis-3-[methyl(7H-pyrrolo[2,3-d]pyrimidin-4-yl)amino]-cyclobutyl}cyclobutanesulfonamide These compounds were prepared using a mixture (~1:1) of cis- and trans-3-(difluoromethyl)cyclobutane-1-sulfonyl chloride. The crude mixture of cis- and trans-isomers was purified by reverse phase chromatography to afford a mixture (0.26 g, 15.82%) of the title compounds as a white solid. The cis- and trans-isomers were then chirally separated by supercritical fluid chromatography (SFC) using (OD-H 30×250 mm col, 5 μm, 32% ethanol, 60 mL/min) column conditions.

trans-3-(Difluoromethyl)-N-{cis-3-[methyl(7H-pyrrolo[2,3-d]pyrimidin-4-yl)amino]cyclobutyl}cyclobutane-sulfonamide Isolation of the first eluting isomer afforded the title compound; Peak 1, trans-isomer: 160.5 mg (46.4%); SFC retention time=8.28 minutes; $^1$H NMR (400 MHz, DMSO-$d_6$) δ 11.72 (br. s., 1H), 8.10 (s, 1H), 7.65 (d, 1H), 7.15 (dd, 1H), 6.64 (dd, 1H), 6.4-6.04 (d, 1H), 4.81-4.94 (m, 1H), 3.77 (t, 1H), 3.51-3.64 (m, 1H), 3.25 (s, 3H), 2.65-2.80 (m, 1H), 2.52-2.63 (m, 2H), 2.15-2.45 (m, 6H); LC/MS (exact mass) calculated for $C_{16}H_{21}F_2N_6O_2S$; 385.44. found (M+H$^+$); 386.1.

cis-3-(Difluoromethyl)-N-{cis-3-[methyl(7H-pyrrolo [2,3-d]pyrimidin-4-yl)amino] cyclobutyl}cyclobutane-sulfonamide Isolation of the second eluting isomer afforded the title compound; Peak 2, cis-isomer: 157.8 mg (45.6%); SFC retention time=8.68 minutes; $^1$H NMR (400 MHz, DMSO-d$_6$) δ 11.62 (br. s., 1H), 8.10 (s, 1H), 7.54 (d, 1H), 7.15 (dd, 1H), 6.64 (dd, 1H), 6.04 (d, 1H), 4.81-4.94 (m, 1H), 3.77 (t, 1H), 3.51-3.64 (m, 1H), 3.25 (s, 3H), 2.65-2.80 (m, 1H), 2.52-2.63 (m, 2H), 2.15-2.33 (m, 6H); LC/MS (exact mass) calculated for $C_{16}H_{21}F_2N_6O_2S$; 385.44. found (M+H$^+$); 386.1.

Step 1: Ethyl 3-oxocyclobutane-1-carboxylate

A mixture of oxocyclobutane-1-carboxylic acid (99.52 g, 0.90 mol) and triethyl orthoacetate (285 g, 1.76 mol) in toluene (2 L) was refluxed overnight. The toluene was removed under reduced pressure; the residue was partitioned between ethyl acetate and water. The aqueous layer was extracted with ethyl acetate (2×500 mL). The combined organic layer was washed with brine (500 mL), dried over sodium sulfate, filtered and concentrated as brown oil. No purification was done before next step. $^1$H NMR (400 MHz, CDCl$_3$) δ 4.21 (q, 2H), 3.34-3.47 (m, 2H), 3.15-3.34 (m, 3H), 1.12-1.36 (t, 3H)

Step 2: Ethyl 3-hydroxycyclobutane-1-carboxylate

To a solution of ethyl 3-oxocyclobutane-1-carboxylate (1010 g, 7235 mmol) in ethanol (12 L) was added sodium borohydride (220 g, 5789 mmol) in portions at 0° C. over a period of 1 hour. The reaction mixture was stirred at room temperature for 2 hours. The reaction was cooled back to 0° C. and quenched using 1N aqueous hydrochloric acid (2 L), which resulted in white precipitate. The mixture was filtered and filtrate was evaporated to dryness. The residue was partitioned between ethyl acetate (10 L) and water (5 L), the organic layer was removed and aqueous phase was extracted again with ethyl acetate (2×5 L). The combined organic layers were washed with brine, dried over sodium sulfate and concentrated to give title compound (710 g, 70%) as colorless oil. $^1$H NMR (400 MHz, CDCl$_3$) δ 3.98-4.23 (q, 3H), 2.46-2.64 (m, 3H), 2.05-2.23 (m, 2H), 1.14-1.30 (t, 3H)

Step 3: Ethyl 3-(tosyloxy)cyclobutane-1-carboxylate

This compound was prepared following Example 42, Step 4, and substituting 3-hydroxycyclobutane-1-carbonitrile for ethyl 3-hydroxycyclobutane-1-carboxylate. The crude compound was purified by chromatography on silica gel eluting with a gradient of petroleum ether and ethyl acetate (0-20%) to afford the title compound (88.3%) as oil. $^1$H NMR (400 MHz, CDCl$_3$) δ 7.78 (m, 2H), 7.34 (m, 2H), 4.73 (m, 1H), 3.98-4.23 (q, 2H), 2.54-2.68 (m, 1H), 2.28-2.54 (m, 7H), 1.14-1.33 (m, 3H)

Step 4: 3-(Hydroxymethyl)cyclobutyl 4-methylbenzenesulfonate

To a solution of ethyl 3-(tosyloxy)cyclobutane-1-carboxylate (3.03 g, 10.31 mmol) in tetrahydrofuran (250 mL) at 0° C. was added lithium aluminum hydride (783.3 mg, 20.61 mmol) in portions. The reaction mixture was stirred at 0° C. for 2 hours. Solid sodium sulfate decahydrate was added, reaction filtered and concentrated to give title compound (1.94 g, 74.62%) as colorless oil. The material was used directly in next step. $^1$H NMR (400 MHz, CDCl$_3$) δ 7.76 (d, 2H), 7.32 (d, 2H), 4.69 (t, 1H), 3.46-3.63 (m, 2H), 2.43 (s, 3H), 2.16-2.33 (m, 2H), 1.77-2.07 (m, 3H)

Step 5: 3-Formylcyclobutyl 4-methylbenzenesulfonate

To a mixture of 3-(hydroxymethyl)cyclobutyl 4-methylbenzenesulfonate (1.94 g, 7.76 mmol) in dichloromethane (200 mL) was added Dess-Martin periodinates (4.31 g, 10.07 mmol) at 0° C. The reaction mixture was stirred at room temperature overnight. The reaction was diluted with saturated aqueous sodium bicarbonate, organic layer extracted, dried over sodium sulfate, and concentrated. The crude compound was purified by chromatography on silica gel eluting with a gradient of petroleum ether and ethyl acetate (0-50%) to afford the title compound (1.76 g, 92%) as colourless oil.
$^1$H NMR (400 MHz, DMSO-d$_6$) δ 9.55 (d, 1H), 7.79 (d, 2H), 7.49 (d, 2H), 4.83 (t, 1H), 2.63-2.90 (m, 1H), 2.43 (s, 3H), 2.26-2.37 (m, 2H), 2.11-2.26 (m, 2H)

Step 6: 3-(Difluoromethyl)cyclobutyl 4-methylbenzenesulfonate

To a solution of 3-formylcyclobutyl 4-methylbenzenesulfonate (883.4 mg, 3.48 mmol) in dichloromethane (150 mL), diethylaminosulfur trifluoride (1.12 g, 6.96 mmol) was added dropwise at −30° C. The reaction mixture was stirred at room temperature overnight. The reaction mixture was poured into mixture of dichloromethane (50 mL) and saturated aqueous ammonium bicarbonate (50 mL). The aqueous layer was extracted with dichloromethane (2×100 mL), the combined organic layer was washed with brine (50 mL), dried over sodium sulfate, filtered and concentrated to give title compound (820.2 mg, 85.76%) as yellow oil. $^1$H NMR (400 MHz, CDCl$_3$) δ 7.75-7.86 (m, 2H), 7.35 (d, 2H), 5.56-5.85 (dd, 1H), 4.70-4.91 (m, 1H), 2.45 (s, 3H), 2.14-2.41 (m, 5H).

Step 7: S-(3-(Difluoromethyl)cyclobutyl) ethanethioate

This compound was prepared following Example 42, Step 5, and substituting 3-(cyanomethyl)-3-methylcyclobutyl 4-methylbenzenesulfonate for 3-(difluoromethyl)cyclobutyl 4-methylbenzenesulfonate. The crude compound was purified by chromatography on silica gel eluting with a gradient of petroleum ether and ethyl acetate (0-25%) to afford the title compound (92%) as yellow oil. $^1$H NMR (400 MHz, CDCl$_3$) δ 5.73 (d, 1H), 4.12 (q, 1H), 2.49-2.82 (m, 3H), 2.27-2.31 (m, 3H), 2.06-2.23 (m, 2H).

Step 8: 3-(Difluoromethyl)cyclobutane-1-sulfonyl chloride

This compound was prepared following Example 42, Step 6, and substituting S-(3-cyanocyclobutyl) ethanethioate for S-(3-(difluoromethyl)cyclobutyl) ethanethioate. The crude compound was purified by chromatography on silica gel eluting with a gradient of petroleum ether and ethyl acetate (0-50%) to afford the title compound (100%) as yellow oil.

¹H NMR (400 MHz, CDCl₃) δ 5.59-6.16 (m, 1H), 4.21-4.55 (m, 1H), 2.73-3.06 (m, 3H), 2.55-2.72 (m, 2H).

Example 54a (Trans) and 54B (Cis)

cis- and trans-1-(3-Cyano-1-methylcyclobutyl)-N-{cis-3-[methyl(7H-pyrrolo[2,3-d]pyrimidin-4-yl)amino]cyclobutyl}methanesulfonamide These compounds were prepared using a mixture (~1:1) of cis- and trans-(3-cyano-1-methylcyclobutyl)methanesulfonyl chloride. The crude mixture of cis- and trans-isomers was purified by chromatography on silica gel eluting with a gradient of dichloromethane and methanol (0-7%) to afford a mixture (0.13 g) of the title compounds as a white solid (16.7%). The cis and trans isomers were then chirally separated by supercritical fluid chromatography (SFC) using (Chiral Pak AD, 30×250 mm col, 5 μm, 55% ethanol, 50 mL/min) column conditions.

1-(trans-3-Cyano-1-methylcyclobutyl)-N-{cis-3 [methyl(7H-pyrrolo[2,3-d]pyrimidin-4-yl)amino] cyclobutyl}-methanesulfonamide Isolation of the first eluting isomer afforded the title compound; Peak 1, trans-isomer: 7.0 mg (5.3%); SFC retention time=3.75 minutes; ¹H NMR (400 MHz, Methanol-d₄) δ 8.12 (s, 1H), 7.14-7.13 (m, 1H), 6.71-6.69 (m, 1H), 4.85-4.84 (m, 1H), 3.75-3.69 (m, 1H), 3.36 (m, 4H), 3.25 (s, 2H), 2.79-2.70 (m, 4H), 2.32-2.29 (m, 2H), 2.21-2.17 (m, 2H), 1.54 (s, 3H); LC/MS (exact mass) calculated for C₁₈H₂₄N₆O₂S; 388.49. found (M+H⁺); 389.0.

1-(cis-3-Cyano-1-methylcyclobutyl)-N-{cis-3-[methyl(7H-pyrrolo[2,3-d]pyrimidin-4-yl)amino] cyclobutyl}-methanesulfonamide Isolation of the second eluting isomer afforded the title compound; Peak 2, cis-isomer: 18.8 mg (14.5%); SFC retention time=4.84 minutes; ¹H NMR (400 MHz, CH₃OH-d₄) δ 8.12 (s, 1H), 7.14-7.13 (m, 1H), 6.71-6.67 (m, 1H), 4.84 (m, 1H), 3.77-3.75 (m, 1H), 3.38 (m, 4H), 3.25 (s, 2H), 2.81-2.77 (m, 2H), 2.56-2.53 (m, 2H), 2.35-2.27 (m, 4H), 1.46 (s, 3H); LC/MS (exact mass) calculated for C₁₈H₂₄N₆O₂S; 388.49. found (M+H⁺); 389.1.

The mixture of cis- and trans-(3-cyano-1-methylcyclobutyl)methanesulfonyl chloride was prepared as follows:

Step 1: 1-Methyl-3-methylenecyclobutanecarbonitrile

To a solution of 3-methylenecyclobutanecarbonitrile (35.0 g, 373.0 mmol) in tetrahydrofuran (200 mL) was added dropwise lithium bis(trimethylsilyl)amide (450 mL, 1M) at −78° C. The solution was stirred for 1 hour at −78° C. and iodomethane (30 mL, 448 mmol) was added to the reaction. After 1 hour, the mixture was warmed to room temperature and stirred overnight. The reaction mixture was quenched with aqueous ammonium chloride (380 mL) and extracted with methyl tert-butyl ether (3×400 mL). The combined organic layers were dried over sodium sulfate and concentrated. The crude product was purified by distillation under reduced pressure to afford the title compound (20 g, 50%) as clear oil. ¹H NMR (400 MHz, CDCl₃): δ 4.90-4.89 (m, 2H), 3.24-3.20 (m, 2H), 2.67-2.62 (m, 2H), 1.50 (s, 3H).

Step 2: 1-Methyl-3-methylenecyclobutanecarboxylic acid

To a solution of 1-methyl-3-methylenecyclobutanecarbonitrile (10.0 g, 93.3 mmol) in water (50 mL) and ethanol (50 mL) was added potassium hydroxide (25.6 g, 466.6 mmol). The reaction mixture was heated to reflux and stirred overnight. The ethanol was removed under reduced pressure, and the solution was cooled to below 10° C., acidified with concentrated hydrochloric acid to pH 1. The aqueous phase was extracted with ethyl acetate (3×150 mL). The combined organic layers were dried over sodium sulfate and concentrated to afford the title compound (9 g, 77%). ¹H NMR (400 MHz, CDCl₃): δ 11.90 (s, 1H), 4.88-4.85 (m, 2H), 3.23-3.17 (m, 2H), 2.53-2.41 (m, 2H), 1.45 (s, 3H)

Step 3: Ethyl 1-methyl-3-methylenecyclobutanecarboxylate

To a solution of 1-methyl-3-methylenecyclobutanecarboxylic acid (6 g, 47.6 mmol) in dichloromethane (30 mL) at 0° C. was added dropwise thionyl chloride (11.0 mL, 143 mmol). The solution was stirred at 0° C. for 1 hour. Three drops of N,N-dimethylformamide were added to the solution. The solution was stirred at 0° C. for 30 minutes. The solvent was evaporated and dichloromethane (20 mL) and ethanol (125 mL) were added to the residue. The resulting solution was stirred for 16 hours at room temperature. The solvent was evaporated and water (20 mL) was added to the residue. The aqueous layer was extracted with dichloromethane (4×20 mL). The combined organic layers were dried over sodium sulfate and concentrated. The crude product was purified by chromatography on silica gel eluting with a gradient of petroleum ether and ethyl acetate (20:1 to 10:1) to afford the title compound (5 g, 68%). ¹H NMR (400 MHz, CDCl₃): δ 4.85-4.83 (m, 2H), 4.17-4.12 (m, 2H), 3.18-3.12 (m, 2H), 2.48-2.42 (m, 2H), 1.41 (s, 3H), 1.27-1.23 (t, 3H).

Step 4: Ethyl 1-methyl-3-oxocyclobutane-1-carboxylate

Ozone gas was bubbled through a solution of ethyl 1-methyl-3-methylenecyclobutane-1-carboxylate (7.7 g, 50 mmol) in dichloromethane (150 mL) at −78° C. for 10 minutes until solution turned blue. After purging the solution with nitrogen gas, dimethylsulfide (10 mL) was added dropwise to the solution at −78° C. The solution was stirred for 30 minutes at −78° C. and the solvent was removed under reduced pressure. The crude product was purified by chromatography on silica gel eluting with a gradient of petroleum ether and ethyl acetate (7:1) to afford the title compound (5.4 g, 69%) as a oil. ¹H NMR (400 MHz, CDCl₃): δ 4.24-4.20 (q, 2H), 3.61-3.54 (m, 2H), 2.92-2.86 (m, 2H), 1.57 (s, 3H), 1.29-1.27 (t, 3H)

Step 5: Ethyl 3-hydroxy-1-methylcyclobutane-1-carboxylate

To a solution of ethyl 1-methyl-3-oxocyclobutane-1-carboxylate (10 g, 64 mmol) in tetrahydrofuran (15 mL) cooled to −20° C. was added sodium borohydride (3.65 g, 96 mmol) in small portions. The mixture was stirred for 4 hours at room temperature. The reaction as warmed to room temperature then quenched with acetone (2 mL). The solvent was evaporated. Water (10 mL) was added to the residue and the aqueous phase was extracted with dichloromethane (4×15 mL). The combined organic layers were dried over sodium sulfate and concentrated. The crude product was purified by chromatography on silica gel eluting with a gradient of petroleum ether and ethyl acetate (6:1) to afford the title compound (6.2 g, 60%) as a colorless oil. $^1$H NMR (400 MHz, CDCl$_3$): δ 4.41-4.37 (m, 1H), 4.15-4.13 (m, 2H), 2.83-2.77 (m, 1H), 2.34-2.23 (m, 2H), 1.90-1.83 (m, 1H), 1.40-1.35 (s, 3H), 1.25-1.23 (m, 3H).

Step 6: Ethyl 1-methyl-3-((methylsulfonyl)oxy)cyclobutane-1-carboxylate

To a solution of ethyl 3-hydroxy-1-methylcyclobutane-1-carboxylate (0.53 g, 3 mmol) in dry dichloromethane (100 mL) at 0° C. was added 4-dimethylaminopyridine (0.6 g, 6 mmol). A solution of methane sulfonyl chloride (0.5 g, 4.5 mmol) was added in dichloromethane (20 mL) was added dropwise. The resulting mixture was stirred at room temperature overnight. The mixture was diluted with water, dichloromethane layer was extracted, washed with brine, dried over magnesium sulfate and concentrated to afford the title compound (0.59 g, 83%) as oil. $^1$H NMR (400 MHz, CDCl$_3$): δ 5.12-5.04 (m, 1H), 4.2-4.15 (q, 2H), 3.01 (s, 3H), 2.99-2.91 (m, 1H), 2.75-2.75 (m, 1H), 2.43-2.40 (m, 1H), 2.28-2.25 (m, 1H), 1.157 (s, 3H), 1.30 (t, 3H)

Step 7: Ethyl 3-cyano-1-methylcyclobutane-1-carboxylate

To a solution of ethyl 1-methyl-3-((methylsulfonyl)oxy)cyclobutane-1-carboxylate (1.56 g, 5 mmol) in dry N'N-dimethylformamide (20 mL) was added potassium carbonate (1.64 g, 6 mmol) and potassium cyanide (0.58 g, 10 mmol). The solution was heated at 120° C. for 2 days. The mixture was diluted with ethyl acetate, washed with brine, dried over magnesium sulfate and concentrated to afford the title compound (0.3 g, 27%) as oil. $^1$H NMR (400 MHz, CDCl$_3$): δ 4.21-4.17 (q, 2H), 3.13-3.09 (m, 1H), 2.86-2.81 (m, 2H), 2.28-2.22 (m, 2H), 1.57 (s, 3H), 1.30-1.24 (t, 3H).

Step 8: 3-(Hydroxymethyl)-3-methylcyclobutane-1-carbonitrile

To a solution of ethyl 3-cyano-1-methylcyclobutane-1-carboxylate (1.67 g, 10 mmol) in tetrahydrofuran (20 mL) was added lithium borohydride (0.44 g, 20 mmol). The mixture was heated at 40° C. and stirred for 2 days. The reaction mixture was quenched with saturated aqueous ammonium chloride; the aqueous phase was extracted with ethyl acetate (2×200 mL). The combined organic layers were dried over magnesium sulfate and concentrated. The crude product was purified by chromatography on silica gel eluting with a gradient of petroleum ether and ethyl acetate (1:1) to afford the title compound (0.9 g, 72%) as a colorless oil. $^1$H NMR (400 MHz, CDCl$_3$): δ 3.46-3.46 (m, 2H), 3.12-3.06 (m, 1H), 2.44-2.38 (m, 2H), 2.37-2.356 (m, 2H), 1.16-1.07 (s, 3H).

Step 9: (3-cyano-1-methylcyclobutyl)methyl 4-methylbenzenesulfonate

This compound was prepared following Example 42, Step 4, and substituting 3-hydroxycyclobutane-1-carbonitrile for 3-(hydroxymethyl)-3-methylcyclobutane-1-carbonitrile. The crude compound was purified by chromatography on silica gel eluting with a gradient of petroleum ether and ethyl acetate (0-20%) to afford the title compound (88.3%) as oil. $^1$H NMR (400 MHz, CDCl$_3$) δ 7.82-7.78 (m, 2H), 7.38-7.36 (m, 2H), 3.85 (s, 2H), 3.11-3.00 (m, 1H), 2.46 (s, 3H), 2.38-2.15 (m, 2H), 2.10-2.07 (m, 2H), 1.18 (s, 3H)

Step 10: S-((3-Cyano-1-methylcyclobutyl)methyl) ethanethioate

This compound was prepared following Example 42, Step 5, and substituting 3-(cyanomethyl)-3-methylcyclobutyl 4-methylbenzenesulfonate for (3-cyano-1-methylcyclobutyl)methyl 4-methylbenzene-sulfonate. The crude compound was purified by chromatography on silica gel eluting with a gradient of petroleum ether and ethyl acetate (0-25%) to afford the title compound (92%) as yellow oil. $^1$H NMR (400 MHz, CDCl$_3$) δ 5.73 (d, 1H), 4.12 (m, 1H), 2.49-2.82 (m, 3H), 2.27-2.31 (m, 3H), 2.06-2.23 (m, 2H).

Step 8: (3-Cyano-1-methylcyclobutyl)methanesulfonyl chloride

This compound was prepared following Example 42, Step 6, and substituting S-(3-cyanocyclobutyl) ethanethioate for S-((3-cyano-1-methylcyclobutyl)methyl) ethanethioate. The crude compound was purified by chromatography on silica gel eluting with a gradient of petroleum ether and ethyl acetate (6:1) to afford the title compound (46%) as yellow oil. $^1$H NMR (400 MHz, CDCl$_3$) δ 3.98 (s, 2H), 3.24-3.17 (m, 1H), 2.73-2.57 (m, 2H), 2.42-2.37 (m, 2H), 1.540 (s, 3H)

Example 55

N-[cis-3-({[3-(Difluoromethyl)azetidin-1-yl]sulfonyl}methyl)cyclobutyl]-N-methyl-7H-pyrrolo[2,3-d]pyrimidin-4-amine The title compound (101 mg) was prepared using 3-(difluoromethyl)azetidine hydrochloride in the sulfonylation step and was de-protected using the method from Example 47, Step 9. The residue was chromatographed by reverse phase preparative chromatography eluting with gradient of water and acetonitrile (90:10 to 70:30)$^1$H NMR (400 MHz, CH$_3$OH-d$_4$): δ 8.15 (s, 1H), 7.18-7.17 (d, 1H), 6.75-6.74 (d, 1H), 6.27-5.98 (m, 1H), 5.09-5.05 (m, 1H), 4.10-4.05 (m, 2H), 3.99-3.95 (m, 1H), 3.38 (s, 3H), 3.30 (m, 2H), 3.14-3.09 (m, 1H), 2.63-2.57 (m, 3H), 2.27-2.22 (m, 2H); LC/MS (exact mass) calculated for C$_{16}$H$_{21}$F$_2$N$_5$O$_2$S; 385.437. found (M+H$^+$); 386.9.

Example 56 (trans) and 57 (cis): cis- and trans-3-Fluoro-N-{cis-3-[methyl(7H-pyrrolo[2,3-d]pyrimidin-4-yl)amino]cyclo-butyl}cyclobutanesulfonamide (trans),(cis)

These compounds were prepared using a mixture (~1:1) of cis- and trans-3-fluorocyclobutane-1-sulfonyl chloride. The crude mixture of cis- and trans-isomers was purified by chromatography on silica gel eluting with a gradient of dichloromethane and methanol (100:0 to 90:10) to afford a mixture (45 mg) of the title compounds as a white solid (25%). The cis and trans isomers were then chirally separated by supercritical fluid chromatography (SFC) using (Chiral Pak AS, 30×250 mm col, 20 μm, 25% ethanol (0.05% concentrated ammonia), 80 mL/min) column conditions.

Trans-3-Fluoro-N-{cis-3-[methyl(7H-pyrrolo[2,3-d]pyrimidin-4-yl)amino]cyclobutyl}cyclobutanesulfonamide Isolation of the first eluting isomer afforded the title compound; Peak 1, trans-isomer: 5.9 mg (16.9%); SFC retention time=4.01 minutes; $^1$H NMR (400 MHz, CH$_3$OH-d$_4$) δ 8.12 (s, 1H), 7.14 (d, 1H), 6.45 (d, 1H), 5.43-5.21 (m, 1H), 3.75-3.69 (m, 1H), 3.52-3.3 (m, 1H), 3.36 (m, 3H), 2.79-2.90 (m, 7H), 2.32-2.29 (m, 2H); LC/MS (exact mass) calculated for C$_{15}$H$_{20}$FN$_5$O$_2$S; 353.42. found (M+H); 354.1.

cis-3-Fluoro-N-{cis-3-[methyl(7H-pyrrolo[2,3-d]pyrimidin-4-yl)amino]cyclobutyl}cyclobutanesulfonamide Isolation of the second eluting isomer afforded the title compound; Peak 2, cis-isomer: 4.3 mg (12.3%); SFC retention time=4.3 minutes; $^1$H NMR (400 MHz, CH$_3$OH-d$_4$) δ 8.22 (s, 1H), 7.21 (d, 1H), 6.65 (d, 1H), 4.54-5.05 (m, 2H), 3.45-3.55 (m, 1H), 3.36 (m, 4H), 2.65-2.80 (m, 4H), 2.42-2.62 (m, 2H), 2.52-2.72 (m, 2H); LC/MS (exact mass) calculated for C$_{15}$H$_{20}$FN$_5$O$_2$S; 353.42. found (M+H); 354.1.

The mixture of cis- and trans-3-fluorocyclobutane-1-sulfonyl chloride was prepared as follows:

Step 1: 3-(Benzyloxy)cyclobutan-1-ol

This compound was prepared following Example 42, Step 3, and substituting 3-hydroxycyclobutane-1-carbonitrile for 3-(benzyloxy)cyclobutan-1-one. The crude compound was purified by chromatography on silica gel eluting with a gradient of petroleum ether and ethyl acetate (100:0 to 60:40) to afford the title compound (3.75 g, 74%) as yellow oil. 1H NMR (400 MHz, CDCl$_3$) δ 7.32-7.38 (m, 5H), 4.42 (s, 2H), 3.88-3.62 (m, 1H), 3.72-3.62 (m, 1H), 2.75-2.65 (m, 2H), 1.98-1.75 (m, 2H), 1.62 (d, 1H)

Step 2: ((3-Fluorocyclobutoxy)methyl)benzene

This compound was prepared following Example 43, Step 6, and substituting 3-formylcyclobutyl 4-methylbenzenesulfonate for 3-(benzyloxy)cyclobutan-1-ol. The crude compound was purified by chromatography on silica gel eluting with a gradient of petroleum ether and ethyl acetate (100:0 to 80:20) to afford the title compound (0.87 g, 23%) as yellow oil. $^1$H NMR (400 MHz, CDCl$_3$) δ 7.45-7.35 (m, 5H), 5.42-5.22 (m, 1H), 4.43 (s, 2H), 4.34-4.25 (m, 1H), 2.55-2.25 (m, 4H)

Step 3: 3-Fluorocyclobutan-1-ol

A mixture of ((3-fluorocyclobutoxy)methyl)benzene (0.87 g, 4.83 mmol) and 10% Pd/C (0.4 g) in methanol (40 mL) was pressurized to 50 psi with hydrogen and stirred at room temperature for 2 days. The mixture was then filtered over Celite™ and concentrated under vacuum to give the mixture of starting material and title compound (0.3 g, 23%) in 1:1 ratio as yellow oil. The crude reaction mixture was used directly in next step.

Step 4: 3-Fluorocyclobutyl 4-methylbenzenesulfonate

This compound was prepared following Example 42, Step 4, and substituting 3-hydroxycyclobutane-1-carbonitrile for 3-fluorocyclobutan-1-ol. The crude compound was purified by chromatography on silica gel eluting with a gradient of petroleum ether and ethyl acetate (0-20%) to afford the title compound (88.3%) as oil. $^1$H NMR (400 MHz, CDCl$_3$) δ 7.72-7.65 (d, 2H), 7.38-7.36 (d, 2H), 5.35-5.25 (m, 0.5H), 5.2-5.1 (m, 0.5H), 5.1-5.0 (m, 1H), 2.63-2.42 (m, 4H), 2.36 (s, 3H)

Step 5: S-(3-Fluorocyclobutyl) ethanethioate

This compound was prepared following Example 42, Step 5, and substituting 3-(cyanomethyl)-3-methylcyclobutyl 4-methylbenzenesulfonate for 3-fluorocyclobutyl 4-methylbenzenesulfonate. The crude compound was purified by chromatography on silica gel eluting with a gradient of petroleum ether and ethyl acetate (8:1) to afford the title compound (100%) as yellow oil.

Step 8: 3-Fluorocyclobutane-1-sulfonyl chloride

This compound was prepared following Example 42, Step 6, and substituting S-(3-cyanocyclobutyl) ethanethioate for S-(3-fluorocyclobutyl) ethanethioate. The crude compound was purified by chromatography on silica gel eluting with a gradient of petroleum ether and ethyl acetate (100:0 to 80:20) to afford the title compound (100%) as colorless oil.

Example 58

3-(2,2-Difluoroethyl)-N-{cis-3-[methyl(7H-pyrrolo[2,3-d]pyrimidin-4-yl)amino]cyclobutyl}-azetidine-1-sulfonamide The following compound, Examples 52, were prepared from N-[cis-3-(methyl{7-[(4-methylphenyl)sulfonyl]-7H-pyrrolo[2,3-d]pyrimidin-4-yl}amino)cyclobutyl]-2-oxo-1,3-oxazolidine-3-sulfonamide (Example 51, Step 1) in a similar manner to that described in Example 51, Step 2, substituting cyclopropanemethylamine for 3-(2,2-difluoroethyl)azetidine and using the deprotection method illustrated in Example 51, Step 3. The crude compound was purified by high performance liquid chromatography to afford the title compound as an off-white solid (32 mg, 26%). $^1$H NMR (400 MHz, methanol-d$_4$): δ 8.11 (s, 1H), 7.28 (s, 1H), 6.42 (d, 1H), 5.75-6.25 (dd, 1H), 4.87-4.86 (m, 1H), 3.87-4.0 (m, 2H), 3.62-3.75 (m, 3H), 3.31 (s, 3H), 2.45-2.74 (m, 3H), 2.23-2.31 (m, 2H), 2.02-2.21 (m, 2H); LC/MS (exact mass) calculated for C$_{16}$H$_{22}$F$_2$N$_6$O$_2$S; 400.452. found (M+H$^+$); 401.1.

Example 59a (Trans) and 59B (Cis)

cis- and trans-3-[({cis-3-[Methyl(7H-pyrrolo[2,3-d]pyrimidin-4-yl)amino]cyclobutyl}methyl)-sulfonyl]cyclobutanecarbonitrile The title compound (40 mg) was prepared starting from S-{[cis-3-(methyl{7-[(4-methylphenyl)-sulfonyl]-7H-pyrrolo[2,3-d]pyrimidin-4-yl}amino)cyclobutyl]methyl}ethanethioate Example 47, Step 5, according to the procedures of Example 53, steps 1 and 2, substituting the appropriate 3-(bromomethyl)-3-methyloxetane for (3-cyanocyclobutyl)methyl 4-methylbenzenesulfonate in Step 1. The compound was purified using preparative thin layer chromatography eluting with dichloromethane and methanol (10:1) to give title compound as white solid. The cis- and trans-isomers were then chirally separated by supercritical fluid chromatography (SFC) using (AD-3, 20×250 mm col, 55% ethanol, 80 mL/min) column conditions.

trans-3-[({cis-3-[Methyl(7H-pyrrolo[2,3-d]pyrimidin-4-yl)amino]cyclobutyl}methyl)sulfonyl]cyclobutanecarbonitrile Isolation of the first eluting isomer afforded the title compound; Peak 1 trans isomer: 5.7 mg (14.3%); SFC retention time=1.728 minutes; $^1$H NMR (400 MHz, CH$_3$OH-d$_4$): δ 8.12 (s, 1H), 7.13-7.12 (d, 1H), 6.70-6.69 (d, 1H), 5.14-5.10 (m, 1H), 3.36 (s, 3H), 3.23-3.14 (m, 6H), 2.64-2.55 (m, 4H), 2.48-2.41 (m, 2H), 2.26-2.22 (m, 2H); LC/MS (exact mass) calculated for C$_{18}$H$_{23}$N$_5$O$_2$S; 373.479. found (M+H$^+$); 374.1.

cis-3-[({cis-3-[methyl(7H-pyrrolo[2,3-d]pyrimidin-4-yl)amino]cyclobutyl}methyl)sulfonyl]cyclobutane-carbonitrile Isolation of the second eluting isomer afforded the title compound; Peak 2 cis isomer: 14.4 mg (36%); SFC retention time=2.248 minutes; $^1$H NMR (400 MHz, CH$_3$OH-d$_4$): δ 8.12 (s, 1H), 7.13-7.12 (d, 1H), 6.70-6.68 (d, 1H), 5.16-5.07 (m, 1H), 3.35 (s, 3H), 3.29-3.21 (m, 5H), 3.00-2.91 (m, 1H), 2.70-2.57 (m, 4H), 2.35-2.30 (m, 2H), 2.30-2.21 (m, 2H); LC/MS (exact mass) calculated for C$_{18}$H$_{23}$N$_5$O$_2$S; 373.479. found (M+H$^+$); 374.1.

Example 120

N-((1S,3S)-3-(((4-(Methoxymethyl)piperidin-1-yl)sulfonyl)methyl)cyclobutyl)-N-methyl-7H-pyrrolo[2,3-d]pyrimidin-4-amine Step 1: N-((1S,3S)-3-(((4-(Methoxymethyl)piperidin-1-yl)sulfonyl)methyl)cyclobutyl)-N-methyl-7-tosyl-7H-pyrrolo[2,3-d]pyrimidin-4-amine To a solution of ((1S,3S)-3-(methyl(7-tosyl-7H-pyrrolo[2,3-d]pyrimidin-4-yl)amino)cyclobutyl) methanesulfonyl chloride, example 25, step 7, (1 g, 2.132 mmol) in dichloromethane cooled to 5° C. was added 4-(methoxymethyl)piperidine (413 mg, 3.2 mmol) and triethylamine (647 mg, 6.40 mmol). The resulting white suspension stirred at 5° C. for 3 hours by which time LCMS confirmed the starting material was consumed and the desired product peak was observed. The yellow suspension was diluted with H$_2$O (80 ml) and extracted with dichloromethane (80 ml×3). The combined organic layers were washed with brine (100 ml×1), dried over Na$_2$SO$_4$, filtered and concentrated. The crude material was purified on silica gel (0-70% EtOAc/petroleum ether) to provide the title material (600 mg, 50% yield) as a white solid. LCMS m/z 562.0 [M+H]$^+$ Step 2: N-((1S,3S)-3-(((4-(Methoxymethyl)piperidin-1-yl)sulfonyl)methyl)cyclobutyl)-N-methyl-7H-pyrrolo[2,3-d]pyrimidin-4-amine To a solution of N-((1S,3S)-3-(((4-(methoxymethyl)piperidin-1-yl)sulfonyl)methyl)cyclobutyl)-N-methyl-7-tosyl-7H-pyrrolo[2,3-d]pyrimidin-4-amine (600 mg, 1.07 mmol) in MeOH (60 ml) at 28° C. was added K$_2$OC$_3$ (443 mg, 3.20 mmol). The white suspension was stirred at 50° C. for 3 h by which time the reaction was deemed complete by TLC. The white suspension was concentrated and diluted with H$_2$O (100 ml). The mixture was extracted with dichloromethane (200 ml×2), washed with brine (100 ml×1), dried over Na$_2$SO$_4$, filtered and concentrated. The crude product was stirred in EtOAc (15 ml) for 2 h by which time the product crystallized from the solution. The crystals were filtered and dried to provide the title compound (380 mg, 87% yield) as a white solid.
$^1$H NMR (400 MHz, DMSO-d6) δ: 11.61 (bs, 1H), 8.10 (s, 1H), 7.14 (m, 1H), 8.62 (m, 1H), 5.07-5.15 (m, 1H), 3.60 (d, J=12.6 Hz, 2H), 3.18-3.25 (m, 10H), 2.73-2.78 (m, 2H), 2.33-2.40 (m, 3H), 2.07-2.15 (m, 2H), 1.63-1.74 (m, 3H), 1.12-1.23 (m, 2H); LCMS m/z 408 [M+H]$^+$ Example 140

N-((1S,3S)-3-(((1-(3-Methoxycyclobutyl)azetidin-3-yl)sulfonyl)methyl)cyclobutyl)-N-methyl-7H-pyrrolo[2,3-d]pyrimidin-4-amine Step 1: t-Butyl 3-((((1S,3S)-3-(methyl(7H-pyrrolo[2,3-d]pyrimidin-4-yl)amino)cyclobutyl)methyl)thio) azetidine-1-carboxylate To a solution of cis-[3-(Methyl{7-[(4-methylphenyl)sulfonyl]-7H-pyrrolo[2,3-d]pyrimidin-4-yl}amino)cyclobutyl]methyl 4-methylbenzenesulfonate, example 25, step 4, (8.5 g, 15.72 mmol) in MeOH (100 mL) was added K$_2$CO$_3$ (6.52 g, 47.2 mmol), t-butyl 3-(acetylthio)azetidine-1-carboxylate (4.36 g, 18.9 mmol) at 0° C. for 30 min under N$_2$ atmosphere. The mixture was stirred at 15° C. for 1 h. Then the mixture was refluxed at 60° C. for 16 h under N$_2$ atmosphere by which time LCMS showed the starting material has been consumed. The reaction was concentrated, diluted with DCM (60 ml) then washed with water (10 mL×3), dried over Na$_2$SO$_4$. The solution was concentrated to afford the crude product which was washed with EtOAc (20 mL) to afford the title compound as a red solid (2600 mg, 41%). The crude material was used in the next step without further purification. Crude reaction LCMS m/z 404 [M+H]$^+$ Step 2: t-Butyl 3-((((1S,3S)-3-(methyl(7H-pyrrolo[2,3-d]pyrimidin-4-yl)amino)cyclobutyl)methyl) sulfonyl) azetidine-1-carboxylate To a solution of t-butyl 3-((((1S,3S)-3-(methyl(7H-pyrrolo[2,3-d]pyrimidin-4-yl)amino)cyclobutyl)methyl)thio) azetidine-1-carboxylate (2600 mg, 6.443 mmol) in a 3:1 mixture of EtOH in H$_2$O (120 mL) was added oxone (5940 mg, 9.66 mmol) in portions at 0° C. for 10 min. The resulting mixture was stirred at 15° C. for 3 hours after which time LCMS showed the starting material had been consumed. The mixture was quenched with saturated Na$_2$SO$_3$ at 0° C. then filtered and concentrated. The solution was diluted with DCM (30 mL×1), washed with water (30 ml×2), dried over Na$_2$SO$_4$ and concentrated to afford the title compound as a white solid (2800 mg, crude) which was used in the next step without further purification. LCMS m/z 436.0 [M+H]$^+$ Step 3: t-Butyl 3-((((1S,3S)-3-(methyl(7-tosyl-7H-pyrrolo[2,3-d]pyrimidin-4-yl)amino)cyclobutyl) methyl) sulfonyl)azetidine-1-carboxylate To a solution of t-butyl 3-((((1S,3S)-3-(methyl(7H-pyrrolo[2,3-d]pyrimidin-4-yl)amino)cyclobutyl)methyl)sulfonyl)azetidine-1-carboxylate (2800 mg, crude) and DMAP (1840 mg, 9.64 mmol) in DCM (200 mL) was added portion-wise TsCl (1840 mg, 9.64 mmol) at 0° C. The reaction mixture was stirred at 20° C. for 24 h upon which time LC-MS showed the starting material was consumed. The reaction was quenched with H$_2$O (60 mL) then extracted with DCM (30 mL×3). The organic layer was washed with brine (100 mL×1), dried over Na$_2$SO$_4$, filtered and concentrated. The crude material was chromatographed on silica gel by eluting with a 0-70% gradient of ethyl acetate and petroleum ether to give the title compound as a white solid (3 g, 78.9% via 2 steps). Crude Reaction LCMS m/z 612 [M+Na]$^+$ Step 4: N-((1S,3S)-3-(((Azetidin-3-ylsulfonyl) methyl)cyclobutyl)-N-methyl-7-tosyl-7H-pyrrolo[2, 3-d]pyrimidin-4-amine To a solution of compound t-butyl 3-(M1S,3S)-3-(methyl (7-tosyl-7H-pyrrolo[2,3-d]pyrimidin-4-yl)amino)cyclobutyl)methyl) sulfonyl)azetidine-1-carboxylate (2800 mg, 4.748 mmol) in dioxane (10 mL) was added HCl/dioxane (10 mL). The resulting mixture stirred at 15° C. for 2 hours upon which time TLC showed that the reaction was completed. Then the mixture was concentrated to afford the product which was combined with an additional batch and washed with DCM (50 mL) to afford the title compound as a white solid (2900 mg, 100%). The crude material was used in the next step without purification. LCMS m/z 490.0 [M+H]$^+$ Step 5: N-((1S,3S)-3-(((1-(3-Methoxycyclobutyl) azetidin-3-yl)sulfonyl)methyl)cyclobutyl)-N-methyl-7-tosyl-7H-pyrrolo[2,3-d]pyrimidin-4-amine To a solution of N-((1S,3S)-3-((azetidin-3-ylsulfonyl) methyl)cyclobutyl)-N-methyl-7-tosyl-7H-pyrrolo[2,3-d]pyrimidin-4-amine (200 mg, 0.408 mmol) in MeOH (20 mL) was added acetic acid (2 mL) and 3-methoxycyclobutan-1-one (164 mg, 1.63 mmol). The resulting solution was stirred at 30° C. for 10 mins. which was followed by the addition of sodium cyanoborohydride (154 mg, 2.45 mmol). This mixture stirred at 30° C. for 16 hours by which time if became colorless. LC-MS showed that the starting material was consumed and desired product (MH+574) was detected as a main peak. The solution was combined with an additional batch and basified by aqueous K$_2$CO$_3$ (20 mL), extracted with DCM (50 mL×2). The combined organic layers were washed with brine (100 mL×1), dried over Na$_2$SO$_4$, filtered and concentrated to afford the title compound as a colorless oil (350 mg). The crude material used in the next step without further purification. LCMS m/z 574.0 [M+H]$^+$ Step 6: N-((1S,3S)-3-(((1-(3-Methoxycyclobutyl) azetidin-3-yl)sulfonyl)methyl)cyclobutyl)-N-methyl-7H-pyrrolo[2,3-d]pyrimidin-4-amine To a mixture of N-((1S,3S)-3-(((1-(3-methoxycyclobutyl) azetidin-3-yl)sulfonyl)methyl)cyclobutyl)-N-methyl-7-tosyl-7H-pyrrolo[2,3-d]pyrimidin-4-amine (350 mg, 0.610 mmol) in THF (4 mL) and EtOH (4 mL) was added a solution of NaOH (122 mg, 3.05 mmol) in H$_2$O (2 mL). The reaction stirred at 60° C. for 2 h by which time the LC-MS showed that the starting material was consumed and desired product (MH+420) was detected as a main peak. The yellow solution was diluted with aqueous HCl (2 mL, 2 N) at 25° C. and concentrated to afford the crude product which was purified by preparative thin layer chromatography to afford the product (50 mg) as a solid. The cis and trans isomers were separated by supercritical fluid chromatography (Column: AD (300 mm*30 mm, 10 μm) Mobile phase: 45% (0.1% NH$_3$/H$_2$O) in EtOH) to provide the title compound (5.73 mg, 3.3% over 2 steps) a yellow solid, which eluted as the second peak. Trans stereochemistry was confirmed by NOE and the spectral data are as follows. $^1$H NMR (400 MHz, CDCl$_3$) δ: 10.35 (b, 1H), 8.32 (s, 1H), 7.08 (m, 1H), 6.58 (m, 1H), 5.14 (quint, J=8.0 Hz, 1H), 4.01 (quint, J=6.5 Hz, 1H), 3.86 (quint, J=7.53 Hz, 1H), 3.61 (t, J=8.03 Hz, 2H), 3.46 (t, J=7.5 Hz, 2H), 3.33 (s, 3H), 3.15-3.22 (m, 4H), 3.11 (d, J=7.0 Hz, 2H), 2.53-2.74 (m, 3H), 1.95-2.16 (m, 6H); LCMS m/z 420.6 [M+H]$^+$ Example 152

N-Methyl-N-((1S,3S)-3-(((3,3,3-trifluoropropyl) sulfonyl)methyl)cyclobutyl)-7H-pyrrolo[2,3-d]pyrimidin-4-amine Step 1: Zinc ((1S,3S)-3-(methyl(7-tosyl-7H-pyrrolo [2,3-d]pyrimidin-4-yl)amino)cyclobutyl)methane sulfinate In three equal batches, a mixture of ((1S,3S)-3-(methyl (7-tosyl-7H-pyrrolo[2,3-d]pyrimidin-4-yl)amino)cyclobutyl)methanesulfonyl chloride, example 25, step 7, (1 g, 2.13 mmol) and Zn dust (209 mg, 3.2 mmol) in anhydrous ethanol (15 mL) was stirred at 75° C. for 1 h at which time LCMS showed the reaction was complete. The three batches were combined, filtered, and concentrated. The crude product was stirred in EtOAc (30 mL) at 18° C. for 16 hours. The mixture was filtered and the filter cake was dried. The resulting filter cake was dissolved in MeCN (10 mL) and H$_2$O (20 mL), the eluent was evaporated to remove organic solvents. The residual aqueous solution was lyophilized to provide the title compound (2.5 g, 89.9%) as a yellow solid. $^1$H NMR (400 MHz, CDCl3) δ: 8.39 (s, 2H), 8.05 (d, J=8.5 Hz, 4H), 7.46 (d, J=4.0 Hz, 2H), 7.28 (m, 4H), 6.63 (d, J=4.0 Hz, 2H), 4.92 (quint, J=7.53 Hz, 2H), 3.23 (s, 6H), 3.01 (d, J=7.0 Hz, 4H), 2.35-2.45 (m, 16H), 2.18-2.27 (m, 2H), 1.89 (q, J=9.5 Hz, 4H); LCMS m/z 434.0 [M+H]+

Step 2: N-Methyl-7-tosyl-N-((1S,3S)-3-(((3,3,3-trifluoropropyl)sulfonyl)methyl)cyclobutyl)-7H-pyrrolo[2,3-d]pyrimidin-4-amine To a solution of Zinc ((1S,3S)-3-(methyl(7-tosyl-7H-pyrrolo[2,3-d]pyrimidin-4-yl)amino)cyclobutyl)-methanesulfinate (100 mg, 0.230 mmol) in DMSO (8 mL) was added 1,1,1-trifluoro-3-iodopropane (129 mg, 0.575 mmol) and K$_2$OC$_3$ (95.4 mg, 0.690 mmol). The solution was stirred at 50° C. for 2 hours by which time LCMS showed the reaction was complete. The mixture was diluted with water (30 mL), extracted with EtOAc (30 mL×2). The combined organic layer was washed with brine (50 mL), dried over Na$_2$SO$_4$, filtered and concentrated. The crude product was purified by silica gel chromatography (EtOAc: PE=2:1) to afford the title compound (45 mg, 37%) as a colorless oil. LCMS m/z 531.1 [M+H]$^+$ Step 3: N-methyl-N-((1S,3S)-3-(((3,3,3-trifluoropropyl)sulfonyl)methyl)cyclobutyl)-7H-pyrrolo[2,3-d] pyrimidin-4-amine To a mixture of N-methyl-7-tosyl-N-((1S,3S)-3-(((3,3,3-trifluoropropyl)sulfonyl)methyl)cyclobutyl)-7H-pyrrolo[2, 3-d]pyrimidin-4-amine (45 mg, 0.085 mmol) in THF (4 mL) and EtOH (4 mL) was added the solution of NaOH (45.1 mg, 1.13 mmol) in H₂O (2 mL). The reaction was stirred at 60° C. for 2 h at which time LCMS showed the reaction was complete. The reaction mixture was quenched with aqueous HCl (1 mL, 2 N) at 25° C. and concentrated. The crude product was purified by prep-HPLC (Column: Phenomenex Gemini C18 250*21.2 mm*8 μm Mobile phase: from 27% MeCN in water (Ammonia (pH 10)) to 47% MeCN in water Ammonia (pH 10))) to afford the title compound (5 mg, 15.7%) as a white solid. ¹H NMR (400 MHz, CDCl3) δ: 9.73 (m, 1H), 8.31 (s, 1H), 7.07 (m, 1H), 6.58 (d, J=3.0 Hz, 1H), 5.16 (quint, J=8.53 Hz, 1H), 3.34 (s, 3H), 3.24 (d, J=7.0 Hz, 2H), 3.16-3.20 (m, 2H), 2.76-2.61 (m, 5H), 2.16 (q, J=9.0 Hz, 2H); LCMS m/z 377.0 [M+H]⁺

The Tables below list some additional examples of compounds of invention (Examples 60-153) that were made using methods, starting materials or intermediates, and preparations described herein.

The following compounds in Table 1 were made starting from cis-[3-(methyl{7-[(4-methylphenyl)sulfonyl]-7H-pyrrolo[2,3-d]pyrimidin-4-yl}amino)cyclobutyl]methanesulfonyl chloride (Example 25, Step 7), according to the procedures of Example 25, Step 8 (sulfonamide formation) and Example 25, step 9 (deprotection), substituting the appropriate amine in Step 8.

TABLE 1

Examples 60-125 (including Method of Preparation, Structures and Physicochemical Data).

| Example Number | Method of Preparation | Structure | 1H NMR (400 MHz, CDCl₃) δ (ppm); Mass spectrum, observed ion m/z [M + H]+ or HPLC retention time; Mass spectrum m/z [M + H]+ (unless otherwise indicated) |
|---|---|---|---|
| 60 | Ex. 120 | 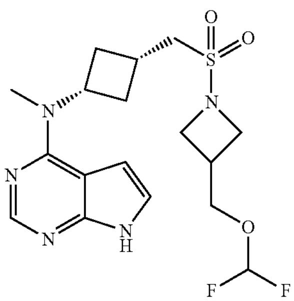 [SMILES: CN(c1ncnc2[nH]ccc12)[C@H]1C[C@@H](CS(=O)(=O)N2CC(COC(F)F)C2)C1] | 3.00 minutes¹; 416 |
| 61 | Ex. 120 | 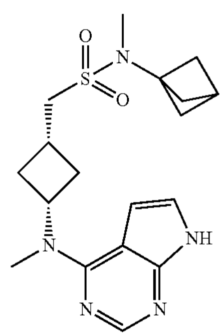 [SMILES: CN(C12CC(C1)C2)S(=O)(=O)C[C@H]1C[C@@H](N(C)c2ncnc3[nH]ccc23)C1] | 2.29 minutes²; 398 |
| 62 | Ex. 120 | 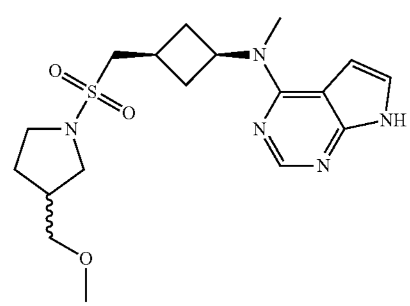 [SMILES: COCC1CCN(S(=O)(=O)C[C@H]2C[C@@H](N(C)c3ncnc4[nH]ccc34)C2)C1] | 2.37 minutes³; 394 |

TABLE 1-continued

Examples 60-125 (including Method of Preparation, Structures and Physicochemical Data).

| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 63 | Ex. 120 | 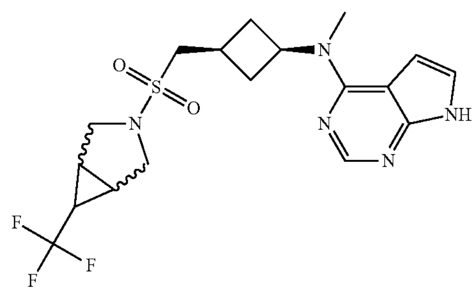 [SMILES: CN(c1ncnc2[nH]ccc12)[C@H]1C[C@@H](CS(=O)(=O)N2CC3C(C2)C3C(F)(F)F)C1] | 2.60 minutes$^2$; 430 |
| 64 | Ex. 120 | Chiral | 2.26 minutes$^2$; 393 |
| 65 | Ex. 120 | 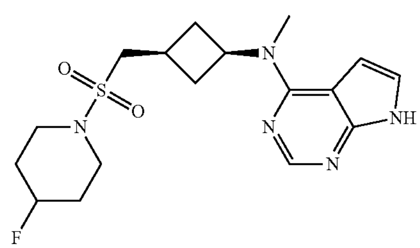 [SMILES: CN(c1ncnc2[nH]ccc12)[C@H]1C[C@@H](CS(=O)(=O)N2CCC(F)CC2)C1] | 2.33 minutes$^2$; 382 |
| 66 | Ex. 120 | 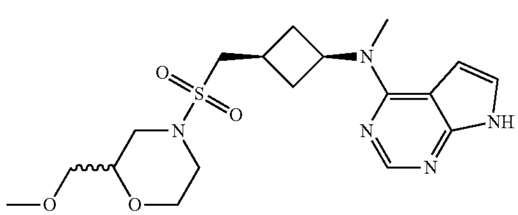 [SMILES: COCC1CN(S(=O)(=O)C[C@H]2C[C@@H](N(C)c3ncnc4[nH]ccc34)C2)CCO1] | 2.20 minutes$^2$; 410 |
| 67 | Ex. 120 | 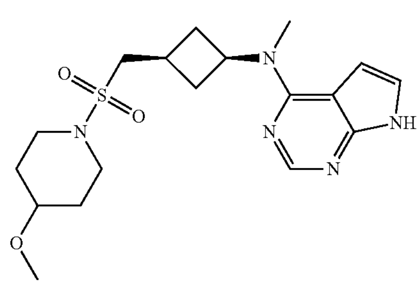 [SMILES: COC1CCN(S(=O)(=O)C[C@H]2C[C@@H](N(C)c3ncnc4[nH]ccc34)C2)CC1] | 2.28 minutes$^2$; 394 |

TABLE 1-continued

Examples 60-125 (including Method of Preparation, Structures and Physicochemical Data).

| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 68 | Ex. 120 | 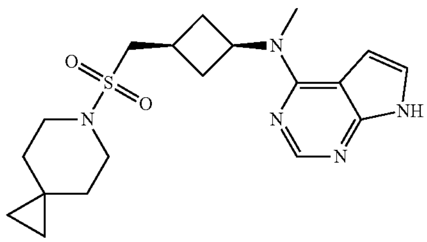 [SMILES: CN(c1ncnc2[nH]ccc12)[C@H]1C[C@@H](CS(=O)(=O)N2CCC3(CC2)CC3)C1] | 2.62 minutes$^2$; 390 |
| 69 | Ex. 120 | 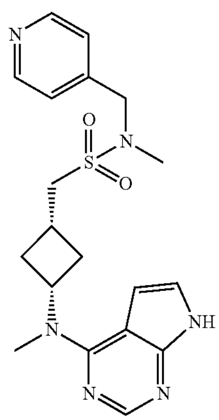 [SMILES: CN(Cc1ccncc1)S(=O)(=O)C[C@H]1C[C@@H](N(C)c2ncnc3[nH]ccc23)C1] | 1.96 minutes$^2$; 401 |
| 70 | Ex. 120 | Chiral | 2.29 minutes$^2$; 398 |
| 71 | Ex. 120 | Chiral | 2.22 minutes$^2$; 380 |

TABLE 1-continued
Examples 60-125 (including Method of Preparation, Structures and Physicochemical Data).
| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 72 | Ex. 120 | Chiral 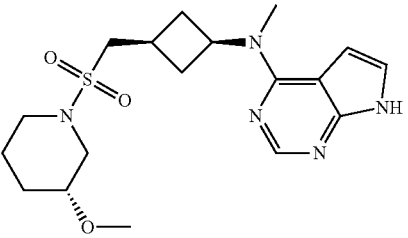 | 2.31 minutes$^2$; 394 |
| 73 | Ex. 120 | Chiral 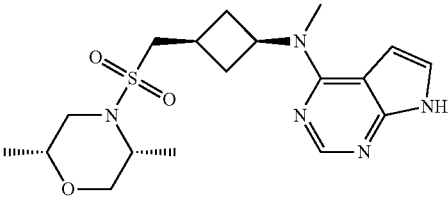 | 2.33 minutes$^2$; 394 |
| 74 | Ex. 120 | 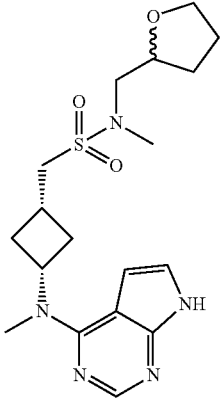 [SMILES: CN(CC1CCCO1)S(=O)(=O)C[C@H]1C[C@@H](N(C)c2ncnc3[nH]ccc23)C1] | 2.32 minutes$^2$; 394 |
| 75 | Ex. 120 | 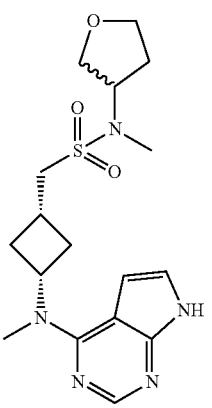 [SMILES: CN(C1CCOC1)S(=O)(=O)C[C@H]1C[C@@H](N(C)c2ncnc3[nH]ccc23)C1] | 2.27 minutes$^2$; 380 |

TABLE 1-continued

Examples 60-125 (including Method of Preparation, Structures and Physicochemical Data).

| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 76 | Ex. 120 | 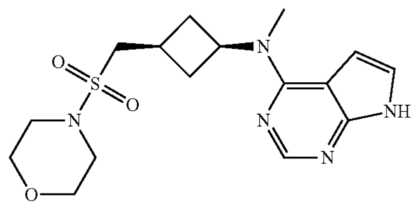 [SMILES: CN(c1ncnc2[nH]ccc12)[C@H]1C[C@@H](CS(=O)(=O)N2CCOCC2)C1] | 2.23 minutes[2]; 366 |
| 77 | Ex. 120 | 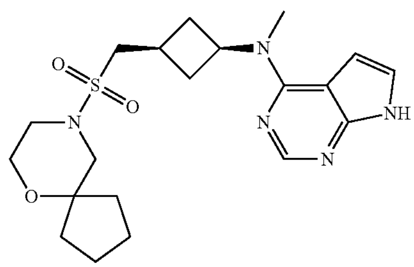 [SMILES: CN(c1ncnc2[nH]ccc12)[C@H]1C[C@@H](CS(=O)(=O)N2CCOC3(CCCC3)C2)C1] | 2.59 minutes[2]; 420 |
| 78 | Ex. 120 | 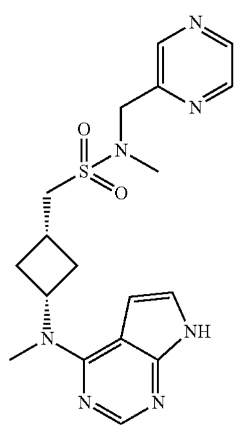 [SMILES: CN(Cc1cnccn1)S(=O)(=O)C[C@H]1C[C@@H](N(C)c2ncnc3[nH]ccc23)C1] | 2.25 minutes[2]; 402 |
| 79 | Ex. 120 | 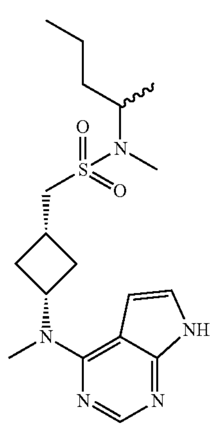 [SMILES: CCCC(C)N(C)S(=O)(=O)C[C@H]1C[C@@H](N(C)c2ncnc3[nH]ccc23)C1] | 2.71 minutes[2]; 380 |

TABLE 1-continued

Examples 60-125 (including Method of Preparation, Structures and Physicochemical Data).

| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 80 | Ex. 120 | 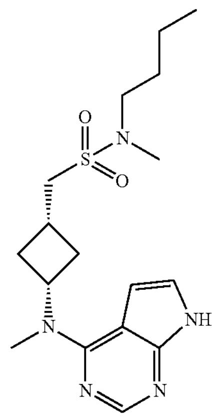 [SMILES: CCCCN(C)S(=O)(=O)C[C@H]1C[C@@H](N(C)c2ncnc3[nH]ccc23)C1] | 2.62 minutes$^2$; 366 |
| 81 | Ex. 120 | 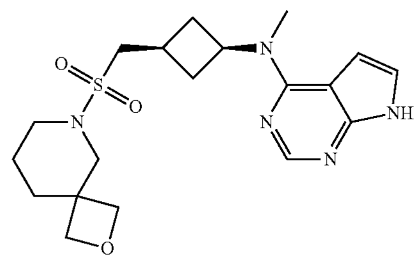 [SMILES: CN(c1ncnc2[nH]ccc12)[C@H]1C[C@@H](CS(=O)(=O)N2CCCC3(COC3)C2)C1] | 2.32 minutes$^2$; 406 |
| 82 | Ex. 120 | Chiral | 2.30 minutes$^2$; 380 |
| 83 | Ex. 120 | 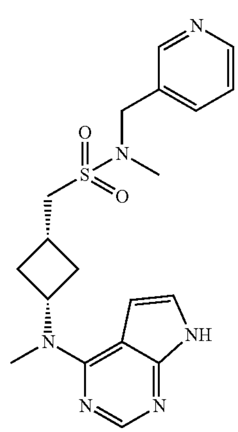 [SMILES: CN(Cc1cccnc1)S(=O)(=O)C[C@H]1C[C@@H](N(C)c2ncnc3[nH]ccc23)C1] | 2.06 minutes$^2$; 401 |

TABLE 1-continued

Examples 60-125 (including Method of Preparation, Structures and Physicochemical Data).

| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 84 | Ex. 120 | 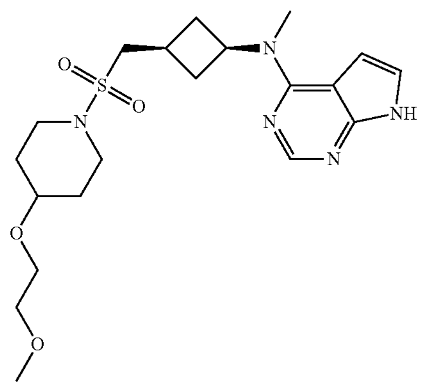 [SMILES: COCCOC1CCN(S(=O)(=O)C[C@H]2C[C@@H](N(C)c3ncnc4[nH]ccc34)C2)CC1] | 2.38 minutes$^2$; 438 |
| 85 | Ex. 120 | 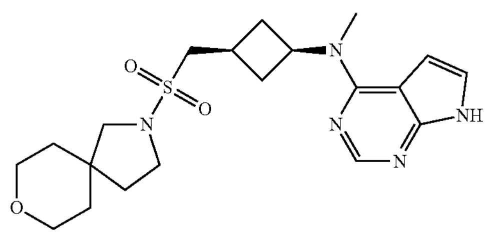 [SMILES: CN(c1ncnc2[nH]ccc12)[C@H]1C[C@@H](CS(=O)(=O)N2CCC3(CCOCC3)C2)C1] | 2.36 minutes$^2$; 429 |
| 86 | Ex. 120 | 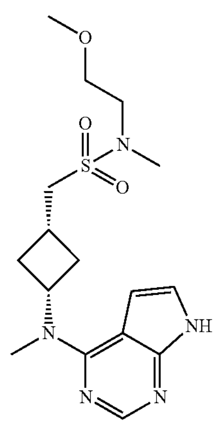 [SMILES: COCCN(C)S(=O)(=O)C[C@H]1C[C@@H](N(C)c2ncnc3[nH]ccc23)C1] | 2.29 minutes$^2$; 368 |
| 87 | Ex. 120 | 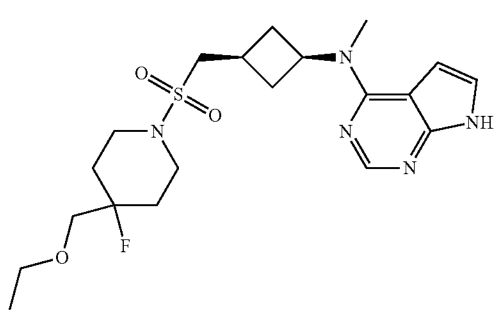 [SMILES: CCOCC1(F)CCN(S(=O)(=O)C[C@H]2C[C@@H](N(C)c3ncnc4[nH]ccc34)C2)CC1] | 2.60 minutes$^2$; 440 |

TABLE 1-continued

Examples 60-125 (including Method of Preparation, Structures and Physicochemical Data).

| Example Number | Method of Preparation | Structure | 1H NMR (400 MHz, CDCl₃) δ (ppm); Mass spectrum, observed ion m/z [M + H]+ or HPLC retention time; Mass spectrum m/z [M + H]+ (unless otherwise indicated) |
|---|---|---|---|
| 88 | Ex. 120 | 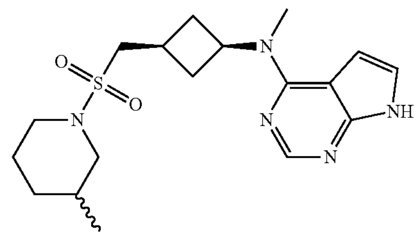 [SMILES: CC1CCCN(S(=O)(=O)C[C@H]2C[C@@H](N(C)c3ncnc4[nH]ccc34)C2)C1] | 2.64 minutes²; 378 |
| 89 | Ex. 120 | 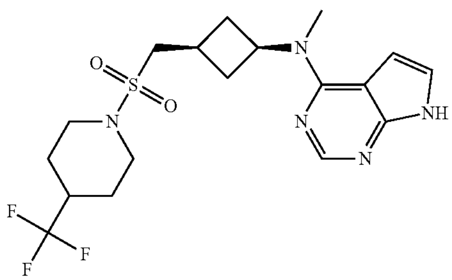 [SMILES: CN(c1ncnc2[nH]ccc12)[C@H]1C[C@@H](CS(=O)(=O)N2CCC(C(F)(F)F)CC2)C1] | 2.69 minutes²; 432 |
| 90 | Ex. 120 | 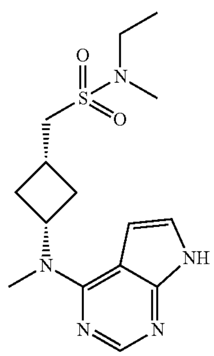 [SMILES: CCN(C)S(=O)(=O)C[C@H]1C[C@@H](N(C)c2ncnc3[nH]ccc23)C1] | 2.36 minutes²; 338 |
| 91 | Ex. 120 | Chiral | 2.31 minutes²; 368 |
| 92 | Ex. 120 | Chiral | 2.34 minutes²; 380 |

TABLE 1-continued

Examples 60-125 (including Method of Preparation, Structures and Physicochemical Data).

| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 93 | Ex. 120 | 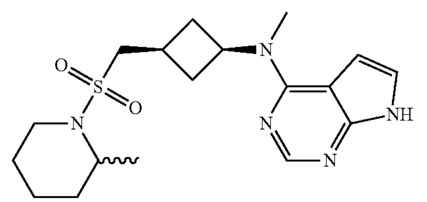 [SMILES: CC1CCCCN1S(=O)(=O)C[C@H]1C[C@@H](N(C)c2ncnc3[nH]ccc23)C1] | 2.59 minutes$^2$; 378 |
| 94 | Ex. 120 | 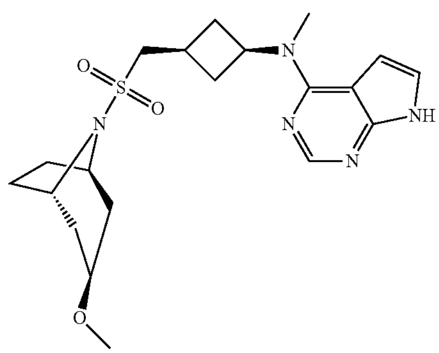 [SMILES: CO[C@@H]1C[C@H]2CC[C@@H](C1)N2S(=O)(=O)C[C@H]1C[C@@H](N(C)c2ncnc3[nH]ccc23)C1] | 2.43 minutes$^2$; 420 |
| 95 | Ex. 120 | 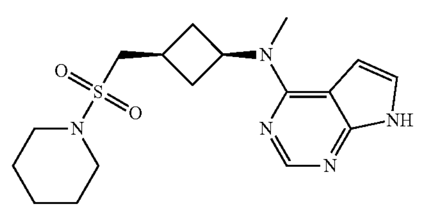 [SMILES: CN(c1ncnc2[nH]ccc12)[C@H]1C[C@@H](CS(=O)(=O)N2CCCCC2)C1] | 2.49 minutes$^2$; 364 |
| 96 | Ex. 120 | Chiral | 2.13 minutes$^2$; 368 |
| 97 | Ex. 120 | Chiral | 2.48 minutes$^2$; 364 |

TABLE 1-continued

Examples 60-125 (including Method of Preparation, Structures and Physicochemical Data).

| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 98 | Ex. 120 | 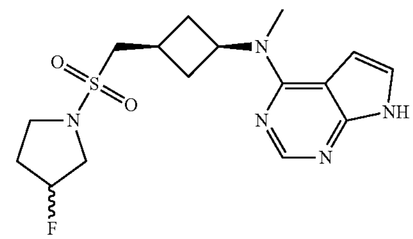 [SMILES: CN(c1ncnc2[nH]ccc12)[C@H]1C[C@@H](CS(=O)(=O)N2CCC(F)C2)C1] | 2.32 minutes$^2$; 368 |
| 99 | Ex. 120 | 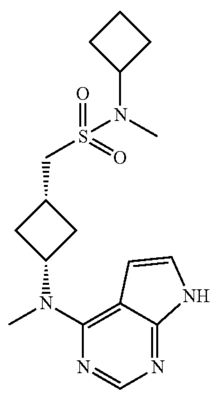 [SMILES: CN(C1CCC1)S(=O)(=O)C[C@H]1C[C@@H](N(C)c2ncnc3[nH]ccc23)C1] | 2.53 minutes$^2$; 364 |
| 100 | Ex. 120 | 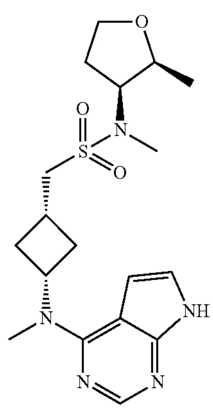 | 2.34 minutes$^2$; 394 |
| 101 | Ex. 120 | 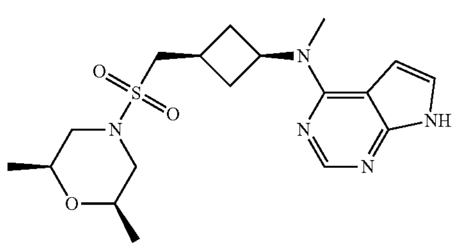 [SMILES: C[C@@H]1CN(S(=O)(=O)C[C@H]2C[C@@H](N(C)c3ncnc4[nH]ccc34)C2)C[C@H](C)O1] | 2.44 minutes$^2$; 394 |

TABLE 1-continued

Examples 60-125 (including Method of Preparation, Structures and Physicochemical Data).

| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 102 | Ex. 120 | 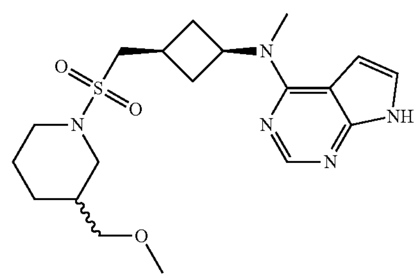 [SMILES: COCC1CCCN(S(=O)(=O)C[C@H]2C[C@@H](N(C)c3ncnc4[nH]ccc34)C2)C1] | 2.51 minutes[2]; 408 |
| 103 | Ex. 120 | 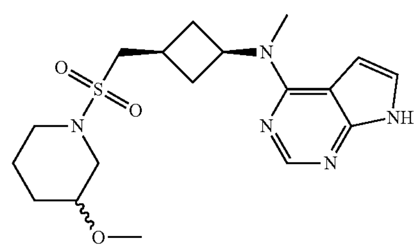 [SMILES: COC1CCCN(S(=O)(=O)C[C@H]2C[C@@H](N(C)c3ncnc4[nH]ccc34)C2)C1] | 2.39 minutes[2]; 394 |
| 104 | Ex. 120 | 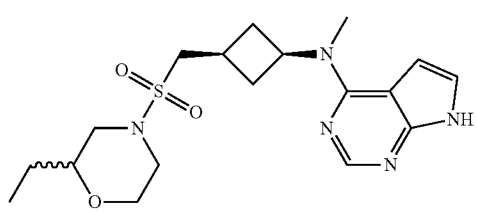 [SMILES: CCC1CN(S(=O)(=O)C[C@H]2C[C@@H](N(C)c3ncnc4[nH]ccc34)C2)CCO1] | 2.49 minutes[2]; 394 |
| 105 | Ex. 120 | 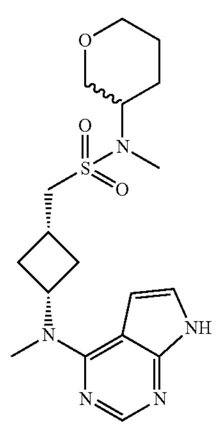 [SMILES: CN(C1CCCOC1)S(=O)(=O)C[C@H]1C[C@@H](N(C)c2ncnc3[nH]ccc23)C1] | 2.37 minutes[2]; 394 |

TABLE 1-continued

Examples 60-125 (including Method of Preparation, Structures and Physicochemical Data).

| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 106 | Ex. 120 | 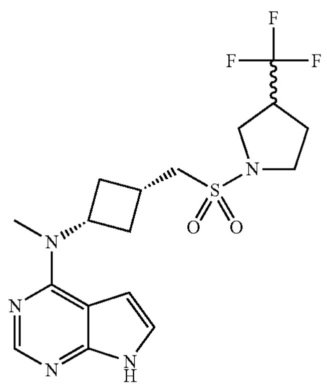 [SMILES: CN(c1ncnc2[nH]ccc12)[C@H]1C[C@@H](CS(=O)(=O)N2CCC(C(F)(F)F)C2)C1] | 2.38 minutes[4]; 418 |
| 107 | Ex. 120 | 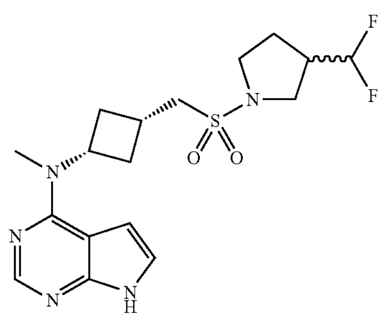 [SMILES: CN(c1ncnc2[nH]ccc12)[C@H]1C[C@@H](CS(=O)(=O)N2CCC(C(F)F)C2)C1] | 2.19 minutes[4]; 400 |
| 108 | Ex. 120 | 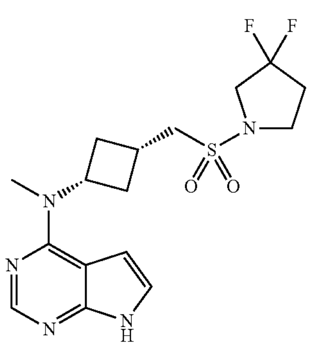 [SMILES: CN(c1ncnc2[nH]ccc12)[C@H]1C[C@@H](CS(=O)(=O)N2CCC(F)(F)C2)C1] | 1.94 minutes[5]; 386 |
| 109 | Ex. 120 | 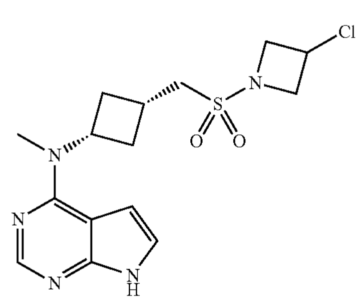 [SMILES: CN(c1ncnc2[nH]ccc12)[C@H]1C[C@@H](CS(=O)(=O)N2CC(Cl)C2)C1] | 2.03 minutes[4]; 370 |

TABLE 1-continued
Examples 60-125 (including Method of Preparation, Structures and Physicochemical Data).
| Example Number | Method of Preparation | Structure | 1H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 110 | Ex. 120 | 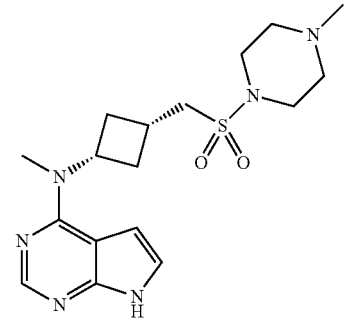 [SMILES: CN1CCN(S(=O)(=O)C[C@H]2C[C@@H](N(C)c3ncnc4[nH]ccc34)C2)CC1] | 2.25 minutes[1]; 379 |
| 111 | Ex. 120 | 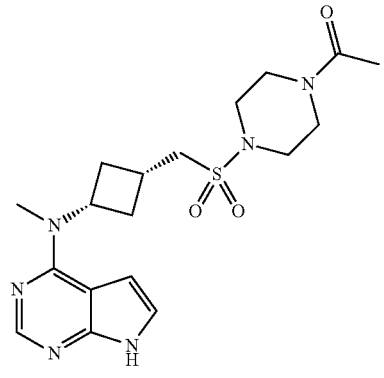 [SMILES: CC(=O)N1CCN(S(=O)(=O)C[C@H]2C[C@@H](N(C)c3ncnc4[nH]ccc34)C2)CC1] | 2.66 minutes[1]; 407 |
| 112 | Ex. 120 | 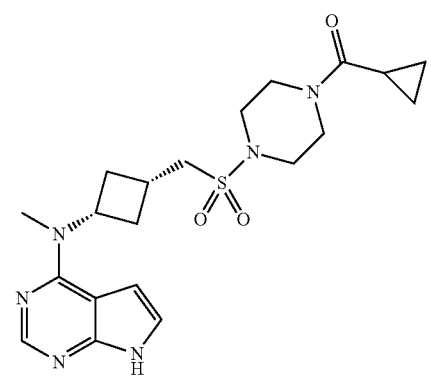 [SMILES: CN(c1ncnc2[nH]ccc12)[C@H]1C[C@@H](CS(=O)(=O)N2CCN(C(=O)C3CC3)CC2)C1] | 2.85 minutes[1]; 433 |
| 113 | Ex. 120 | 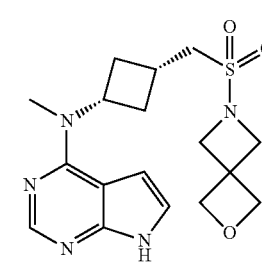 | 2.61 minutes[1]; 378 |

TABLE 1-continued

Examples 60-125 (including Method of Preparation, Structures and Physicochemical Data).

| Example Number | Method of Preparation | Structure | 1H NMR (400 MHz, CDCl₃) δ (ppm); Mass spectrum, observed ion m/z [M + H]+ or HPLC retention time; Mass spectrum m/z [M + H]+ (unless otherwise indicated) |
|---|---|---|---|
| 114 | Ex. 120 | 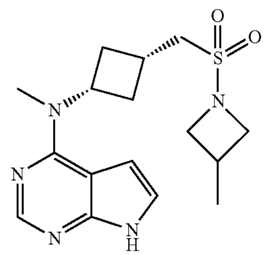 [SMILES: CC1CN(S(=O)(=O)C[C@H]2C[C@@H](N(C)c3ncnc4[nH]ccc34)C2)C1] | 2.86 minutes[1]; 350 |
| 115 | Ex. 120 | 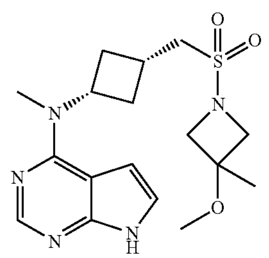 [SMILES: COC1(C)CN(S(=O)(=O)C[C@H]2C[C@@H](N(C)c3ncnc4[nH]ccc34)C2)C1] | 2.82 minutes[1]; 380 |
| 116 | Ex. 120 | 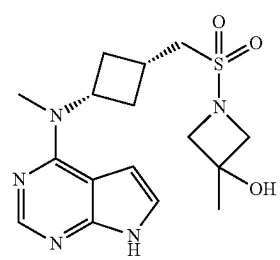 [SMILES: CN(c1ncnc2[nH]ccc12)[C@H]1C[C@@H](CS(=O)(=O)N2CC(C)(O)C2)C1] | 2.57 minutes[1]; 366 |
| 117 | Ex. 120 | 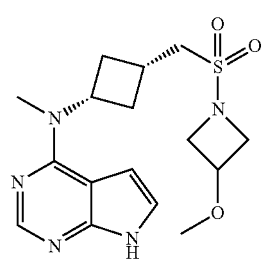 [SMILES: COC1CN(S(=O)(=O)C[C@H]2C[C@@H](N(C)c3ncnc4[nH]ccc34)C2)C1] | 2.71 minutes[1]; 366 |
| 118 | Ex. 120 | 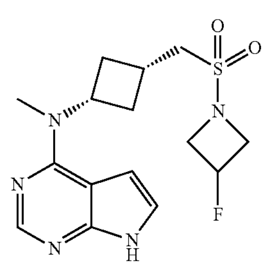 [SMILES: CN(c1ncnc2[nH]ccc12)[C@H]1C[C@@H](CS(=O)(=O)N2CC(F)C2)C1] | 2.71 minutes[1]; 354 |

TABLE 1-continued

Examples 60-125 (including Method of Preparation, Structures and Physicochemical Data).

| Example Number | Method of Preparation | Structure | 1H NMR (400 MHz, CDCl₃) δ (ppm); Mass spectrum, observed ion m/z [M + H]+ or HPLC retention time; Mass spectrum m/z [M + H]+ (unless otherwise indicated) |
|---|---|---|---|
| 119 | Ex. 120 | 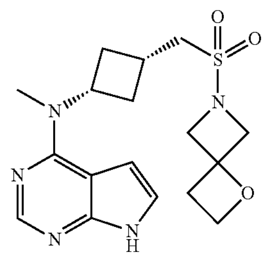 [SMILES: CN(c1ncnc2[nH]ccc12)[C@H]1C[C@@H](CS(=O)(=O)N2CC3(CCO3)C2)C1] | 2.69 minutes[1]; 378 |
| 120 | Ex. 120 | 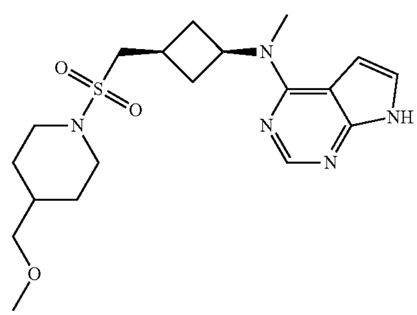 [SMILES: COCC1CCN(S(=O)(=O)C[C@H]2C[C@@H](N(C)c3ncnc4[nH]ccc34)C2)CC1] | ¹H NMR (400 MHz, DMSO-d6) δ 11.61 (bs, 1H), 8.10 (s, 1H), 7.14 (m, 1H), 8.62 (m, 1H), 5.07-5.15 (m, 1H), 3.60 (d, J = 12.6 Hz, 2H), 3.18-3.25 (m, 10H), 2.73-2.78 (m, 2H), 2.33-2.40 (m, 3H), 2.07-2.15 (m, 2H), 1.63-1.74 (m, 3H), 1.12-1.23 (m, 2H); 2.408 minutes[1]; 408 |
| 121 | Ex. 120 | 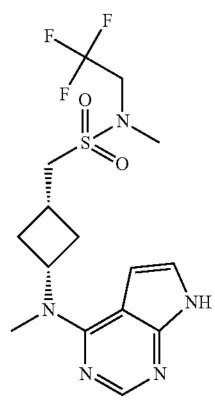 [SMILES: CN(CC(F)(F)F)S(=O)(=O)C[C@H]1C[C@@H](N(C)c2ncnc3[nH]ccc23)C1] | 2.53 minutes[2]; 392 |
| 122 | Ex. 120 | 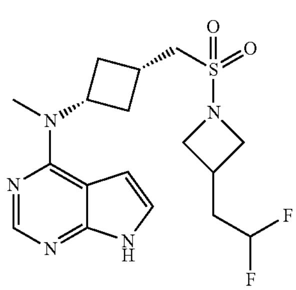 [SMILES: CN(c1ncnc2[nH]ccc12)[C@H]1C[C@@H](CS(=O)(=O)N2CC(CC(F)F)C2)C1] | 10.22 (b, 1H), 8.32 (s, 1H), 7.08 (d, J = 3.5 Hz, 1H), 6.59 (d, J = 3.5 Hz, 1H), 5.86 (tt, J = 55.0, 4.0 Hz, 1H), 4.04 (t, J = 8.0 Hz, 2H), 3.79 (t, J = 7.5 Hz, 2H), 3.33 (s, 3H), 3.11 (d, J = 7.0 Hz, 2H), 2.90 (sept, J = 7.1 Hz, 1H), 2.49-2.70 (m, 3H), 2.07-2.24 (m, 4H); 2.98 minutes[1], 399.9 |

TABLE 1-continued

Examples 60-125 (including Method of Preparation, Structures and Physicochemical Data).

| Example Number | Method of Preparation | Structure | 1H NMR (400 MHz, CDCl₃) δ (ppm); Mass spectrum, observed ion m/z [M + H]+ or HPLC retention time; Mass spectrum m/z [M + H]+ (unless otherwise indicated) |
|---|---|---|---|
| 123 | Ex. 120 | 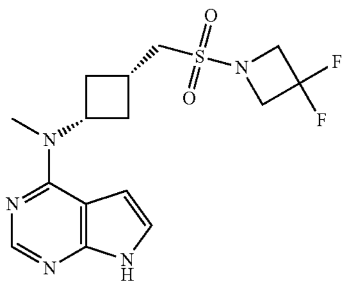 [SMILES: CN(c1ncnc2[nH]ccc12)[C@H]1C[C@@H](CS(=O)(=O)N2CC(F)(F)C2)C1] | 10.32 (b, 1H), 8.33 (s, 1H), 7.08 (d, J = 2.0 Hz, 1H), 6.58 (d, J = 3.0 Hz, 1H), 5.12-5.20 (m, 1H), 4.33 (t, J = 12.1 Hz, 4H), 3.34 (s, 3H), 3.21 (d, J = 7.0 Hz, 2H), 2.63-2.70 (m, 2H), 2.52-2.61 (m, 1H), 2.08-2.16 (m, 2H); 2.87 minutes[1], 372 |
| 124 | Ex. 120 | 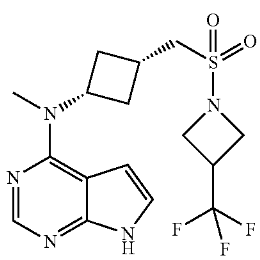 [SMILES: CN(c1ncnc2[nH]ccc12)[C@H]1C[C@@H](CS(=O)(=O)N2CC(C(F)(F)F)C2)C1] | 10.04 (b, 1H), 8.32 (s, 1H), 7.07 (2, J = 3.51 Hz, 1H), 6.58 (d, J = 3.5, 1H), 5.11-5.19 (m, 1H), 4.19 (t, J = 9.0 Hz, 2H), 4.02 (dd, J = 9.0, 6.0 Hz, 2H), 3.21-3.34 (m, 4H), 3.04 (d, J = 7.0 Hz, 2H), 2.48-2.69 (m, 3H), 2.11 (qd, J = 9.5, 2.5 Hz, 2H); 3.07 minutes[1], 404 |
| 125 | Ex. 120 | 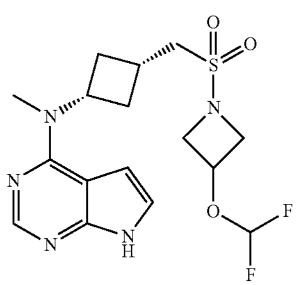 [SMILES: CN(c1ncnc2[nH]ccc12)[C@H]1C[C@@H](CS(=O)(=O)N2CC(OC(F)F)C2)C1] | 10.15 (b, 1H), 8.32 (s, 1H), 7.07 (m, 1H), 6.58 (m, 1H), 6.25 (t, J = 72 Hz, 1H), 5.15 (m, 1H), 4.96 (m, 1H), 4.08-4.17 (m, 4H), 3.33 (s, 3H), 3.15 (d, J = 7.0 Hz, 2H), 2.51-2.69 (m, 3H), 2.07-2.14 (m, 2H); 2.97 minutes[1], 402 |

[1] Conditions for analytical HPLC. Column: Xtimate C18 5 × 30 mm, 3 um; Mobile phase: 0.0375% trifluoroacetic acid in water (v/v); Mobile phase B; 0.0187% trifluoroacetic acid in acetonitrile (v/v); gradient: 99.0% H₂O/1.0% acetonitrile linear to 95% H₂O/5% acetonitrile in 1.0 min, then from 95.0% H₂O/5.0% acetonitrile linear to 0% H₂O/100% acetonitrile in 5 min, HOLD at 0% H₂O/100% acetonitrile to 8 min.; Flow: 1.2 ml/min.
[2] Conditions for analytical HPLC. Column: Xbridge C18 2.1 × 50 mm, 5 um; Mobile phase A: 0.0375% TFA in H₂O; Mobile phase B: 0.01875% TFA in acetonitrile; Gradient 99% H₂O/1% acetonitrile to 100% acetonitrile in 4 min.; Flow rate = 0.8 ml/min.
3. Conditions for analytical HPLC. Column Xbridge C18 2.1 × 50 mm, 5 um; Mobile phase A: 0.05% NH₄OH in H₂O; Mobile phase B: 100% acetonitrile; Gradient 95% H₂O/5% acetonitrile to 100% acetonitrile in 3.40 mins., HOLD at 100% acetonitrile for 0.8 min.; Flow 0.8 ml/min.
[4] Conditions for analytical HPLC. Column: Waters XBridge C18, 4.6 × 50 mm, 5 μm; Mobile phase A: 0.03% NH₄OH in water; Mobile phase B: 0.03% NH₄OH in acetonitrile; Gradient: 95% H₂O/5.0% acetonitrile linear to 5% H₂O/95% acetonitrile in 4.0 min, HOLD at 5% H₂O/95% acetonitrile to 5.0 min; Flow rate: 2 ml/min.
[5] Conditions for analytical HPLC. Column: Waters XBridge C18, 4.6 × 50 mm, 5 μm; Mobile phase A: 0.03% NH₄OH in water; Mobile phase B: 0.03% NH₄OH in acetonitrile; Gradient: 95% H₂O/5.0% acetonitrile linear to 5% H₂O/95% acetonitrile in 4.0 min, HOLD at 5% H₂O/95% acetonitrile to 5.0 min; Flow rate: 2 ml/min.

The following compounds in Table 2 were made starting from cis-[3-(Methyl{7-[(4-methylphenyl)sulfonyl]-7H-pyrrolo[2,3-d]pyrimidin-4-yl}amino)cyclobutyl]methyl 4-methylbenzenesulfonate (Example 25, Step 4), according to the procedures of Example 140 Step 1 (tosylate displacement with thioacetate reagent) and Example 33, step 2 (oxidation), substituting the appropriate thioacetate in Step 1

In certain cases, the compounds are further elaborated such as in Example 140, step 5, using the appropriate electrophile.

TABLE 2

Examples 126-140 (including Method of Preparation, Structures and Physicochemical Data).

| Example | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 126 | Ex. 140 | 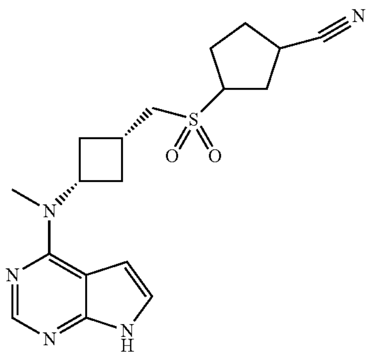 [SMILES: CN(c1ncnc2[nH]ccc12)[C@H]1C[C@@H](CS(=O)(=O)C2CCC(C#N)C2)C1] | 2.72 minutes[1]; 374 |
| 127 | Ex. 140 | 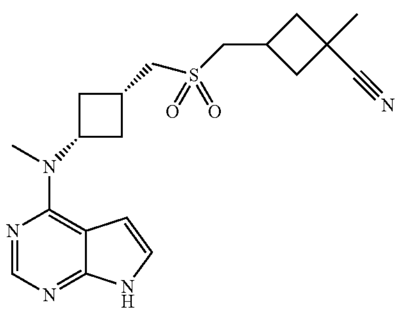 [SMILES: CN(c1ncnc2[nH]ccc12)[C@H]1C[C@@H](CS(=O)(=O)CC2CC(C)(C#N)C2)C1] | 2.87 minutes[1]; 388 |
| 128 | Ex. 140 | 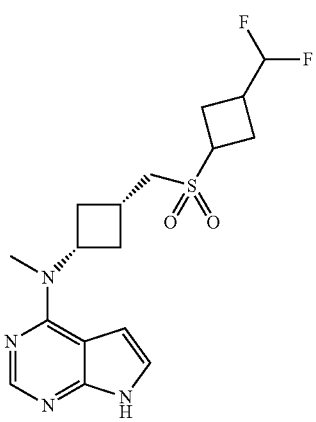 [SMILES: CN(c1ncnc2[nH]ccc12)[C@H]1C[C@@H](CS(=O)(=O)C2CC(C(F)F)C2)C1] | 2.86 minutes[1]; 385 |
| 129 | Ex. 140 | 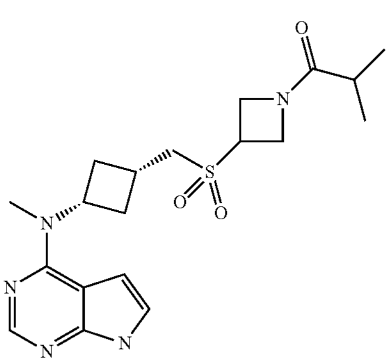 [SMILES: CC(C)C(=O)N1CC(S(=O)(=O)C[C@H]2C[C@@H](N(C)c3ncnc4[nH]ccc34)C2)C1] | 2.74 minutes[1]; 406 |

TABLE 2-continued
Examples 126-140 (including Method of Preparation, Structures and Physicochemical Data).
| Example | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 130 | Ex. 140 | 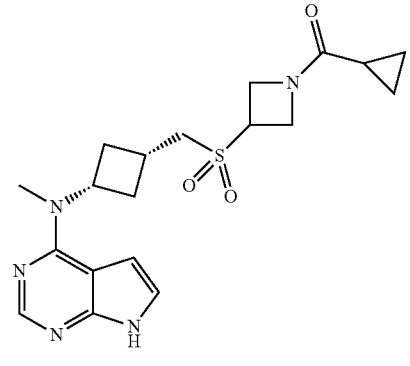 [SMILES: CN(c1ncnc2[nH]ccc12)[C@H]1C[C@@H](CS(=O)(=O)C2CN(C(=O)C3CC3)C2)C1] | 2.68 minutes$^1$; 404 |
| 131 | Ex. 140 | 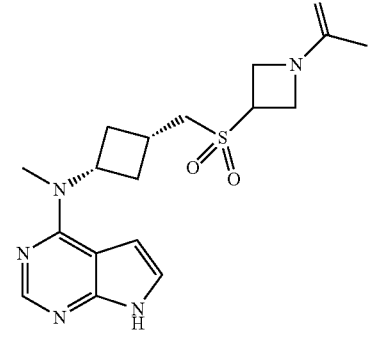 | 2.49 minutes$^1$; 378 |
| 132 | Ex. 140 | 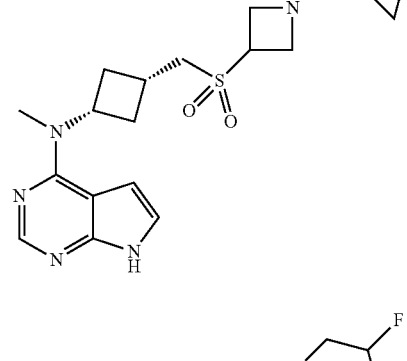 | 2.39 minutes$^1$; 390 |
| 133 | Ex. 140 | 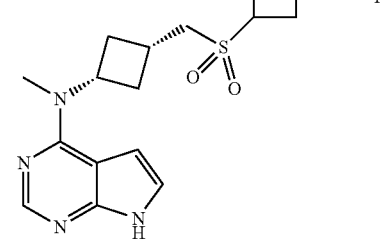 | 2.38 minutes$^1$; 400 |

TABLE 2-continued

Examples 126-140 (including Method of Preparation, Structures and Physicochemical Data).

| Example | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 134 | Ex. 140 | 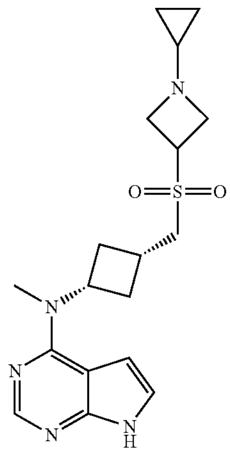 [SMILES: CN(c1ncnc2[nH]ccc12)[C@H]1C[C@@H](CS(=O)(=O)C2CN(C3CC3)C2)C1] | 2.23 minutes$^1$; 376 |
| 135 | Ex. 140 | 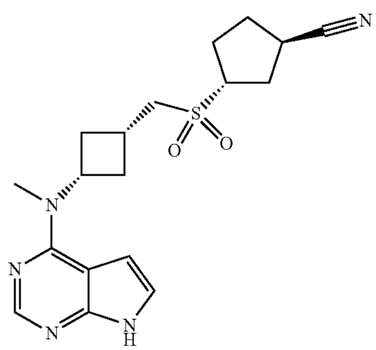 [SMILES: CN(c1ncnc2[nH]ccc12)[C@H]1C[C@@H](CS(=O)(=O)[C@@H]2CC[C@@H](C#N)C2)C1] | 2.70 minutes$^1$; 374 |
| 136 | Ex. 140 | 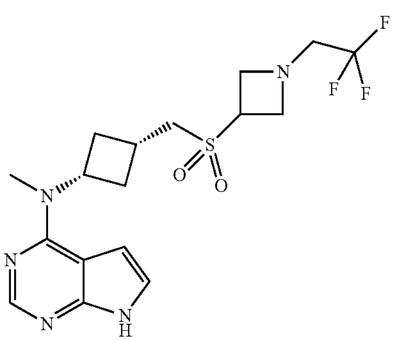 [SMILES: CN(c1ncnc2[nH]ccc12)[C@H]1C[C@@H](CS(=O)(=O)C2CN(CC(F)(F)F)C2)C1] | 2.86 minutes$^1$; 418 |
| 137 | Ex. 140 | 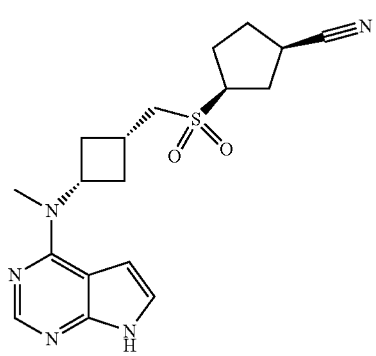 [SMILES: CN(c1ncnc2[nH]ccc12)[C@H]1C[C@@H](CS(=O)(=O)[C@H]2CC[C@@H](C#N)C2)C1] | 2.66 minutes$^1$; 374 |

TABLE 2-continued

Examples 126-140 (including Method of Preparation, Structures and Physicochemical Data).

| Example | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 138 | Ex. 140 | 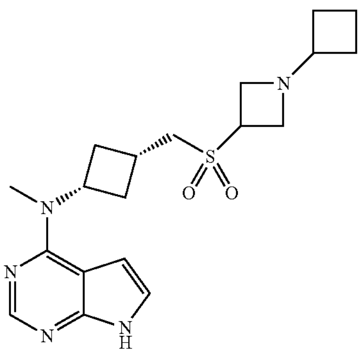 [SMILES: CN(c1ncnc2[nH]ccc12)[C@H]1C[C@@H](CS(=O)(=O)C2CN(C3CCC3)C2)C1] | 2.36 minutes[1]; 390 |
| 139 | Ex. 140 | 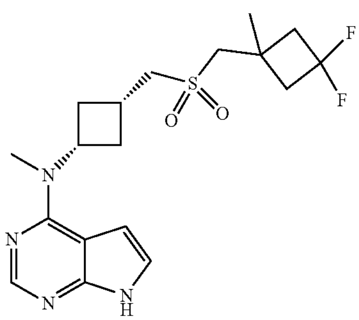 [SMILES: CN(c1ncnc2[nH]ccc12)[C@H]1C[C@@H](CS(=O)(=O)CC2(C)CC(F)(F)C2)C1] | 9.96 (m, 1H), 8.31 (s, 1H), 7.06 (d, J = 3.0 Hz, 1H), 6.58 (d, J = 3.5 Hz, 1H), 5.16 (quint, J = 7.0 Hz, 1H), 3.33 (s, 3H), 3.16-3.18 (m, 4H), 2.50-2.83 (m, 7H), 2.15 (q, J = 10.5 Hz, 2H), 1.59 (s, 3H); 3.13 minutes[1], 399 |
| 140 | Ex. 140 | 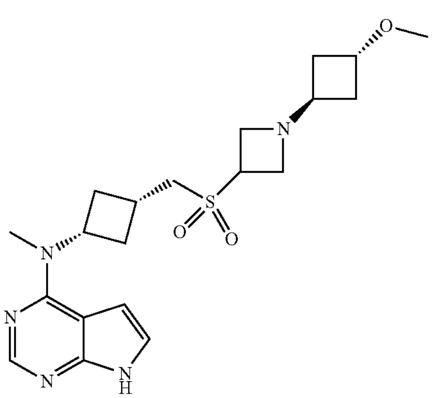 [SMILES: CO[C@H]1C[C@H](N2CC(S(=O)(=O)C[C@H]3C[C@@H](N(C)c4ncnc5[nH]ccc45)C3)C2)C1] | 10.35 (b, 1H), 8.32 (s, 1H), 7.08 (m, 1H), 6.58 (m, 1H), 5.14 (quint, J = 8.0 Hz, 1H), 4.01 (quint, J = 6.5 Hz, 1H), 3.86 (quint, J = 7.53 Hz, 1H), 3.61 (t, J = 8.03 Hz, 2H), 3.46 (t, J = 7.5 Hz, 2H), 3.33 (s, 3H), 3.15-3.22 (m, 4H), 3.11 (d, J = 7.0 Hz, 2H), 2.53-2.74 (m, 3H), 1.95-2.16 (m, 6H); 2.405 minutes[1], 420 |

[1]Conditions for analytical HPLC Column: Xtimate C18 5 × 30 mm, 3 μm; Mobile phase: 0.0375% trifluoroacetic acid in water (v/v); Mobile phase B; 0.0187% trifluoroacetic acid in acetonitrile (v/v); gradient: 99.0% H$_2$O/1.0% acetonitrile linear to 95% H$_2$O/5% acetonitrile in 1.0 min, then from 95.0% H$_2$O/5.0% acetonitrile linear to 0% H$_2$0/100% acetonitrile in 5 min, HOLD at 0% H$_2$O/100% acetonitrile to 8 min.; Flow: 1.2 ml/min.

The following compounds in Table 3 were made starting from cis-[3-(methyl{7-[(4-methylphenyl)sulfonyl]-7H-pyrrolo[2,3-d]pyrimidin-4-yl}amino)cyclobutyl]methanesulfonyl chloride (Example 25, Step 7), according to the procedures of Example 152, Step 1 (sodium sulfinate formation) and Step 2 (alkylation), substituting the appropriate electrophile in Step 2.

TABLE 3

Examples 141-153 (including Method of Preparation, Structures and Physicochemical Data).

| Example Number | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 141 | Ex. 152 | 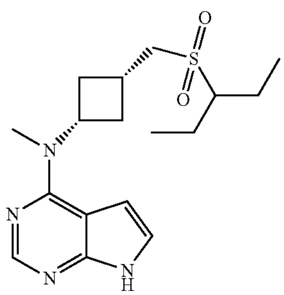 [SMILES: CCC(CC)S(=O)(=O)C[C@H]1C[C@@H](N(C)c2ncnc3[nH]ccc23)C1] | 1.83 minutes$^1$; 351 |
| 142 | Ex. 152 | 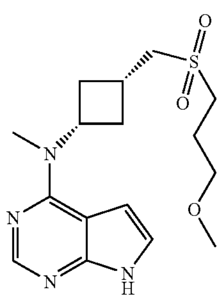 [SMILES: COCCCS(=O)(=O)C[C@H]1C[C@@H](N(C)c2ncnc3[nH]ccc23)C1] | 1.43 minutes$^1$; 353 |
| 143 | Ex. 152 | 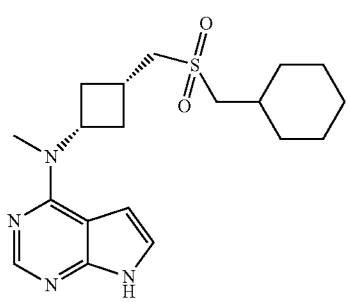 [SMILES: CN(c1ncnc2[nH]ccc12)[C@H]1C[C@@H](CS(=O)(=O)CC2CCCCC2)C1] | 2.18 minutes$^1$; 377 |
| 144 | Ex. 152 | 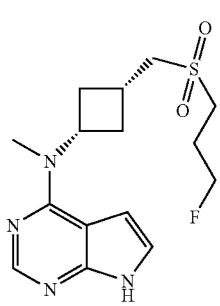 [SMILES: CN(c1ncnc2[nH]ccc12)[C@H]1C[C@@H](CS(=O)(=O)CCCF)C1] | 1.44 minutes$^1$; 341 |

TABLE 3-continued

Examples 141-153 (including Method of Preparation, Structures and Physicochemical Data).

| Example Number | Method of Preparation | Structure | ¹H NMR (400 MHz, CDCl₃) δ (ppm); Mass spectrum, observed ion m/z [M + H]+ or HPLC retention time; Mass spectrum m/z [M + H]+ (unless otherwise indicated) |
|---|---|---|---|
| 145 | Ex. 152 | 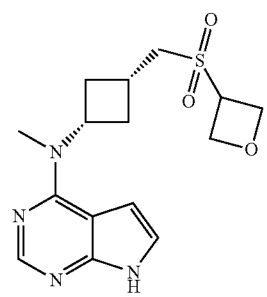 [SMILES: CN(c1ncnc2[nH]ccc12)[C@H]1C[C@@H](CS(=O)(=O)C2COC2)C1] | 1.27 minutes[1]; 337 |
| 146 | Ex. 152 | 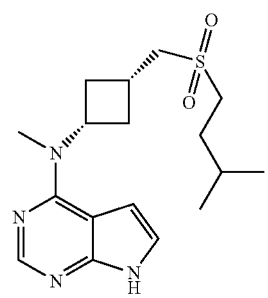 [SMILES: CC(C)CCS(=O)(=O)C[C@H]1C[C@@H](N(C)c2ncnc3[nH]ccc23)C1] | 1.95 minutes[1]; 351 |
| 147 | Ex. 152 | 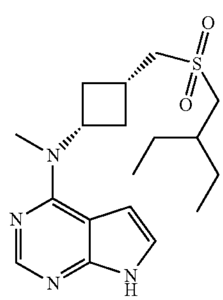 [SMILES: CCC(CC)CS(=O)(=O)C[C@H]1C[C@@H](N(C)c2ncnc3[nH]ccc23)C1] | 1.94 minutes[1]; 365 |
| 148 | Ex. 152 | 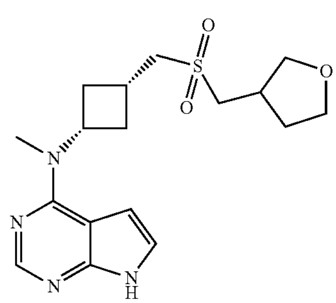 [SMILES: CN(c1ncnc2[nH]ccc12)[C@H]1C[C@@H](CS(=O)(=O)CC2CCOC2)C1] | 1.39 minutes[1]; 365 |

TABLE 3-continued

Examples 141-153 (including Method of Preparation, Structures and Physicochemical Data).

| Example Number | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 149 | Ex. 152 | 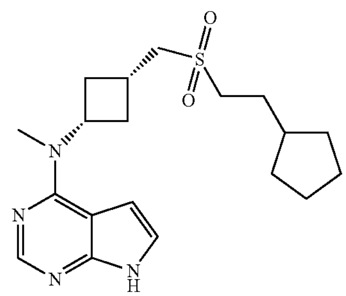 [SMILES: CN(c1ncnc2[nH]ccc12)[C@H]1C[C@@H](CS(=O)(=O)CCC2CCCC2)C1] | 2.23 minutes[1]; 377 |
| 150 | Ex. 152 | 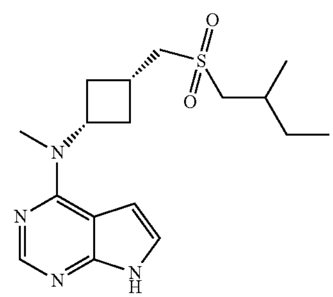 [SMILES: CCC(C)CS(=O)(=O)C[C@H]1C[C@@H](N(C)c2ncnc3[nH]ccc23)C1] | 1.94 minutes[1]; 351 |
| 151 | Ex. 152 | 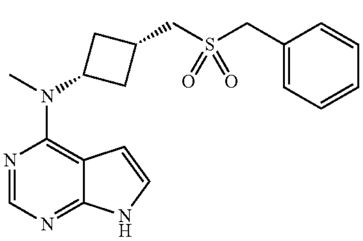 [SMILES: CN(c1ncnc2[nH]ccc12)[C@H]1C[C@@H](CS(=O)(=O)Cc2ccccc2)C1] | 2.19 minutes[2]; 371 |
| 152 | Ex. 152 | 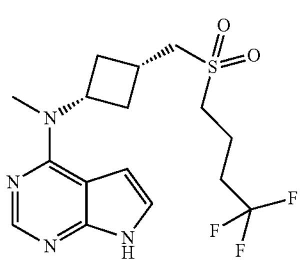 [SMILES: CN(c1ncnc2[nH]ccc12)[C@H]1C[C@@H](CS(=O)(=O)CCCC(F)(F)F)C1] | 9.39 (b, 1H), 8.31 (s, 1H), 7.06 (m, 1H), 6.58 (d, J = 2.51 Hz, 1H), 5.15 (quint, J = 7.5 Hz, 1H), 3.33 (s, 3H), 3.19 (d, J = 7.0 Hz, 2H), 3.04 (t, J = 7.5 Hz, 2H), 2.59-2.75 (m, 3H), 2.30-2.40 (m, 2H), 2.11-2.22 (m, 4H); 2.99 minutes[1], 391 |

TABLE 3-continued

Examples 141-153 (including Method of Preparation, Structures and Physicochemical Data).

| Example Number | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 153 | Ex. 152 | 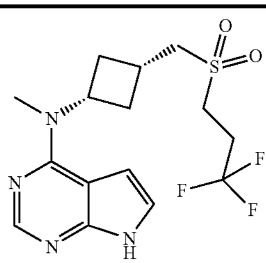 | 9.73 (m, 1H), 8.31 (s, 1H), 7.07 (m, 1H), 6.58 (d, J = 3.0 Hz, 1H), 5.16 (quint, J = 8.53 Hz, 1H), 3.34 (s, 3H), 3.24 (d, J = 7.0 Hz, 2H), 3.16-3.20 (m, 2H), 2.76-2.61 (m, 5H), 2.16 (q, J = 9.0 Hz, 2H); 2.88 minutes[1], 376 |

[1]Conditions for analytical HPLC Column: Waters Atlantis dC18 4.6 × 50, 5 μm; Mobile Phase A: 0.05% TFA in H$_2$O (v/v); Mobile phase B: TFA in acetonitrile (v/v); Gradient: 95.0% H$_2$O/5.0% acetonitrile linear to 5% H$_2$O/95% acetonitrile in 4.0 min., HOLD at 5% H$_2$O/95% acetonitrile for 5 min. Flow: 2 ml/min.
[2]Conditions for analytical HPLC. Column: Waters XBridge C18, 4.6 × 50 mm, 5 μm; Mobile phase A: 0.03% NH$_4$OH in water; Mobile phase B: 0.03% NH$_4$OH in acetonitrile; Gradient: 95% H$_2$O/5.0% acetonitrile linear to 5% H$_2$O/95% acetonitrile in 4.0 min, HOLD at 5% H$_2$O/95% acetonitrile to 5.0 min; Flow rate: 2 ml/min.

Example 239 cis-N-((1S,3S)-3-(((3,3-Difluorocyclobutyl)sulfonyl) methyl)cyclobutyl)-N-methyl-7H-pyrrolo[2,3-d]pyrimidin-4-amine Step 1: 2-((3,3-difluorocyclobutyl)thio)benzo[d]thiazole To a suspension of 2,2'-dibenzthiazolyl disulfide (677 mg, 2.04 mmol) and 3,3-difluorocyclobutanol (220 mg, 2.04 mmol, 1 eq.) in THF (5 ml) was added triphenylphosphine (747 mg, 2.85 mmol, 1.4 eq.) at 20° C. In 30 minutes, LCMS analysis of the resulting yellow solution indicated the reaction was complete. The reaction was diluted with DCM (25 ml) and washed with 1 N NaOH (aq) (2×10 ml). The combined aqueous was extracted with DCM (1×15 ml) and the combined organics were dried over MgSO$_4$, filtered and concentrated to provide a crude product as an off white solid which was purified via SiO$_2$ chromatography (EtOAc, Hep 5-30% gradient) to provide the desired material as a white solid (421 mg, 80% yield, 60% pure) which was used as is in the next step.
Crude $^1$H NMR (400 MHz, CHLOROFORM-d) δ 7.85-7.94 (m, 1H), 7.75-7.83 (m, 1H), 7.45 (ddd, J=1.37, 7.24, 8.22 Hz, 1H), 7.29-7.38 (m, 1H), 4.16-4.32 (m, 1H), 3.19-3.38 (m, 2H), 2.69-2.87 (m, 2H)

Step 2: 2-((3,3-difluorocyclobutyl)sulfonyl)benzo[d]thiazole

To a solution of 2-((3,3-difluorocyclobutyl)sulfonyl) benzo[d]thiazole (421 mg, 0.98 mmol based on 60% purity) in DCM (20 mL) was added mCPBA (550 mg, 2.45 mmol, 2.5 eq.) in one portion. The resulting reaction was stirred for 12 hours until starting material was consumed as determined by LCMS. The mixture was diluted with 10 ml DCM and washed with saturated Na$_2$CO$_3$ (3×10 ml). The organic layer was separated and the aqueous was extracted with DCM (1×10 ml). The combined organic layers were dried over MgSO4 filtered and then adsorbed onto celite and purified via column chromatography (ISCO SiO$_2$, 10-30% EtOAc/hexanes) to provide a crude white solid. An additional purification via column chromatography (10-25% EtOAc/Hex) provided 2-((3,3-difluorocyclobutyl)thio)benzo[d]thiazole (186 mg, 65%) as a white solid.
$^1$H NMR (400 MHz, CHLOROFORM-d) δ 8.23 (dd, J=1.37, 7.61 Hz, 1H), 8.05 (dd, J=1.40, 7.60 Hz, 1H), 7.61-7.70 (m, 2H), 4.13-4.23 (m, 1H), 3.26-3.40 (m, 2H), 2.93-3.06 (m, 2H)

Step 3: Preparation of the Sodium Sulfinate

To a solution of 2-((3,3-difluorocyclobutyl)thio)benzo[d]thiazole (186 mg, 0.643 mmol) in MeOH was added NaOMe (0.5 M solution, 1.54 ml, 0.771 mmol, 1.2 eq.) and the resulting solution stirred at RT for 20 minutes by which time TLC indicated SM was consumed. The reaction was concentrated and then slurried with heptane (40 ml). The white solid was filtered and dried under vacuum to provide the desired compound as a crude solid that was used as is in the next step. Crude $^1$H NMR (400 MHz, DMSO-d$_6$) δ 2.52-2.66 (m, 2H), 2.32-2.44 (m, 1H), 2.18-2.31 (m, 2H)

Step 4: cis-N-((1S,3S)-3-(((3,3-difluorocyclobutyl) sulfonyl)methyl)cyclobutyl)-N-methyl-7H-pyrrolo [2,3-d]pyrimidin-4-amine To a 2 dram vile containing N-((1S,3S)-3-(iodomethyl) cyclobutyl)-N-methyl-7-tosyl-7H-pyrrolo[2,3-d]pyrimidin-4-amine (111 mg, 0.212 mmol. 1 eq.), crude sulfinate (75 mg, 0.423 mmol, 2.0 eq.) and K$_2$CO$_3$ (146 mg, 1.06 mmol, 5 eq.) was added DMSO (1 ml). The resulting mixture was stirred at 50° C. for 2 h where the reaction was judged to be complete by LCMS. MeOH (0.5 ml) was added and the reaction was stirred for an additional 30 minutes at 50° C. by which time LCMS indicated the major peak correlated to deprotected product. The reaction was concentrated and partitioned between water (10 ml) and DCM (25 ml). The aqueous was extracted with DCM (1×25 ml). Combined organics were dried over MgSO$_4$ filtered and concentrated to a clear oil. The resulting crude material was purified via reversed phase HPLC.

¹H NMR (400 MHz, CHLOROFORM-d) δ 13.83 (br. s., 1H) 8.23 (s, 1H) 7.17 (dd, J=3.51, 2.34 Hz, 1H) 6.65 (dd, J=3.51, 1.95 Hz, 1H) 5.12-5.30 (m, 1H) 3.51-3.62 (m, 1H) 3.46 (s, 3H) 3.06-3.23 (m, 2H) 3.14 (d, J=11.71 Hz, 2H) 2.87-3.00 (m, 2H) 2.60-2.84 (m, 3H) 2.15-2.26 (m, 2H). LCMS m/z 371 [M+H]⁺

TABLE 3a

Examples 155-181, 184, 185, 190, 194, 195, 219, 228, 232, 239, 243, 245, 246, 248, 254, and 256 (including Method of Preparation, Structures and Physicochemical Data).

| Example Number | Method of Preparation | Structure | ¹H NMR (400 MHz, CDCl₃) δ (ppm); Mass spectrum, observed ion m/z [M + H]+ or HPLC retention time; Mass spectrum m/z [M + H]+ (unless otherwise indicated) |
|---|---|---|---|
| 155 | 140 | 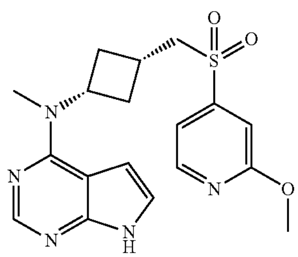 [SMILES: COc1cc(S(=O)(=O)C[C@H]2C[C@@H](N(C)c3ncnc4[nH]ccc34)C2)ccn1] | 3.16 minutes¹; 388 |
| 156 | 152 | 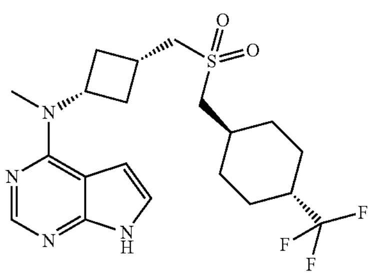 [SMILES: CN(c1ncnc2[nH]ccc12)[C@H]1C[C@@H](CS(=O)(=O)C[C@H]2CC[C@H](C(F)(F)F)CC2)C1] | 3.52 minutes¹; 445 |
| 158 | 140 | 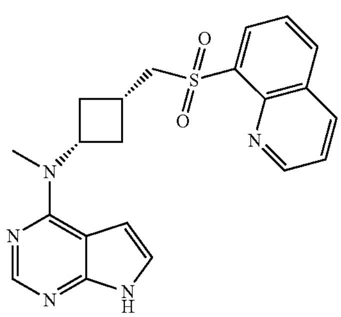 [SMILES: CN(c1ncnc2[nH]ccc12)[C@H]1C[C@@H](CS(=O)(=O)c2cccc3cccnc23)C1] | 1.74 minutes²; 408 |
| 159 | 120 | 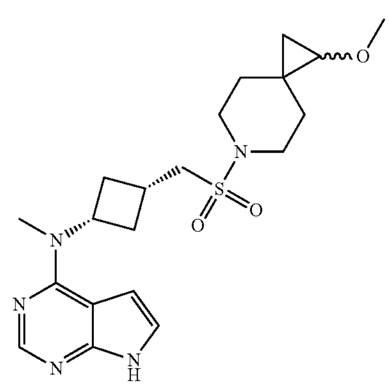 [SMILES: COC1CC12CCN(S(=O)(=O)C[C@H]1C[C@@H](N(C)c3ncnc4[nH]ccc34)C1)CC2] | 1.99 minutes²; 420 |

TABLE 3a-continued

Examples 155-181, 184, 185, 190, 194, 195, 219, 228, 232, 239, 243, 245, 246, 248, 254, and 256 (including Method of Preparation, Structures and Physicochemical Data).

| Example Number | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 160 | 152 | 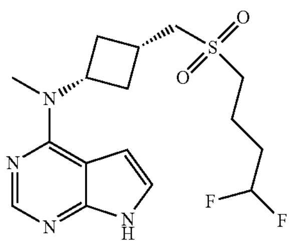 [SMILES: CN(c1ncnc2[nH]ccc12)[C@H]1C[C@@H](CS(=O)(=O)CCCC(F)F)C1] | 2.88 minutes$^1$; 373 |
| 161 | 152 | 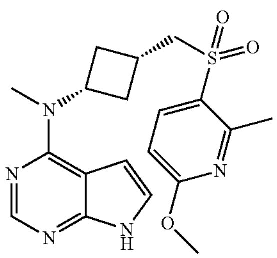 [SMILES: COc1ccc(S(=O)(=O)C[C@H]2C[C@@H](N(C)c3ncnc4[nH]ccc34)C2)c(C)n1] | 3.30 minutes$^1$; 402 |
| 163 | 120 | 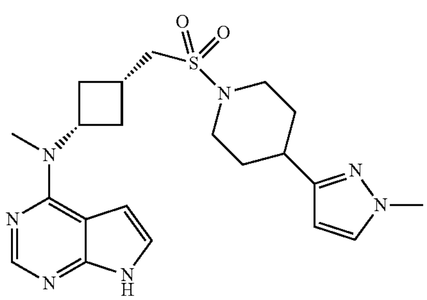 [SMILES: Cn1ccc(C2CCN(S(=O)(=O)C[C@H]3C[C@@H](N(C)c4ncnc5[nH]ccc45)C3)CC2)n1] | 3.04 minutes$^1$; 444 |
| 165 | 140 | 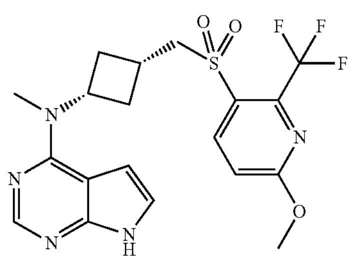 [SMILES: COc1ccc(S(=O)(=O)C[C@H]2C[C@@H](N(C)c3ncnc4[nH]ccc34)C2)c(C(F)(F)F)n1] | 3.50 minutes$^1$; 456 |
| 166 | 140 | 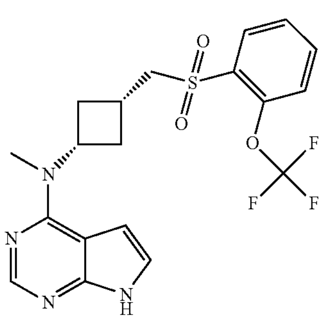 [SMILES: CN(c1ncnc2[nH]ccc12)[C@H]1C[C@@H](CS(=O)(=O)c2ccccc2OC(F)(F)F)C1] | 1.92 minutes$^2$; 415 |

TABLE 3a-continued

Examples 155-181, 184, 185, 190, 194, 195, 219, 228, 232, 239, 243, 245, 246, 248, 254, and 256 (including Method of Preparation, Structures and Physicochemical Data).

| Example Number | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 168 | 140 | 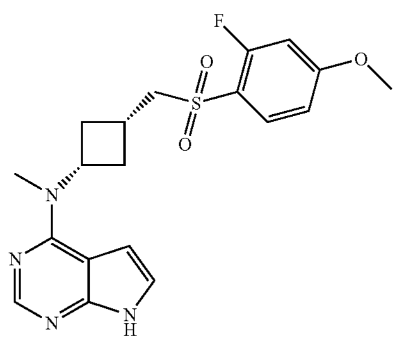 [SMILES: COc1ccc(S(=O)(=O)C[C@H]2C[C@@H](N(C)c3ncnc4[nH]ccc34)C2)c(F)c1] | 1.94 minutes$^2$; 405 |
| 170 | 140 | 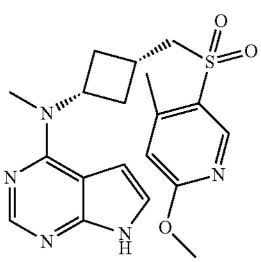 [SMILES: COc1cc(C)c(S(=O)(=O)C[C@H]2C[C@@H](N(C)c3ncnc4[nH]ccc34)C2)cn1] | 3.22 minutes$^1$; 402 |
| 171 | 140 | 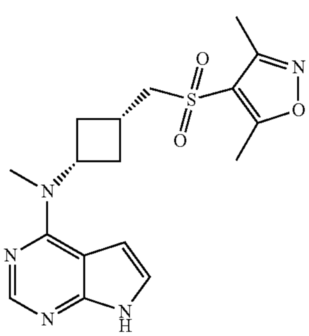 [SMILES: Cc1noc(C)c1S(=O)(=O)C[C@H]1C[C@@H](N(C)c2ncnc3[nH]ccc23)C1] | 1.75 minutes$^2$; 376 |
| 173 | 152 | 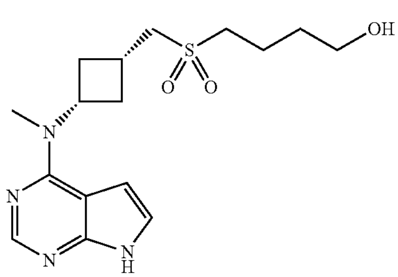 [SMILES: CN(c1ncnc2[nH]ccc12)[C@H]1C[C@@H](CS(=O)(=O)CCCCO)C1] | 0.994 minutes$^1$; 353 |

TABLE 3a-continued

Examples 155-181, 184, 185, 190, 194, 195, 219, 228, 232, 239, 243, 245, 246, 248, 254, and 256 (including Method of Preparation, Structures and Physicochemical Data).

| Example Number | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 174 | 152 | 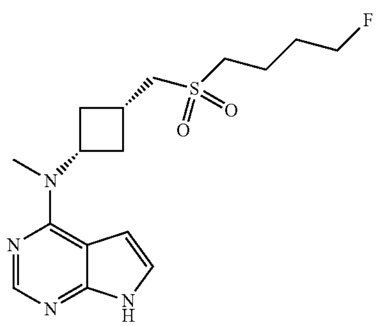 [SMILES: CN(c1ncnc2[nH]ccc12)[C@H]1C[C@@H](CS(=O)(=O)CCCCF)C1] | 2.72 minutes$^1$; 355 |
| 176 | 140 | 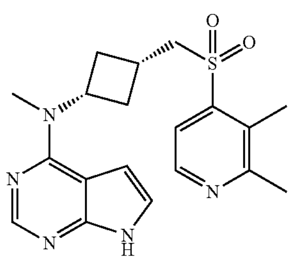 [SMILES: Cc1nccc(S(=O)(=O)C[C@H]2C[C@@H](N(C)c3ncnc4[nH]ccc34)C2)c1C] | 2.96 minutes$^1$; 385.9 |
| 178 | 140 | 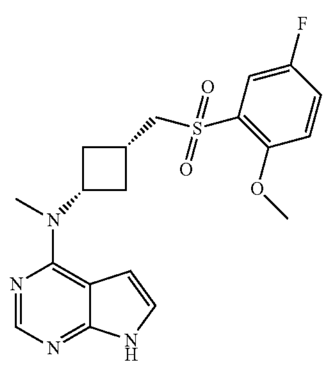 [SMILES: COc1ccc(F)cc1S(=O)(=O)C[C@H]1C[C@@H](N(C)c2ncnc3[nH]ccc23)C1] | 1.88 minutes$^2$; 405 |
| 180 | 140 | 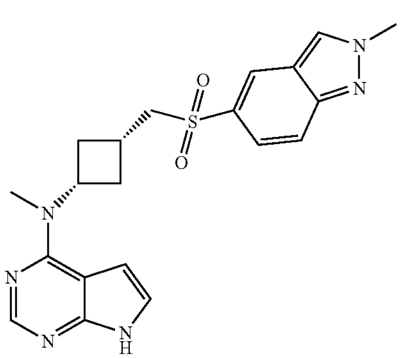 [SMILES: Cn1cc2cc(S(=O)(=O)C[C@H]3C[C@@H](N(C)c4ncnc5[nH]ccc45)C3)ccc2n1] | 1.78 minutes$^2$; 418 |

TABLE 3a-continued

Examples 155-181, 184, 185, 190, 194, 195, 219, 228, 232, 239, 243, 245, 246, 248, 254, and 256 (including Method of Preparation, Structures and Physicochemical Data).

| Example Number | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 181 | 152 | 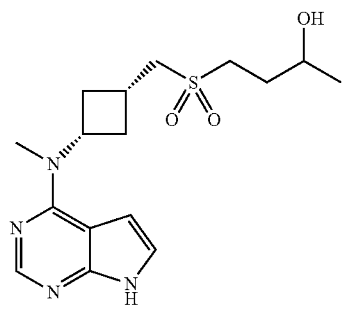 [SMILES: CC(O)CCS(=O)(=O)C[C@H]1C[C@@H](N(C)c2ncnc3[nH]ccc23)C1] | 2.45 minutes$^3$; 353 |
| 184 | 140 | 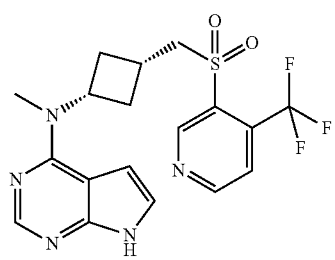 [SMILES: CN(c1ncnc2[nH]ccc12)[C@H]1C[C@@H](CS(=O)(=O)c2cnccc2C(F)(F)F)C1] | 3.05 minutes$^1$; 426 |
| 185 | 152 | 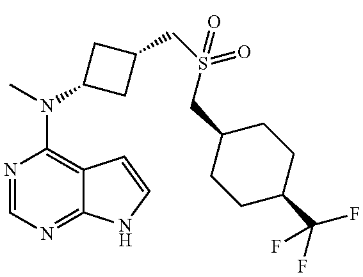 [SMILES: CN(c1ncnc2[nH]ccc12)[C@H]1C[C@@H](CS(=O)(=O)C[C@H]2CC[C@@H](C(F)(F)F)CC2)C1] | 3.47 minutes$^1$; 445 |
| 190 | 140 | 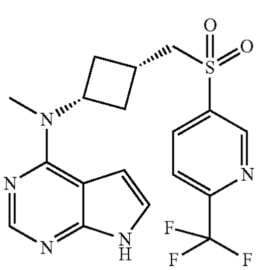 [SMILES: CN(c1ncnc2[nH]ccc12)[C@H]1C[C@@H](CS(=O)(=O)c2ccc(C(F)(F)F)nc2)C1] | 3.36 minutes$^1$; 426 |

TABLE 3a-continued

Examples 155-181, 184, 185, 190, 194, 195, 219, 228, 232, 239, 243, 245, 246, 248, 254, and 256 (including Method of Preparation, Structures and Physicochemical Data).

| Example Number | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 194 | 152 | 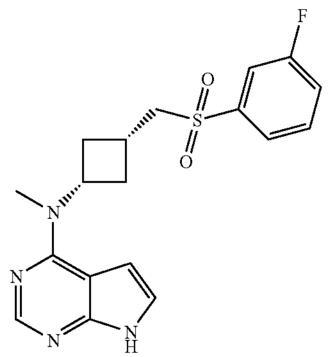 [SMILES: CN(c1ncnc2[nH]ccc12)[C@H]1C[C@@H](CS(=O)(=O)c2cccc(F)c2)C1] | 3.15 minutes[2]; 375 |
| 195 | 120 | 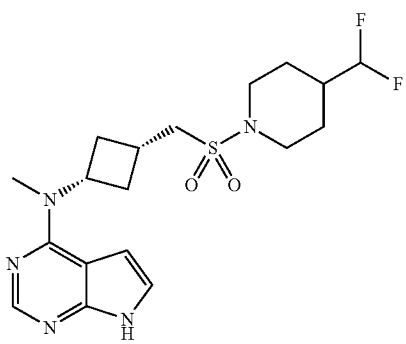 [SMILES: CN(c1ncnc2[nH]ccc12)[C@H]1C[C@@H](CS(=O)(=O)N2CCC(C(F)F)CC2)C1] | 3.14 minutes[1]; 414 |
| 219 | 152 | 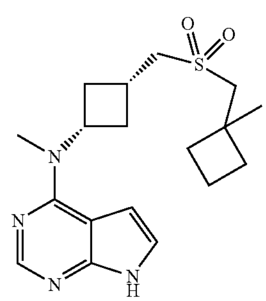 [SMILES: CN(c1ncnc2[nH]ccc12)[C@H]1C[C@@H](CS(=O)(=O)CC2(C)CCC2)C1] | 3.196 minutes[1]; 362 |
| 228 | 152 | 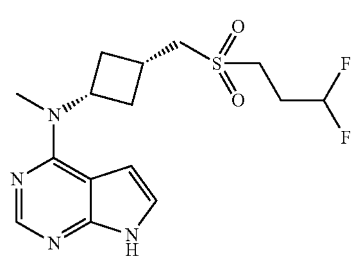 [SMILES: CN(c1ncnc2[nH]ccc12)[C@H]1C[C@@H](CS(=O)(=O)CCC(F)F)C1] | 2.67 minutes[1]; 359 |

TABLE 3a-continued

Examples 155-181, 184, 185, 190, 194, 195, 219, 228, 232, 239, 243, 245, 246, 248, 254, and 256 (including Method of Preparation, Structures and Physicochemical Data).

| Example Number | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 232 | 120 | 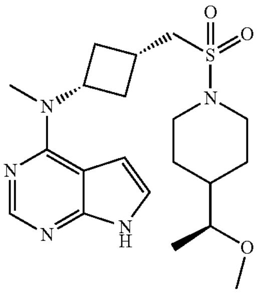 [SMILES: CO[C@@H](C)C1CCN(S(=O)(=O)C[C@H]2C[C@@H](N(C)c3ncnc4[nH]ccc34)C2)CC1] | 3.20 minutes[1]; 422 |
| 239 | 239 | 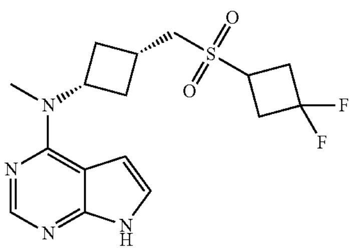 [SMILES: CN(c1ncnc2[nH]ccc12)[C@H]1C[C@@H](CS(=O)(=O)C2CC(F)(F)C2)C1] | 13.83 (br. s., 1H) 8.23 (s, 1H) 7.17 (dd, J = 3.51, 2.34 Hz, 1H) 6.65 (dd, J = 3.51, 1.95 Hz, 1H) 5.12-5.30 (m, 1H) 3.51-3.62 (m, 1H) 3.46 (s, 3H) 3.06-3.23 (m, 2H) 3.14 (d, J = 11.71 Hz, 2H) 2.87-3.00 (m, 2H) 2.60-2.84 (m, 3H) 2.15-2.26 (m, 2H), 1.87 minutes[3]; 371 |
| 243 | 239 | 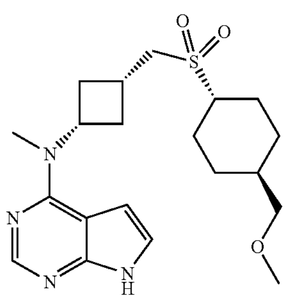 [SMILES: COC[C@H]1CC[C@H](S(=O)(=O)C[C@H]2C[C@@H](N(C)c3ncnc4[nH]ccc34)C2)CC1] | 3.06 minutes[1]; 407 |
| 245 | 152 | 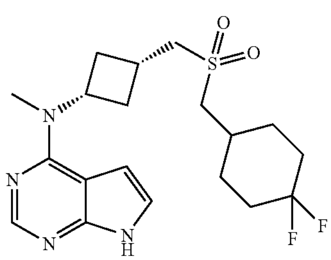 [SMILES: CN(c1ncnc2[nH]ccc12)[C@H]1C[C@@H](CS(=O)(=O)CC2CCC(F)(F)CC2)C1] | 3.19 minutes[1]; 413 |
| 246 | 152 | 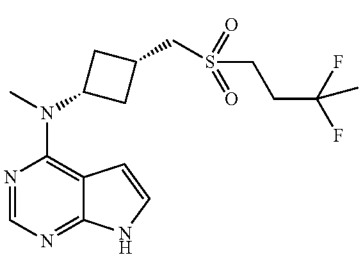 [SMILES: CN(c1ncnc2[nH]ccc12)[C@H]1C[C@@H](CS(=O)(=O)CCC(C)(F)F)C1] | 2.90 minutes[1]; 373 |

TABLE 3a-continued

Examples 155-181, 184, 185, 190, 194, 195, 219, 228, 232, 239, 243, 245, 246, 248, 254, and 256 (including Method of Preparation, Structures and Physicochemical Data).

| Example Number | Method of Preparation | Structure | $^1$H NMR (400 MHz, CDCl$_3$) δ (ppm); Mass spectrum, observed ion m/z [M + H]+ or HPLC retention time; Mass spectrum m/z [M + H]+ (unless otherwise indicated) |
|---|---|---|---|
| 248 | 152 | 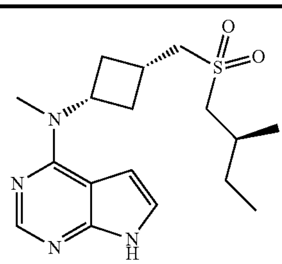 | 3.13 minutes[1]; 351 |
| 254 | 120 | 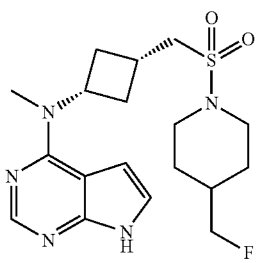 [SMILES: CN(c1ncnc2[nH]ccc12)[C@H]1C[C@@H](CS(=O)(=O)N2CCC(CF)CC2)C1] | 3.06 minutes[1]; 396 |
| 256 | 120 | 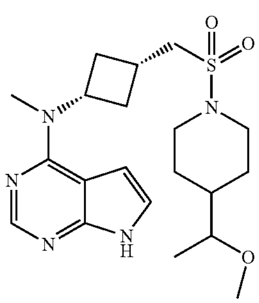 [SMILES: COC(C)C1CCN(S(=O)(=O)C[C@H]2C[C@@H](N(C)c3ncnc4[nH]ccc34)C2)CC1] | 3.20 minutes[1]; 422 |

[1] Conditions for analytical HPLC. Column: Xtimate C18 5 × 30 mm, 3 μm; Mobile phase: 1.0% ACN in water (0.1% TFA) to 5% ACN in water (0.1% TFA) in 1 min; then from 5.0% ACN in water (0.1%TFA to 100% ACN (0.1% TFA) in 5 minutes; HOLD at 100% ACN (0.1% TFA) for 2 minutes; back to 1.0% ACN in water (0.1% TFA) at 8.01 min, and HOLD two minutes. Flow rate: 1.2 ml/min.
[2] Conditions for analytical HPLC. Column: Waters Atlantis dC18 4.6 × 50 mm, 5μ; Mobile phase A: 0.05% TFA in water (v/v); Mobile phase B: 0.05% TFA in acetonitrile (v/v); 95.0% H$_2$O/5.0% Acetonitrile linear to 5% H$_2$O/95% Acetonitrile in 4.0 min, HOLD at 5% H$_2$O/95% Acetonitrile to 5.0 min. Flow: 2 mL/min.
[3] Conditions for analytical HPLC.: Waters Atlantis dC18 4.6 × 50 mm, 5μ; Mobile phase A: 0.05% TFA in water (v/v); Mobile phase B: 0.05% TFA in acetonitrile (v/v); Gradient: 95.0% H$_2$O/5.0% Acetonitrile linear to 5% H$_2$O/95% Acetonitrile in 4.0 min, HOLD at 5% H$_2$O/95% Acetonitrile to 5.0 min. Flow: 2 mL/min.

Biological Evaluation

JAK Caliper Enzyme Assay at 1 mM ATP

Test article was solubilized in dimethyl sulfoxide (DMSO) to a stock concentration of 30 mM. An 11-point half log dilution series was created in DMSO with a top concentration of 600 μM. The test compound plate also contained positive control wells containing a known inhibitor to define 100% inhibition and negative control wells containing DMSO to define no inhibition. The compound plates were diluted 1 to 60 resulting in a top final assay compound concentration of 10 μM and a 2% DMSO concentration.

Test article and assay controls were added to a 384-well plate. Reaction mixtures contained 20 mM HEPES, pH 7.4, 10 mM magnesium chloride, 0.01% bovine serum albumin (BSA), 0.0005% Tween 20, 1 mM ATP and 1 μM peptide substrate. The JAK1 and TYK2 assays contained 1 μM of the IRStide peptide (5FAM-KKSRGDYMTMQID) and the JAK2 and JAK3 assays contained 1 μM of the JAKtide peptide (FITC-KGGEEEEYFELVKK). The assays were initiated by the addition of 20 nM JAK1, 1 nM JAK2, 1 nM JAK3 or 1 nM TYK2 enzyme and were incubated at room temperature for three hours for JAK1, 60 minutes for JAK2, 75 minutes for JAK3 or 135 minutes for TYK2. Enzyme concentrations and incubation times were optimized for each new enzyme preps and were modified slightly over time to ensure 20%-30% phosphorylation. The assays were stopped with a final concentration of 10 mM EDTA, 0.1% Coating Reagent and 100 mM HEPES, pH=7.4. The assay plates were placed on a Caliper Life Science Lab Chip 3000 (LC3000) instrument, and each well was sampled using appropriate separation conditions to measure the unphosphorylated and phosphorylated peptide.

TABLE 4

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| (structure) | 1 | 0.022 | 0.381 | >9.220 | 1.020 |
| (structure) | 2 | 0.029 | 0.803 | >10.000 | 1.250 |
| (structure) | 3 | 0.014 | 0.542 | >10.000 | 0.479 |
| 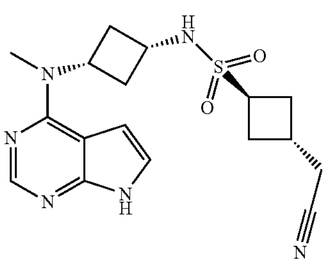 [SMILES: CN(c1ncnc2[nH]ccc12)[C@H]1C[C@@H](NS(=O)(=O)[C@H]2C[C@H](CC#N)C2)C1] | 4B | 0.006 | 0.607 | >10.000 | 0.965 |
| (structure) | 4A | 0.018 | 1.400 | >10.000 | 2.710 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 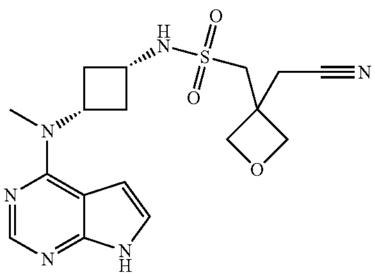 [SMILES: CN(c1ncnc2[nH]ccc12)[C@H]1C[C@@H](NS(=O)(=O)CC2(CC#N)COC2)C1] | 5 | 0.006 | 0.313 | 8.090 | 0.878 |
| 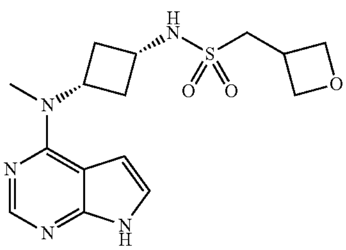 [SMILES: CN(c1ncnc2[nH]ccc12)[C@H]1C[C@@H](NS(=O)(=O)CC2COC2)C1] | 6 | 0.028 | 0.933 | >10.000 | 2.380 |
| 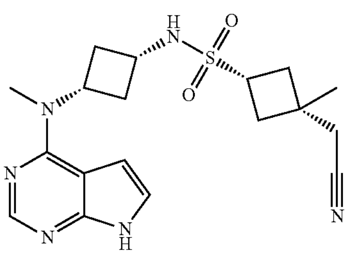 [SMILES: CN(c1ncnc2[nH]ccc12)[C@H]1C[C@@H](NS(=O)(=O)[C@H]2C[C@@](C)(CC#N)C2)C1] | 7A | 0.031 | 2.020 | >10.000 | 5.240 |
| 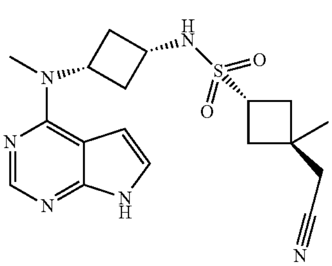 [SMILES: CN(c1ncnc2[nH]ccc12)[C@H]1C[C@@H](NS(=O)(=O)[C@H]2C[C@](C)(CC#N)C2)C1] | 7B | 0.016 | 0.750 | >10.000 | 2.440 |
| 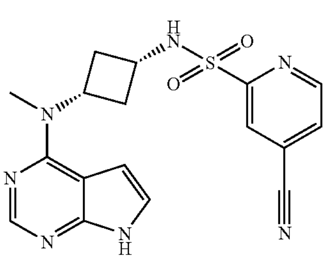 [SMILES: CN(c1ncnc2[nH]ccc12)[C@H]1C[C@@H](NS(=O)(=O)c2cc(C#N)ccn2)C1] | 8 | 0.003 | 0.700 | >10.000 | 0.260 |

TABLE 4-continued
Data for JAK Caliper™ Enzyme assay at 1 mM ATP.
| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 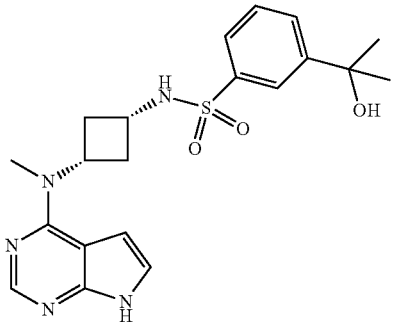 [SMILES: CN(c1ncnc2[nH]ccc12)[C@H]1C[C@@H](NS(=O)(=O)c2cccc(C(C)(C)O)c2)C1] | 9 | 0.231 | 5.630 | >10.000 | 6.670 |
| 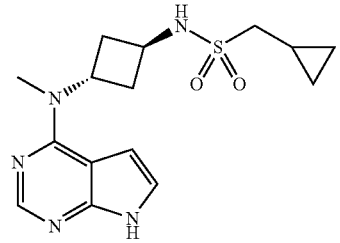 [SMILES: CN(c1ncnc2[nH]ccc12)[C@H]1C[C@H](NS(=O)(=O)CC2CC2)C1] | 10 | 1.030 | 7.180 | >10.000 | >10.000 |
| 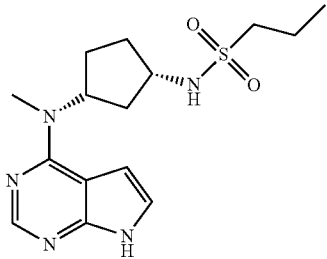 | 11 | 0.029 | 0.574 | 5.950 | 2.040 |
| 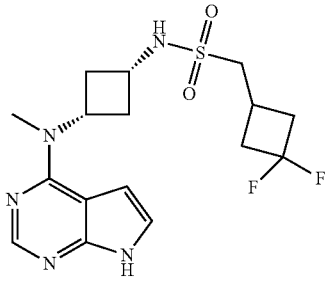 [SMILES: CN(c1ncnc2[nH]ccc12)[C@H]1C[C@@H](NS(=O)(=O)CC2CC(F)(F)C2)C1] | 12 | 0.006 | 0.413 | >9.670 | 0.770 |
| 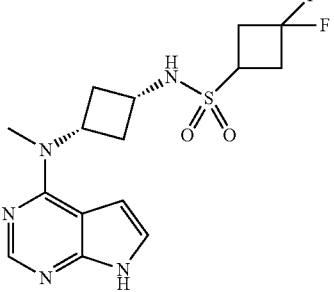 | 13 | 0.005 | 0.177 | 8.840 | 0.323 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 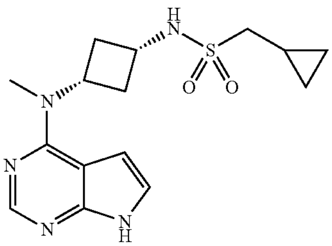 [SMILES: CN(c1ncnc2[nH]ccc12)[C@H]1C[C@@H](NS(=O)(=O)CC2CC2)C1] | 14 | 0.042 | 1.200 | >10.000 | 1.870 |
| 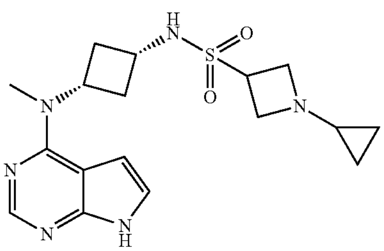 [SMILES: CN(c1ncnc2[nH]ccc12)[C@H]1C[C@@H](NS(=O)(=O)C2CN(C3CC3)C2)C1] | 15 | 0.006 | 0.597 | >10.000 | 4910 |
| 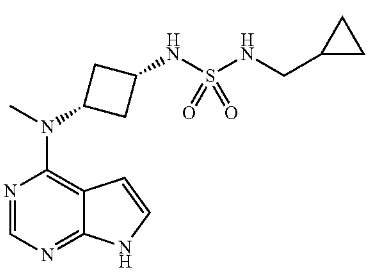 [SMILES: CN(c1ncnc2[nH]ccc12)[C@H]1C[C@@H](NS(=O)(=O)NCC2CC2)C1] | 16 | 0.051 | 1.100 | >10.000 | 1.780 |
| 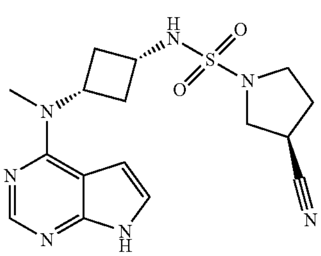 [SMILES: CN(c1ncnc2[nH]ccc12)[C@H]1C[C@@H](NS(=O)(=O)N2CC[C@@H](C#N)C2)C1] | 17A | 0.005 | 0.308 | >10.000 | 0.337 |
| 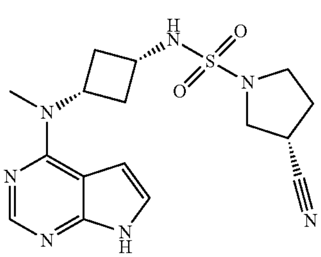 [SMILES: CN(c1ncnc2[nH]ccc12)[C@H]1C[C@@H](NS(=O)(=O)N2CC[C@H](C#N)C2)C1] | 17B | 0.013 | 0.434 | >9.770 | 1.120 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 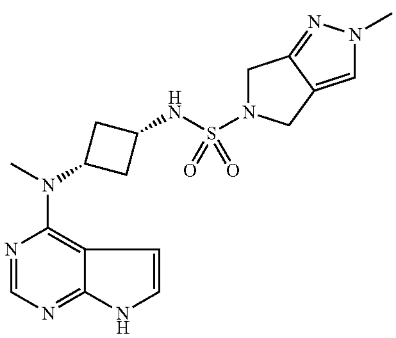 [SMILES: Cn1cc2c(n1)CN(S(=O)(=O)N[C@H]1C[C@@H](N(C)c3ncnc4[nH]ccc34)C1)C2] | 18 | 0.046 | 1.080 | >10.000 | 7.380 |
| 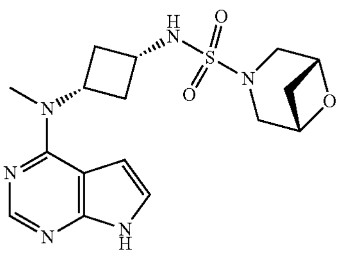 [SMILES: CN(c1ncnc2[nH]ccc12)[C@H]1C[C@@H](NS(=O)(=O)N2C[C@H]3C[C@@H](C2)O3)C1] | 19 | 0.034 | 1.150 | >10.000 | 2.030 |
| 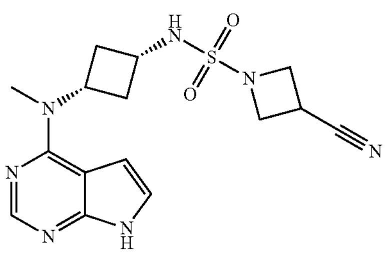 [SMILES: CN(c1ncnc2[nH]ccc12)[C@H]1C[C@@H](NS(=O)(=O)N2CC(C#N)C2)C1] | 20 | 0.004 | 0.171 | 5.500 | 0.332 |
| 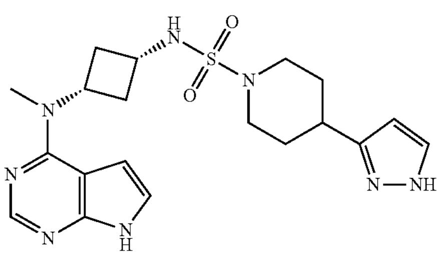 [SMILES: CN(c1ncnc2[nH]ccc12)[C@H]1C[C@@H](NS(=O)(=O)N2CCC(c3cc[nH]n3)CC2)C1] | 21 | 0.001 | 0.052 | 3.120 | 0.365 |
| 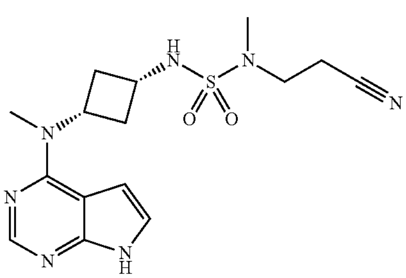 [SMILES: CN(CCC#N)S(=O)(=O)N[C@H]1C[C@@H](N(C)c2ncnc3[nH]ccc23)C1] | 22 | 0.022 | 0.412 | >10.000 | 1.190 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 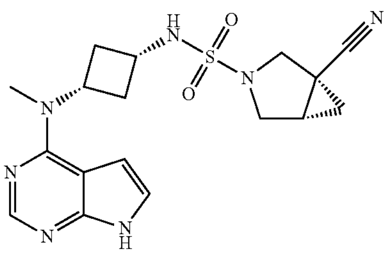 [SMILES: CN(c1ncnc2[nH]ccc12)[C@H]1C[C@@H](NS(=O)(=O)N2C[C@H]3C[C@@]3(C#N)C2)C1] | 23 | 0.008 | 0.551 | >10.000 | 0.565 |
| 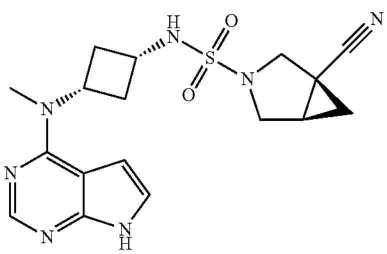 [SMILES: CN(c1ncnc2[nH]ccc12)[C@H]1C[C@@H](NS(=O)(=O)N2C[C@@H]3C[C@]3(C#N)C2)C1] | 27 | 0.017 | 0.987 | >10.000 | 1.970 |
| 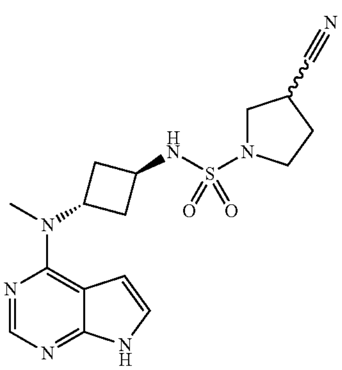 [SMILES: CN(c1ncnc2[nH]ccc12)[C@H]1C[C@H](NS(=O)(=O)N2CCC(C#N)C2)C1] | 24 | 0.241 | 3.370 | >10.000 | 7.870 |
| 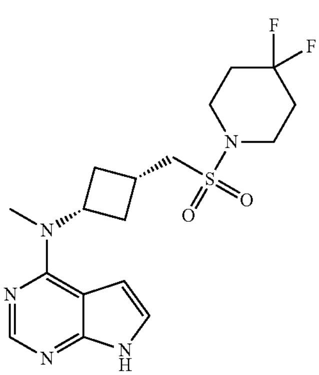 [SMILES: CN(c1ncnc2[nH]ccc12)[C@H]1C[C@@H](CS(=O)(=O)N2CCC(F)(F)CC2)C1] | 25 | 0.009 | 0.373 | >10.000 | 0.713 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 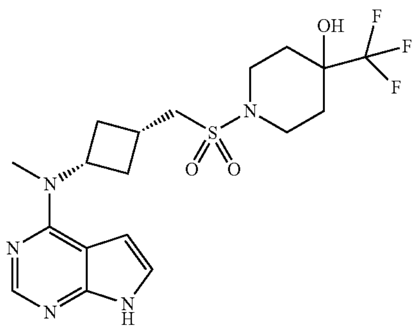 [SMILES: CN(c1ncnc2[nH]ccc12)[C@H]1C[C@@H](CS(=O)(=O)N2CCC(O)(C(F)(F)F)CC2)C1] | 26 | 0.006 | 0.088 | 1.880 | 0.358 |
| 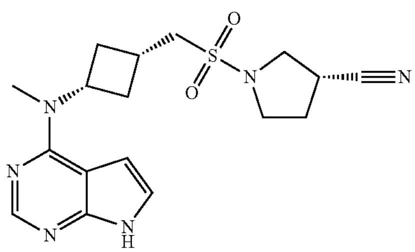 [SMILES: CN(c1ncnc2[nH]ccc12)[C@H]1C[C@@H](CS(=O)(=O)N2CC[C@@H](C#N)C2)C1] | 28 | 0.005 | 0.179 | 5.270 | 0.444 |
| 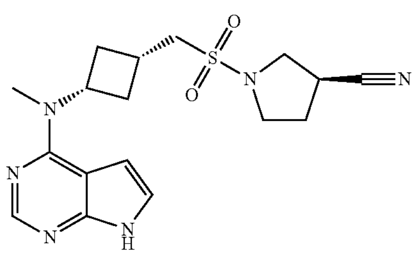 [SMILES: CN(c1ncnc2[nH]ccc12)[C@H]1C[C@@H](CS(=O)(=O)N2CC[C@H](C#N)C2)C1] | 29 | 0.017 | 0.372 | >9.930 | 1.100 |
| 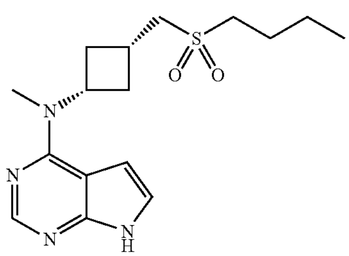 [SMILES: CCCCS(=O)(=O)C[C@H]1C[C@@H](N(C)c2ncnc3[nH]ccc23)C1] | 30 | 0.009 | 0.220 | >6.710 | 0.553 |
| 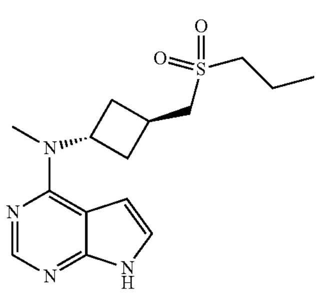 [SMILES: CCCS(=O)(=O)C[C@H]1C[C@H](N(C)c2ncnc3[nH]ccc23)C1] | 31 | 0.067 | 0.946 | >10.000 | 3.610 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 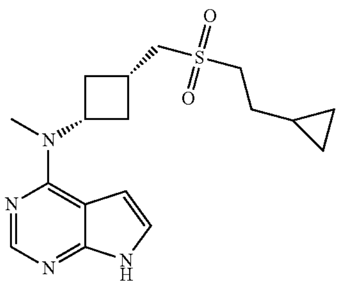 [SMILES: CN(c1ncnc2[nH]ccc12)[C@H]1C[C@@H](CS(=O)(=O)CCC2CC2)C1] | 32 | 0.014 | 0.426 | >10.000 | 1.460 |
| 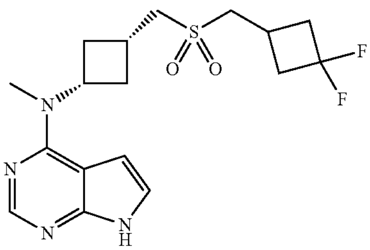 [SMILES: CN(c1ncnc2[nH]ccc12)[C@H]1C[C@@H](CS(=O)(=O)CC2CC(F)(F)C2)C1] | 33 | 0.005 | 0.161 | 6.570 | 0.582 |
| 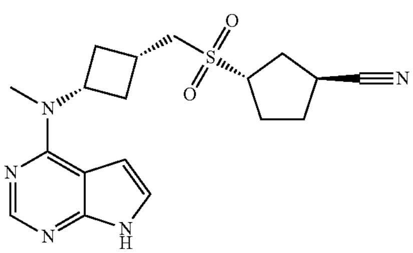 [SMILES: CN(c1ncnc2[nH]ccc12)[C@H]1C[C@@H](CS(=O)(=O)[C@H]2CC[C@H](C#N)C2)C1] | 34B | 0.009 | 0.309 | >10.000 | 0.840 |
| 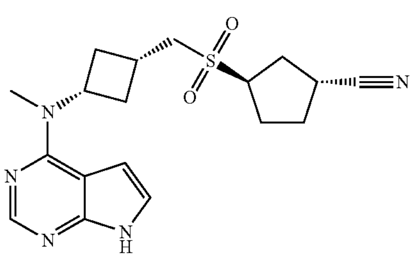 [SMILES: CN(c1ncnc2[nH]ccc12)[C@H]1C[C@@H](CS(=O)(=O)[C@@H]2CC[C@@H](C#N)C2)C1] | 34A | 0.037 | 0.801 | >10.000 | 3.280 |
| 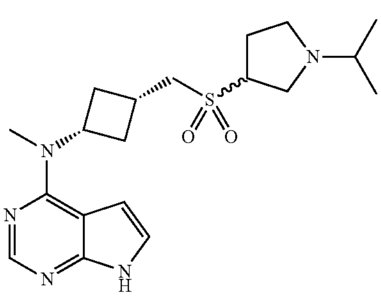 [SMILES: CC(C)N1CCC(S(=O)(=O)C[C@H]2C[C@@H](N(C)c3ncnc4[nH]ccc34)C2)C1] | 35 | 0.106 | 3.760 | >10.000 | >10.000 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 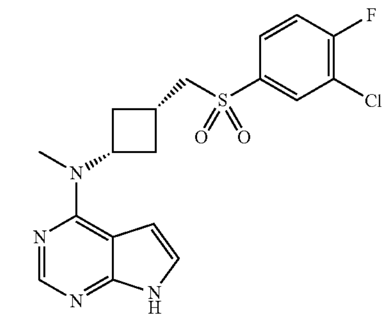 [SMILES: CN(c1ncnc2[nH]ccc12)[C@H]1C[C@@H](CS(=O)(=O)c2ccc(F)c(Cl)c2)C1] | 36 | 0.004 | 0.085 | 3.190 | 0.242 |
| 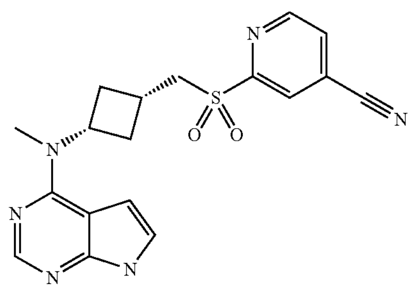 [SMILES: CN(c1ncnc2[nH]ccc12)[C@H]1C[C@@H](CS(=O)(=O)c2cc(C#N)ccn2)C1] | 37 | 0.006 | 0.569 | >8.880 | 0.418 |
| 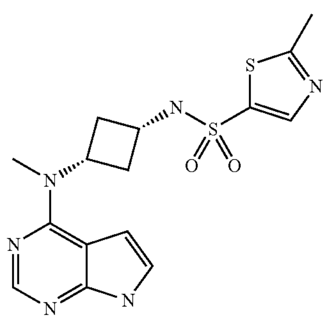 [SMILES: Cc1ncc(S(=O)(=O)N[C@H]2C[C@@H](N(C)c3ncnc4[nH]ccc34)C2)s1] | 38 | 0.0046 | 0.512 | >10.000 | 0.546 |
| 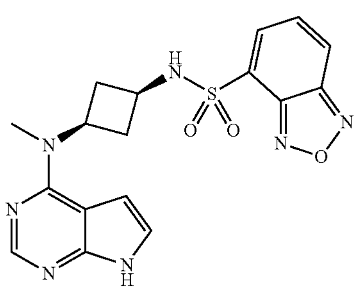 [SMILES: CN(c1ncnc2[nH]ccc12)[C@H]1C[C@@H](NS(=O)(=O)c2cccc3nonc23)C1] | 39 | 0.001 | 0.061 | 4.264 | 0.013 |
| 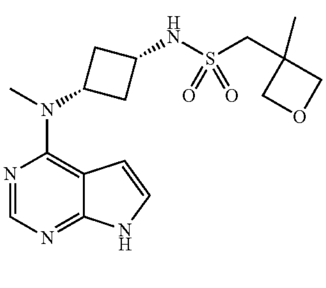 [SMILES: CN(c1ncnc2[nH]ccc12)[C@H]1C[C@@H](NS(=O)(=O)CC2(C)COC2)C1] | 40 | 0.007 | 0.559 | 7.282 | 0.864 |

TABLE 4-continued
Data for JAK Caliper™ Enzyme assay at 1 mM ATP.
| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 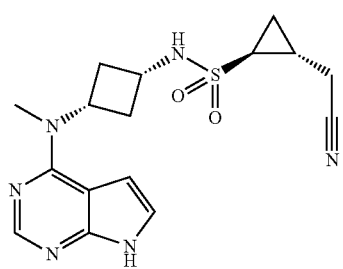 [SMILES: CN(c1ncnc2[nH]ccc12)[C@H]1C[C@@H](NS(=O)(=O)[C@H]2C[C@@H]2CC#N)C1] | 41A | 0.007 | 0.150 | 5.228 | 0.415 |
| 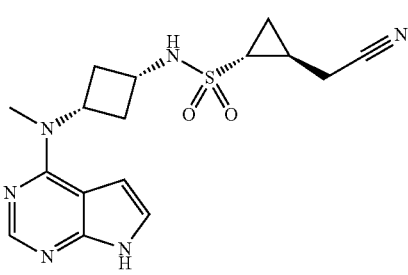 [SMILES: CN(c1ncnc2[nH]ccc12)[C@H]1C[C@@H](NS(=O)(=O)[C@@H]2C[C@H]2CC#N)C1] | 41B | 0.006 | 0.362 | >10.000 | 0.667 |
| 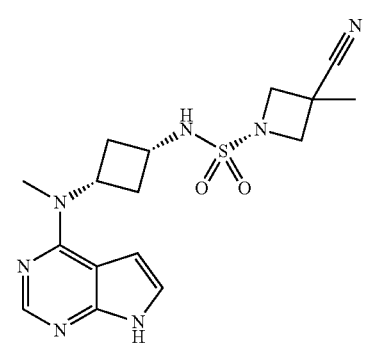 | 42 | 0.004 | 0.276 | >8.299 | 0.576 |
| 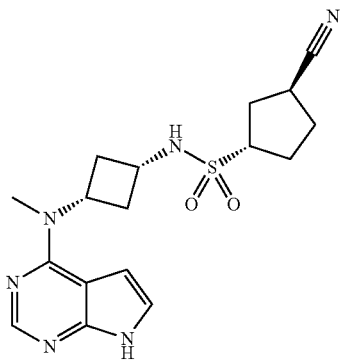 [SMILES: CN(c1ncnc2[nH]ccc12)[C@H]1C[C@@H](NS(=O)(=O)[C@H]2CC[C@H](C#N)C2)C1] | 43A | 0.023 | 0.909 | >10.000 | 2.398 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 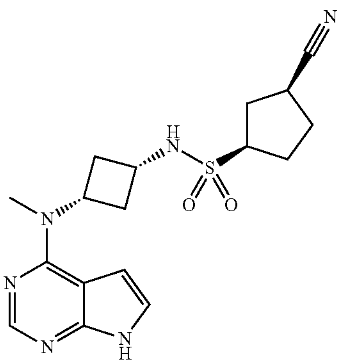 [SMILES: CN(c1ncnc2[nH]ccc12)[C@H]1C[C@@H](NS(=O)(=O)[C@@H]2CC[C@H](C#N)C2)C1] | 43B | 0.007 | 0.553 | >10.000 | 0.445 |
| 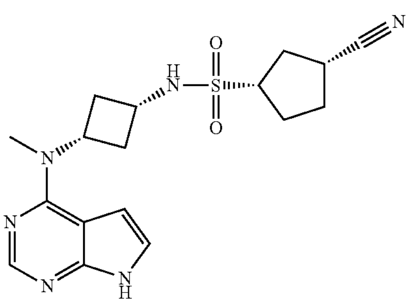 [SMILES: CN(c1ncnc2[nH]ccc12)[C@H]1C[C@@H](NS(=O)(=O)[C@H]2CC[C@@H](C#N)C2)C1] | 43C | 0.026 | 1.021 | >10.000 | 1.575 |
| 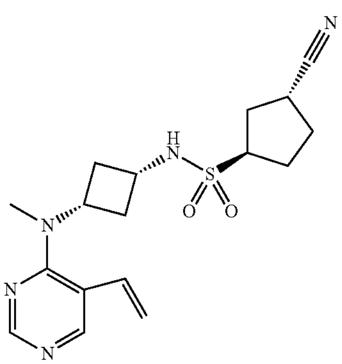 [SMILES: C=Cc1cncnc1N(C)[C@H]1C[C@@H](NS(=O)(=O)[C@@H]2CC[C@@H](C#N)C2)C1] | 43D | 0.008 | 0.805 | >10.000 | 1.024 |
| 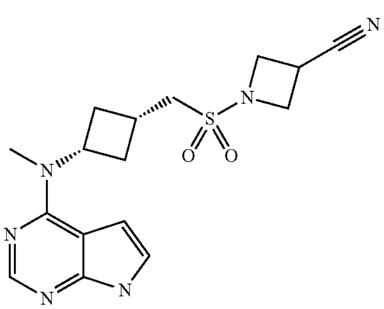 [SMILES: CN(c1ncnc2[nH]ccc12)[C@H]1C[C@@H](CS(=O)(=O)N2CC(C#N)C2)C1] | 44 | 0.006 | 0.133 | 5.824 | 0.485 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 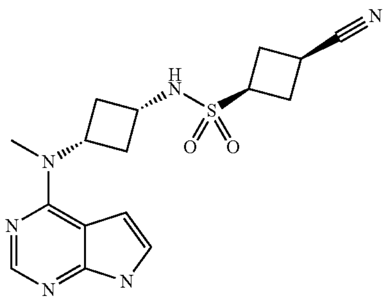 [SMILES: CN(c1ncnc2[nH]ccc12)[C@H]1C[C@@H](NS(=O)(=O)[C@H]2C[C@@H](C#N)C2)C1] | 45 | 0.011 | 0.361 | 8.782 | 0.899 |
| 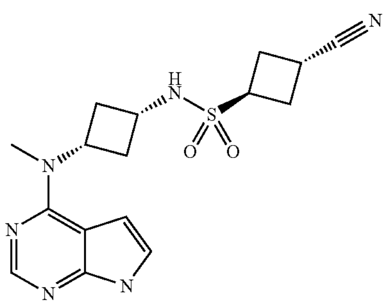 [SMILES: CN(c1ncnc2[nH]ccc12)[C@H]1C[C@@H](NS(=O)(=O)[C@H]2C[C@H](C#N)C2)C1] | 46 | 0.008 | 0.447 | >10.000 | 1.035 |
| 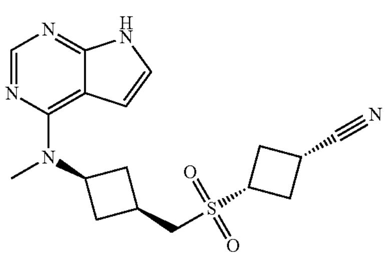 [SMILES: CN(c1ncnc2[nH]ccc12)[C@H]1C[C@@H](CS(=O)(=O)[C@H]2C[C@@H](C#N)C2)C1] | 47 | 0.009 | 0.474 | >10.000 | 2.134 |
| 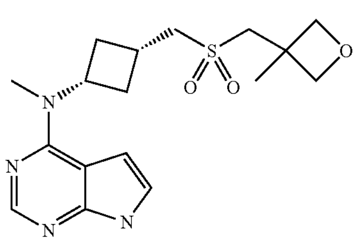 [SMILES: CN(c1ncnc2[nH]ccc12)[C@H]1C[C@@H](CS(=O)(=O)CC2(C)COC2)C1] | 48 | 0.009 | 0.231 | >10.000 | 1.085 |
| 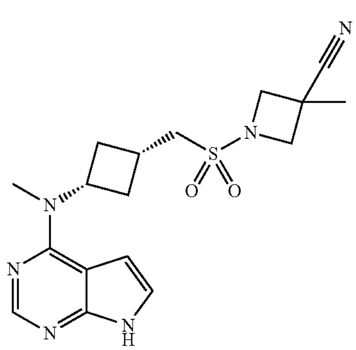 [SMILES: CN(c1ncnc2[nH]ccc12)[C@H]1C[C@@H](CS(=O)(=O)N2CC(C)(C#N)C2)C1] | 49 | 0.003 | 0.115 | 3.491 | 0.682 |

TABLE 4-continued
Data for JAK Caliper™ Enzyme assay at 1 mM ATP.
| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 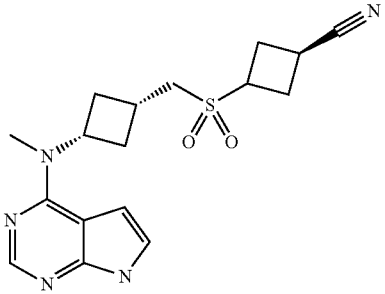 | 50 | 0.004 | 0.136 | 7.155 | 0.570 |
| 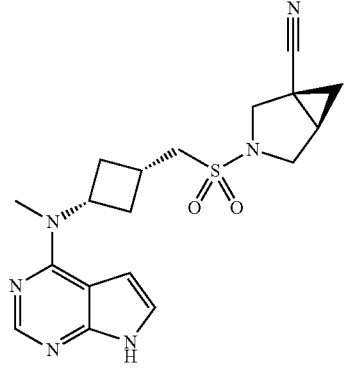 [SMILES: CN(c1ncnc2[nH]ccc12)[C@H]1C[C@@H](CS(=O)(=O)N2C[C@@H]3C[C@]3(C#N)C2)C1] | 51 | 0.012 | 0.293 | >10.000 | 0.777 |
| 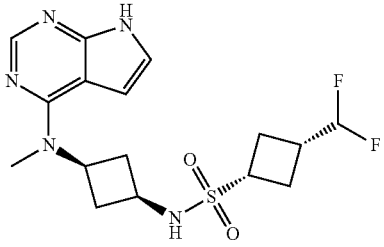 [SMILES: CN(c1ncnc2[nH]ccc12)[C@H]1C[C@@H](NS(=O)(=O)[C@H]2C[C@@H](C(F)F)C2)C1] | 52 | 0.001 | 0.083 | 5.244 | 0.185 |
| 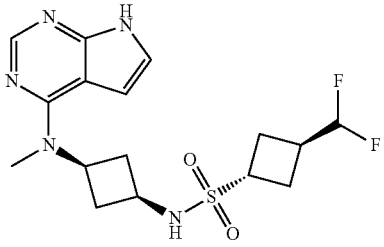 [SMILES: CN(c1ncnc2[nH]ccc12)[C@H]1C[C@@H](NS(=O)(=O)[C@H]2C[C@H](C(F)F)C2)C1] | 53 | 0.003 | 0.226 | >9.859 | 0.376 |
| 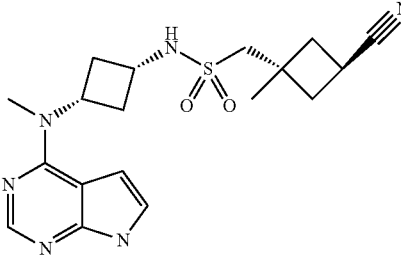 | 54A | 0.002 | 0.132 | 4.599 | 0.246 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 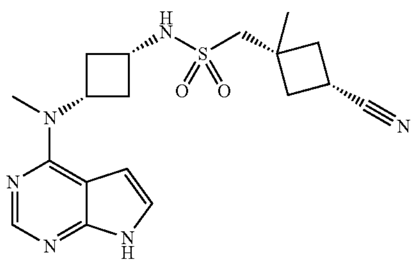 [SMILES: CN(c1ncnc2[nH]ccc12)[C@H]1C[C@@H](NS(=O)(=O)C[C@]2(C)C[C@H](C#N)C2)C1] | 54B | 0.002 | 0.466 | >10.000 | 0.825 |
| 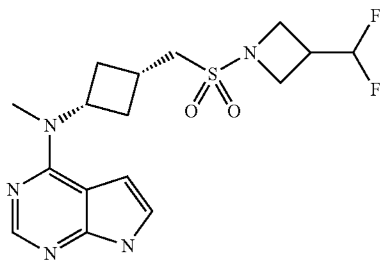 [SMILES: CN(c1ncnc2[nH]ccc12)[C@H]1C[C@@H](CS(=O)(=O)N2CC(C(F)F)C2)C1] | 55 | 0.007 | 0.150 | 5.228 | 0.415 |
| 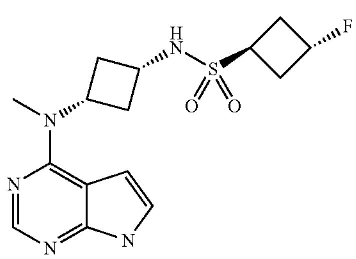 [SMILES: CN(c1ncnc2[nH]ccc12)[C@H]1C[C@@H](NS(=O)(=O)[C@H]2C[C@H](F)C2)C1] | 56 | 0.018 | 0.670 | >10.000 | 0.630 |
| 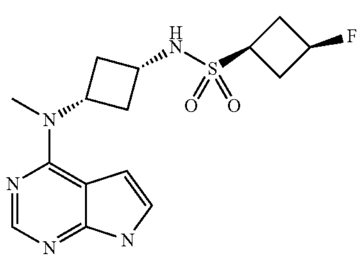 [SMILES: CN(c1ncnc2[nH]ccc12)[C@H]1C[C@@H](NS(=O)(=O)[C@H]2C[C@@H](F)C2)C1] | 57 | 0.008 | 0.266 | >10.000 | 0.238 |
| 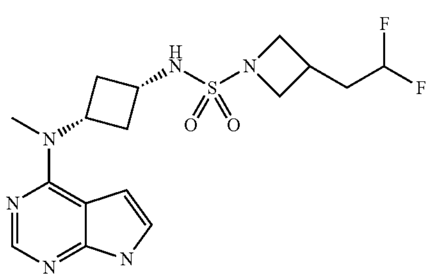 [SMILES: CN(c1ncnc2[nH]ccc12)[C@H]1C[C@@H](NS(=O)(=O)N2CC(CC(F)F)C2)C1] | 58 | 0.003 | 0.318 | >9.567 | 0.687 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 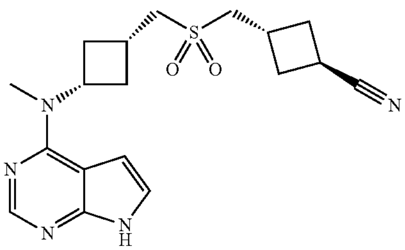 [SMILES: CN(c1ncnc2[nH]ccc12)[C@H]1C[C@@H](CS(=O)(=O)C[C@H]2C[C@H](C#N)C2)C1] | 59A | 0.02 | 0.585 | >10.00 | 2.883 |
| 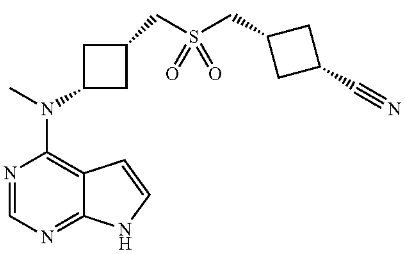 [SMILES: CN(c1ncnc2[nH]ccc12)[C@H]1C[C@@H](CS(=O)(=O)C[C@H]2C[C@@H](C#N)C2)C1] | 59B | 0.009 | 0.474 | >10.000 | 2.134 |
| 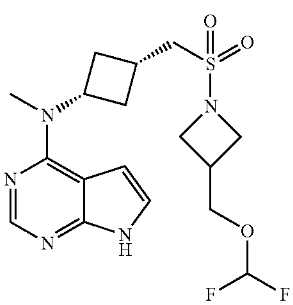 [SMILES: CN(c1ncnc2[nH]ccc12)[C@H]1C[C@@H](CS(=O)(=O)N2CC(COC(F)F)C2)C1] | 60 | 0.019 | 0.571 | 10.000 | 3.829 |
| 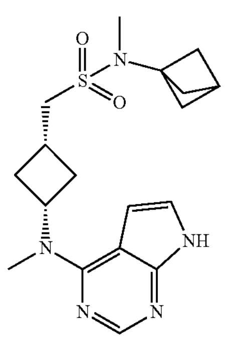 [SMILES: CN(C12CC(C1)C2)S(=O)(=O)C[C@H]1C[C@@H](N(C)c2ncnc3[nH]ccc23)C1] | 61 | 0.028 | 0.523 | 10.000 | 0.832 |
| 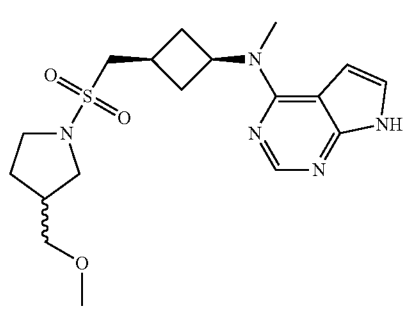 [SMILES: COCC1CCN(S(=O)(=O)C[C@H]2C[C@@H](N(C)c3ncnc4[nH]ccc34)C2)C1] | 62 | 0.092 | 2.330 | 10.000 | 5.401 |

TABLE 4-continued
Data for JAK Caliper™ Enzyme assay at 1 mM ATP.
| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 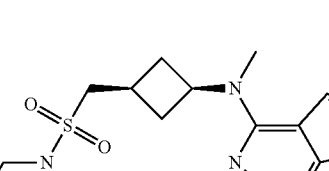 | 63 | 0.096 | 2.896 | 10.000 | 8.507 |
| Chiral 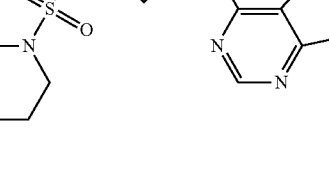 | 64 | 0.070 | 1.165 | 10.000 | 2.631 |
| 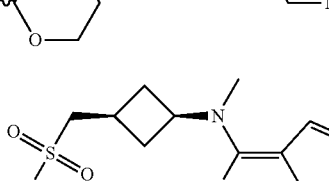 | 65 | 0.024 | 0.464 | 10.000 | 1.167 |
| 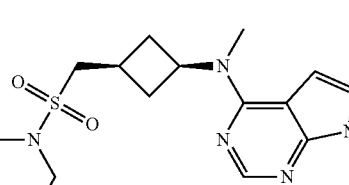 | 66 | 0.064 | 1.468 | 10.000 | 2.833 |
| 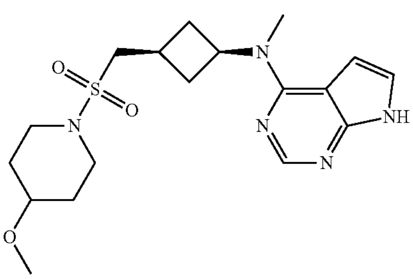 [SMILES: COC1CCN(S(=O)(=O)C[C@H]2C[C@@H](N(C)c3ncnc4[nH]ccc34)C2)CC1] | 67 | 0.086 | 2.500 | 10.000 | 5.895 |
| 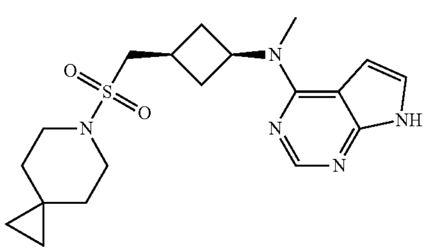 [SMILES: CN(c1ncnc2[nH]ccc12)[C@H]1C[C@@H](CS(=O)(=O)N2CCC3(CC2)CC3)C1] | 68 | 0.020 | 0.632 | 10.000 | 3.657 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 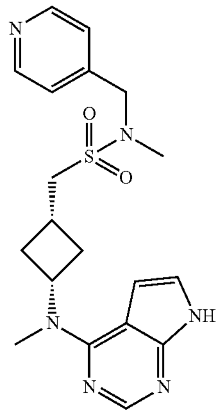 [SMILES: CN(Cc1ccncc1)S(=O)(=O)C[C@H]1C[C@@H](N(C)c2ncnc3[nH]ccc23)C1] | 69 | 0.086 | 1.059 | 10.000 | 3.664 |
| Chiral | 70 | 0.039 | 0.563 | 10.000 | 1.339 |
| Chiral | 71 | 0.096 | 1.368 | 10.000 | 2.199 |
| Chiral | 72 | 0.047 | 1.302 | 10.000 | 2.900 |
| Chiral | 73 | 0.085 | 1.287 | 10.000 | 2.630 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 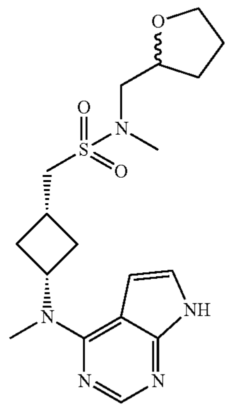 [SMILES: CN(CC1CCCO1)S(=O)(=O)C[C@H]1C[C@@H](N(C)c2ncnc3[nH]ccc23)C1] | 74 | 0.062 | 2.363 | 10.000 | 7.717 |
| 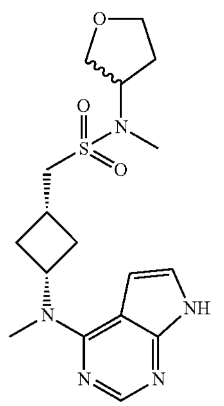 [SMILES: CN(C1CCOC1)S(=O)(=O)C[C@H]1C[C@@H](N(C)c2ncnc3[nH]ccc23)C1] | 75 | 0.042 | 1.043 | 10.000 | 2.342 |
| 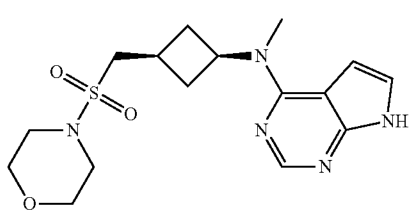 [SMILES: CN(c1ncnc2[nH]ccc12)[C@H]1C[C@@H](CS(=O)(=O)N2CCOCC2)C1] | 76 | 0.042 | 0.971 | 10.000 | 1.586 |
| 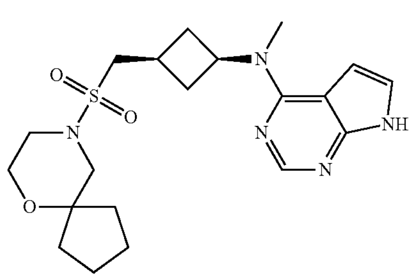 [SMILES: CN(c1ncnc2[nH]ccc12)[C@H]1C[C@@H](CS(=O)(=O)N2CCOC3(CCCC3)C2)C1] | 77 | 0.086 | 2.401 | 10.000 | 3.853 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 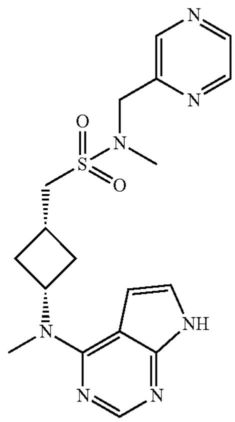 [SMILES: CN(Cc1cnccn1)S(=O)(=O)C[C@H]1C[C@@H](N(C)c2ncnc3[nH]ccc23)C1] | 78 | 0.070 | 1.706 | 10.000 | 5.981 |
| 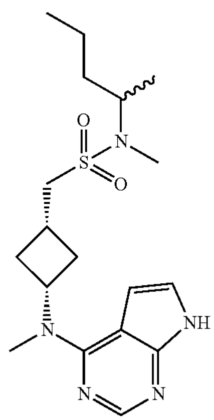 [SMILES: CCCC(C)N(C)S(=O)(=O)C[C@H]1C[C@@H](N(C)c2ncnc3[nH]ccc23)C1] | 79 | 0.056 | 3.324 | 10.000 | 2.923 |
| 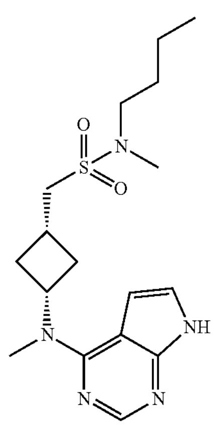 [SMILES: CCCCN(C)S(=O)(=O)C[C@H]1C[C@@H](N(C)c2ncnc3[nH]ccc23)C1] | 80 | 0.017 | 0.886 | 10.000 | 2.203 |
| 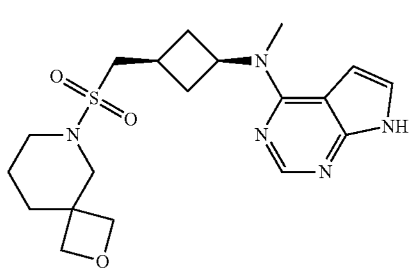 [SMILES: CN(c1ncnc2[nH]ccc12)[C@H]1C[C@@H](CS(=O)(=O)N2CCCC3(COC3)C2)C1] | 81 | 0.013 | 0.455 | 10.000 | 1.109 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| (Chiral) | 82 | 0.054 | 1.483 | 10.000 | 2.499 |
| 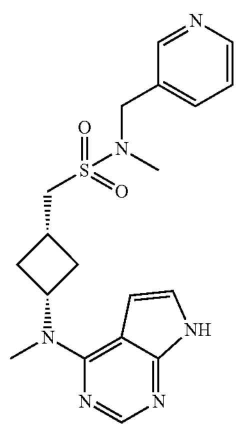 [SMILES: CN(Cc1cccnc1)S(=O)(=O)C[C@H]1C[C@@H](N(C)c2ncnc3[nH]ccc23)C1] | 83 | 0.059 | 1.028 | 10.000 | 2.281 |
| 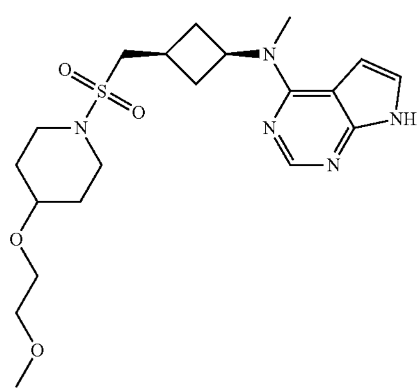 [SMILES: COCCOC1CCN(S(=O)(=O)C[C@H]2C[C@@H](N(C)c3ncnc4[nH]ccc34)C2)CC1] | 84 | 0.028 | 0.963 | 10.000 | 1.262 |
| 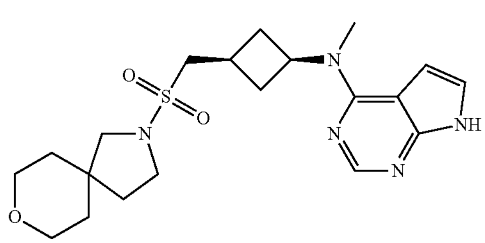 [SMILES: CN(c1ncnc2[nH]ccc12)[C@H]1C[C@@H](CS(=O)(=O)N2CCC3(CCOCC3)C2)C1] | 85 | 0.099 | 2.608 | 10.000 | 10.000 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 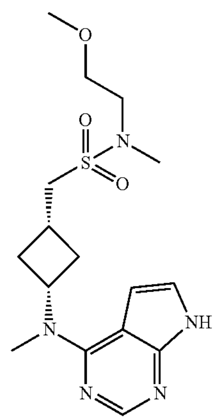 [SMILES: COCCN(C)S(=O)(=O)C[C@H]1C[C@@H](N(C)c2ncnc3[nH]ccc23)C1] | 86 | 0.094 | 1.833 | 10.000 | 5.160 |
| 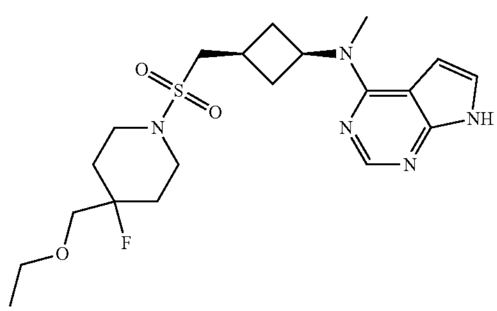 [SMILES: CCOCC1(F)CCN(S(=O)(=O)C[C@H]2C[C@@H](N(C)c3ncnc4[nH]ccc34)C2)CC1] | 87 | 0.077 | 2.393 | 10.000 | 10.000 |
| 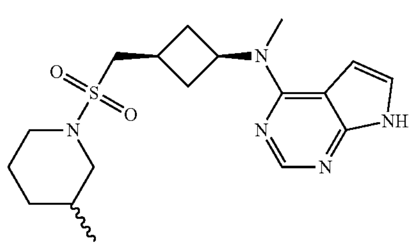 [SMILES: CC1CCCN(S(=O)(=O)C[C@H]2C[C@@H](N(C)c3ncnc4[nH]ccc34)C2)C1] | 88 | 0.016 | 0.623 | 10.000 | 0.830 |
| 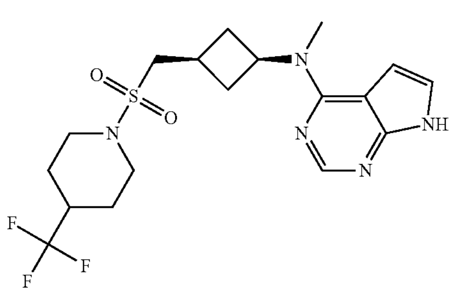 [SMILES: CN(c1ncnc2[nH]ccc12)[C@H]1C[C@@H](CS(=O)(=O)N2CCC(C(F)(F)F)CC2)C1] | 89 | 0.015 | 0.835 | 10.000 | 1.780 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 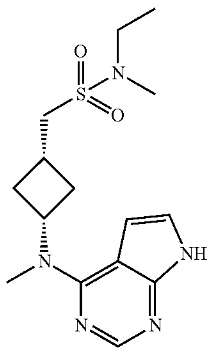 [SMILES: CCN(C)S(=O)(=O)C[C@H]1C[C@@H](N(C)c2ncnc3[nH]ccc23)C1] | 90 | 0.066 | 0.518 | 10.000 | 0.946 |
| Chiral | 91 | 0.056 | 0.566 | 10.000 | 1.652 |
| Chiral | 92 | 0.046 | 1.259 | 10.000 | 2.381 |
| 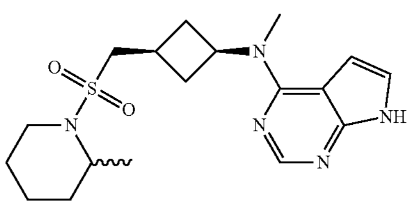 [SMILES: CC1CCCCN1S(=O)(=O)C[C@H]1C[C@@H](N(C)c2ncnc3[nH]ccc23)C1] | 93 | 0.057 | 1.130 | 10.000 | 1.460 |
| 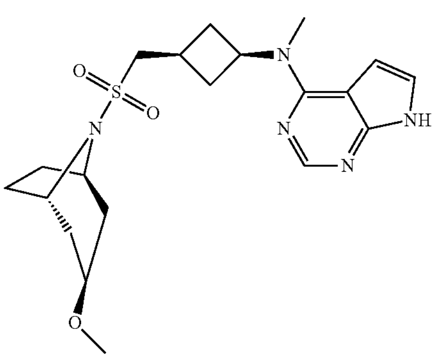 [SMILES: CO[C@@H]1C[C@H]2CC[C@@H](C1)N2S(=O)(=O)C[C@H]1C[C@@H](N(C)c2ncnc3[nH]ccc23)C1] | 94 | 0.064 | 2.068 | 10.000 | 8.954 |

TABLE 4-continued
Data for JAK Caliper™ Enzyme assay at 1 mM ATP.
| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 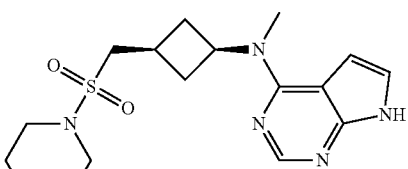 | 95 | 0.027 | 0.555 | 10.000 | 0.930 |
| Chiral 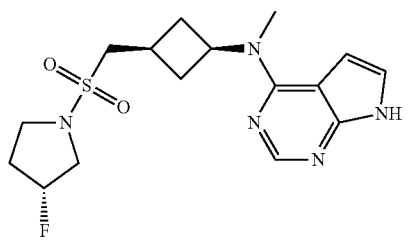 [SMILES: CN(c1ncnc2[nH]ccc12)[C@H]1C[C@@H](CS(=O)(=O)N2CCC(F)C2)C1] | 96 | 0.023 | 0.295 | 10.000 | 0.551 |
| Chiral 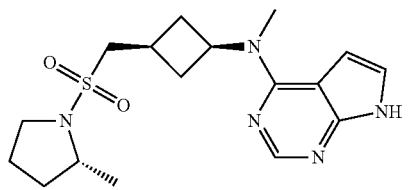 | 97 | 0.028 | 0.504 | 10.000 | 0.325 |
| 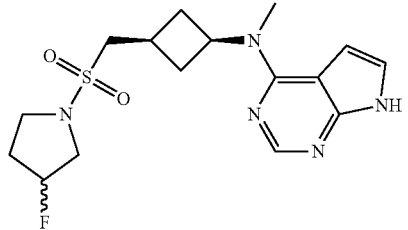 | 98 | 0.031 | 0.414 | 10.000 | 0.812 |
| 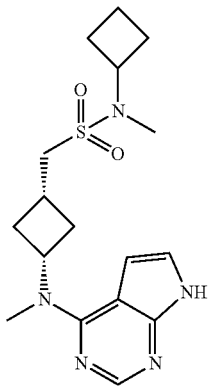 [SMILES: CN(C1CCC1)S(=O)(=O)C[C@H]1C[C@@H](N(C)c2ncnc3[nH]ccc23)C1] | 99 | 0.013 | 0.351 | 10.000 | 0.507 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 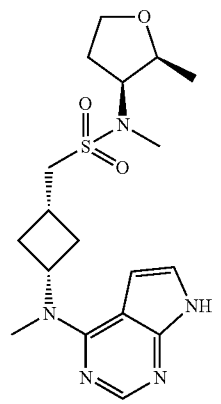 | 100 | 0.078 | 1.723 | 10.000 | 5.535 |
| 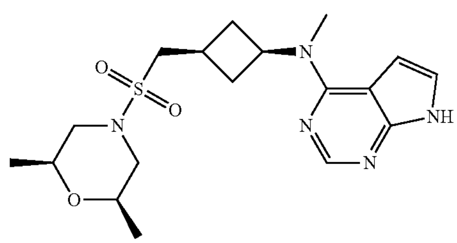 [SMILES: C[C@@H]1CN(S(=O)(=O)C[C@H]2C[C@@H](N(C)c3ncnc4[nH]ccc34)C2)C[C@H](C)O1] | 101 | 0.022 | 0.523 | 10.000 | 2.835 |
| 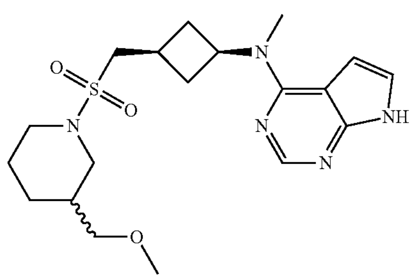 [SMILES: COCC1CCCN(S(=O)(=O)C[C@H]2C[C@@H](N(C)c3ncnc4[nH]ccc34)C2)C1] | 102 | 0.028 | 1.009 | 10.000 | 1.185 |
| 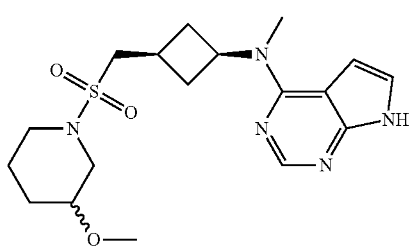 [SMILES: COC1CCCN(S(=O)(=O)C[C@H]2C[C@@H](N(C)c3ncnc4[nH]ccc34)C2)C1] | 103 | 0.056 | 2.151 | 10.000 | 4.797 |
| 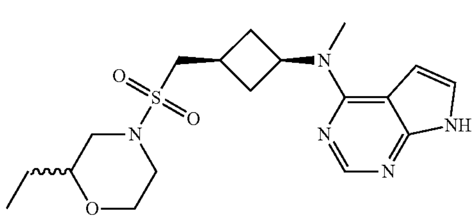 [SMILES: CCC1CN(S(=O)(=O)C[C@H]2C[C@@H](N(C)c3ncnc4[nH]ccc34)C2)CCO1] | 104 | 0.093 | 2.324 | 10.000 | 4.249 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 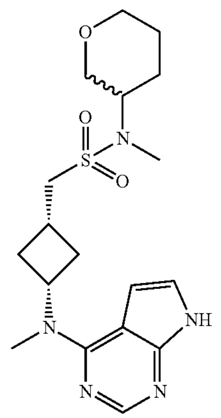 [SMILES: CN(C1CCCOC1)S(=O)(=O)C[C@H]1C[C@@H](N(C)c2ncnc3[nH]ccc23)C1] | 105 | 0.040 | 1.971 | 10.000 | 4.121 |
| 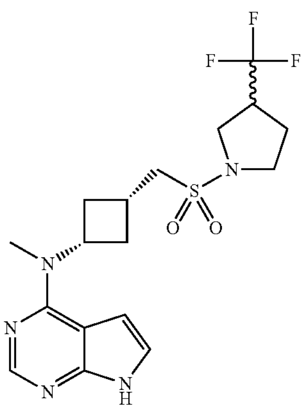 [SMILES: CN(c1ncnc2[nH]ccc12)[C@H]1C[C@@H](CS(=O)(=O)N2CCC(C(F)(F)F)C2)C1] | 106 | 0.015 | 0.573 | 10.000 | 1.415 |
| 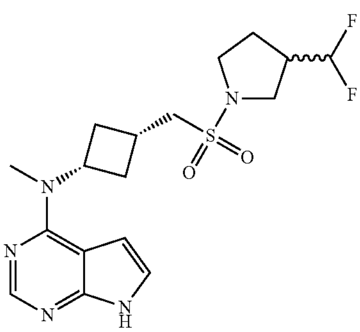 [SMILES: CN(c1ncnc2[nH]ccc12)[C@H]1C[C@@H](CS(=O)(=O)N2CCC(C(F)F)C2)C1] | 107 | 0.014 | 0.463 | 10.000 | 1.105 |
| 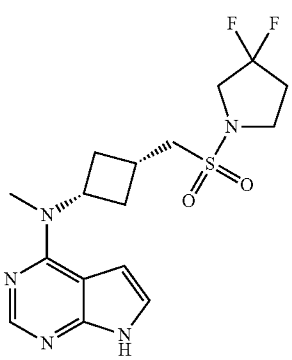 [SMILES: CN(c1ncnc2[nH]ccc12)[C@H]1C[C@@H](CS(=O)(=O)N2CCC(F)(F)C2)C1] | 108 | 0.010 | 0.228 | 10.000 | 0.340 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 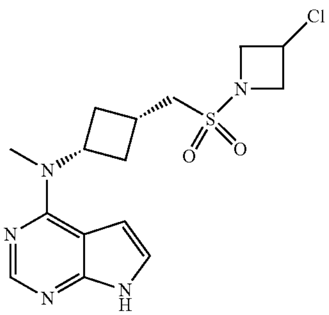 [SMILES: CN(c1ncnc2[nH]ccc12)[C@H]1C[C@@H](CS(=O)(=O)N2CC(Cl)C2)C1] | 109 | 0.004 | 0.060 | 5.848 | 0.228 |
| 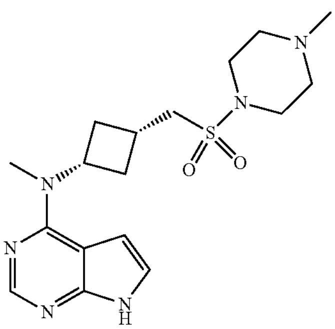 [SMILES: CN1CCN(S(=O)(=O)C[C@H]2C[C@@H](N(C)c3ncnc4[nH]ccc34)C2)CC1] | 110 | 0.094 | 2.338 | 10.000 | 7.124 |
| 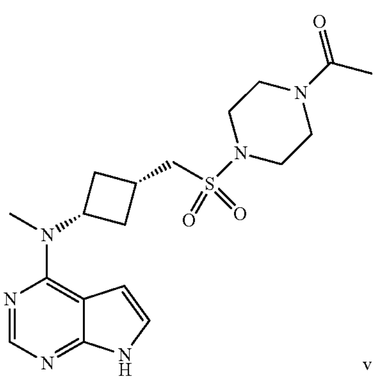 [SMILES: CC(=O)N1CCN(S(=O)(=O)C[C@H]2C[C@@H](N(C)c3ncnc4[nH]ccc34)C2)CC1] | 111 | 0.027 | 1.292 | 10.000 | 0.975 |
| 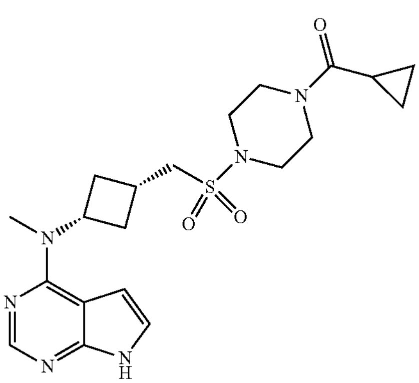 [SMILES: CN(c1ncnc2[nH]ccc12)[C@H]1C[C@@H](CS(=O)(=O)N2CCN(C(=O)C3CC3)CC2)C1] | 112 | 0.052 | 2.331 | 10.000 | 2.102 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 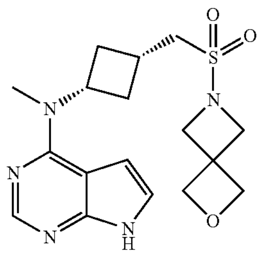 [SMILES: CN(c1ncnc2[nH]ccc12)[C@H]1C[C@@H](CS(=O)(=O)N2CC3(COC3)C2)C1] | 113 | 0.062 | 1.564 | 10.000 | 4.772 |
| 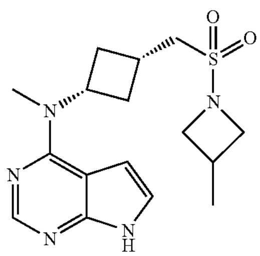 [SMILES: CC1CN(S(=O)(=O)C[C@H]2C[C@@H](N(C)c3ncnc4[nH]ccc34)C2)C1] | 114 | 0.022 | 0.465 | 10.000 | 1.061 |
| 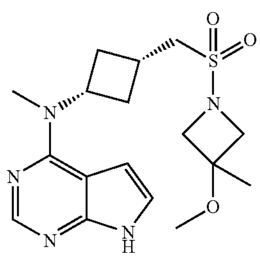 | 115 | 0.096 | 2.040 | 10.000 | 6.184 |
| 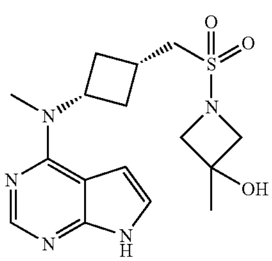 [SMILES: CN(c1ncnc2[nH]ccc12)[C@H]1C[C@@H](CS(=O)(=O)N2CC(C)(O)C2)C1] | 116 | 0.037 | 0.601 | 10.000 | 1.823 |
| 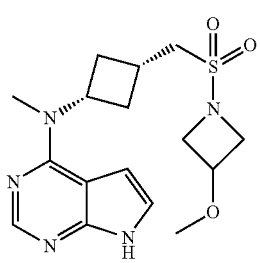 [SMILES: COC1CN(S(=O)(=O)C[C@H]2C[C@@H](N(C)c3ncnc4[nH]ccc34)C2)C1] | 117 | 0.077 | 1.662 | 10.000 | 4.794 |
| 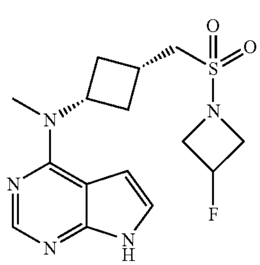 | 118 | 0.018 | 0.171 | 9.218 | 0.363 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 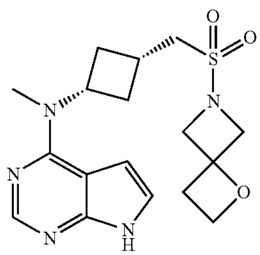 | 119 | 0.056 | 1.134 | 10.000 | 4.189 |
| 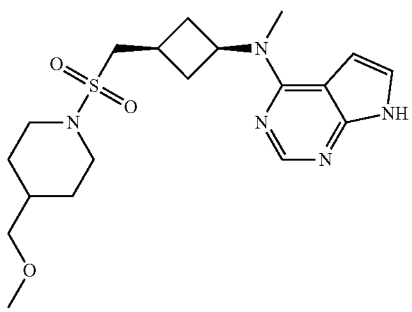 [SMILES: COCC1CCN(S(=O)(=O)C[C@H]2C[C@@H](N(C)c3ncnc4[nH]ccc34)C2)CC1] | 120 | 0.009 | 1.037 | >10.000 | 2.676 |
| 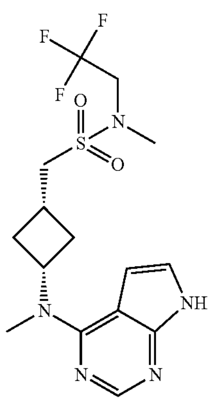 [SMILES: CN(CC(F)(F)F)S(=O)(=O)C[C@H]1C[C@@H](N(C)c2ncnc3[nH]ccc23)C1] | 121 | 0.006 | 0.162 | 10.000 | 0.179 |
| 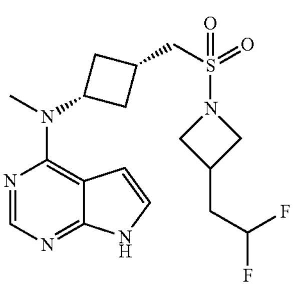 [SMILES: CN(c1ncnc2[nH]ccc12)[C@H]1C[C@@H](CS(=O)(=O)N2CC(CC(F)F)C2)C1] | 122 | 0.006 | 0.250 | 9.487 | 1.013 |
| 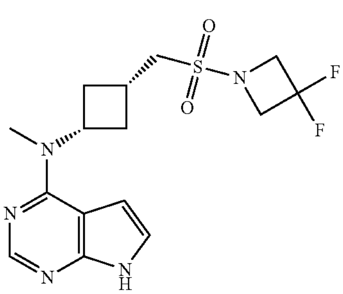 [SMILES: CN(c1ncnc2[nH]ccc12)[C@H]1C[C@@H](CS(=O)(=O)N2CC(F)(F)C2)C1] | 123 | 0.008 | 0.116 | 4.653 | 0.292 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 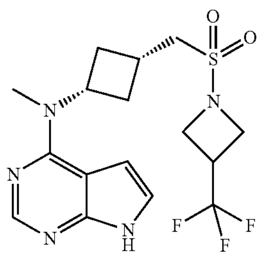 [SMILES: CN(c1ncnc2[nH]ccc12)[C@H]1C[C@@H](CS(=O)(=O)N2CC(C(F)(F)F)C2)C1] | 124 | 0.006 | 0.256 | 10.000 | 0.719 |
| 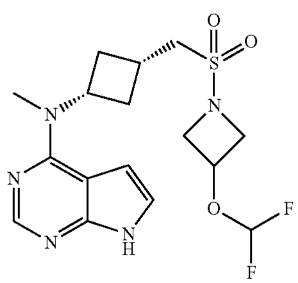 [SMILES: CN(c1ncnc2[nH]ccc12)[C@H]1C[C@@H](CS(=O)(=O)N2CC(OC(F)F)C2)C1] | 125 | 0.009 | 0.245 | 10.000 | 0.882 |
| 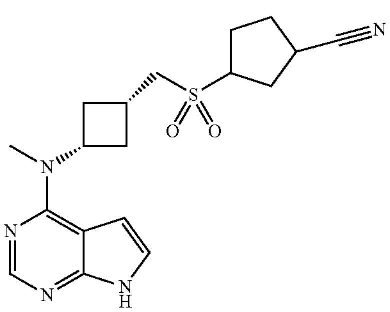 [SMILES: CN(c1ncnc2[nH]ccc12)[C@H]1C[C@@H](CS(=O)(=O)C2CCC(C#N)C2)C1] | 126 | 0.008 | 0.319 | 10.000 | 0.668 |
| 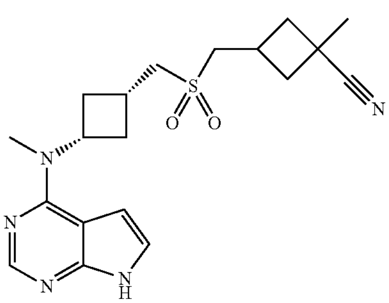 [SMILES: CN(c1ncnc2[nH]ccc12)[C@H]1C[C@@H](CS(=O)(=O)CC2CC(C)(C#N)C2)C1] | 127 | 0.011 | 0.604 | 10.000 | 0.837 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 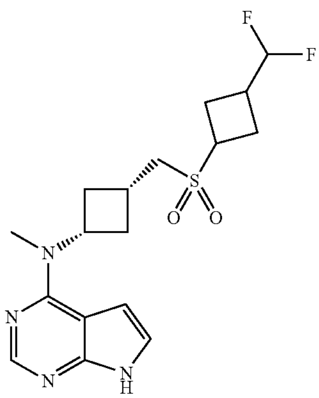 [SMILES: CN(c1ncnc2[nH]ccc12)[C@H]1C[C@@H](CS(=O)(=O)C2CC(C(F)F)C2)C1] | 128 | 0.002 | 0.027 | 2.812 | 0.113 |
| 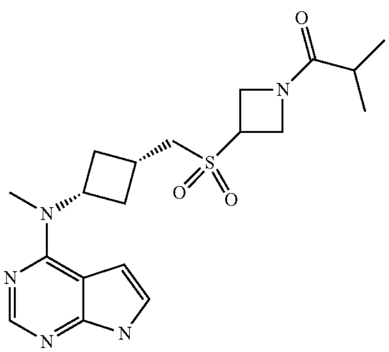 [SMILES: CC(C)C(=O)N1CC(S(=O)(=O)C[C@H]2C[C@@H](N(C)c3ncnc4[nH]ccc34)C2)C1] | 129 | 0.097 | 3.226 | 10.000 | 6.949 |
| 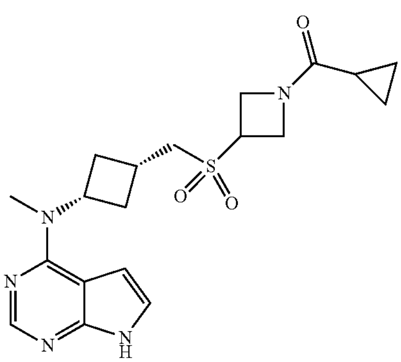 [SMILES: CN(c1ncnc2[nH]ccc12)[C@H]1C[C@@H](CS(=O)(=O)C2CN(C(=O)C3CC3)C2)C1] | 130 | 0.051 | 1.686 | 10.000 | 3.440 |
| 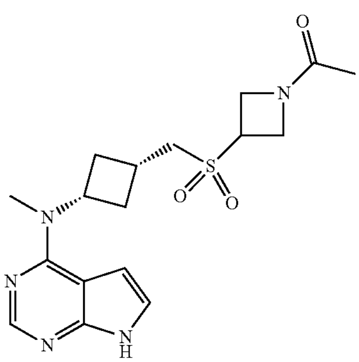 [SMILES: CC(=O)N1CC(S(=O)(=O)C[C@H]2C[C@@H](N(C)c3ncnc4[nH]ccc34)C2)C1] | 131 | 0.033 | 0.991 | 10.000 | 3.947 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 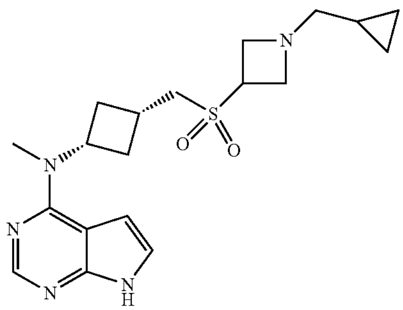 [SMILES: CN(c1ncnc2[nH]ccc12)[C@H]1C[C@@H](CS(=O)(=O)C2CN(CC3CC3)C2)C1] | 132 | 0.089 | 2.110 | 10.000 | 10.000 |
| 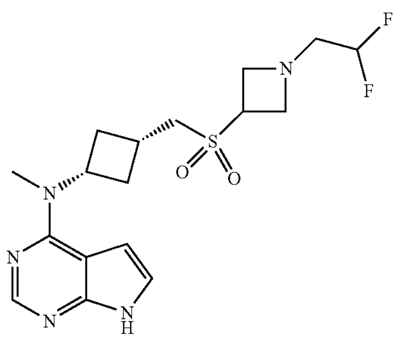 [SMILES: CN(c1ncnc2[nH]ccc12)[C@H]1C[C@@H](CS(=O)(=O)C2CN(CC(F)F)C2)C1] | 133 | 0.009 | 0.353 | 10.000 | 1.790 |
| 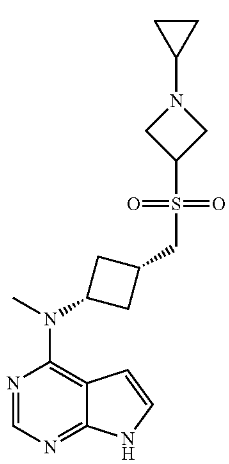 [SMILES: CN(c1ncnc2[nH]ccc12)[C@H]1C[C@@H](CS(=O)(=O)C2CN(C3CC3)C2)C1] | 134 | 0.007 | 0.445 | 10.000 | 3.959 |
| 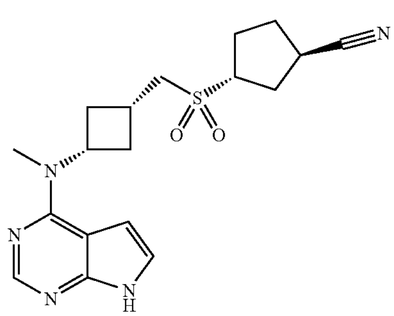 [SMILES: CN(c1ncnc2[nH]ccc12)[C@H]1C[C@@H](CS(=O)(=O)[C@@H]2CC[C@@H](C#N)C2)C1] | 135 | 0.008 | 0.286 | 10.000 | 0.682 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 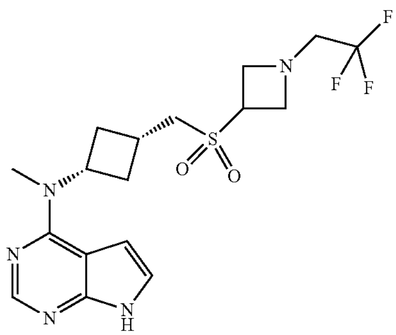 [SMILES: CN(c1ncnc2[nH]ccc12)[C@H]1C[C@@H](CS(=O)(=O)C2CN(CC(F)(F)F)C2)C1] | 136 | 0.045 | 1.695 | 10.000 | 6.460 |
| 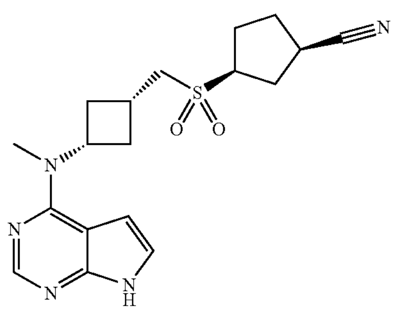 [SMILES: CN(c1ncnc2[nH]ccc12)[C@H]1C[C@@H](CS(=O)(=O)[C@H]2CC[C@@H](C#N)C2)C1] | 137 | 0.018 | 0.588 | 10.000 | 0.979 |
| 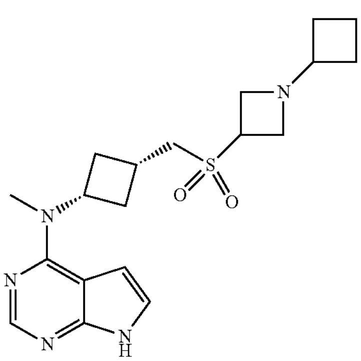 [SMILES: CN(c1ncnc2[nH]ccc12)[C@H]1C[C@@H](CS(=O)(=O)C2CN(C3CCC3)C2)C1] | 138 | 0.022 | 0.702 | 10.000 | 6.615 |
| 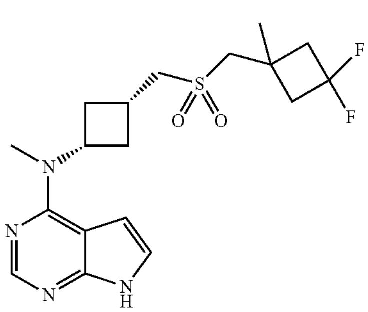 [SMILES: CN(c1ncnc2[nH]ccc12)[C@H]1C[C@@H](CS(=O)(=O)CC2(C)CC(F)(F)C2)C1] | 139 | 0.002 | 0.069 | 5.804 | 0.276 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 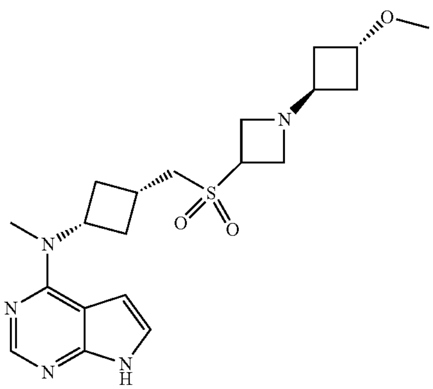 [SMILES: CO[C@H]1C[C@H](N2CC(S(=O)(=O)C[C@H]3C[C@@H](N(C)c4ncnc5[nH]ccc45)C3)C2)C1] | 140 | 0.007 | 0.234 | 10.000 | 8.172 |
| 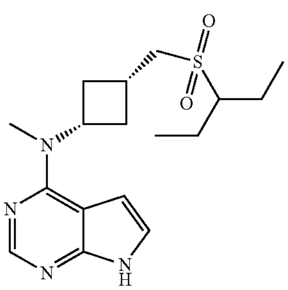 [SMILES: CCC(CC)S(=O)(=O)C[C@H]1C[C@@H](N(C)c2ncnc3[nH]ccc23)C1] | 141 | 0.075 | 1.081 | 10.000 | 1.414 |
| 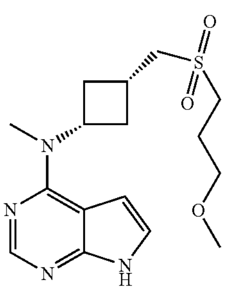 [SMILES: COCCCS(=O)(=O)C[C@H]1C[C@@H](N(C)c2ncnc3[nH]ccc23)C1] | 142 | 0.053 | 1.324 | 10.000 | 6.788 |
| 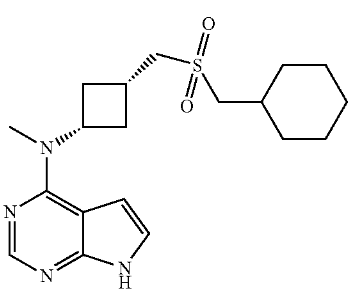 [SMILES: CN(c1ncnc2[nH]ccc12)[C@H]1C[C@@H](CS(=O)(=O)CC2CCCCC2)C1] | 143 | 0.014 | 0.434 | 10.000 | 2.544 |
| 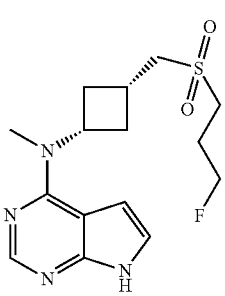 [SMILES: CN(c1ncnc2[nH]ccc12)[C@H]1C[C@@H](CS(=O)(=O)CCCF)C1] | 144 | 0.007 | 0.130 | 10.000 | 0.310 |

TABLE 4-continued
Data for JAK Caliper™ Enzyme assay at 1 mM ATP.
| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 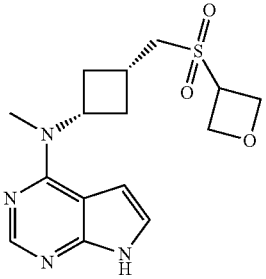 [SMILES: CN(c1ncnc2[nH]ccc12)[C@H]1C[C@@H](CS(=O)(=O)C2COC2)C1] | 145 | 0.024 | 0.533 | 10.000 | 1.216 |
| 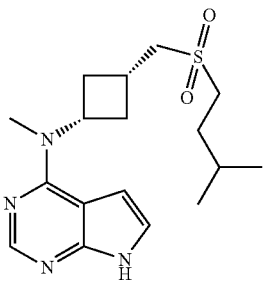 [SMILES: CC(C)CCS(=O)(=O)C[C@H]1C[C@@H](N(C)c2ncnc3[nH]ccc23)C1] | 146 | 0.032 | 0.888 | 10.000 | 2.751 |
| 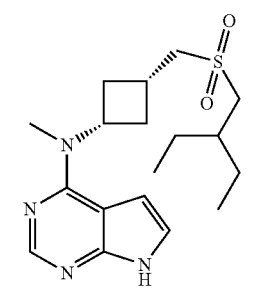 [SMILES: CCC(CC)CS(=O)(=O)C[C@H]1C[C@@H](N(C)c2ncnc3[nH]ccc23)C1] | 147 | 0.007 | 0.157 | 10.000 | 0.372 |
| 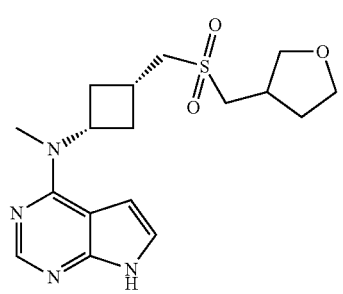 [SMILES: CN(c1ncnc2[nH]ccc12)[C@H]1C[C@@H](CS(=O)(=O)CC2CCOC2)C1] | 148 | 0.024 | 0.671 | 10.000 | 3.124 |
| 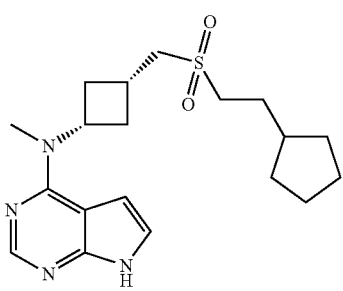 [SMILES: CN(c1ncnc2[nH]ccc12)[C@H]1C[C@@H](CS(=O)(=O)CCC2CCCC2)C1] | 149 | 0.022 | 0.758 | 10.000 | 3.530 |

TABLE 4-continued

Data for JAK Caliper™ Enzyme assay at 1 mM ATP.

| Structure | Example | JAK1 IC$_{50}$ (uM) | JAK2 IC$_{50}$ (uM) | JAK3 IC$_{50}$ (uM) | Tyk2 IC$_{50}$ (uM) |
|---|---|---|---|---|---|
| 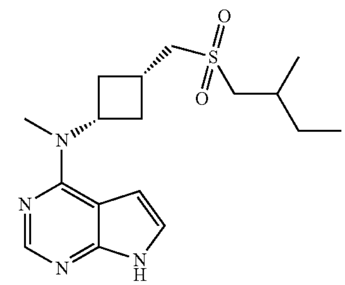 [SMILES: CCC(C)CS(=O)(=O)C[C@H]1C[C@@H](N(C)c2ncnc3[nH]ccc23)C1] | 150 | 0.008 | 0.187 | 10.000 | 0.448 |
| 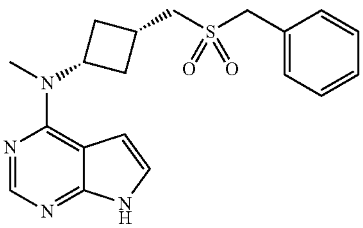 [SMILES: CN(c1ncnc2[nH]ccc12)[C@H]1C[C@@H](CS(=O)(=O)Cc2ccccc2)C1] | 151 | 0.049 | 1.128 | 10.000 | 3.653 |
| 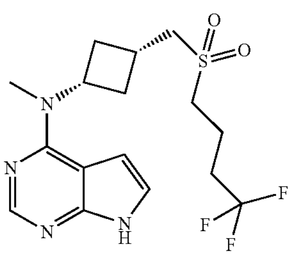 [SMILES: CN(c1ncnc2[nH]ccc12)[C@H]1C[C@@H](CS(=O)(=O)CCCC(F)(F)F)C1] | 152 | 0.009 | 0.211 | 9.162 | 0.804 |
| 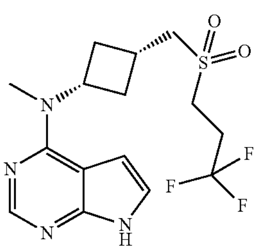 [SMILES: CN(c1ncnc2[nH]ccc12)[C@H]1C[C@@H](CS(=O)(=O)CCC(F)(F)F)C1] | 153 | 0.009 | 0.258 | 10.000 | 0.700 |

TABLE 5

Data for JAK Caliper™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 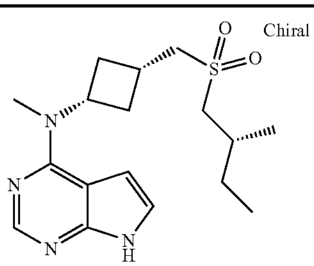 | 154 | 0.012 | 0.170 | 10.000 | 0.365 |

TABLE 5-continued
Data for JAK Caliper ™ Enzyme assay at 1 mM ATP.
| Structure | Example | JAK1 IC50 (nM) | JAK2 IC50 (nM) | JAK3 IC50 (nM) | Tyk2 IC50 (nM) |
|---|---|---|---|---|---|
| 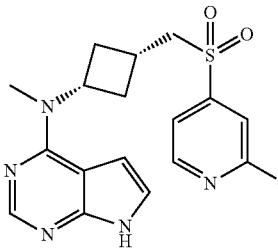 | 155 | 0.008 | 0.115 | 10.000 | 2.412 |
| 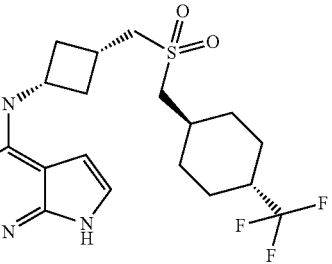 | 156 | 0.091 | 3.799 | 10.000 | 10.000 |
| 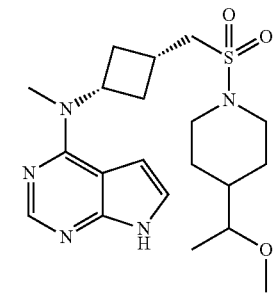 [SMILES: COC(C)C1CCN(S(=O)(=O)C[C@H]2C[C@@H](N(C)c3ncnc4[nH]ccc34)C2)CC1] | 157 | 0.011 | 1.206 | 10.000 | 1.875 |
| 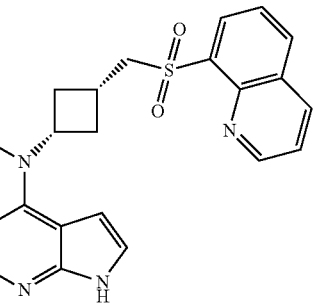 | 158 | 0.083 | 1.833 | 10.000 | 5.433 |
| 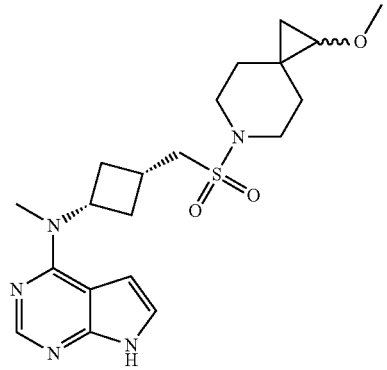 [SMILES: COC1CC12CCN(S(=O)(=O)C[C@H]1C[C@@H](N(C)c3ncnc4[nH]ccc34)C1)CC2] | 159 | 0.081 | 2.273 | 10.000 | 9.881 |

TABLE 5-continued

Data for JAK Caliper™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 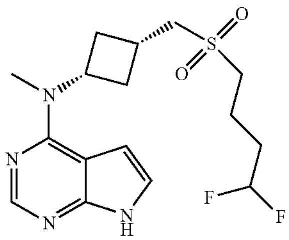 [SMILES: CN(c1ncnc2[nH]ccc12)[C@H]1C[C@@H](CS(=O)(=O)CCCC(F)F)C1] | 160 | 0.007 | 0.174 | 8.023 | 0.742 |
| 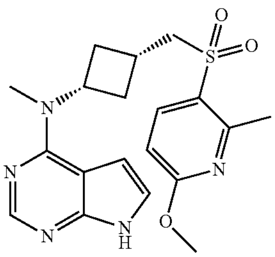 [SMILES: COc1ccc(S(=O)(=O)C[C@H]2C[C@@H](N(C)c3ncnc4[nH]ccc34)C2)c(C)n1] | 161 | 0.014 | 0.258 | 10.000 | 0.385 |
| 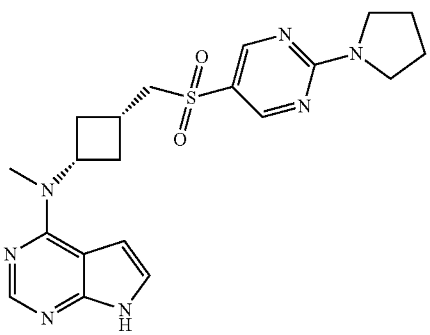 [SMILES: CN(c1ncnc2[nH]ccc12)[C@H]1C[C@@H](CS(=O)(=O)c2cnc(N3CCCC3)nc2)C1] | 162 | 0.071 | 0.860 | 10.000 | 1.863 |
| 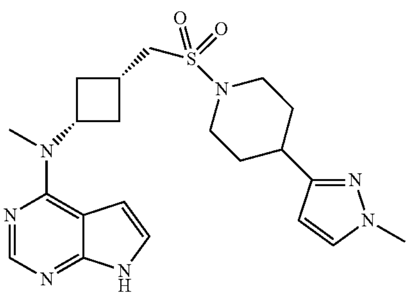 [SMILES: Cn1ccc(C2CCN(S(=O)(=O)C[C@H]3C[C@@H](N(C)c4ncnc5[nH]ccc45)C3)CC2)n1] | 163 | 0.003 | 0.066 | 5.774 | 0.231 |
| 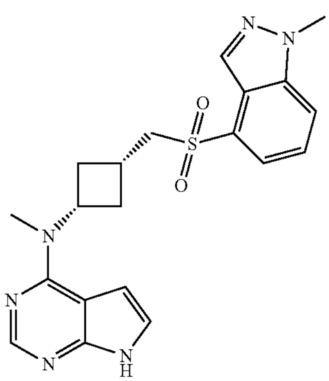 [SMILES: Cn1ncc2c(S(=O)(=O)C[C@H]3C[C@@H](N(C)c4ncnc5[nH]ccc45)C3)cccc21] | 164 | 0.067 | 0.963 | 10.000 | 5.906 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 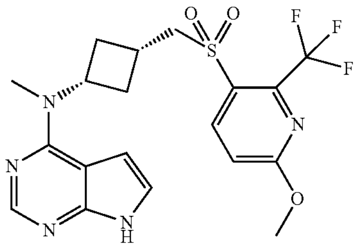 [SMILES: COc1ccc(S(=O)(=O)C[C@H]2C[C@@H](N(C)c3ncnc4[nH]ccc34)C2)c(C(F)(F)F)n1] | 165 | 0.011 | 0.189 | 10.000 | 0.407 |
| 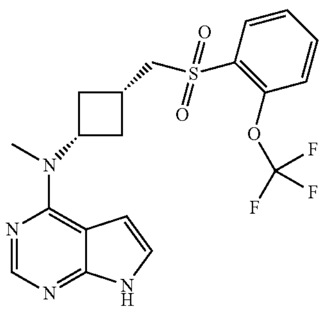 [SMILES: CN(c1ncnc2[nH]ccc12)[C@H]1C[C@@H](CS(=O)(=O)c2ccccc2OC(F)(F)F)C1] | 166 | 0.057 | 2.312 | 10.000 | 7.987 |
| 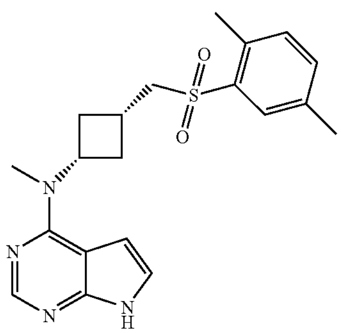 [SMILES: Cc1ccc(C)c(S(=O)(=O)C[C@H]2C[C@@H](N(C)c3ncnc4[nH]ccc34)C2)c1] | 167 | 0.056 | 0.838 | 10.000 | 1.832 |
| 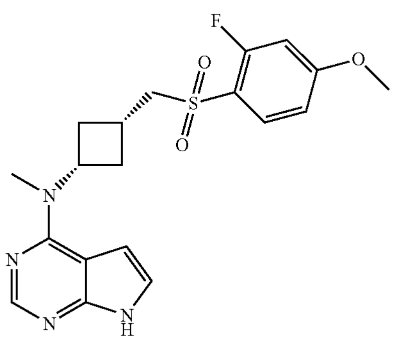 [SMILES: COc1ccc(S(=O)(=O)C[C@H]2C[C@@H](N(C)c3ncnc4[nH]ccc34)C2)c(F)c1] | 168 | 0.018 | 0.398 | 10.000 | 0.846 |
| 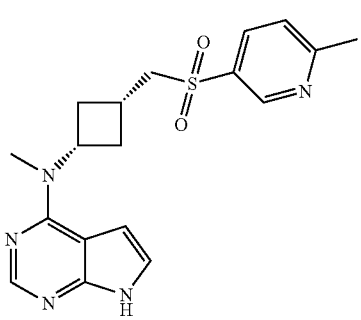 [SMILES: Cc1ccc(S(=O)(=O)C[C@H]2C[C@@H](N(C)c3ncnc4[nH]ccc34)C2)cn1] | 169 | 0.049 | 1.024 | 10.000 | 3.214 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 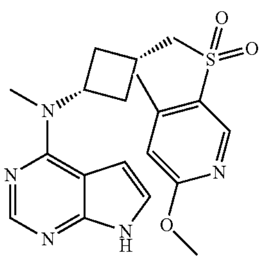 [SMILES: COc1cc(C)c(S(=O)(=O)C[C@H]2C[C@@H](N(C)c3ncnc4[nH]ccc34)C2)cn1] | 170 | 0.005 | 0.113 | 7.530 | 1.141 |
| 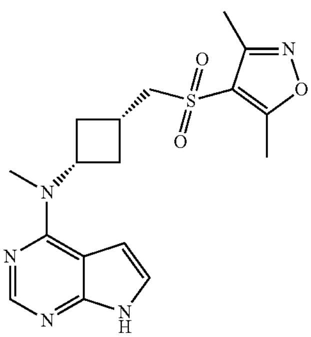 [SMILES: Cc1noc(C)c1S(=O)(=O)C[C@H]1C[C@@H](N(C)c2ncnc3[nH]ccc23)C1] | 171 | 0.042 | 0.377 | 10.000 | 0.798 |
| 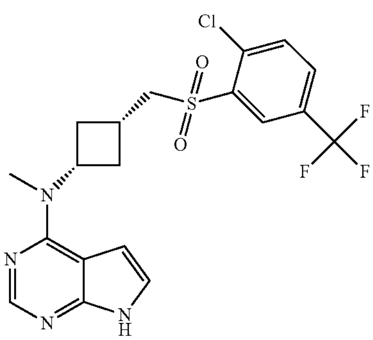 [SMILES: CN(c1ncnc2[nH]ccc12)[C@H]1C[C@@H](CS(=O)(=O)c2cc(C(F)(F)F)ccc2Cl)C1] | 172 | 0.041 | 0.685 | 10.000 | 2.736 |
| 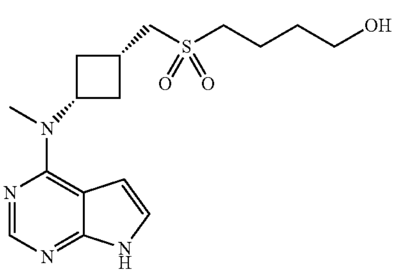 [SMILES: CN(c1ncnc2[nH]ccc12)[C@H]1C[C@@H](CS(=O)(=O)CCCCO)C1] | 173 | 0.039 | 1.291 | 9.320 | 5.813 |
| 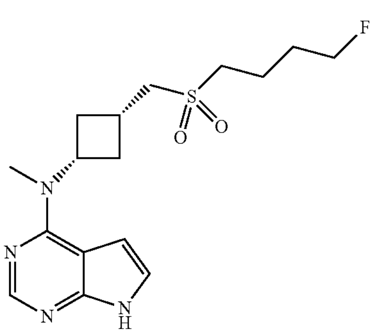 [SMILES: CN(c1ncnc2[nH]ccc12)[C@H]1C[C@@H](CS(=O)(=O)CCCCF)C1] | 174 | 0.008 | 0.357 | 10.000 | 1.131 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 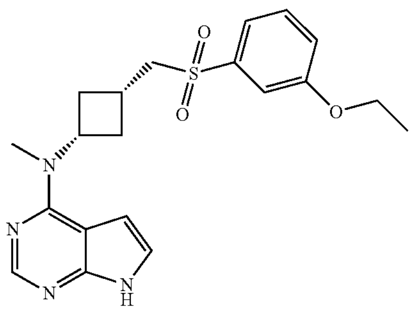 [SMILES: CCOc1cccc(S(=O)(=O)C[C@H]2C[C@@H](N(C)c3ncnc4[nH]ccc34)C2)c1] | 175 | 0.018 | 0.344 | 10.000 | 0.304 |
| 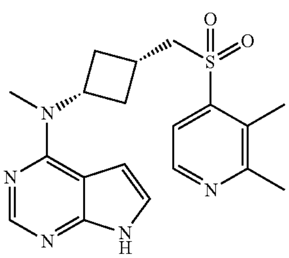 [SMILES: Cc1nccc(S(=O)(=O)C[C@H]2C[C@@H](N(C)c3ncnc4[nH]ccc34)C2)c1C] | 176 | 0.005 | 0.131 | 10.000 | 0.243 |
| 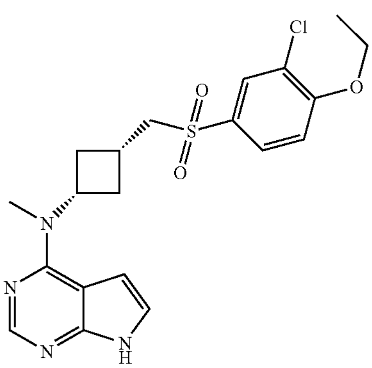 [SMILES: CCOc1ccc(S(=O)(=O)C[C@H]2C[C@@H](N(C)c3ncnc4[nH]ccc34)C2)cc1Cl] | 177 | 0.022 | 0.517 | 10.000 | 3.554 |
| 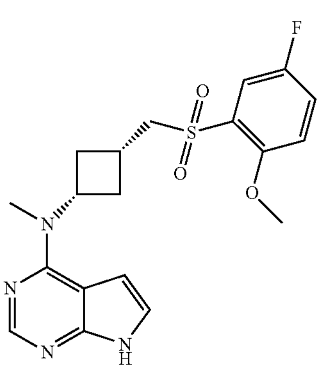 [SMILES: COc1ccc(F)cc1S(=O)(=O)C[C@H]1C[C@@H](N(C)c2ncnc3[nH]ccc23)C1] | 178 | 0.032 | 0.309 | 10.000 | 1.135 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 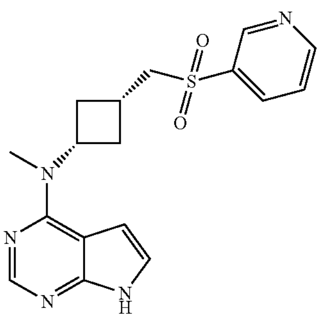 [SMILES: CN(c1ncnc2[nH]ccc12)[C@H]1C[C@@H](CS(=O)(=O)c2cccnc2)C1] | 179 | 0.013 | 0.164 | 9.967 | 0.486 |
| 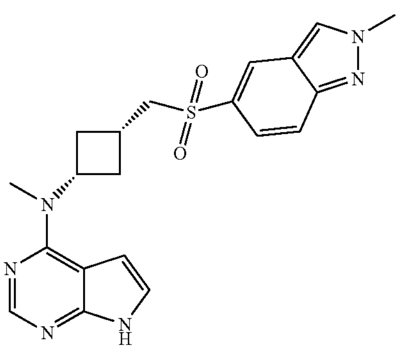 [SMILES: Cn1cc2cc(S(=O)(=O)C[C@H]3C[C@@H](N(C)c4ncnc5[nH]ccc45)C3)ccc2n1] | 180 | 0.019 | 0.145 | 10.000 | 3.373 |
| 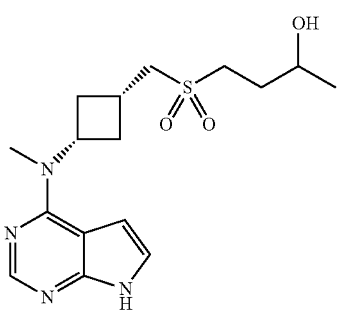 [SMILES: CC(O)CCS(=O)(=O)C[C@H]1C[C@@H](N(C)c2ncnc3[nH]ccc23)C1] | 181 | 0.031 | 0.955 | 10.000 | 3.948 |
| 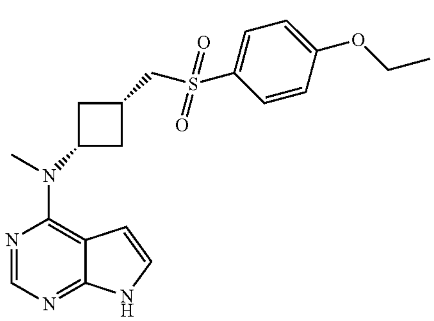 [SMILES: CCOc1ccc(S(=O)(=O)C[C@H]2C[C@@H](N(C)c3ncnc4[nH]ccc34)C2)cc1] | 182 | 0.027 | 0.524 | 10.000 | 3.155 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 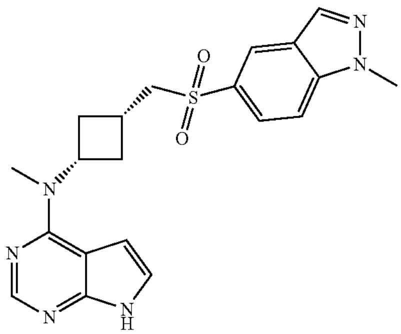 [SMILES: Cn1ncc2cc(S(=O)(=O)C[C@H]3C[C@@H](N(C)c4ncnc5[nH]ccc45)C3)ccc21] | 183 | 0.025 | 0.567 | 10.000 | 1.208 |
| 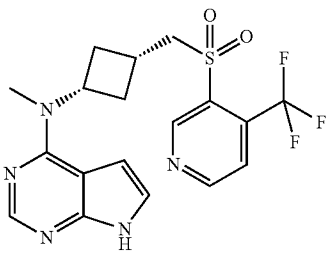 [SMILES: CN(c1ncnc2[nH]ccc12)[C@H]1C[C@@H](CS(=O)(=O)c2cnccc2C(F)(F)F)C1] | 184 | 0.019 | 0.464 | 10.000 | 0.958 |
| 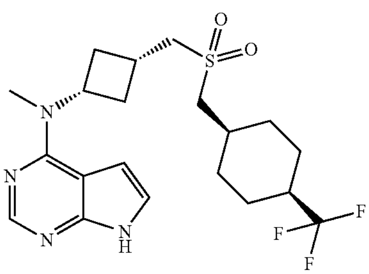 [SMILES: CN(c1ncnc2[nH]ccc12)[C@H]1C[C@@H](CS(=O)(=O)C[C@H]2CC[C@@H](C(F)(F)F)CC2)C1] | 185 | 0.017 | 1.113 | 10.000 | 4.552 |
| 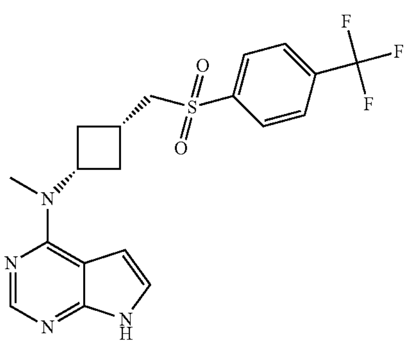 [SMILES: CN(c1ncnc2[nH]ccc12)[C@H]1C[C@@H](CS(=O)(=O)c2ccc(C(F)(F)F)cc2)C1] | 186 | 0.020 | 0.617 | 10.000 | 2.381 |
| 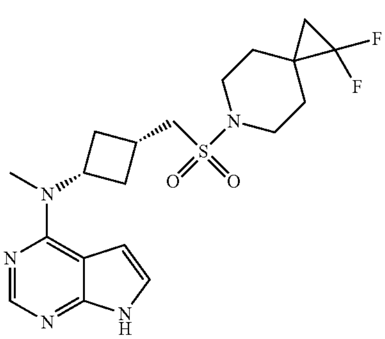 [SMILES: CN(c1ncnc2[nH]ccc12)[C@H]1C[C@@H](CS(=O)(=O)N2CCC3(CC2)CC3(F)F)C1] | 187 | 0.019 | 0.626 | 10.000 | 2.457 |

TABLE 5-continued
Data for JAK Caliper ™ Enzyme assay at 1 mM ATP.
| Structure | Example | JAK1 IC50 (nM) | JAK2 IC50 (nM) | JAK3 IC50 (nM) | Tyk2 IC50 (nM) |
|---|---|---|---|---|---|
| 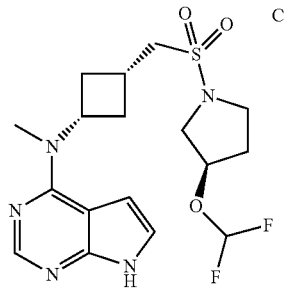 Chiral | 188 | 0.007 | 0.307 | 10.000 | 0.685 |
| 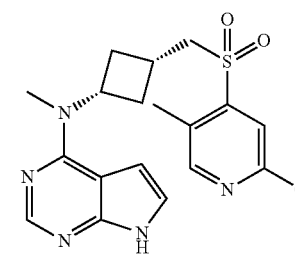 | 189 | 0.019 | 0.317 | 10.000 | 3.043 |
| 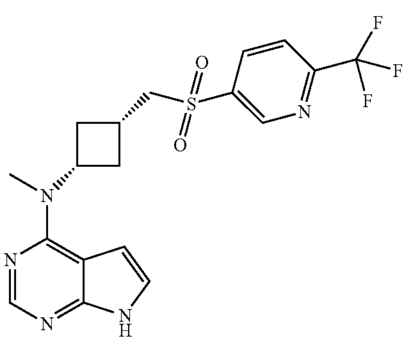 [SMILES: CN(c1ncnc2[nH]ccc12)[C@H]1C[C@@H](CS(=O)(=O)c2ccc(C(F)(F)F)nc2)C1] | 190 | 0.011 | 0.172 | 10.000 | 0.260 |
| 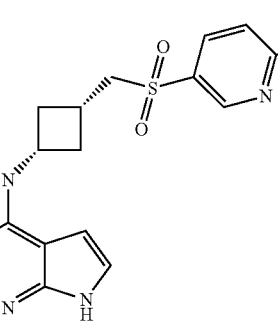 | 191 | 0.032 | 0.422 | 10.000 | 2.084 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 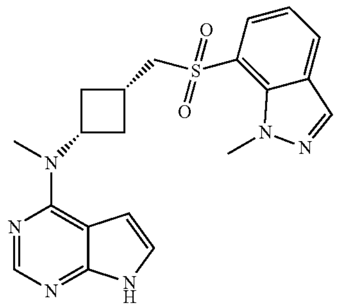 [SMILES: Cn1ncc2cccc(S(=O)(=O)C[C@H]3C[C@@H](N(C)c4ncnc5[nH]ccc45)C3)c21] | 192 | 0.009 | 0.148 | 9.132 | 0.468 |
| 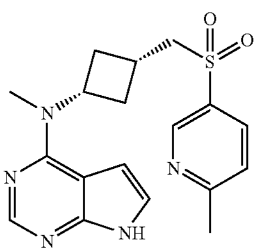 [SMILES: Cc1ccc(S(=O)(=O)C[C@H]2C[C@@H](N(C)c3ncnc4[nH]ccc34)C2)cn1] | 193 | 0.017 | 0.446 | 10.000 | 2.371 |
| 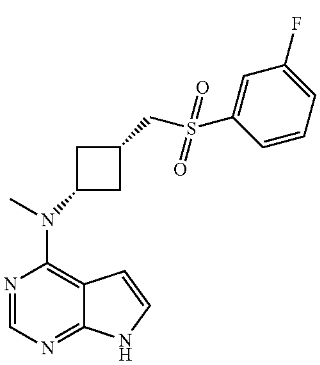 [SMILES: CN(c1ncnc2[nH]ccc12)[C@H]1C[C@@H](CS(=O)(=O)c2cccc(F)c2)C1] | 194 | 0.005 | 0.064 | 3.884 | 0.077 |
| 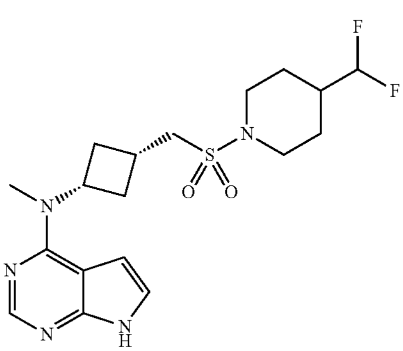 [SMILES: CN(c1ncnc2[nH]ccc12)[C@H]1C[C@@H](CS(=O)(=O)N2CCC(C(F)F)CC2)C1] | 195 | 0.006 | 0.194 | 9.452 | 0.573 |

TABLE 5-continued
Data for JAK Caliper ™ Enzyme assay at 1 mM ATP.
| Structure | Example | JAK1 IC50 (nM) | JAK2 IC50 (nM) | JAK3 IC50 (nM) | Tyk2 IC50 (nM) |
|---|---|---|---|---|---|
| 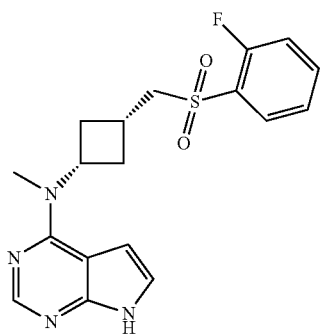 [SMILES: CN(c1ncnc2[nH]ccc12)[C@H]1C[C@@H](CS(=O)(=O)c2ccccc2F)C1] | 196 | 0.015 | 0.458 | 10.000 | 0.365 |
| 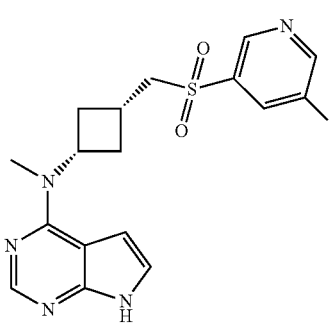 | 197 | 0.015 | 0.236 | 10.000 | 0.354 |
| 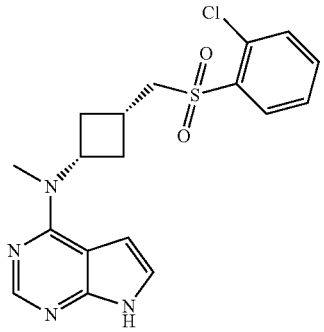 [SMILES: CN(c1ncnc2[nH]ccc12)[C@H]1C[C@@H](CS(=O)(=O)c2ccccc2Cl)C1] | 198 | 0.014 | 0.238 | 10.000 | 0.425 |
| 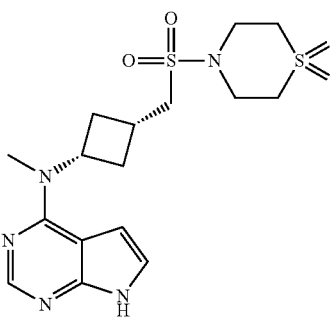 | 199 | 0.009 | 0.187 | 9.010 | 0.508 |

TABLE 5-continued
Data for JAK Caliper ™ Enzyme assay at 1 mM ATP.
| Structure | Example | JAK1 IC50 (nM) | JAK2 IC50 (nM) | JAK3 IC50 (nM) | Tyk2 IC50 (nM) |
|---|---|---|---|---|---|
| 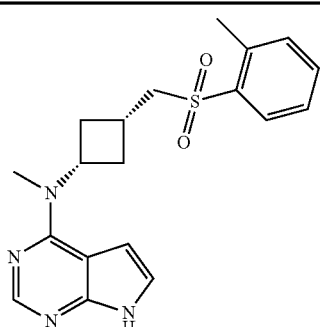 | 200 | 0.013 | 0.247 | 10.000 | 0.680 |
| 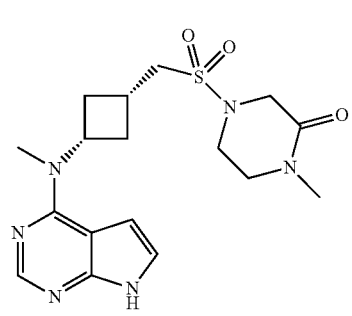 [SMILES: CN1CCN(S(=O)(=O)C[C@H]2C[C@@H](N(C)c3ncnc4[nH]ccc34)C2)CC1=O] | 201 | 0.063 | 1.235 | 10.000 | 2.330 |
| 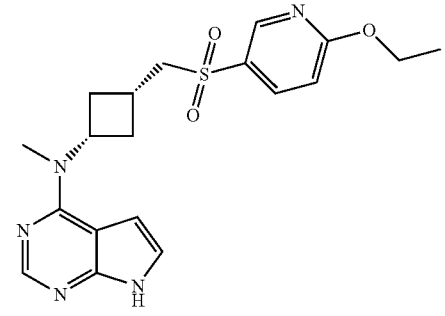 [SMILES: CCOc1ccc(S(=O)(=O)C[C@H]2C[C@@H](N(C)c3ncnc4[nH]ccc34)C2)cn1] | 202 | 0.013 | 0.254 | 7.266 | 2.491 |
| 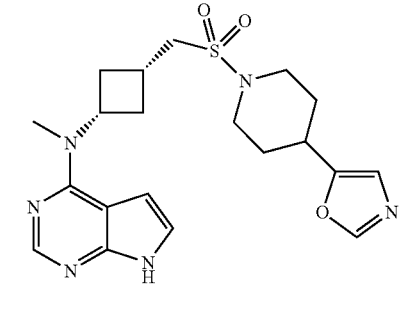 [SMILES: CN(c1ncnc2[nH]ccc12)[C@H]1C[C@@H](CS(=O)(=O)N2CCC(c3cnco3)CC2)C1] | 203 | 0.013 | 0.497 | 10.000 | 1.560 |
| 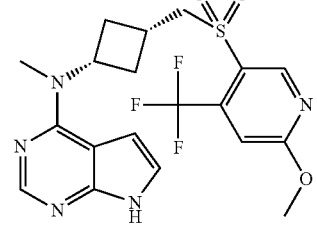 | 204 | 0.045 | 0.521 | 10.000 | 1.724 |

TABLE 5-continued
Data for JAK Caliper ™ Enzyme assay at 1 mM ATP.
| Structure | Example | JAK1 IC50 (nM) | JAK2 IC50 (nM) | JAK3 IC50 (nM) | Tyk2 IC50 (nM) |
|---|---|---|---|---|---|
| 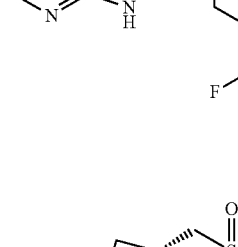 | 205 | 0.012 | 0.727 | 10.000 | 2.285 |
| 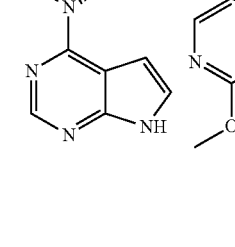 | 206 | 0.012 | 0.155 | 7.815 | 0.656 |
| 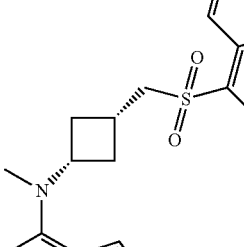 | 207 | 0.012 | 0.574 | 10.000 | 2.220 |
| 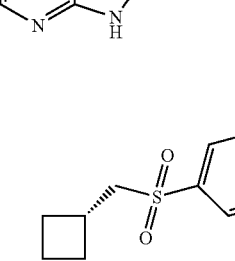 | 208 | 0.012 | 0.225 | 10.000 | 0.381 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 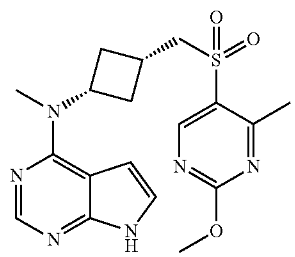 [SMILES: COc1ncc(S(=O)(=O)C[C@H]2C[C@@H](N(C)c3ncnc4[nH]ccc34)C2)c(C)n1] | 209 | 0.011 | 0.187 | 8.226 | 0.600 |
| 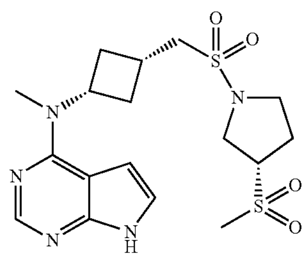 [SMILES: CN(c1ncnc2[nH]ccc12)[C@H]1C[C@@H](CS(=O)(=O)N2CC[C@H](S(C)(=O)=O)C2)C1] | 210 | 0.011 | 0.393 | 10.000 | 0.710 |
| 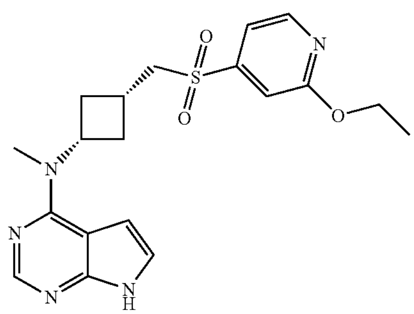 [SMILES: CCOc1cc(S(=O)(=O)C[C@H]2C[C@@H](N(C)c3ncnc4[nH]ccc34)C2)ccn1] | 211 | 0.011 | 0.330 | 10.000 | 0.885 |
| 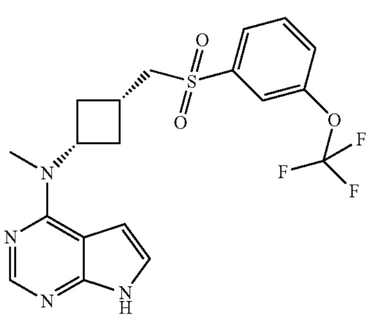 [SMILES: CN(c1ncnc2[nH]ccc12)[C@H]1C[C@@H](CS(=O)(=O)c2cccc(OC(F)(F)F)c2)C1] | 212 | 0.037 | 1.284 | 10.000 | 3.852 |
| 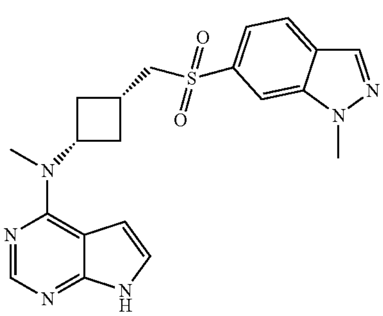 [SMILES: Cn1ncc2ccc(S(=O)(=O)C[C@H]3C[C@@H](N(C)c4ncnc5[nH]ccc45)C3)cc21] | 213 | 0.011 | 0.240 | 10.000 | 0.329 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 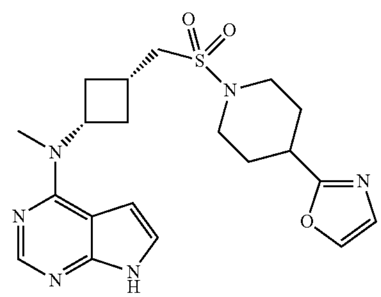 [SMILES: CN(c1ncnc2[nH]ccc12)[C@H]1C[C@@H](CS(=O)(=O)N2CCC(c3ncco3)CC2)C1] | 214 | 0.004 | 0.159 | 9.843 | 1.025 |
| 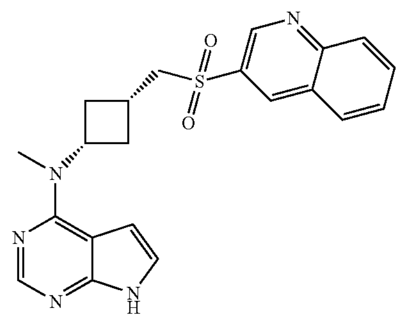 [SMILES: CN(c1ncnc2[nH]ccc12)[C@H]1C[C@@H](CS(=O)(=O)c2cnc3ccccc3c2)C1] | 215 | 0.009 | 0.216 | 7.930 | 0.634 |
| 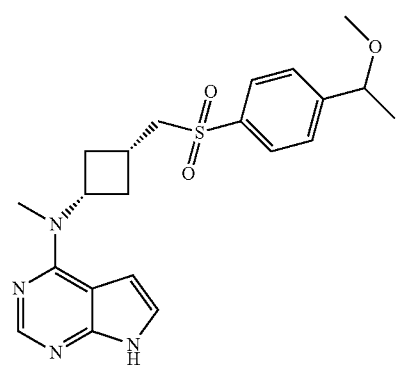 [SMILES: COC(C)c1ccc(S(=O)(=O)C[C@H]2C[C@@H](N(C)c3ncnc4[nH]ccc34)C2)cc1] | 216 | 0.009 | 0.170 | 9.054 | 0.908 |
| 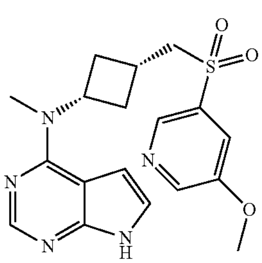 [SMILES: COc1cncc(S(=O)(=O)C[C@H]2C[C@@H](N(C)c3ncnc4[nH]ccc34)C2)c1] | 217 | 0.009 | 0.092 | 8.970 | 0.269 |
| 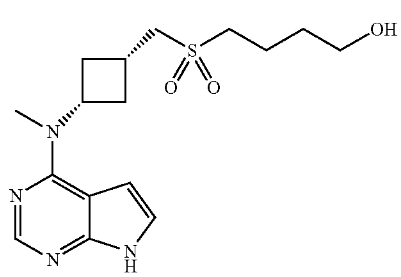 [SMILES: CN(c1ncnc2[nH]ccc12)[C@H]1C[C@@H](CS(=O)(=O)CCCCO)C1] | 218 | 0.039 | 0.778 | 10.000 | 3.485 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 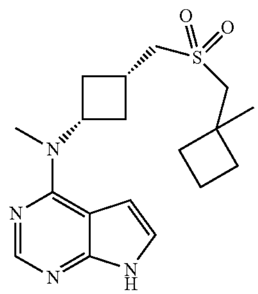 [SMILES: CN(c1ncnc2[nH]ccc12)[C@H]1C[C@@H](CS(=O)(=O)CC2(C)CCC2)C1] | 219 | 0.003 | 0.050 | 4.324 | 0.216 |
| 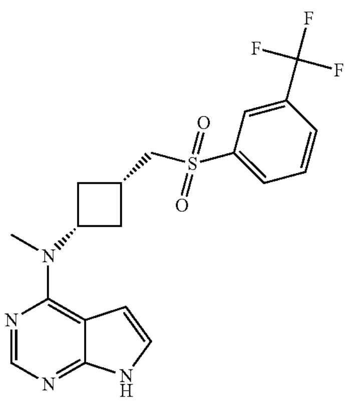 [SMILES: CN(c1ncnc2[nH]ccc12)[C@H]1C[C@@H](CS(=O)(=O)c2cccc(C(F)(F)F)c2)C1] | 220 | 0.009 | 0.136 | 10.000 | 0.322 |
| 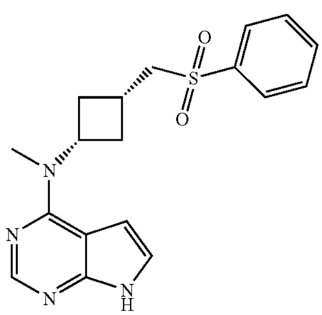 [SMILES: CN(c1ncnc2[nH]ccc12)[C@H]1C[C@@H](CS(=O)(=O)c2ccccc2)C1] | 221 | 0.009 | 0.240 | 10.000 | 0.168 |
| 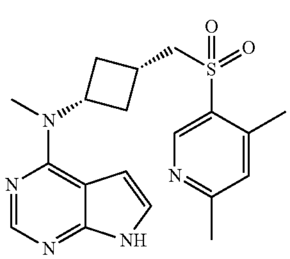 [SMILES: Cc1cc(C)c(S(=O)(=O)C[C@H]2C[C@@H](N(C)c3ncnc4[nH]ccc34)C2)cn1] | 222 | 0.007 | 0.279 | 10.000 | 1.294 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 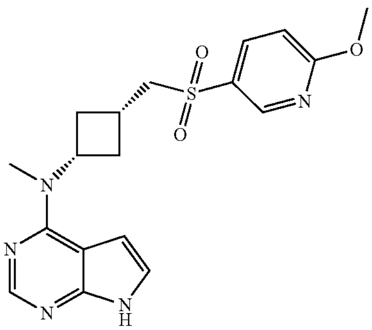 [SMILES: COc1ccc(S(=O)(=O)C[C@H]2C[C@@H](N(C)c3ncnc4[nH]ccc34)C2)cn1] | 223 | 0.008 | 0.081 | 5.994 | 0.220 |
| 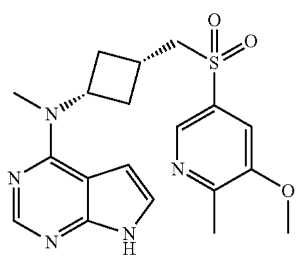 [SMILES: COc1cc(S(=O)(=O)C[C@H]2C[C@@H](N(C)c3ncnc4[nH]ccc34)C2)cnc1C] | 224 | 0.008 | 0.180 | 10.000 | 3.033 |
| 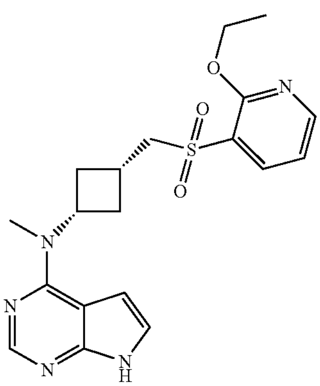 [SMILES: CCOc1ncccc1S(=O)(=O)C[C@H]1C[C@@H](N(C)c2ncnc3[nH]ccc23)C1] | 225 | 0.008 | 0.530 | 10.000 | 1.227 |
| 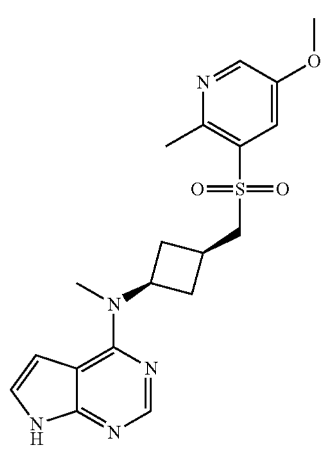 [SMILES: COc1cnc(C)c(S(=O)(=O)C[C@H]2C[C@@H](N(C)c3ncnc4[nH]ccc34)C2)c1] | 226 | 0.037 | 0.647 | 10.000 | 3.890 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
| --- | --- | --- | --- | --- | --- |
| 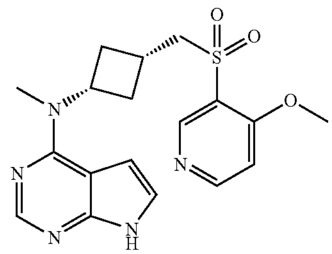 [SMILES: COc1ccncc1S(=O)(=O)C[C@H]1C[C@@H](N(C)c2ncnc3[nH]ccc23)C1] | 227 | 0.075 | 0.894 | 10.000 | 2.897 |
| 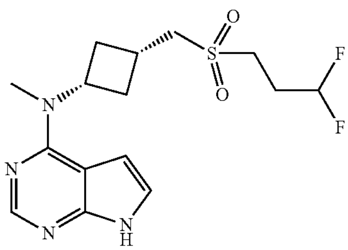 [SMILES: CN(c1ncnc2[nH]ccc12)[C@H]1C[C@@H](CS(=O)(=O)CCC(F)F)C1] | 228 | 0.005 | 0.110 | 5.250 | 0.282 |
| 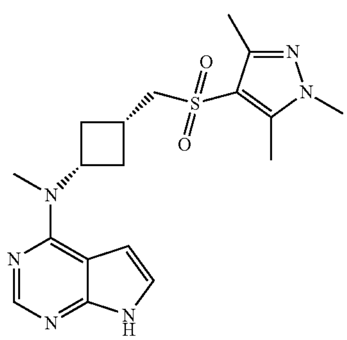 [SMILES: Cc1nn(C)c(C)c1S(=O)(=O)C[C@H]1C[C@@H](N(C)c2ncnc3[nH]ccc23)C1] | 229 | 0.149 | 1.442 | >10 | 0.798 |
| 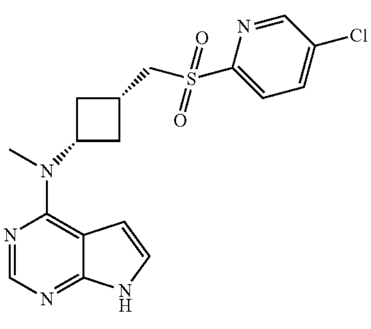 [SMILES: CN(c1ncnc2[nH]ccc12)[C@H]1C[C@@H](CS(=O)(=O)c2ccc(Cl)cn2)C1] | 230 | 0.069 | 1.472 | 10.000 | 6.132 |
| 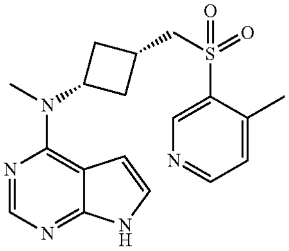 [SMILES: Cc1ccncc1S(=O)(=O)C[C@H]1C[C@@H](N(C)c2ncnc3[nH]ccc23)C1] | 231 | 0.005 | 0.112 | 8.671 | 0.153 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 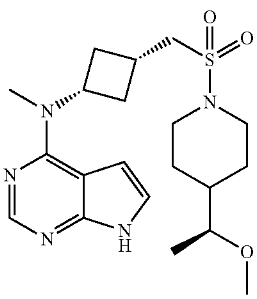 [SMILES: CO[C@@H](C)C1CCN(S(=O)(=O)C[C@H]2C[C@@H](N(C)c3ncnc4[nH]ccc34)C2)CC1] | 232 | 0.006 | 0.822 | 10.000 | 1.030 |
| 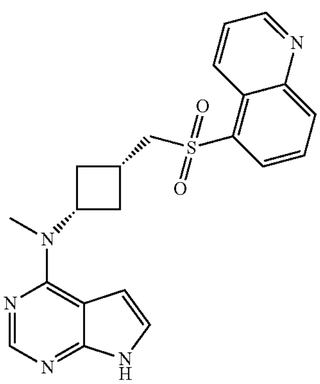 [SMILES: CN(c1ncnc2[nH]ccc12)[C@H]1C[C@@H](CS(=O)(=O)c2cccc3ncccc23)C1] | 233 | 0.018 | 0.194 | 10.000 | 0.788 |
| 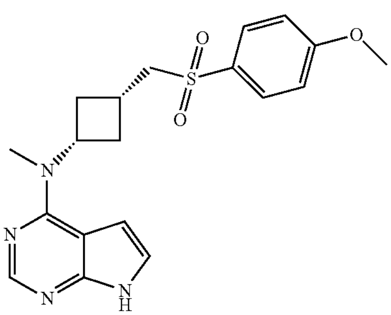 [SMILES: COc1ccc(S(=O)(=O)C[C@H]2C[C@@H](N(C)c3ncnc4[nH]ccc34)C2)cc1] | 234 | 0.015 | 0.230 | 10.000 | 0.597 |
| 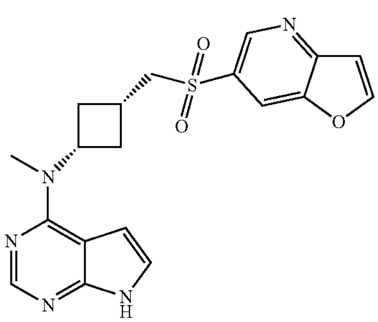 [SMILES: CN(c1ncnc2[nH]ccc12)[C@H]1C[C@@H](CS(=O)(=O)c2cnc3ccoc3c2)C1] | 235 | 0.015 | 0.203 | 10.000 | 1.510 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 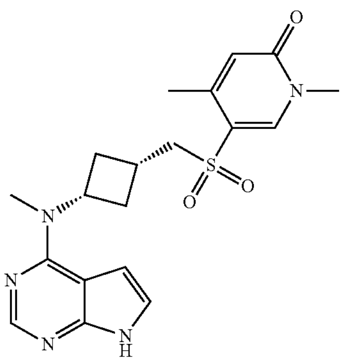 [SMILES: Cc1cc(=O)n(C)cc1S(=O)(=O)C[C@H]1C[C@@H](N(C)c2ncnc3[nH]ccc23)C1] | 236 | 0.003 | 0.100 | 10.000 | 0.088 |
| 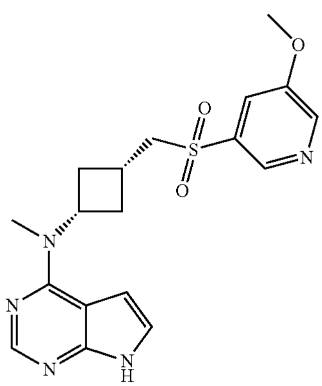 [SMILES: COc1cncc(S(=O)(=O)C[C@H]2C[C@@H](N(C)c3ncnc4[nH]ccc34)C2)c1] | 237 | 0.003 | 0.164 | 9.354 | 0.278 |
| 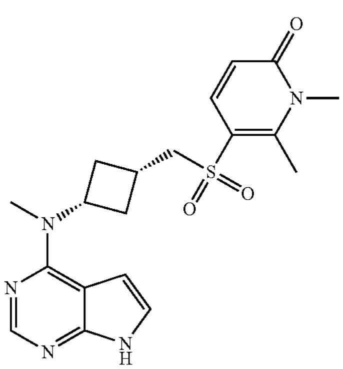 [SMILES: Cc1c(S(=O)(=O)C[C@H]2C[C@@H](N(C)c3ncnc4[nH]ccc34)C2)ccc(=O)n1C] | 238 | 0.097 | 1.304 | 10.000 | 2.007 |
| 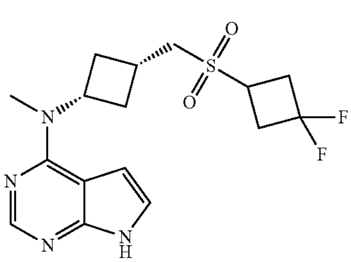 [SMILES: CN(c1ncnc2[nH]ccc12)[C@H]1C[C@@H](CS(=O)(=O)C2CC(F)(F)C2)C1] | 239 | 0.003 | 0.070 | 5.698 | 0.185 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 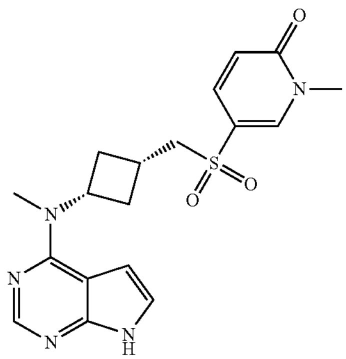 [SMILES: Cn1cc(S(=O)(=O)C[C@H]2C[C@@H](N(C)c3ncnc4[nH]ccc34)C2)ccc1=O] | 240 | 0.005 | 0.116 | 8.609 | 0.135 |
| 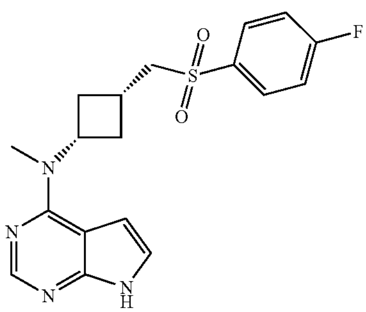 [SMILES: CN(c1ncnc2[nH]ccc12)[C@H]1C[C@@H](CS(=O)(=O)c2ccc(F)cc2)C1] | 241 | 0.006 | 0.108 | 7.161 | 0.231 |
| 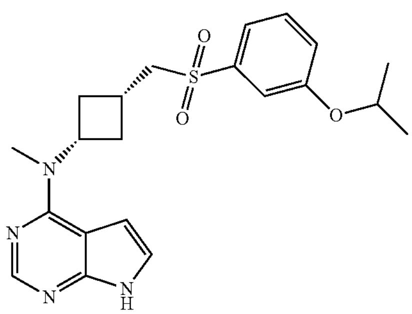 [SMILES: CC(C)Oc1cccc(S(=O)(=O)C[C@H]2C[C@@H](N(C)c3ncnc4[nH]ccc34)C2)c1] | 242 | 0.117 | 1.525 | >10 | 1.675 |
| 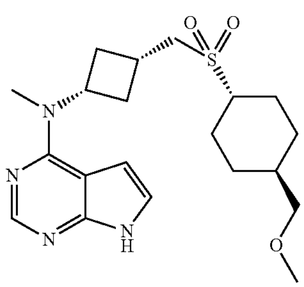 [SMILES: COC[C@H]1CC[C@H](S(=O)(=O)C[C@H]2C[C@@H](N(C)c3ncnc4[nH]ccc34)C2)CC1] | 243 | 0.009 | 0.340 | 10.000 | 5.398 |
| 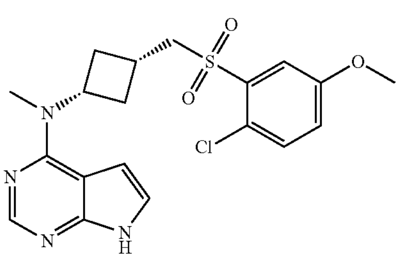 [SMILES: COc1ccc(Cl)c(S(=O)(=O)C[C@H]2C[C@@H](N(C)c3ncnc4[nH]ccc34)C2)c1] | 244 | 0.077 | 0.639 | 10.000 | 3.258 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 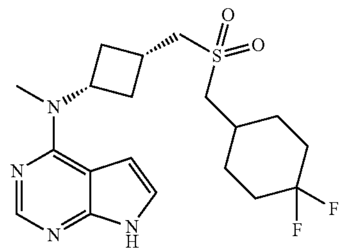 [SMILES: CN(c1ncnc2[nH]ccc12)[C@H]1C[C@@H](CS(=O)(=O)CC2CCC(F)(F)CC2)C1] | 245 | 0.012 | 0.601 | 10.000 | 3.275 |
| 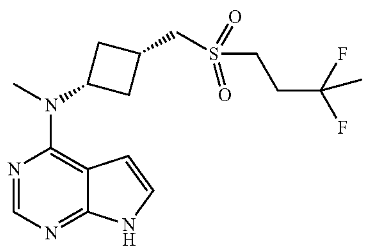 [SMILES: CN(c1ncnc2[nH]ccc12)[C@H]1C[C@@H](CS(=O)(=O)CCC(C)(F)F)C1] | 246 | 0.013 | 0.577 | 10.000 | 1.845 |
| 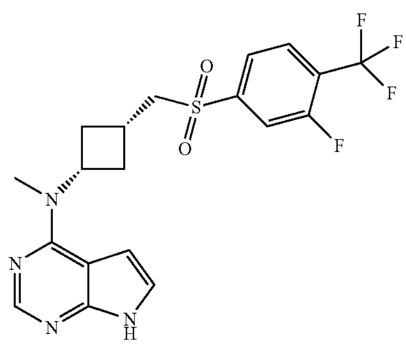 [SMILES: CN(c1ncnc2[nH]ccc12)[C@H]1C[C@@H](CS(=O)(=O)c2ccc(C(F)(F)F)c(F)c2)C1] | 247 | 0.086 | 0.970 | 10.000 | 2.506 |
| 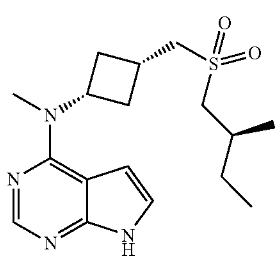 [SMILES: CC[C@H](C)CS(=O)(=O)C[C@H]1C[C@@H](N(C)c2ncnc3[nH]ccc23)C1] | 248 | 0.006 | 0.153 | 10.000 | 0.302 |
| 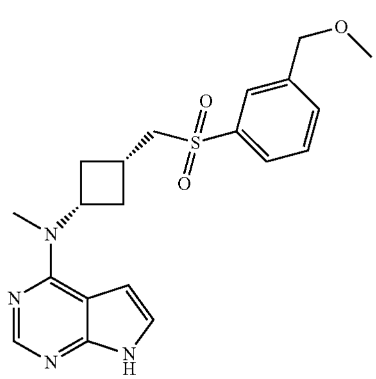 [SMILES: COCc1cccc(S(=O)(=O)C[C@H]2C[C@@H](N(C)c3ncnc4[nH]ccc34)C2)c1] | 249 | 0.038 | 0.780 | 10.000 | 1.168 |

TABLE 5-continued
Data for JAK Caliper ™ Enzyme assay at 1 mM ATP.
| Structure | Example | JAK1 IC50 (nM) | JAK2 IC50 (nM) | JAK3 IC50 (nM) | Tyk2 IC50 (nM) |
|---|---|---|---|---|---|
| 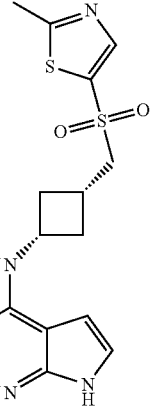 | 250 | 0.022 | 0.497 | 10.000 | 1.741 |
| 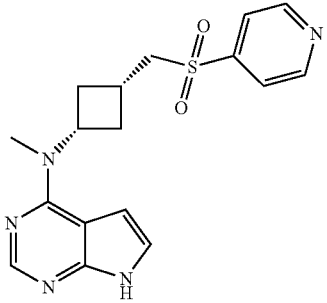 [SMILES: CN(c1ncnc2[nH]ccc12)[C@H]1C[C@@H](CS(=O)(=O)c2ccncc2)C1] | 251 | 0.010 | 0.150 | 9.264 | 0.307 |
| 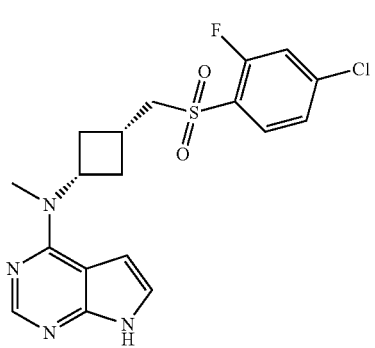 [SMILES: CN(c1ncnc2[nH]ccc12)[C@H]1C[C@@H](CS(=O)(=O)c2ccc(Cl)cc2F)C1] | 252 | 0.004 | 0.131 | 6.929 | 0.382 |
| 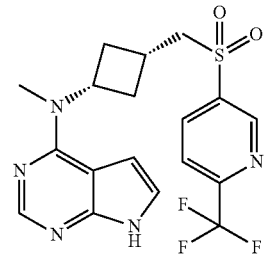 [SMILES: CN(c1ncnc2[nH]ccc12)[C@H]1C[C@@H](CS(=O)(=O)c2ccc(C(F)(F)F)nc2)C1] | 253 | 0.012 | 0.561 | 8.615 | 2.979 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 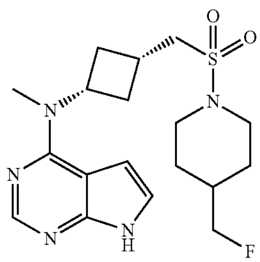 [SMILES: CN(c1ncnc2[nH]ccc12)[C@H]1C[C@@H](CS(=O)(=O)N2CCC(CF)CC2)C1] | 254 | 0.008 | 0.299 | 10.000 | 1.072 |
| 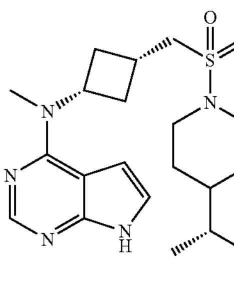 | 255 | 0.051 | 2.746 | 10.000 | 6.206 |
| 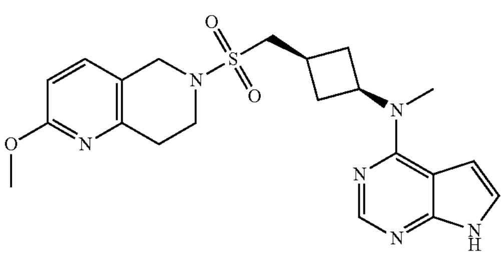 [SMILES: COc1ccc2c(n1)CCN(S(=O)(=O)C[C@H]1C[C@@H](N(C)c3ncnc4[nH]ccc34)C1)C2] | 256 | 0.017 | 0.503 | >10.000 | 1.366 |
| 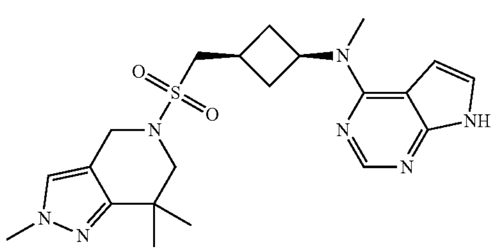 [SMILES: Cn1cc2c(n1)C(C)(C)CN(S(=O)(=O)C[C@H]1C[C@@H](N(C)c3ncnc4[nH]ccc34)C1)C2] | 257 | 0.009 | 0.356 | >10.000 | 1.210 |
| 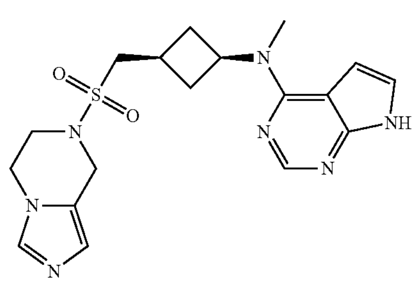 [SMILES: CN(c1ncnc2[nH]ccc12)[C@H]1C[C@@H](CS(=O)(=O)N2CCn3cncc3C2)C1] | 258 | 0.014 | 0.336 | >10.000 | 0.885 |

TABLE 5-continued

Data for JAK Caliper ™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 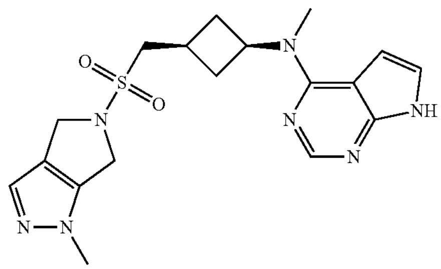 [SMILES: Cn1ncc2c1CN(S(=O)(=O)C[C@H]1C[C@@H](N(C)c3ncnc4[nH]ccc34)C1)C2] | 259 | 0.006 | 0.211 | 9.426 | 0.355 |
| 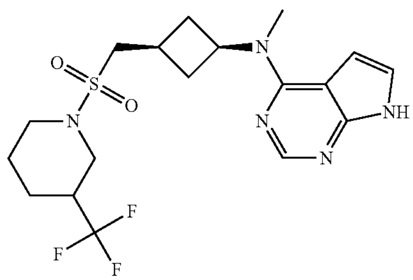 [SMILES: CN(c1ncnc2[nH]ccc12)[C@H]1C[C@@H](CS(=O)(=O)N2CCCC(C(F)(F)F)C2)C1] | 260 | 0.005 | 0.248 | >10.000 | 0.416 |
| 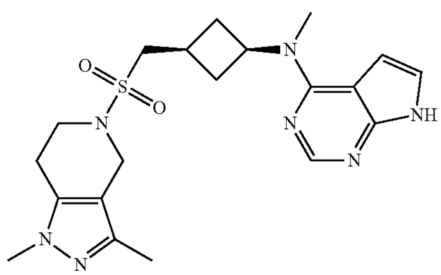 [SMILES: Cc1nn(C)c2c1CN(S(=O)(=O)C[C@H]1C[C@@H](N(C)c3ncnc4[nH]ccc34)C1)CC2] | 261 | 0.013 | 0.646 | >10.000 | 2.043 |
| 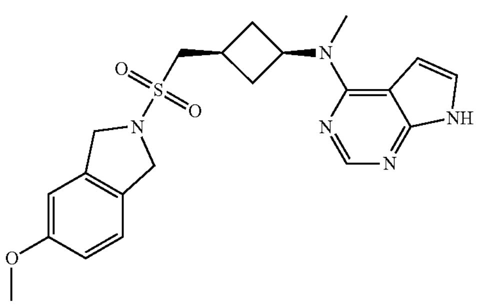 [SMILES: COc1ccc2c(c1)CN(S(=O)(=O)C[C@H]1C[C@@H](N(C)c3ncnc4[nH]ccc34)C1)C2] | 262 | 0.005 | 0.128 | >10.000 | 0.799 |
| 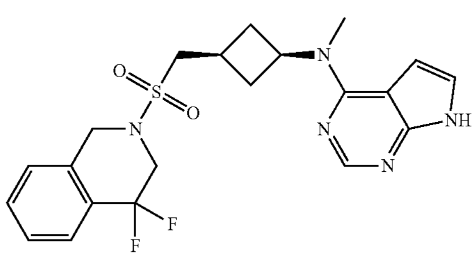 [SMILES: CN(c1ncnc2[nH]ccc12)[C@H]1C[C@@H](CS(=O)(=O)N2Cc3ccccc3C(F)(F)C2)C1] | 263 | 0.002 | 0.061 | 7.848 | 0.109 |

TABLE 5-continued

Data for JAK Caliper™ Enzyme assay at 1 mM ATP.

| Structure | Example | JAK1 IC50 (nM) | JAK2 IC50 (nM) | JAK3 IC50 (nM) | Tyk2 IC50 (nM) |
|---|---|---|---|---|---|
| 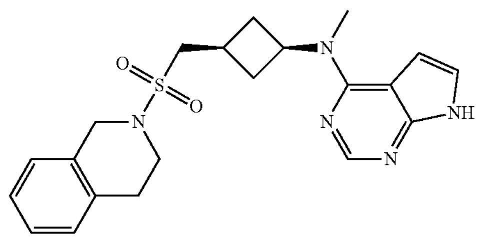 [SMILES: CN(c1ncnc2[nH]ccc12)[C@H]1C[C@@H](CS(=O)(=O)N2CCc3ccccc3C2)C1] | 264 | 0.005 | 0.119 | >10.000 | 0.293 |
| 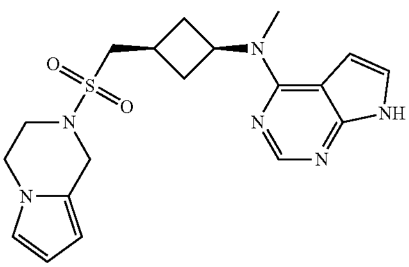 [SMILES: CN(c1ncnc2[nH]ccc12)[C@H]1C[C@@H](CS(=O)(=O)N2CCn3cccc3C2)C1] | 265 | 0.002 | 0.043 | 3.370 | 0.114 |

HWB INF Alpha Induced STAT3 Phosphorylation Assay

Test articles were prepared as 30 mM stocks in 100% DMSO, and then diluted to 5 mM. A 10-point 2.5 dilution series was created in DMSO with a top concentration of 5 mM. Further dilution was done by adding 4 µL of the above test article solutions into 96 µL of PBS with a top concentration of 200 µM.

To a 96-well polypropylene plate (VWR 82007-292) 90 µl of HWB was added per well, followed by addition of 5 µl test article solutions prepared above to give a top concentration of 10 µM. The plate was mixed and incubated for 45 minutes at 37° C. To each well was added 5 µl of human IFN alpha (Universal Type I IFN, R&D Systems #11200-2; final concentration of 5000 U/ml) or D-PBS (unstimulated control), mixed and incubated 15 minutes at 37° C. The reaction was quenched by adding Lyse/Fix Buffer [BD Phosflow 5× Lyse/Fix Buffer (BD #558049)] to all wells at 1000 µl/well and incubated for 20 minutes at 37° C.; after washing with FACS buffer [D-PBS (Invitrogen cat #14190) containing 0.1% BSA and 0.1% sodium azide], 400 µl ice cold 90% methanol/water was added to each well and incubated on ice for 30 minutes. One more wash was done with cold FACS buffer and all samples were finally resuspended in 250 µl/well of the desired Alexa Fluor 647 conjugated anti-phospho-STAT3 (pY705) antibody (BD #557815) at 1:125 dilution in FACS buffer. After overnight incubation at 4 degree all the samples were transferred into a 96-well polypropylene U-bottom plate (Falcon #353077) and checked by flow cytometry machine. The following examples have $IC_{50}$'s between 19 and 297 nM in the HWB IFNa assay;

1-3, 4B, 5, 6, 7B, 8, 12-15, 17A, 17B, 19-23, 25, 26, 28-30, 32, 33, 34B, 37-40, 41B, 42, 43B, 43C, 43D, 44-46, 48-53, 54A, 54B, 55-58, 59A, and 59B.

Canine In Vitro T-Cell Proliferation Assay

T-cell activation plays a key role in a variety of inflammatory and autoimmune disorders as well as asthma, allergies and pruritus. Since T-cell activation can, in part, can be triggered by cytokines that signal through the JAK-STAT pathway, a JAK inhibitor could be effective against such diseases involving aberrant T-cell activation.

Methods: Canine whole blood was collected in sodium heparin tubes from 29 beagle dogs and 23 mixed breed dogs. Whole blood (20 µL) was plated in 96-well plates (Costar 3598) with 180 µL of medium (RPMI 1640, Gibco #21870-076, with 1% heat inactivated fetal bovine serum, Gibco #10082-39, 292 µg/ml L-glutamine, Gibco #250030-081, 100 u/ml penicillin and 100 µg streptomycin per ml, Gibco #15140-122) containing vehicle control or test compound (0.001 to 10 µM), concanavalin A (ConA; 1 µg/ml, Sigma C5275), and canine interleukin-2 (IL-2; 50 ng/ml, R&D Systems 1815-CL/CF). Wells containing whole blood, medium with vehicle control and no ConA or IL-2 were used as background controls. Plates were incubated at 37° C. for 48 hours. Tritiated thymidine, 0.4 µCi/well (Perkin Elmer, Net027A-005MC), was added for 20 additional hours. Plates were frozen and then thawed, washed and filtered using a Brandel MLR-96 cell harvester and pre-wet filter mats (Wallac 1205-401, Perkin Elmer). Filters were dried at 60° C. for one hour (Precision 16EG convection oven) and placed into filter sample bags (Wallac 1205-411, Perkin Elmer) with 10 mL of scintillant (Wallac 1205-440, Perkin Elmer). Sealed filters were counted on a LKB Wallac 1205 Betaplate liquid scintillation counter. Data were collected via Gterm Betaplate program v1.1 and transformed into percent inhibition, calculated using the following formula:

$$100 - \frac{[(\text{Mean Drug Treatment } cpm) - (\text{Mean } BCK\ cpm)]}{[(\text{Mean Non Drug Treatment } cpm) - (\text{Mean } BCK\ cpm)]} \times 100 = \%\ \text{Inhibition}$$

Data were graphically displayed as percent inhibition using GraphPad Prism 4.0, and $IC_{50}$ curves were fitted using a point to point analysis.

Example 38 had an $IC_{50}$ of 48.5 nM in this assay. This data suggests that the compounds of the present invention are effective in inhibiting T-cell proliferation, a key feature in diseases resulting from JAK dysregulation.

Neuropharmacokinetic Studies in Mice

Test substances were administered to C57/BL6 mice via subcutaneous administration to the lower back region. Mice weighed between 0.020 and 0.035 kg. Blood, brain and cerebrospinal fluid (CSF) were collected at either 1 or 4 time points following dose administration. Animals were anesthetized with isoflurane prior to sample collection. Blood was collected via cardiac puncture, CSF was collected from the cisterna magna and brain was collected following decapitation. Blood was centrifuged to separate plasma and plasma was transferred to a clean vial. Brains were rinsed with saline and blotted dry before transfer to a collection vial. When studies were run to collect only one time point samples were collected at 1 hr post dose. When studies were run to collect four time points samples were collected at 0.5, 1, 2 and 4 hr post dose.

Samples were analyzed for drug using LC-MS-MS analysis. Pharmacokinetic (PK) analysis was only done on studies with 4 time points for measurement of Cmax, Tmax, half-life ($T_{1/2}$), area under the curve 0–Tlast)(AUCO–Tlast) and area under the curve extrapolated (AUC Extrap). Data was analyzed by comparing the AUC Extrap, Brain over AUC Extrap, Plasma. Free fraction in both brain and plasma were incorporated to yield a free brain to free plasma ratio ($C_{b,u}/C_{p,u}$). These ratios allowed us to assess the level of brain impairment in a mouse. For studies with only one time point, impairment was assessed by generating a $C_{b,u}/C_{p,u}$ with the drug exposure values at 1 hr (not an AUC Extrap ratio).

| Ex. | IUPAC Name | Number of time points | Mouse $C_{b,u}/C_{p,u}$ |
|---|---|---|---|
| 30 | N-{cis-3-(butylsulfonyl)methyl]-cyclobutyl}-N-methyl-7H-pyrrolo[2,3-d]pyrimidin-4-amine | 4 | 0.4 |
| 33 | N-[cis-3-({[(3,3-difluorocyclo-butyl)methyl]sulfonyl}methyl)cyclobutyl]-N-methyl-7H-pyrrolo[2,3-d]pyrimidin-4-amine | 4 | 0.08 |
| 55 | N-[cis-3-({[3-(difluoromethyl)azetidin-1-yl]sulfonyl}methyl)cyclobutyl]-N-methyl-7H-pyrrolo[2,3-d]pyrimidin-4-amine | 4 | 0.9 |
| 122 | N-[cis-3-({[3-(2,2-difluoroethyl)-azetidin-1-yl]sulfonyl}methyl)-cyclobutyl]-N-methyl-7H-pyrrolo[2,3-d]pyrimidin-4-amine | 4 | 0.05 |
| 123 | N-(cis-3-{[(3,3-difluoroazetidin-1-yl)sulfonyl]methyl}cyclobutyl)-N-methyl-7H-pyrrolo[2,3-d]pyrimidin-4-amine | 4 | 0.39 |
| 124 | N-methyl-N-[cis-3-({[3-(trifluoromethyl)azetidin-1-yl]sulfonyl}methyl)cyclobutyl]-7H-pyrrolo[2,3-d]pyrimidin-4-amine | 4 | 0.16 |
| 125 | N-[cis-3-({[3-(difluoromethoxy)-azetidin-1-yl]sulfonyl}methyl)cyclobutyl]-N-methyl-7H-pyrrolo[2,3-d]pyrimidin-4-amine | 1 | 0.11 |
| 153 | N-methyl-N-(cis-3-{[(3,3,3-trifluoropropyl)sulfonyl]methyl}-cyclobutyl)-7H-pyrrolo[2,3-d]pyrimidin-4-amine | 1 | 0.16 |

What is claimed is:

1. A compound selected from the group consisting of:
[2,2,2-Trifluoro-N-{cis-3-[methyl(7H-pyrrolo[2,3-d]pyrimidin-4-yl)amino]cyclo-butyl}ethanesulfonamide;]
N-{cis-3-[Methyl(7H-pyrrolo[2,3-d]pyrimidin-4-yl)amino]cyclobutyl}-propane-1-sulfonamide;
2-Methyl-N-{cis-3-[methyl(7H-pyrrolo[2,3-d]pyrimidin-4-yl)amino]-cyclobutyl}propane-1-sulfonamide;
cis-3-(Cyanomethyl)-N-{cis-3-[methyl(7H-pyrrolo[2,3-d]pyrimidin-4-yl)amino]cyclobutyl}cyclo-butanesulfonamide;
trans-3-(Cyanomethyl)-N-{cis-3-[methyl(7H-pyrrolo[2,3-d]pyrimidin-4-yl)amino]cyclobutyl}cyclo-butanesulfonamide;
[N-{cis-3-[methyl(7H-pyrrolo[2,3-d]pyrimidin-4-yl)amino]cyclobutyl}-1-oxetan-3-ylmethane-sulfonamide;]
cis-3-(Cyanomethyl)-3-methyl-N-{cis-3-[methyl(7H-pyrrolo[2,3-d]pyrimidin-4-yl)amino]cyclo-butyl}cyclobutanesulfonamide;
trans-3-(Cyanomethyl)-3-methyl-N-{cis-3-[methyl(7H-pyrrolo[2,3-d]pyrimidin-4-yl)amino]cyclo-butyl}cyclobutanesulfonamide;
3-(1-Hydroxy-1-methylethyl)-N-{cis-3-[methyl(7H-pyrrolo[2,3-d]pyrimidin-4-yl)amino]cyclo-butyl}benzenesulfonamide;
N-{(1S,3R)-3-[Methyl(7H-pyrrolo[2,3-d]pyrimidin-4-yl)amino]cyclopentyl}propane-1-sulfonamide;
3,3-Difluoro-N-{cis-3-[methyl(7H-pyrrolo[2,3-d]pyrimidin-4-yl)amino]cyclobutyl}cyclobutane-sulfonamide;
N-(2-Cyanoethyl)-N-methyl-N'-{cis-3-[methyl(7H-pyrrolo[2,3-d]pyrimidin-4-yl)amino]cyclo-butyl}sulfamide;
N-{cis-3-[(Butylsulfonyl)methyl]cyclobutyl}-N-methyl-7H-pyrrolo[2,3-d]pyrimidin-4-amine;
N-Methyl-N-(trans-3-((propylsulfonyl)methyl)cyclobutyl)-7H-pyrrolo[2,3-d]pyrimidin-4-amine;
N-(cis-3-{[(2-Cyclopropylethyl)sulfonyl]methyl}cyclobutyl)-N-methyl-7H-pyrrolo[2,3-d]pyrimidin-4-amine;
N-[cis-3-({[(3,3-Difluorocyclobutyl)methyl]sulfonyl}-methyl)cyclobutyl]-N-methyl-7H-pyrrolo[2,3-d]pyrimidin-4-amine;
(1R, 3R)-[({cis-3-[methyl(7H-pyrrolo[2,3-d]pyrimidin-4-yl)amino]cyclobutyl}methyl)sulfon-yl]cyclopentane-carbonitrile;
(1S, 3S)-[({cis-3-[methyl(7H-pyrrolo[2,3-d]pyrimidin-4-yl)amino]cyclobutyl}methyl)sulfon-yl]cyclopentane-carbonitrile;
N-(cis-3-{[(3-Chloro-4-fluorophenyl)sulfonyl]methyl}cyclobutyl)-N-methyl-7H-pyrrolo[2,3-d]pyrimidin-4-amine;
[(1S,2S)-trans-2-(cyanomethyl)-N-{cis-3-[methyl(7H-pyrrolo[2,3-d]pyrimidin-4-yl)amino]cyclo-butyl}cyclopropanesulfonamide;
(1R,2R)-trans-2-(cyanomethyl)-N-{cis-3-[methyl(7H-pyrrolo[2,3-d]pyrimidin-4-yl)amino]cyclo-butyl}cyclopropanesulfonamide]
3-Cyano-3-methyl-N-{cis-3-[methyl(7H-pyrrolo[2,3-d]pyrimidin-4-yl)amino]cyclobutyl}azet-idine-1-sulfonamide;
cis-3-Cyano-N-{cis-3-[methyl(7H-pyrrolo[2,3-d]pyrimidin-4-yl)amino]cyclobutyl}cyclopentanesulfonamide;
trans-3-Cyano-N-{cis-3-[methyl(7H-pyrrolo[2,3-d]pyrimidin-4-yl)amino]cyclobutyl}cyclopentane-sulfonamide;
1-[({cis-3-[Methyl(7H-pyrrolo[2,3-d]pyrimidin-4-yl)amino]cyclobutyl}methyl)-sulfonyl]azetidine-3-carbonitrile;

cis-3-Cyano-N-{cis-3-[methyl(7H-pyrrolo[2,3-d]pyrimidin-4-yl)amino]cyclobutyl}-cyclobutanesulfonamide;
trans-3-Cyano-N-{cis-3-[methyl(7H-pyrrolo[2,3-d]pyrimidin-4-yl)amino]cyclobutyl}cyclobutane-sulfonamide;
cis-3-[({cis-3-[Methyl(7H-pyrrolo[2,3-d]pyrimidin-4-yl)amino]cyclobutyl}methyl)sulfonyl]cyclo-butanecarbonitrile;
trans-3-[({cis-3-[Methyl(7H-pyrrolo[2,3-d]pyrimidin-4-yl)amino]cyclobutyl}methyl)sulfonyl]cyclo-butanecarbonitrile;
3-Methyl-1-[({cis-3-[methyl(7H-pyrrolo[2,3-d]pyrimidin-4-yl)amino]cyclobutyl}methyl)sulfon-yl]azetidine-3-carbonitrile;
(1R,5R)-3-[({cis-3-[Methyl(7H-pyrrolo[2,3-d]pyrimidin-4-yl)amino]cyclobutyl}methyl)-sulfonyl]-3-azabicyclo[3.1.0]hexane-1-carbonitrile;
cis-3-(Difluoromethyl)-N-{cis-3-[methyl(7H-pyrrolo[2,3-d]pyrimidin-4-yl)amino]cyclobutyl}cyclo-butanesulfonamide;
trans-3-(Difluoromethyl)-N-{cis-3-[methyl(7H-pyrrolo[2,3-d]pyrimidin-4-yl)amino]cyclobutyl}cyclo-butanesulfonamide;
cis-1-(3-Cyano-1-methylcyclobutyl)-N-{cis-3-[methyl(7H-pyrrolo[2,3-d]pyrimidin-4-yl)amino]cyclobutyl}methanesulfonamide;
trans-1-(3-Cyano-1-methylcyclobutyl)-N-{cis-3-[methyl(7H-pyrrolo[2,3-d]pyrimidin-4-yl)amino]-cyclobutyl}-methanesulfonamide;
cis-3-Fluoro-N-{cis-3-[methyl(7H-pyrrolo[2,3-d]pyrimidin-4-yl)amino]cyclobutyl}cyclo-butanesulfonamide;
trans-3-Fluoro-N-{cis-3-[methyl(7H-pyrrolo[2,3-d]pyrimidin-4-yl)amino]cyclo-butyl}cyclobutane-sulfonamide;
cis-3-[({cis-3-[Methyl(7H-pyrrolo[2,3-d]pyrimidin-4-yl)amino]cyclobutyl}methyl)sulfonyl]cyclo-butanecarbonitrile;
trans-3-[({cis-3-[Methyl(7H-pyrrolo[2,3-d]pyrimidin-4-yl)amino]cyclobutyl}methyl)sulfonyl]cyclo-butanecarbonitrile;
N-Methyl-N-((1S,3S)-3-(((3,3,3-trifluoropropyl)sulfonyl)methyl)cyclobutyl)-7H-pyrrolo[2,3-d]pyrimidin-4-amine;
N-Methyl-N-[cis-3-({[3-(trifluoromethyl)pyrrolidin-1-yl]sulfonyl}methyl)cyclobutyl]-7H-pyrrolo[2,3-d]pyrimidin-4-amine;
N-[cis-3-({[3-(Difluoromethyl)pyrrolidin-1-yl]sulfonyl}methyl)cyclobutyl]-N-methyl-7H-pyrrolo[2,3-d]pyrimidin-4-amine;
N-(cis-3-{[(3,3-Difluoropyrrolidin-1-yl)sulfonyl]methyl}cyclobutyl)-N-methyl-7H-pyrrolo[2,3-d]pyrimidin-4-amine;
3-[({cis-3-[Methyl(7H-pyrrolo[2,3-d]pyrimidin-4-yl)amino]cyclobutyl}methyl)sulfonyl]cyclo-pentanecarbonitrile;
N-{cis-3-[(Benzylsulfonyl)methyl]cyclobutyl}-N-methyl-7H-pyrrolo[2,3-d]pyrimidin-4-amine;
1-methyl-3-{[({cis-3-[Methyl(7H-pyrrolo[2,3-d]pyrimidin-4-yl)amino]cyclobutyl}methyl)sulfon-yl]methyl}cyclobutanecarbonitrile;
N-[cis-3-({[3-(Difluoromethyl)cyclobutyl]sulfonyl}methyl)cyclobutyl]-N-methyl-7H-pyrrolo[2,3-d]pyrimidin-4-amine;
2-methyl-1-{3-[({cis-3-[Methyl(7H-pyrrolo[2,3-d]pyrimidin-4-yl)amino]cyclobutyl}methyl)sulfon-yl]azetidin-1-yl}propan-1-one;
(1R,3R)-3-[({cis-3-[Methyl(7H-pyrrolo[2,3-d]pyrimidin-4-yl)amino]cyclobutyl}methyl)sulfonyl]cyclo-pentanecarbonitrile;
N-Methyl-N-{cis-3-[(2-oxa-6-azaspiro[3.3]hept-6-ylsulfonyl)methyl]cyclobutyl}-7H-pyrrolo[2,3-d]pyrimidin-4-amine;
(1R,3S)-3-[({cis-3-[Methyl(7H-pyrrolo[2,3-d]pyrimidin-4-yl)amino]cyclobutyl}methyl)sulfonyl]cyclo-pentanecarbonitrile;
N-Methyl-N-{cis-3-[(pentan-3-ylsulfonyl)methyl]cyclobutyl}-7H-pyrrolo[2,3-d]pyrimidin-4-amine;
N-(cis-3-{[(3-Methoxypropyl)sulfonyl]methyl}cyclobutyl)-N-methyl-7H-pyrrolo[2,3-d]pyrimidin-4-amine;
N-(cis-3-{[(Cyclohexylmethyl)sulfonyl]methyl}cyclobutyl)-N-methyl-7H-pyrrolo[2,3-d]pyrimidin-4-amine;
N-(cis-3-{[(3-Fluoropropyl)sulfonyl]methyl}cyclobutyl)-N-methyl-7H-pyrrolo[2,3-d]pyrimidin-4-amine;
N-Methyl-N-(cis-3-{[(3-methylbutyl)sulfonyl]methyl}cyclobutyl)-7H-pyrrolo[2,3-d]pyrimidin-4-amine;
N-(cis-3-{[(2-Ethylbutyl)sulfonyl]methyl}cyclobutyl)-N-methyl-7H-pyrrolo[2,3-d]pyrimidin-4-amine;
N-(cis-3-{[(2-Cyclopentylethyl)sulfonyl]methyl}cyclobutyl)-N-methyl-7H-pyrrolo[2,3-d]pyrimidin-4-amine;
N-Methyl-N-(cis-3-{[(2-methylbutyl)sulfonyl]methyl}cyclobutyl)-7H-pyrrolo[2,3-d]pyrimidin-4-amine;
N-(Bicyclo[1.1.1]pent-1-yl)-N-methyl-1-{cis-3-[methyl(7H-pyrrolo[2,3-d]pyrimidin-4-yl)amino]cyclobutyl}methanesulfonamide;
N-Methyl-1-{cis-3-[methyl(7H-pyrrolo[2,3-d]pyrimidin-4-yl)amino]cyclobutyl}-N-(pentan-2-yl)methanesulfonamide;
N-Butyl-N-methyl-1-{cis-3-[methyl(7H-pyrrolo[2,3-d]pyrimidin-4-yl)amino]cyclobutyl}methane-sulfonamide;
N-(2-Methoxyethyl)-N-methyl-1-{cis-3-[methyl(7H-pyrrolo[2,3-d]pyrimidin-4-yl)amino]cyclobutyl}methanesulfonamide;
N-Ethyl-N-methyl-1-{cis-3-[methyl(7H-pyrrolo[2,3-d]pyrimidin-4-yl)amino]cyclobutyl}methanesulfonamide;
N-Cyclobutyl-N-methyl-1-{cis-3-[methyl(7H-pyrrolo[2,3-d]pyrimidin-4-yl)amino]cyclobutyl}meth-anesulfonamide;
2,5-Anhydro-1,3,4-trideoxy-3-{methyl[({cis-3-[methyl(7H-pyrrolo[2,3-d]pyrimidin-4-yl)amino]cyclobutyl}methyl)sulfonyl]amino}-L-threo-pentitol;
N-[cis-3-({[(3,3-Difluoro-1-methylcyclobutyl)methyl]sulfonyl}methyl)cyclobutyl]-N-methyl-7H-pyrrolo[2,3-d]pyrimidin-4-amine;
N-Methyl-N-(cis-3-{[(4,4,4-trifluorobutyl)sulfonyl]methyl}cyclobutyl)-7H-pyrrolo[2,3-d]pyrimidin-4-amine;
N-Methyl-N-(cis-3-{[(3,3,3-Trifluoropropyl)sulfonyl]methyl}cyclobutyl)-7H-pyrrolo[2,3-d]pyrimidin-4-amine;
or,
a pharmaceutically acceptable salt thereof.

2. A pharmaceutical or a veterinary composition comprising a compound of claim 1, or a pharmaceutically acceptable salt thereof, and a pharmaceutically acceptable carrier.

* * * * *